US011193132B2

(12) United States Patent
Ajjawi et al.

(10) Patent No.: US 11,193,132 B2
(45) Date of Patent: Dec. 7, 2021

(54) GENETIC MODULATION OF PHOTOSYNTHETIC ORGANISMS FOR IMPROVED GROWTH

(71) Applicant: Synthetic Genomics, Inc., La Jolla, CA (US)

(72) Inventors: Imad Ajjawi, San Diego, CA (US); Fedor I. Kuzminov, La Mesa, CA (US); Randor R. Radakovits, Poway, CA (US); John H. Verruto, San Diego, CA (US); Sarah Potts, San Diego, CA (US); Roberto Spreafico, La Jolla, CA (US); William F. Lambert, San Diego, CA (US); Jessica Greiner, San Diego, CA (US)

(73) Assignee: Synthetic Genomics, Inc., La Jolla, CA (US)

(*) Notice: Subject to any disclaimer, the term of this patent is extended or adjusted under 35 U.S.C. 154(b) by 0 days.

(21) Appl. No.: 16/234,209

(22) Filed: Dec. 27, 2018

(65) Prior Publication Data

US 2019/0203221 A1 Jul. 4, 2019

Related U.S. Application Data

(60) Provisional application No. 62/612,251, filed on Dec. 29, 2017, provisional application No. 62/690,205, filed on Jun. 26, 2018.

(51) Int. Cl.

*C12N 15/82* (2006.01)
*A61K 36/02* (2006.01)
*C12N 15/62* (2006.01)
*C12N 15/10* (2006.01)

(52) U.S. Cl.

CPC .......... *C12N 15/8222* (2013.01); *A61K 36/02* (2013.01); *C12N 15/8269* (2013.01); *C12N 15/102* (2013.01); *C12N 15/62* (2013.01); *C12N 15/8201* (2013.01); *C12N 15/8243* (2013.01)

(58) Field of Classification Search

CPC .................................................. C12N 15/8205
See application file for complete search history.

(56) References Cited

U.S. PATENT DOCUMENTS 10,544,424 B2* 1/2020 DiPetrillo .......... C12N 15/8247
2010/0115666 A1 5/2010 Schmulling et al.
2012/0278948 A1 11/2012 Sakakibara et al.
2015/0143581 A1 5/2015 Liu et al.
2015/0232874 A1 8/2015 Hatzfeld et al.
2016/0032309 A1 2/2016 Kashihara et al.
2016/0304896 A1* 10/2016 DiPetrillo ............... C12P 7/649
2017/0073695 A1 3/2017 Verruto et al.
2018/0186842 A1* 7/2018 Moellering ............... C12R 1/89

OTHER PUBLICATIONS httpswww.ncbi.nlm.nih.govStructure_PF00072.pdf (Year: 2020).*
Paquet et al (Efficient introduction of specific homozygous and heterozygous mutations using CRISPR/Cas9. Nature 533:125-129, 2016). (Year: 2016).*
Walter et al (*Arabidopsis thaliana* mutants lacking cpFtsY or cpSRP54 exhibit different defects in photosystemII repair. Frontiers in Plant Science, 6: 1-9, 2015). (Year: 2015).*
International Search Report dated Apr. 24, 2019, regarding PCT/US2018/067712.
Jeong et al.: "*Loss of CpSRP54 function leads to a truncated light-harvesting antenna size in Chlamydomonas reinhardtii,*"; Biochimica et Blophysica Acta—Bioenergetics, Jan. 31, 2017, vol. 1858, Issue 1, pp. 45-55.
Braun et al., "Effects of light and circadian clock on growth and chlorophyll accumulation of N annochloropsis gaditana", Journal of Phycology, Apr. 2014, 50(3):515-525.
Database UniProt [Online] Nov. 30, 2016, "RecName: Full= Response regulatory domain-containing protein {ECO:0000259|PROSITE:P850110};" XP55838280, retrieved from EBI accession No. UNIPROT:A0A1D2A709, DB accession No. A0A1D2A709.
EP Supplementary Partial European Search Report in European Application No. EP18897385, dated Sep. 21, 2021, 17 pages.
Nakamiohi et al., "Pseudo-Response Regulators, PRR9, PRR7 and PRR5, Together Play Essential Roles Close to the Circadian Clock of *Arabidopsis thaliana*", Plant and Cell Physiology, May 2005, 46(5):686-698.

* cited by examiner

*Primary Examiner* — Ashley K Buran
*Assistant Examiner* — Wayne Zhong
(74) *Attorney, Agent, or Firm* — DLA Piper LLP (US)

(57) ABSTRACT

Mutant photosynthetic organisms having reduced chlorophyll and increased photosynthetic efficiency are provided. The mutant strains have mutated or attenuated: chloroplastic SRP54 gene and SGI1 gene; chloroplastic SRP54 gene and SGI2 gene; chloroplastic SRP54 gene, SGI1, and SGI2 genes are disclosed. The mutant photosynthetic organisms exhibit increased productivity with respect to wild-type strains. Also provided are mutant photosynthetic organisms having mutated or attenuated cytosolic SRP54 genes. Provided herein are methods of producing biomass and other products such as lipids using strains having mutations in an SRP54 gene, SGI1, SGI2 genes, a combination of SGI1/SRP54, and a combination of SGI2 and SRP54 genes. Also included are constructs and methods for attenuating or disrupting SRP54, SGI1, and SGI2 genes.

25 Claims, 17 Drawing Sheets

Specification includes a Sequence Listing.

Figure 5
Protein family membership
None predicted.
Homologous superfamilies
Domains and repeats
Detailed signature matches
Chey-like superfamily
Signal transduction response regulator, receiver domain
no IPR
Unintegrated signatures
GO term prediction
Biological Process
phosphorelay signal transduction system
Molecular Function
None predicted.
Cellular Component
None predicted.

GENETIC MODULATION OF PHOTOSYNTHETIC ORGANISMS FOR IMPROVED GROWTH

CROSS-REFERENCE TO RELATED APPLICATIONS

This application claims benefit of priority under 35 U.S.C. § 119(e) of U.S. Ser. No. 62/612,251, filed Dec. 29, 2017 and U.S. Ser. No. 62/690,205, filed Jun. 26, 2018, the entire contents of which are incorporated herein by reference in their entireties.

INCORPORATION OF SEQUENCE LISTING

The material in the accompanying sequence listing is hereby incorporated by reference into this application. The accompanying sequence listing text file, name SGI2140_2_Sequence_Listing.txt was created on Dec. 18, 2018, and is 419 kb. The file can be accessed using Microsoft Word on a computer that uses Windows OS.

BACKGROUND OF THE INVENTION

Improvements in biomass productivity of photosynthetic organisms are relevant to various commercial applications—from biofuels to high-value products. Genetic manipulation to increase the total protein content of biomass is highly desirable, but strategies to do so are not apparent in the art.

Engineering photosynthetic organisms to increase photosynthetic efficiency for higher productivity is a long-standing goal of plant and algal biologists. US 2014/0220638 and US 2016/030489, both of which are incorporated herein by reference, describe mutant screens to obtain algal mutants having reduced chlorophyll that are impaired in their ability to low light acclimation, that is, they retain the low chlorophyll state of high light adapted cells even in low light. US 2014/0220638 describes algal mutants having mutations in the Light Acclimation Regulator LAR1, LAR2, and LAR3 genes, and US 2016/0304896 discloses algal mutants having mutations in the chloroplastic SRP54 gene.

SUMMARY OF THE INVENTION

Disclosed herein are photosynthetic organisms comprising modulated genes having increased photosynthetic efficiency and productivity, their use in producing products under photoautotrophic conditions, and methods of producing such photosynthetic organisms, and nucleic acid molecules and constructs for modulating such genes.

In one aspect, provided are mutant photosynthetic organisms comprising a mutated or attenuated gene encoding significant growth improvement gene 2 (SGI2).

In one aspect, provided are mutant photosynthetic organisms comprising a mutated or attenuated gene encoding a chloroplastic signal recognition protein 54 (cpSRP54) and a mutated or attenuated significant growth improvement gene 2 (SGI2).

In one aspect, provided are mutant photosynthetic organisms comprising a mutated or attenuated gene encoding a chloroplastic signal recognition protein 54 (cpSRP54) and a mutated or attenuated significant growth improvement gene 1 (SGI1).

In one aspect provided are mutant photosynthetic organism comprising a mutated or attenuated gene encoding a chloroplastic signal recognition protein 54 (cpSRP54), a mutated or attenuated significant growth improvement gene 1 (SGI1), and a mutated or attenuated significant growth improvement gene 2 (SGI2).

In one aspect, provided are mutant photosynthetic organisms comprising a mutated or attenuated gene encoding a cytosolic signal recognition protein 54 (cytoSRP54) and a mutated or attenuated significant growth improvement gene 2 (SGI2).

In one aspect, provided are mutant photosynthetic organisms comprising a mutated or attenuated gene encoding a cytosolic signal recognition protein 54 (cytoSRP54) and a mutated or attenuated significant growth improvement gene 1 (SGI1).

In one aspect, provided are mutant photosynthetic organisms comprising a mutated or attenuated gene encoding a cytosolic signal recognition protein 54 (cytoSRP54) a mutated or attenuated significant growth improvement gene 1 (SGI1), and a mutated or attenuated significant growth improvement gene 2 (SGI2).

In one aspect, provided are biomass comprising mutant photosynthetic organisms in which the mutant photosynthetic organisms comprise a mutated or attenuated gene encoding a chloroplastic signal recognition protein 54 (cpSRP54), and a mutated or attenuated significant growth improvement gene 1 (SGI1) and/or a mutated or attenuated significant growth improvement gene 2 (SGI2).

In one aspect, provided are methods of producing a biological product. The methods include culturing mutant photosynthetic organisms in which the mutant photosynthetic organisms comprise a mutated or attenuated gene encoding a chloroplastic signal recognition protein 54 (cpSRP54), and a mutated or attenuated significant growth improvement gene 1 (SGI1) and/or a mutated or attenuated significant growth improvement gene 2 (SGI2); and isolating at least one product from the culture.

In one aspect, provided are methods of inserting a single copy of a CRISPR gene into a selected locus of a microorganism. In some embodiments, the CRISPR gene is codon optimized for expression in the microorganism. In some embodiments, the inserted CRISPR gene comprises multiple heterologous introns. In some embodiments, the number of heterologous introns can be at least 5, 6, 7, 8, 9, 10, 11, 12, 13, 14, 15, 16, 17, 18, 19, 20, 21, 22, 23, 24, 25, 26, 27, 28, 29, 30, 35, 40, or more. Non-limiting examples of the CRISPR gene include Cas9 and Cpf1. In some embodiments, the CRISPR gene can be operably linked to a promoter native to the microorganism. In some embodiments, the promoter is inducible. In some embodiments, the CRISPR gene can be operably linked to a promoter heterologous to the microorganism.

In some embodiments, the biological product is a lipid, a protein, a peptide, one or more amino acids, an amino acid, one or more nucleotides, a vitamin, a cofactor, a hormone, an antioxidant, or a pigment or colorant. In some embodiments, the biological product is a biomass. In some embodiments, the mutant photosynthetic organism is algae and the biomass is algal biomass.

In some embodiments, the mutant photosynthetic organism is engineered to include at least one exogenous gene encoding a polypeptide that participates in the production of a lipid. In some embodiments, the mutant photosynthetic organism is cultured phototrophically. In some embodiments, the mutant photosynthetic organism is algae, and the algae are cultured in pond or raceway.

In one aspect, provided are nucleic acid molecule constructs for homologous recombination comprising a nucleotide sequence from or adjacent to a naturally-occurring photosynthetic organism gene encoding SGI2 protein, wherein the SGI2 protein comprises an amino acid sequence having at least 55% identity to an amino acid sequence selected from the group consisting of SEQ ID NO: 5, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, and SEQ ID NO: 56 prior to mutation or attenuation of the gene.

In one aspect, provided are plurality of nucleic acid molecule constructs for homologous recombination comprising a nucleotide sequence from or adjacent to a naturally-occurring photosynthetic organism gene encoding a cpSRP54 protein and a photosynthetic organism gene encoding a SGI1 protein, wherein the cpSRP54 protein comprises an amino acid sequence having at least 55% identity to SEQ ID NO: 68, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, and SEQ ID NO:85 prior to mutation or attenuation of the gene., and wherein the SGI1 gene encodes a polypeptide having an amino acid sequence comprises an amino acid sequence having at least 55% identity to an amino acid sequence selected from the group consisting of SEQ ID NO:3, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 34, SEQ ID NO: 35, SEQ ID NO: 36, SEQ ID NO: 37, SEQ ID NO: 38, and SEQ ID NO: 39 prior to mutation or attenuation of the SGI1 gene.

In one aspect, provided are plurality of nucleic acid molecule constructs for homologous recombination comprising a nucleotide sequence from or adjacent to a naturally-occurring photosynthetic organism gene encoding a cpSRP54 protein and a photosynthetic organism gene encoding SGI2 protein, wherein the cpSRP54 protein comprises an amino acid sequence having at least 55% identity to SEQ ID NO: 68, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, or SEQ ID NO:85 prior to mutation or attenuation of the gene, and wherein the SGI2 protein comprises an amino acid sequence having at least 55% identity to SEQ ID NO: 5, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, or SEQ ID NO: 56 prior to mutation or attenuation of the gene.

In one aspect, provided are nucleic acid molecule constructs for expression of an antisense RNA, shRNA, microRNA, or ribozyme comprising a nucleotide sequence complementary to at least a portion of a naturally-occurring a photosynthetic organism gene encoding SGI2 protein, wherein the SGI2 protein comprises an amino acid sequence having at least 55% identity to SEQ ID NO: 5, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, or SEQ ID NO: 56 prior to mutation or attenuation of the gene.

In one aspect, provided are plurality of nucleic acid molecule constructs for expression of an antisense RNA, shRNA, microRNA, or ribozyme comprising a nucleotide sequence complementary to at least a portion of a naturally-occurring a photosynthetic organism gene encoding a cpSRP54 protein and a photosynthetic organism gene encoding SGI1 protein, wherein the cpSRP54 protein comprises an amino acid sequence having at least 55% identity to SEQ ID NO: 68, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, or SEQ ID NO:85 prior to mutation or attenuation of the gene, and wherein the SGI1 protein comprises an amino acid sequence having at least 55% identity to SEQ ID NO:3, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 34, SEQ ID NO: 35, SEQ ID NO: 36, SEQ ID NO: 37, SEQ ID NO: 38, or SEQ ID NO: 39 prior to mutation or attenuation of the SGI1 gene.

In some embodiments, the construct comprises at least a portion of a 5'UTR of a cpSRP54, SGI1, SGI2, or a combination of two or more of the genes, at least a portion of the promoter region of a cpSRP54, SGI1, SGI2, or a combination of two or more of the genes, and/or at least a portion of a 3' UTR of a cpSRP54, SGI1, SGI2, or a combination of two or more of the genes. In some examples, the construct can be an RNAi, ribozyme, or antisense construct and can include a sequence from the transcribed region of the cpSRP54, SGI1, SGI2, or a combination of two or more of the genes in either sense or antisense orientation. In further examples, a construct can be designed for the in vitro or in vivo expression of a guide RNA designed to target a cpSRP54, SGI1, SGI2, or a combination of two or more of the genes, and can include a sequence homologous to a portion of any of the genes, including, for example, an intron, a 5'UTR, a promoter region, and/or a 3' UTR of the gene. In yet further examples, a construct for attenuating expression a gene encoding a cpSRP54, SGI1, or SGI2 polypeptide can be a guide RNA or antisense oligonucleotide, where the sequence having homology to a transcribed region of a cpSRP54, SGI1, SGI2, or a combination of two or more genes in antisense orientation.

In one aspect, provided are plurality of nucleic acid molecule constructs for expression of an antisense RNA, shRNA, microRNA, or ribozyme comprising a nucleotide sequence complementary to at least a portion of a naturally-occurring a photosynthetic organism gene encoding a cpSRP54 protein and a photosynthetic organism gene encoding SGI2 protein, wherein the cpSRP54 encodes a protein that comprises an amino acid sequence having at least 55% identity to SEQ ID NO: 68, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, or SEQ ID NO:85 prior to mutation or attenuation of the gene, and wherein the SGI2 gene encodes a protein that comprises an amino acid sequence having at least 55% identity to SEQ ID NO: 5, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, or SEQ ID NO: 56 prior to mutation or attenuation of the gene.

In one aspect, provided are plurality nucleic acid molecules encoding a guide RNAs, wherein the guide RNAs comprises at least a portion of a naturally-occurring a photosynthetic organism gene SGI2, wherein SGI2 gene encodes a protein that comprises an amino acid sequence having at least 55% identity to SEQ ID NO: 5, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, or SEQ ID NO: 56 prior to mutation or attenuation of the gene.

In one aspect, provided are plurality nucleic acid molecules encoding at least two guide RNAs, wherein the guide RNAs comprises at least a portion of a naturally-occurring a photosynthetic organism gene encoding a cpSRP54 and a photosynthetic organism gene encoding SGI1, wherein the cpSRP54 encodes a protein that comprises an amino acid sequence having at least 55% identity to SEQ ID NO: 68, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, or SEQ ID NO:85 prior to mutation or attenuation of the gene, and wherein the SGI1 gene comprises an amino acid sequence having at least 55% identity to SEQ ID NO:3, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 34, SEQ ID NO: 35, SEQ ID NO: 36, SEQ ID NO: 37, SEQ ID NO: 38, or SEQ ID NO: 39 prior to mutation or attenuation of the SGI1 gene.

In one aspect, provided are plurality nucleic acid molecules encoding at least two guide RNAs, wherein the guide RNAs comprises at least a portion of a naturally-occurring a photosynthetic organism cpSRP54 gene and a photosynthetic organism gene SGI2 gene, wherein the cpSRP54 gene encodes a protein that comprises an amino acid sequence having at least 55% identity to SEQ ID NO: 68, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, or SEQ ID NO:85 prior to mutation or attenuation of the gene, and wherein the SGI2 gene comprises an amino acid sequence having at least SEQ ID NO: 5, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, or SEQ ID NO: 56 prior to mutation or attenuation of the gene.

In one aspect, provided are methods of increasing the biomass of a photosynthetic organism, comprising modulating the SGI2 gene.

In one aspect, provided are method of increasing the biomass of a photosynthetic organism, comprising modulating the chloroplastic signal recognition protein 54 (cpSRP54) and Significant Growth Improvement Gene 1 (SGI1), wherein the cpSRP54 gene encodes a protein that comprises an amino acid sequence having at least 55% identity to SEQ ID NO: 68, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, or SEQ ID NO:85 prior to mutation or attenuation of the gene, and wherein the SGI1 gene comprises an amino acid sequence having at least SEQ ID NO:3, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 34, SEQ ID NO: 35, SEQ ID NO: 36, SEQ ID NO: 37, SEQ ID NO: 38, or SEQ ID NO: 39 prior to mutation or attenuation of the SGI1 gene.

In one aspect, provided are method of increasing the biomass of a photosynthetic organism, comprising modulating the chloroplastic signal recognition protein 54 gene (cpSRP54) and Significant Growth Improvement Gene 2 (SGI2), wherein the cpSRP54 gene encodes a protein that comprises an amino acid sequence having at least 55% identity to SEQ ID NO: 68, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, or SEQ ID NO:85 prior to mutation or attenuation of the gene, and wherein the SGI2 gene comprises an amino acid sequence having at least SEQ ID NO: 5, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, or SEQ ID NO: 56 prior to mutation or attenuation of the gene.

In one aspect, provided are method of increasing the biomass of a photosynthetic organism, comprising modulating the cytosolic signal recognition protein 54 (cytoSRP54) and Significant Growth Improvement Gene 2 (SGI2), wherein the SGI2 gene encodes a protein that comprises an amino acid sequence having at least SEQ ID NO: 5, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, or SEQ ID NO: 56 prior to mutation or attenuation of the gene.

In some embodiments, the culture of the mutant photosynthetic organism exhibits greater biomass productivity than does a culture of a control photosynthetic organism of the same species. In some embodiments, the mutant photosynthetic organism demonstrates greater biomass productivity in photoautotrophic culture. In some embodiments, the mutant photosynthetic organism exhibits greater biomass productivity than does a culture of a control photosynthetic organism of the same species under continuous light conditions. In some embodiments, the mutant photosynthetic organism exhibits greater biomass productivity than does a culture of a control photosynthetic organism of the same species under diel cycle conditions. In some embodiments, the mutant photosynthetic organism exhibits greater biomass productivity than does a culture of a control photosynthetic organism of the same species under diel cycle conditions in which the light profile mimics a natural daylight profile.

In some embodiments, increasing the biomass of a photosynthetic organism comprises an increase in total organic carbon. In some embodiments, increasing the biomass of a photosynthetic organism comprises an increase in total lipid content. In some embodiments, increasing the biomass of a photosynthetic organism comprises an increase in total nitrogen content.

In some embodiments, mutant photosynthetic organism exhibits a reduction in chlorophyll under low light conditions and higher maximum quantum yield of photochemistry in photosystem II ($F_V/F_M$) at all physiologically relevant irradiances above 100, 125, 150, 200, or 250 μE $m^{-2}s^{-1}$ with respect to a control photosynthetic organism of the same species. In some embodiments, the reduction in chlorophyll is at least 20%, 30%, 40%, 50%, 60%, or 70% reduction with respect to a control photosynthetic organism of the same species. In some embodiments, the mutant photosynthetic organism exhibits lower nonphotochemical quenching (NPQ) at all physiologically relevant irradiances above 125, 150, 200, or 250 μE $m^{-2}$ $s^{-1}$ with respect to a control photosynthetic organism of the same species.

In some embodiments, the mutant photosynthetic organism exhibits a higher rate of carbon fixation on a per chlorophyll basis than does a control photosynthetic organism of the same species. In some embodiments, the rate of carbon fixation is at least 50%, 60%, 70%, 80%, 90%, or 100% higher than a control photosynthetic organism of the same species.

In some embodiments, the mutant photosynthetic organism exhibits at least 100%, 150%, 200%, 300%, 400% or higher rate of oxygen evolution per mg chlorophyll than a control photosynthetic organism of the same species. In some embodiments, the mutant photosynthetic organism exhibits at least 100%, 150%, 200%, 300%, 400% or higher rate of oxygen evolution per □g of total organic carbon (TOC).

In some embodiments, the mutant photosynthetic organism exhibits greater lipid productivity than does a culture of a control photosynthetic organism of the same species. In some embodiments, the mutant photosynthetic organism exhibits greater lipid productivity in photoautotrophic culture. In some embodiments, the mutant photosynthetic organism is algae.

In some embodiments, the mutant photosynthetic organisms are generated by modulating the SGI2 genes of the organisms. In some embodiments, the mutant photosynthetic organisms are generated by modulating the cpSRP54 gene together with the SGI1 gene or SGI2 gene of the organisms. In some embodiments, modulating the genes comprises UV radiation, gamma radiation, or chemical mutagenesis. In some embodiments, modulating the genes comprises base substitution mutation, insertional mutagenesis, gene replacement, RNAi, antisense RNA, meganuclease genome engineering, one or more ribozymes, and/or a CRISPR/Cas system in the cpSRP54 gene, SGI1 gene, SGI2 gene, or a combination of the genes.

In some embodiments, the mutant photosynthetic organisms comprise a cpSRP54 gene encoding a protein having an amino acid sequence that is at least 50%, 55%, 60%, 65%, 70%, 75%, 80%, 85%, 90%, or 95% identity to an amino acid sequence selected from the group consisting of SEQ ID NO: 68, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, or SEQ ID NO:85 prior to mutation or attenuation of the gene. In some embodiments, the mutant photosynthetic organisms comprise a cpSRP54 gene encodes a protein having an amino acid sequence that is at least 50%, 55%, 60%, 65%, 70%, 75%, 80%, 85%, 90%, or 95% identity to at least 30, 35, 40, 45, 50, 60, 70, 80, 100, 150, 200, 250, 300 amino acids, or to the entire length of an amino acid sequence selected from the group consisting of SEQ ID NO: 68, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, or SEQ ID NO:85 prior to mutation or attenuation of the gene.

In some embodiments, the mutant photosynthetic organisms comprise a mutation in the cpSRP54 gene that occurs outside the sequence encoding the first 169 amino acids of the cpSRP54 GTPase domain. In some embodiments, the mutation in the cpSRP54gene encoding an SRP54 protein occurs outside the sequence encoding the cpSRP54 GTPase domain. In some embodiments, the mutation in the cpSRP54 gene does not include a gene-disrupting mutation in the cpSRP54 GTPase domain.

In some embodiments, the SGI2 gene of the mutant photosynthetic organisms encoding a protein having an amino acid sequence that is at least 50%, 65%, 70%, 75%, 80%, 85%, 90%, 95% identity to an amino acid sequence of SEQ ID NO: 5, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, or SEQ ID NO: 56 prior to mutation or attenuation of the gene. In some embodiments, the SGI2 gene of the mutant photosynthetic organisms encoding a protein having an amino acid sequence that is at least 50%, 65%, 70%, 75%, 80%, 85%, 90%, 95% identity to at least 30, 35, 40, 45, 50, 60, 70, 80, 100, 150, 200, 250, 300 amino acids, or to the entire length of an amino acid sequence of SEQ ID NO: 5, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, or SEQ ID NO: 56 prior to mutation or attenuation of the gene.

In some embodiments, the SGI1 gene of the mutant photosynthetic organisms encoding a protein having an amino acid sequence that is at least 50%, 65%, 70%, 75%, 80%, 85%, 90%, 95% identity to an amino acid sequence of SEQ ID NO:3, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 34, SEQ ID NO: 35, SEQ ID NO: 36, SEQ ID NO: 37, SEQ ID NO: 38, or SEQ ID NO: 39 prior to mutation or attenuation of the SGI1 gene. In some embodiments, the SGI1 gene of the mutant photosynthetic organisms encoding a protein having an amino acid sequence that is at least 50%, 65%, 70%, 75%, 80%, 85%, 90%, 95% identity to at least 30, 35, 40, 45, 50, 60, 70, 80, 100, 150, 200, 250, 300 amino acids, or to the entire length of an amino acid sequence of SEQ ID NO:3, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 34, SEQ ID NO: 35, SEQ ID NO: 36, SEQ ID NO: 37, SEQ ID NO: 38, or SEQ ID NO: 39 prior to mutation or attenuation of the SGI1 gene.

In some embodiments of the above aspects, the photosynthetic organism is multiploidy, e.g., diploid, triploid, tetraploid. In some embodiments, one or more copies of the gene: cpSRP54, SGI1, or SGI2 is mutated or attenuated leaving other copies of the genes unaltered or unattenuated to generate a mutant photosynthetic organism. In some embodiments, the mutant photosynthetic organism thus generated, exhibit a reduction in chlorophyll under low light conditions and higher maximum quantum yield of photochemistry in photosystem II ($F_v/F_M$) at all physiologically relevant irradiances above 100, 125, 150, 200, or 250 μE $m^{-2}s^{-1}$ with respect to a control photosynthetic organism of the same species. In some embodiments, the mutant photosynthetic organism thus generated, exhibits greater biomass productivity than a control photosynthetic organism of the same species. In some embodiments, the mutant photosynthetic organism thus generated, exhibits greater lipid productivity than a control photosynthetic organism of the same species.

In some embodiments of the above aspects, the mutant photosynthetic organism is algae. In some embodiments, the algae belong to genus *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Gloeothamnion, Haematococcus, Halocafeteria, Heterosigma, Hymenomonas, Isochrysis, Lepocinclis, Micractinium, Monodus, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Skeletonema, Spyrogyra, Stichococcus, Tetraselmis, Thalassiosira, Tribonema, Vaucheria, Viridiella, Vischeria*, and *Volvox*. In some embodiments, the mutant photosynthetic organism is a member of the chlorophytes or charophytes, and may be, for example, a member of any of the Chlorophyte classes Chlorophyceae, Trebouxiophyceae, Chlorodendrophyceae, Ulvophyceae, Pedinophyceae, or Prasinophyceae. For example, the algal mutant can be a species belonging to Chlorophyceae, Trebouxiophyceae, or Chlorodendrophyceae. In some embodiments, the mutant algal cell is a Chlorophyte algal cell, and may be a Chlorophyte algal cell of the Trebouxiophyceae class, for example, an algal cell of a species of a genus such as *Botryococcus, Chlorella, Auxenochlorella, Heveochlorella, Marinichlorella, Parachlorella, Pseudochlorella, Tetrachlorella, Eremosphaera, Franceia, Micractinium, Nannochloris, Oocystis, Picochlorum*, or *Prototheca*. In some embodiments, the mutant alga can be a species belonging to a species of *Auxenochlorella, Chlorella, Heveochlorella, Marinichlorella, Parachlorella, Pseudochlorella* or *Tetrachlorella*.

In some embodiments, the mutant photosynthetic microorganism is a cyanobacterium. In some embodiments, the cyanobacterium is an *Acaryochloris, Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, thermosynechocystis, Tolypothrix, Trichodesmium, Tychonema*, or *Xenococcus* species.

In some embodiments, the mutant photosynthetic microorganism is a plant. Non-limiting examples of plants include monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot potato, sugar beets, yam), leafy vegetable crops (e.g., lettuce, spinach); flowering plants (e.g., petunia, rose, chrysanthemum), conifers and pine trees (e.g., pine fir, spruce), plants used in phytoremediation (e.g., heavy metal accumulating plants); oil crops (e.g., sunflower, rapeseed) and plants used for experimental purposes (e.g., *Arabidopsis*).

Non-limiting examples of mutated dicotyledonous plants include plants belonging to the orders *Magniolales, Miciales, Laurales, Piperales, Aristochiales, Nymphaeales, Ranunculales, Papeverales, Sarraceniaceae, Trochodendrales, Hamamelidales, Eucomiales, Leitneriales, Myricales, Fagales, Casuarinales, Caryophyllales, Batales, Polygonales, Plumbaginales, Dilleniales, Theales, Malvales, Urticales, Lecythidales, Violales, Salicales, Capparales, Ericales, Diapensales, Ebenales, Primulales, Rosales, Fabales, Podostemales, Haloragales, Myrtales, Cornales, Proteales, San tales, Rafflesiales, Celastrales, Euphorbiales, Rhamnales, Sapindales, Juglandales, Geraniales, Polygalales, Umbellales, Gentianales, Polemoniales, Lamiales, Plantaginales, Scrophulariales, Campanulales, Rubiales, Dipsacales*, and *Asterales*.

Non-limiting examples of mutated monocotyledonous plants include plants belonging to the orders *Alismatales, Hydrocharitales, Najadales, Triuridales, Commelinales, Eriocaulales, Restionales, Poales, Juncales, Cyperales, Typhales, Bromeliales, Zingiberales, Arecales, Cyclanthales, Pandanales, Arales, Lilliales*, and *Orchid ales*, or with plants belonging to Gymnospermae, e.g., those belonging to the orders *Pinales, Ginkgoales, Cycadales, Araucariales, Cupressales* and *Gnetales*.

In some embodiments, the mutated plants can be *Arabidopsis arenicola, Arabidopsis arenosa, Arabidopsis cebennensis, Arabidopsis croatica, Arabidopsis halleri, Arabidopsis lyrata, Arabidopsis neglecta, Arabidopsis pedemontana, Arabidopsis suecica, Arabidopsis thaliana, Zea mays, Oryza sativa, Triticum aestivum, Solanum tuberosum, Allium cepa, Allium sativum, Glycine max, Solanum lycopersicum, Gossypium hirsutum, Gossypium herbaceum, Gossypium arboreum, Gossypium tomentosum, Brassica nigra*, or *Brassica* sp.

In some embodiments, modulation of SRP54, SGI1, SGI2, or a combination of one or more of the genes in a plant can be tissue specific. In some embodiments, the plant tissue can be leaf, stem, or roots. In some embodiments, the modulation of the tissue-specific genes can be achieved by modulating the tissue-specific non-coding regions of the genes, for example, promoters, enhancers, introns, 3'- or 5'-untranslated regions. In some embodiments, modulation of SRP54, SGI1, SGI2, or a combination of one or more of the genes in a plant can be made at different developmental stages of the plant.

These and other objects and features of the invention will become more fully apparent when the following detailed description of the invention is read in conjunction with the accompanying drawings.

DETAILED DESCRIPTION OF THE INVENTION

Figure 1:
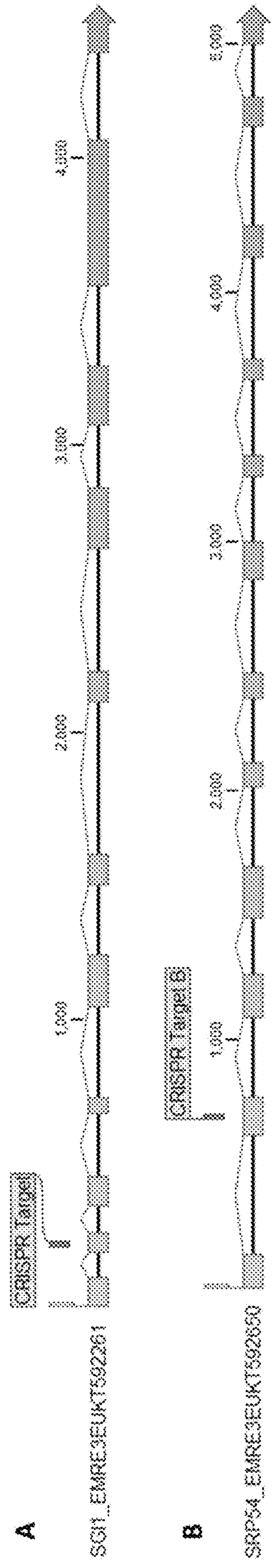
FIG. 1A shows a schematics of the SGI1 gene. A putative location of the gRNA designed to disrupt the SGI1 gene (CRISPR target) is indicated.
FIG. 1B shows a schematics of the SPR54 gene. A putative location of the gRNA designed to disrupt the SPR54 gene (CRISPR target) is indicated.

Inventors of the present application surprisingly and unexpectedly found that modulating the SGI1 and SGI2 genes in photosynthetic organisms result in a reduction in chlorophyll under low light conditions and higher maximum quantum yield of photochemistry in photosystem II ($F_V/F_M$) at all physiologically relevant irradiances. In some embodiments, the mutant photosynthetic organism comprising a mutated or attenuated SGI1 or SGI2 gene exhibits lower nonphotochemical quenching (NPQ) at all physiologically relevant irradiances. In some embodiments, the mutant photosynthetic organism comprising a mutated or attenuated SGI1 or SGI2 gene exhibits increased biomass than does a control photosynthetic organism of the same species. In some embodiments, the mutant photosynthetic organism comprising a mutated or attenuated SGI1 or SGI2 gene exhibits a higher rate of carbon fixation on a per chlorophyll basis than does a control photosynthetic organism of the same species. In some embodiments, the mutant photosynthetic organism comprising a mutated or attenuated SGI1 or SGI2 gene exhibits a higher rate of carbon fixation per TOC basis than does a control photosynthetic organism of the same species. In some embodiments, the mutant photosynthetic organism comprising a mutated or attenuated SGI1 or SGI2 gene exhibits a higher rate of oxygen evolution per mg chlorophyll than a control photosynthetic organism of the same species. In some embodiments, the mutant photosynthetic organism comprising a mutated or attenuated SGI1 or SGI2 gene exhibits a higher rate of oxygen evolution per TOC basis than a control photosynthetic organism of the same species. In some embodiments, the mutant photosynthetic organism comprising a mutated or attenuated SGI1 or SGI2 gene exhibits greater lipid productivity than does a culture of a control photosynthetic organism of the same species. In some embodiments, the mutant photosynthetic organism comprising a mutated or attenuated SGI1 or SGI2 gene exhibits greater lipid productivity in photoautotrophic culture.

Inventors of the present application also surprisingly found a synergistic effect upon modulating SGI1 or SGI2 genes together with modulating SRP54 gene in photosynthetic organisms. In some embodiments, the chlorophyll is further reduced, more increased biomass, greater carbon fixation on a per chlorophyll basis, greater carbon fixation per TOC basis, greater lipid productivity in a mutant photosynthetic organism where SRP54 and SGI1 or SGI2 genes are modulated as compared to a mutant photosynthetic organism where only SGI1 or SGI2 genes are modulated.

SGI1 Gene

As described herein, Significant Growth Improvement Gene 1 (SGI1) polypeptides are polypeptides that include two domains: a Response Receiver or "RR" domain (Pfam PF00072) and a Myb domain (Pfam PF00249), where the RR domain is positioned N-terminal to the Myb domain. The RR domain and Myb domain are separated by an amino acid sequence that is found to be poorly conserved or not conserved among SGI1 polypeptides, sometimes referred to herein as a linker between the two domains, where the linker and may range in length from one to 300 amino acids, or from ten to 200 amino acids, for example. The linker region can optionally include a nuclear localization sequence (NLS).

The presence of a Response Receiver "RR" domain (Pfam PF00072) is responsible for its bioinformatic annotation as a CheY-like polypeptide. This RR domain extends from approximately amino acid 36 to amino acid 148 of the *Parachlorella* SGI1 polypeptide (SEQ ID NO:3), and is also characterized as a "signal receiver domain", cd00156, in the conserved domain database (CDD), extending approximately from amino acid 37 through amino acid 154. It is also characterized as a "CheY-like receiver (REC) domain", COG0784, in the Clusters of Orthologous Groups of proteins database and as an Interpro "CheY-like superfamily" domain, IPR011006, with both of these characterized domains extending from approximately amino acid 33 to approximately amino acid 161 of the *Parachlorella* SGI1 polypeptide of SEQ ID NO:3. The RR domain is found in bacterial two-component regulatory systems (like the bacterial chemotaxis two-component system that includes a polypeptide known as CheY), in which it receives a signal from a sensor partner. The RR domain of such systems is often found N-terminal to a DNA binding domain and includes a phosphoacceptor site that can be phosphorylated, which may be responsible for its activation or deactivation.

An RR domain within an SGI1 protein can be characterized, for example, as Pfam PF00072, or as a "signal receiver domain" or simply "receiver domain", and/or can be classified as cd00156 in the conserved domain database (CDD), as COG0784 in the Clusters of Orthologous Groups of proteins database, or as an Interpro "CheY-like superfamily" domain, IPR011006. The RR domain is found in bacterial two-component regulatory systems (like the bacterial chemotaxis two-component system that includes a polypeptide known as CheY), in which it receives a signal from a sensor partner. The RR domain of such systems is often found N-terminal to a DNA binding domain and includes a phosphoacceptor site that can be phosphorylated, which may be responsible for its activation or deactivation.

A myb domain within an SGI1 protein can be characterized, for example, as pfamPF00249: "Myb-like DNA-binding domain", and/or may be identified as conserved domain TIGR01557 "myb-like DNA-binding domain, SHAQKYF class ("SHAQKYF" disclosed as SEQ ID NO: 102)", or as an Interpro Homeobox-like domain superfamily domain (IPR009057) and/or an Interpro Myb domain (IPR017930).

In addition to having an RR domain N-terminal to a myb domain, an SGI1 protein as provided herein can have a score of 300 or higher, 320 or higher, 340 or higher, 350 or higher, 360 or higher, or 370 or higher when scanned with a Hidden Markov Model (HMM) designed to score proteins on the basis of how well the query protein amino acid sequence matches the conserved amino acids of a region of SGI1 homologs in algae, where highly conserved amino acid positions are weighted more heavily than poorly conserved amino acid positions within a compared region of the polypeptides to arrive at the score. Polypeptides having scores of 350 or greater, such as 370 or greater, when scanned with an HMM model based on protein sequences of algal SGI1 polypeptides that include a single continuous sequence that includes the RR domain, linker, and myb domain developed using include, without limitation, polypeptides of the algal and plant species *Parachlorella* sp. 1185 (SEQ ID NO:3), *Coccomyxa subellipsoidea* (SEQ ID NO:9), *Ostreococcus lucimarinus* (SEQ ID NO:10), *Chlamydomonas reinhardtii* (SEQ ID NO:11), *Volvox carteri* (SEQ ID NO:13), *Tetraselmis* sp. 105 (SEQ ID NOs:14, 15, and 16), *Oocystis* sp. (SEQ ID NO:17), *Micromonas* sp. RCC299 (SEQ ID NO:18), *Micromonas pusilla* (SEQ ID NO:19), *Sphagnum fallax* (SEQ ID NO:20), *Physcomitrella patens* (SEQ ID NO:21), *Arabidopsis thaliana* ((SEQ ID NO:22), *Arabidopsis halleri* (SEQ ID NO:23), *Arabidopsis lyrata* (SEQ ID NO:24), *Helianthus annuus* (SEQ ID NO:25), *Vitis vinifera* (SEQ ID NO:26), *Amborella trichopoda* (SEQ ID NO:27), *Ricinus communis* (SEQ ID NO:28), *Solanum lycopersicum* (SEQ ID NO:29), *Solanum tuberosum* (SEQ ID NO:30), *Gossypium hirsutum* (SEQ ID NO:31), *Theobroma cacao* (SEQ ID NO:32), *Phaeolis vulgaris* (SEQ ID NO:33), *Glycine max* (SEQ ID NO:34), *Chenopodium quinoa* (SEQ ID NO:35), *Malus domesticus* (SEQ ID NO:36), *Zea mays* (SEQ ID NO:37), *Brassica rapa* (SEQ ID NO:38), and *Oryza sativa* (SEQ ID NO:39), as well as polypeptides having at least 50%, at least 55%, at least 60%, at least 65%, at least 70%, at least 75%, at least 80%, at least 85%, at least 90%, at least 95%, at least 96%, at least 97%, at least 98%, or at least 99% identity to any of the aforegoing, where the polypeptide has an RR domain and a myb domain, and the RR domain is N-terminal to the myb domain. In various embodiments, the SGI1 polypeptide is from a plant or algal species. A gene encoding an SGI1 polypeptide as provided herein, for example a gene that is disrupted or whose expression is attenuated in a mutant as provided herein can be, in various embodiments, a naturally-occurring gene of a plant or algal species that encodes a polypeptide as disclosed herein.

In some embodiments, an SGI1 polypeptide as provided herein is an algal SGI1 polypeptide, for example, having the sequence of a naturally-occurring algal SGI1 polypeptide, where the algal polypeptide includes an RR domain and a myb domain, and the RR domain is N-terminal to the myb domain. The algal polypeptide can optionally have at least 50%, at least 55%, at least 60%, at least 65%, at least 70%, at least 75%, at least 80%, at least 85%, at least 90%, at least 95%, at least 96%, at least 97%, at least 98%, or at least 99% identity to any of the algal SGI1 polypeptides disclosed herein. In some embodiments, an SGI1 gene can be a gene encoding an algal SGI1 polypeptide, such as for example, a polypeptide having the sequence of a naturally-occurring algal SGI1 polypeptide. An SGI1 gene that encodes a polypeptide having the sequence of a naturally-occurring algal SGI polypeptide can be a gene having a naturally-occurring gene sequence of gene-encoding sequence, or can have a sequence that varies from the sequence of a naturally-occurring gene. In various embodiments, an SGI1 gene that is attenuated, mutated, or disrupted in mutant photosynthetic organisms as disclosed herein can be a gene that is identified through BLAST, for example, using sequences disclosed herein, and/or by HMM scanning, where the HMM is based on a contiguous amino acid sequence, for example derived by comparison of at least six SGI polypeptides, where the contiguous amino acid sequence includes an RR domain and a myb domain, where the RR domain is N-terminal to the myb domain, and where there is a linker sequence between the RR and myb domains that does not belong to either domain.

In some embodiments, an SGI polypeptide has the sequence of an algal SGI1 polypeptide or is a variant of a naturally-occurring algal SGI1 polypeptide having at least 85%, at least 90%, or at least 95% identity to a naturally-occurring algal SGI1 polypeptide and/or has at least 50%, at least 55%, at least 60%, at least 65%, at least 70%, at least 75%, at least 80%, at least 85%, at least 90%, at least 95%, at least 96%, at least 97%, at least 98%, or at least 99% identity to any of SEQ ID NO:3, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, or SEQ ID NO:19.

In some embodiments, an SGI polypeptide has the sequence of a plant SGI1 polypeptide or is a variant of a naturally-occurring plant SGI1 polypeptide having at least 85%, at least 90%, or at least 95% identity to a naturally-occurring algal SGI polypeptide and/or has at least 50%, at least 55%, at least 60%, at least 65%, at least 70%, at least 75%, at least 80%, at least 85%, at least 90%, at least 95%, at least 96%, at least 97%, at least 98%, or at least 99% identity to any of SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, or SEQ ID NO:39.

A *Parachlorella* SGI1 gene sequence is provided as SEQ ID NO:1 was found to encode a polypeptide (SEQ ID NO:3) that includes two major functional domains, both occurring in the N-terminal half of the 619 amino acid protein. An exemplary *Parachlorella* SGI1 cDNA sequence is provided as SEQ ID NO: 2.

No conserved protein domains could be found in the region of the SGI1 polypeptide C-terminal to the myb domain, i.e., in the C-terminal (approximately) half of the protein. The RR and Myb domains, on the other hand, where the myb domain is positioned C-terminal to the RR domain, can be found in many proteins coded for in Viridiplantae (green plant, encompassing algae) genomes. Bioinformatic analysis was used to identify likely orthologs of SGI1 in additional plant and algal species.

To identify a class of SGI1 proteins in additional photosynthetic organisms, a Hidden Markov Model (HMM) was built for the RR domain—myb domain architecture found in *Parachlorella* SGI1. As a first step, the *Parachlorella* SGI1 polypeptide sequence (SEQ ID NO:3) was used to BLAST search the JGI Phytozome database v.12 that included the genomes of plants and algae. Four proprietary algal genomes (from *Parachlorella, Nannochloropsis, Tetraselmis*, and *Oocystis* species) were also added to the database that was searched. The search was halted when it reached approximately 2,000 hits. These results were then analyzed by InterProScan (available from the EMBL-EBI [European Molecular Biology Laboratories-European Bioinformatics Institute, for example, at ebi.ac.uk]) to ensure that selected results had both the Interpro CheY-like superfamily domain (IPR011006) and the Interpro Homeobox-like or Myb domain (IPR009057 or IPR017930). This step reduced the number of selected hits to between 900 and 1,000, with polypeptides having the two domain architecture (RR domain N-terminal to myb domain) clearly identified in polypeptides of both algae and higher plants. The resulting sequences were used to assemble a phylogenetic tree based on sequence homology. The phylogenetic tree showed a clear grouping of related polypeptides from algal species, including SGI1 homologs of *Parachlorella, Tetraselmis, Oocystis, Chlamydomonas, Volvox, Ostreococcus, Micromonas*, and *Coccomyxa*.

TABLE

SGI1 Orthologs in Algal species

| Organism | Polypeptide Sequence | HMM Score |
|---|---|---|
| *Parachlorella* sp. 1185 | SEQ ID NO: 3 | 400.20 |
| *Coccomyxa subellipsoidea* | SEQ ID NO: 9 | 403.0 |
| *Ostreococcus lucimarinus* | SEQ ID NO: 10 | 425.8 |
| *Chlamydomonas reinhardtii* | SEQ ID NO: 11 | 413.3 |
| *Chromochloris zofingiensis* | SEQ ID NO: 12 | 292.6 |
| *Volvox carteri* | SEQ ID NO: 13 | 441.4 |
| *Tetraselmis* sp. 105 | SEQ ID NO: 14 | 403.6 |
| *Tetraselmis* sp. 105 | SEQ ID NO: 15 | 403.0 |
| *Tetraselmis* sp. 105 | SEQ ID NO: 16 | 402.9 |
| *Oocystis* sp. | SEQ ID NO: 17 | 426.9 |
| *Micromonas* sp. RC299 | SEQ ID NO: 18 | 418.4 |
| *Micromonas pusilla* | SEQ ID NO: 19 | 405.9 |

To establish a criterion for likely SGI1 orthologs in other photosynthetic organisms then, a Hidden Markov Model (HMM) was developed based on the algal cluster of SGI1 polypeptide sequences. The HMM was developed based on the N-terminal portion of the SGI1 polypeptide that encompasses both the RR and myb domains, including the linker region between the two conserved domains. The sequence of the polypeptides C-terminal to the myb domain that did not include any recognizable conserved structure were excluded from the model-building. HMMER 3.1b2 was used to build the HMM using Multiple Sequence Alignments (MSAs) from proprietary sequences of *Parachlorella, Oocystis*, and *Tetraselmis* polypeptides as well as sequences of public databases of polypeptides of *Chlamydomonas reinhardtii, Volvox carteri, Chromochloris zofingiensis, Coccomyxa subellipsoidea, Micromonas* sp. RCC299, and *Ostreococcus* luminarinus. Multiple sequence alignments (MSAs) of the N-terminal half of the protein were generated using the ETE3 toolkit and eggnog41 workflow. This program internally uses the programs Muscle, MAFFT, Clustal Omega, and M-coffee for alignment, trimAI for alignment trimming, and PhyML for phylogeny interference. An HMM, unlike a single protein sequence used for homology comparison, for example, captures information from multiple protein sequences and is therefore able to distinguish highly conserved from highly divergent residues and take that into account when determining relatedness of sequences. When an HMM is used to score a sequence, highly conserved residues receive more weight that highly divergent residues, thereby providing superior sensitivity and accuracy than simpler PSAs.

The SGI1 HHM was used to assign a score to the polypeptides identified in the BLAST search that also were verified as having the two conserved domain (RR and myb). The highest scores, found almost in algal species and a single plant polypeptide, in a bioinformatic search allowed identification of proteins of interest in other algal species (Table 1). These represent likely orthologs whose genes may be attenuated or knocked out to provide high productivity mutants in other organisms.

TABLE 2

| SGI1 Orthologs in Plant species | | |
|---|---|---|
| Organism | Polypeptide Sequence | HMM Score |
| *Sphagnum fallax* | SEQ ID NO: 20 | 397.3 |
| *Physcomitrella patens* | SEQ ID NO: 21 | 372.3 |
| *Arabidopsis_thaliana* | SEQ ID NO: 22 | 371.1 |
| *Arabidopsis halleri* | SEQ ID NO: 23 | 475.9 |
| *Arabidopsis lyrata* | SEQ ID NO: 24 | 395.5 |
| *Helianthus annuus* | SEQ ID NO: 25 | 391.2 |
| *Vitis vinifera* | SEQ ID NO: 26 | 390.6 |
| *Amborella trichopoda* | SEQ ID NO: 27 | 390.1 |
| *Ricinus communis* | SEQ ID NO: 28 | 390.1 |
| *Solanum lycopersicum* | SEQ ID NO: 29 | 388.4 |
| *Solanum tuberosum* | SEQ ID NO: 30 | 387.2 |
| *Gossypium hirsutum* | SEQ ID NO: 31 | 385.8 |
| *Theobroma cacao* | SEQ ID NO: 32 | 383.0 |
| *Phaseolus vulgaris* | SEQ ID NO: 33 | 381.6 |
| *Glycine max* | SEQ ID NO: 34 | 381.4 |
| *Chenopodium quino* | SEQ ID NO: 35 | 373.7 |
| *Malus domestica* | SEQ ID NO: 36 | 372.6 |
| *Zea mays* | SEQ ID NO: 37 | 371.5 |
| *Brassica rapa* | SEQ ID NO: 38 | 370.5 |
| *Oryza sativa* | SEQ ID NO: 39 | 369.6 |

A schematics of SGI1 gene is shown in FIG. 1A.

In some embodiments, modulations the SGI1 gene such as mutation, attenuation, or a knockout of the SGI1 gene in algal species, e.g., increases the maximum quantum yield of photochemistry in photosystem II ($F_V/F_M$) (by about 10-14%) while exhibiting reduced antenna size (i.e., functional absorption cross-section) as compared to the wild-type strain from which they were derived.

In some embodiments, modulations the SGI1 gene may also cause reduced antenna size (i.e., functional absorption cross-section) of photosystem II (PSII) and photosystem I (PSI) (down 40-50% with respect to wild-type), high rates of electron transport on the acceptor side of PSII (1/τ'Qa) under saturating light (increased between about 35% and about 130%, and by at least approximately 100% with respect to wild-type in the engineered mutants) and high rates of carbon fixation (Pmax) (up at least 30-40% with respect to wild-type), while, as determined by Multiple Reaction Monitoring protein determination, the number of photosystems on a per TOC basis is maintained.

SGI2 Gene

Inventors of the present application have identified Significant Growth Improvement Gene 2 (SGI2) as orthologs present in photosynthetic organisms, e.g., algae, plants of a class of regulatory genes called two-component systems (TCS) because they are known to regulate important cellular processes including bacterial cell cycle progression and development (Skerker et al. 2015; Two-component signal transduction pathways regulating growth and cell cycle progression in a bacterium: a system-level analysis, PLoS Biology. 3 (10): e334), nitrogen sensing (Sanders et al., 1992; Phosphorylation site of NtrC, a protein phosphatase whose covalent intermediate activates transcription. Journal of Bacteriology. 174 (15): 5117-22), and bacterial chemotaxis (Sanders et al. 1989; Identification of the site of phosphorylation of the chemotaxis response regulator protein, CheY; The Journal of Biological Chemistry. 264 (36): 21770-8). In bacteria, these proteins typically consist of a histidine kinase that senses a specific environmental stimulus and a corresponding response regulator domain (PF00072) that mediates the cellular response, mostly through differential expression of target genes. However, in the photosynthetic organisms, the SGI2 genes comprise the corresponding response regulator domain (PF00072) and lacks the other domain of the two-component system.

Figure 2:
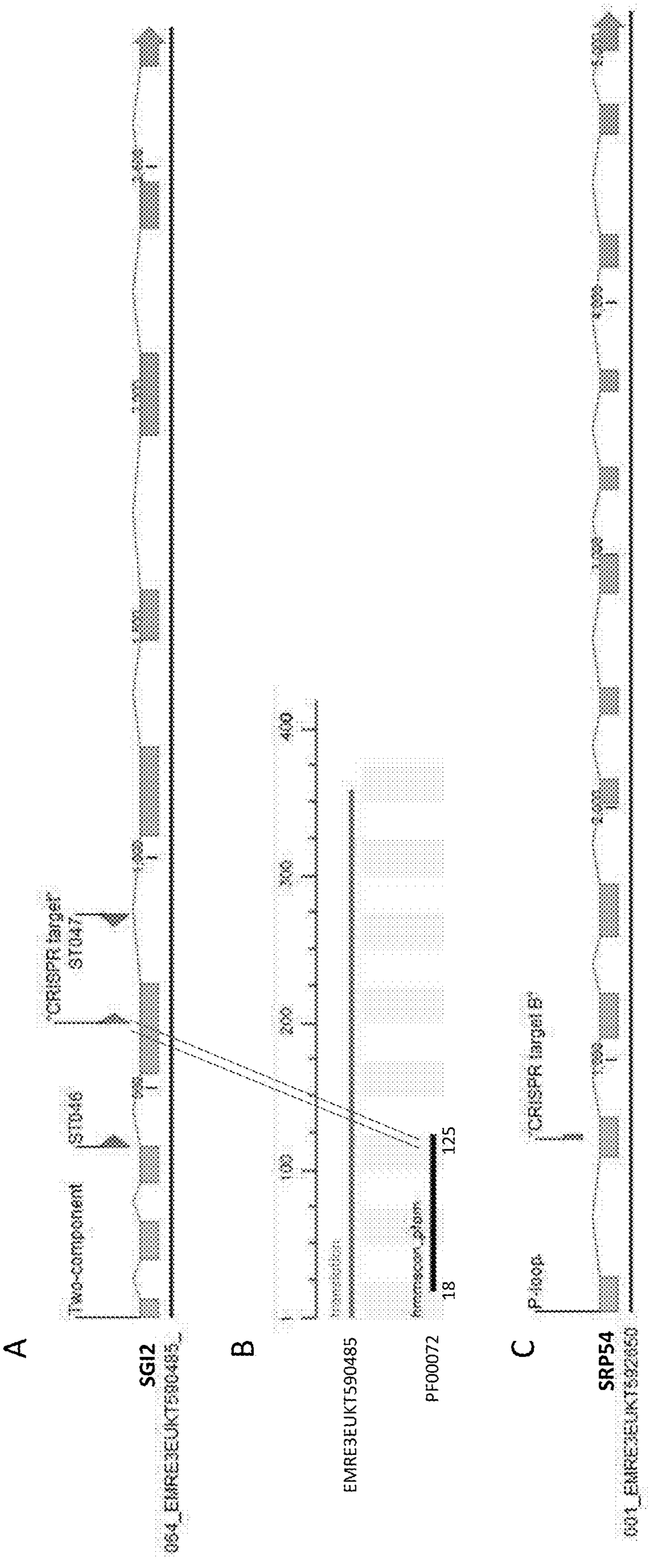
FIG. 2A shows a schematics of the SGI1 gene. A putative location of the gRNA designed to disrupt the SGI1 gene (CRISPR target) is indicated.
FIG. 2B shows a schematics of the SGI1 protein.
FIG. 2C shows a schematics of the SPR54 gene. A putative location of the gRNA designed to disrupt the SPR54 gene (CRISPR target) is indicated.
Figure 3:
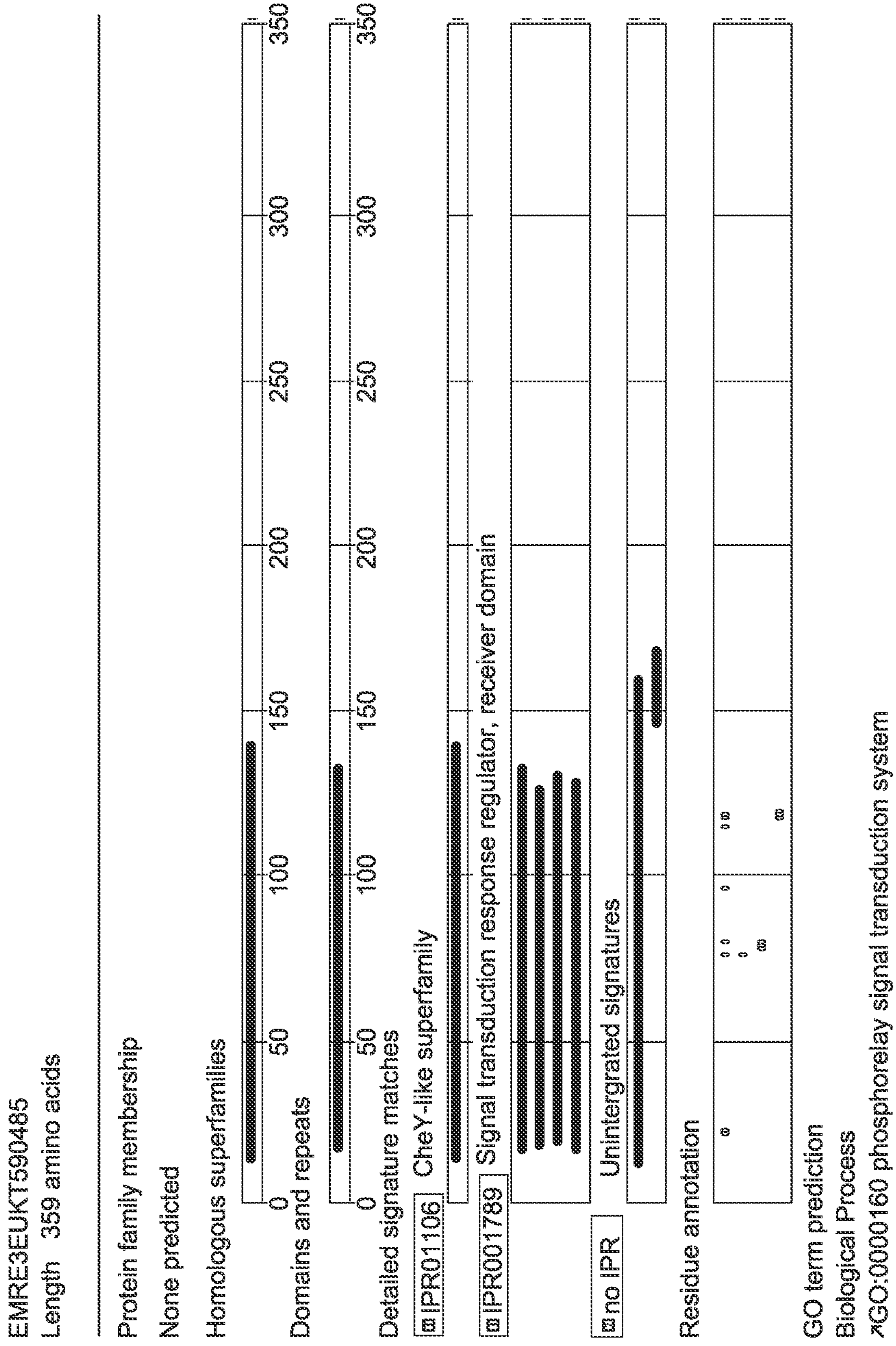
FIG. 3 shows an exemplary domain architecture analysis of *Parachorella* sp. SGI2 protein.
Figure 4:
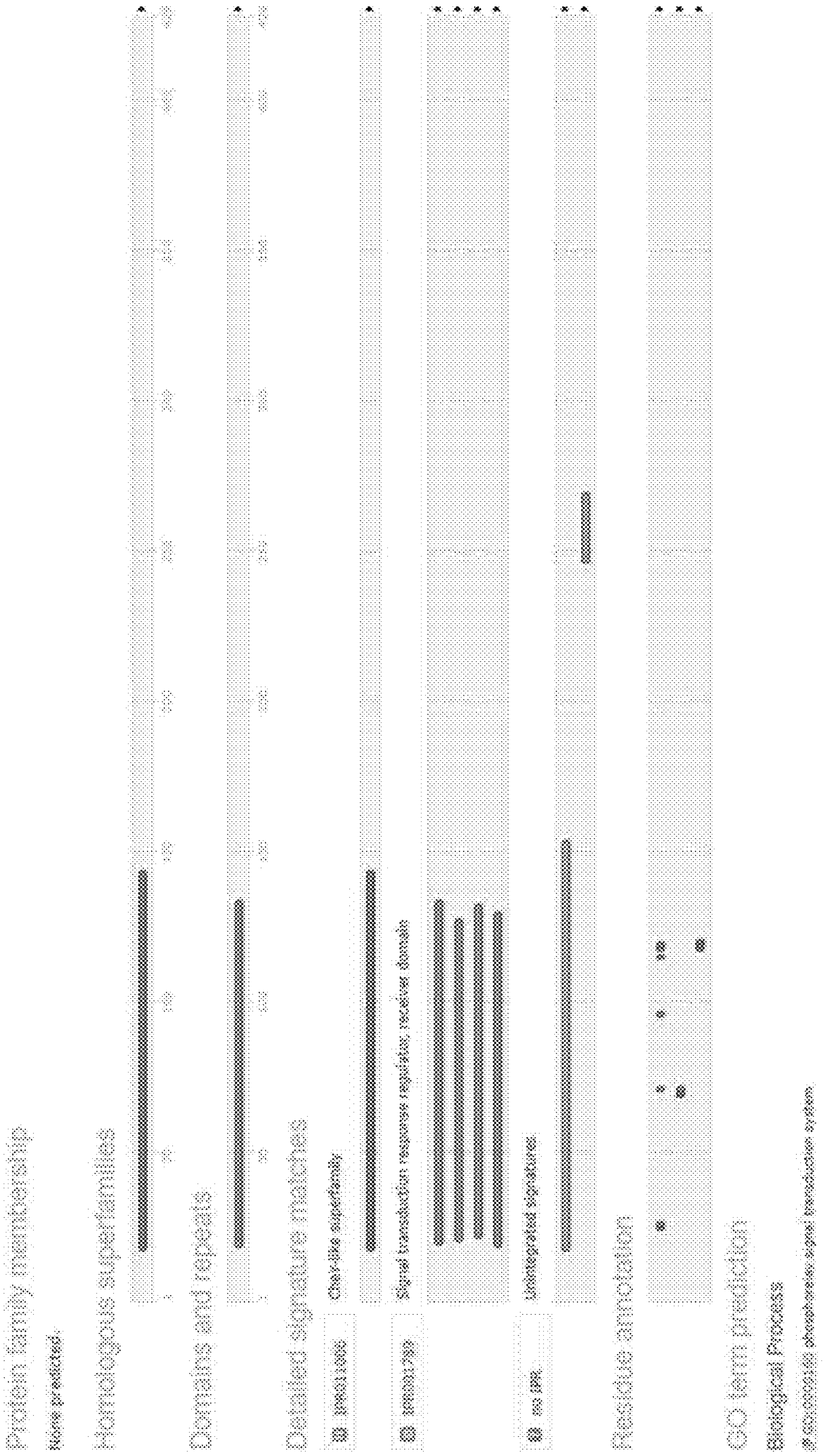
FIG. 4 shows an exemplary domain architecture analysis of *Oocystis* sp. SGI2 protein.
Figure 5:
FIG. 5 shows an exemplary domain architecture analysis of *Tetraselmis* sp. SGI2 protein.
Figure 6:
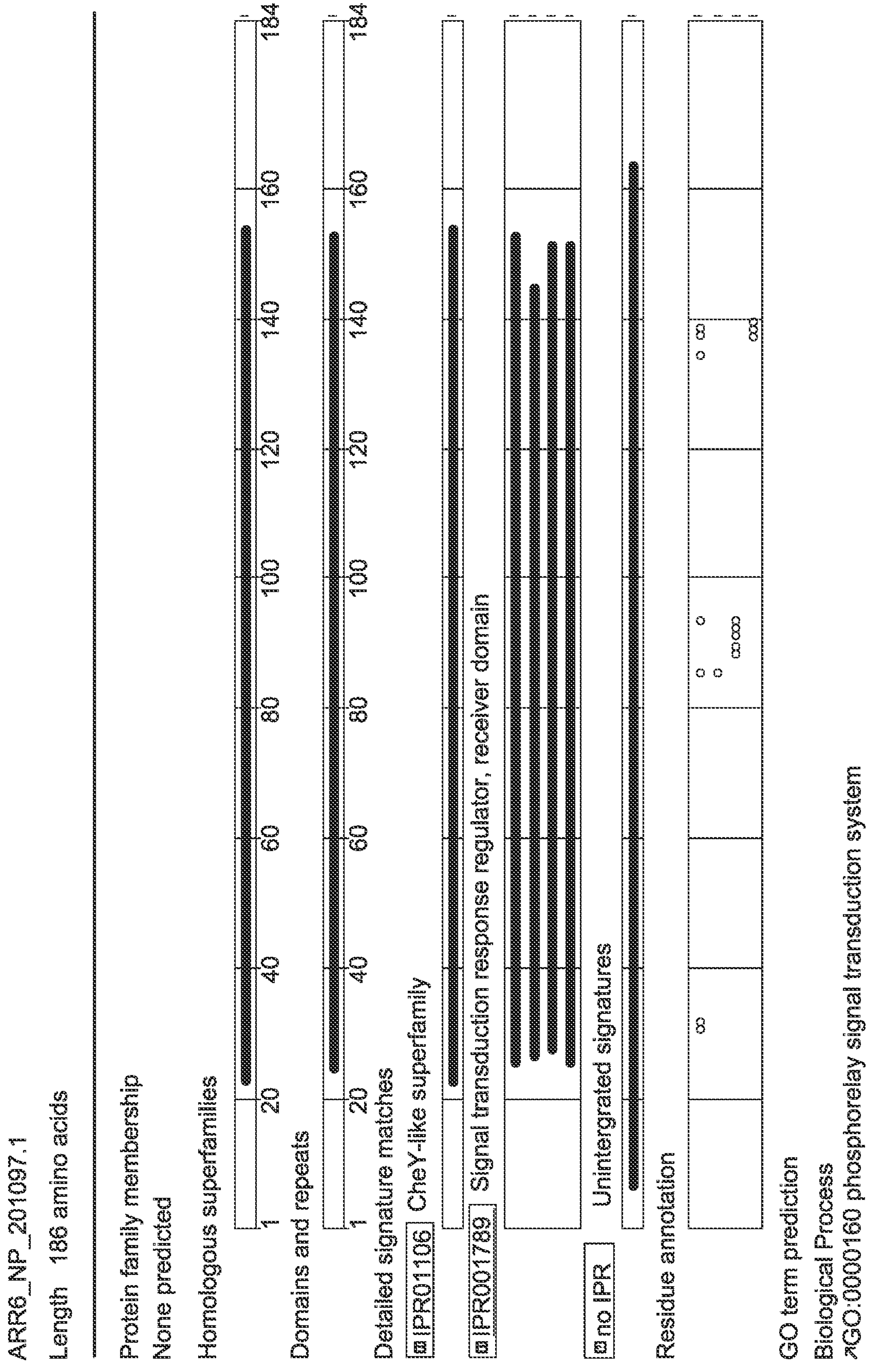
FIG. 6 shows an exemplary domain architecture analysis of *Arabidopsis thaliana* SGI2 protein.
Figure 7:
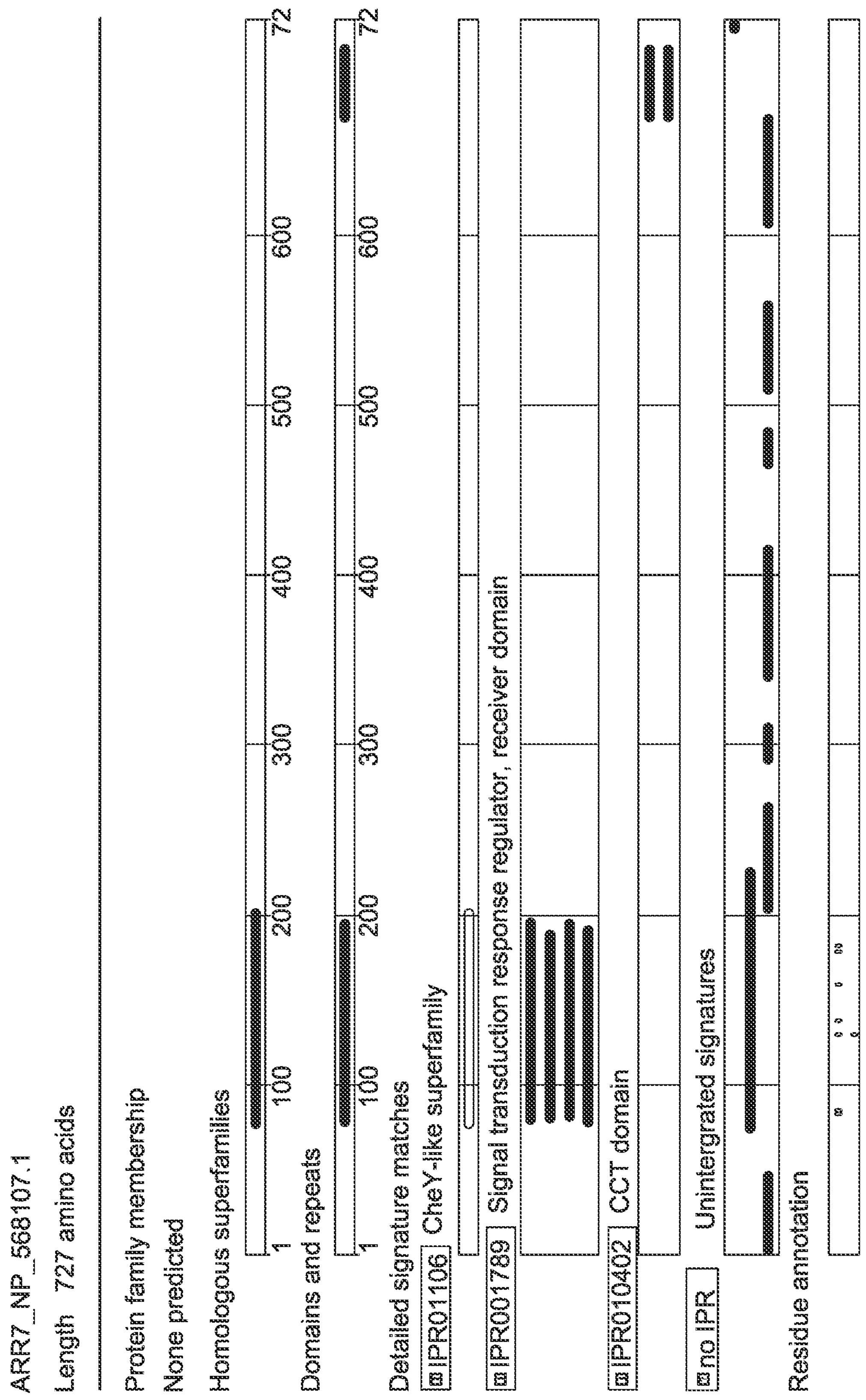
FIG. 7 shows an exemplary domain architecture analysis of *Arabidopsis thaliana* SGI2 protein.
Figure 8:
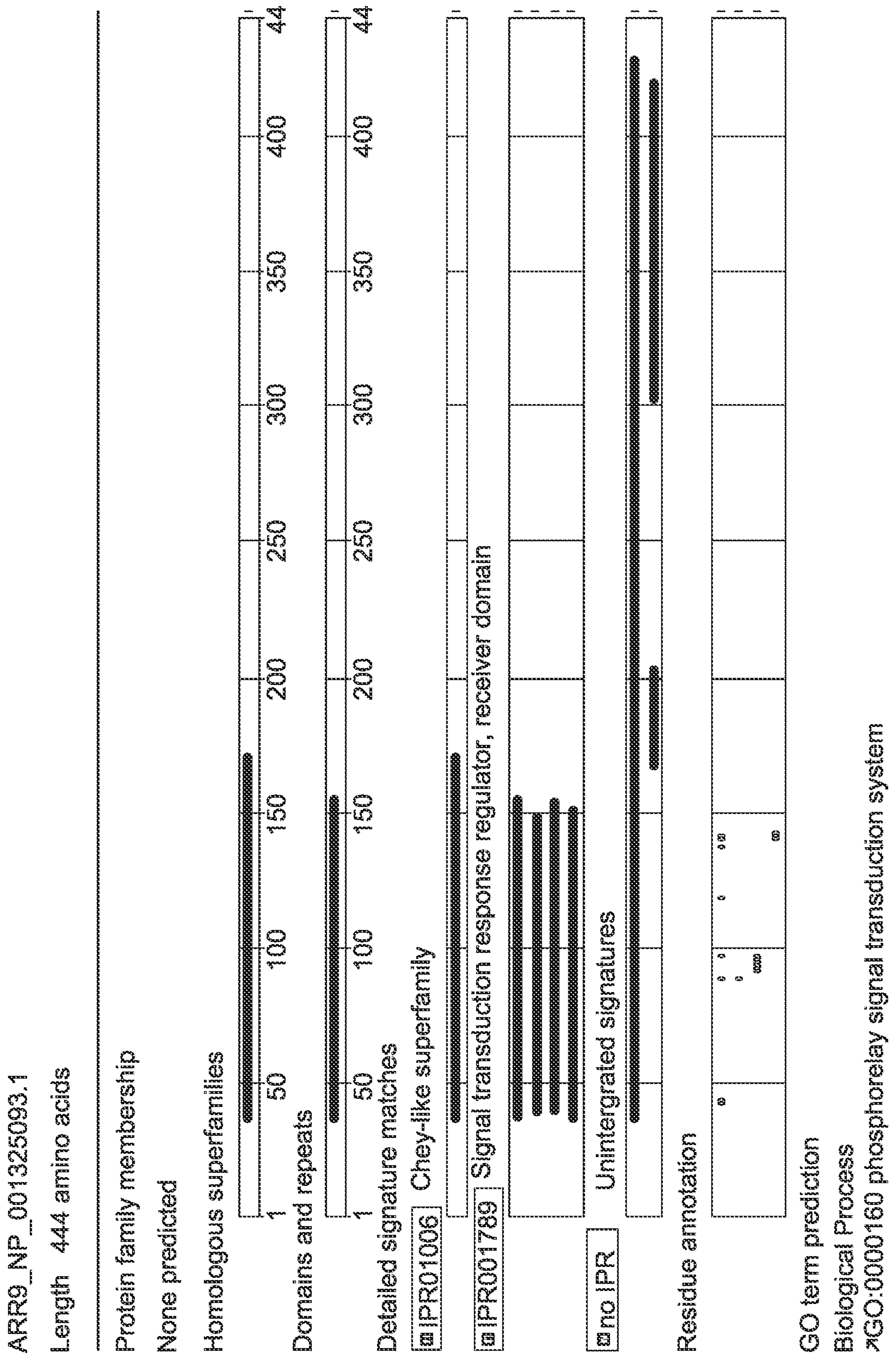
FIG. 8 shows an exemplary domain architecture analysis of *Arabidopsis thaliana* SGI2 protein.
Figure 9:
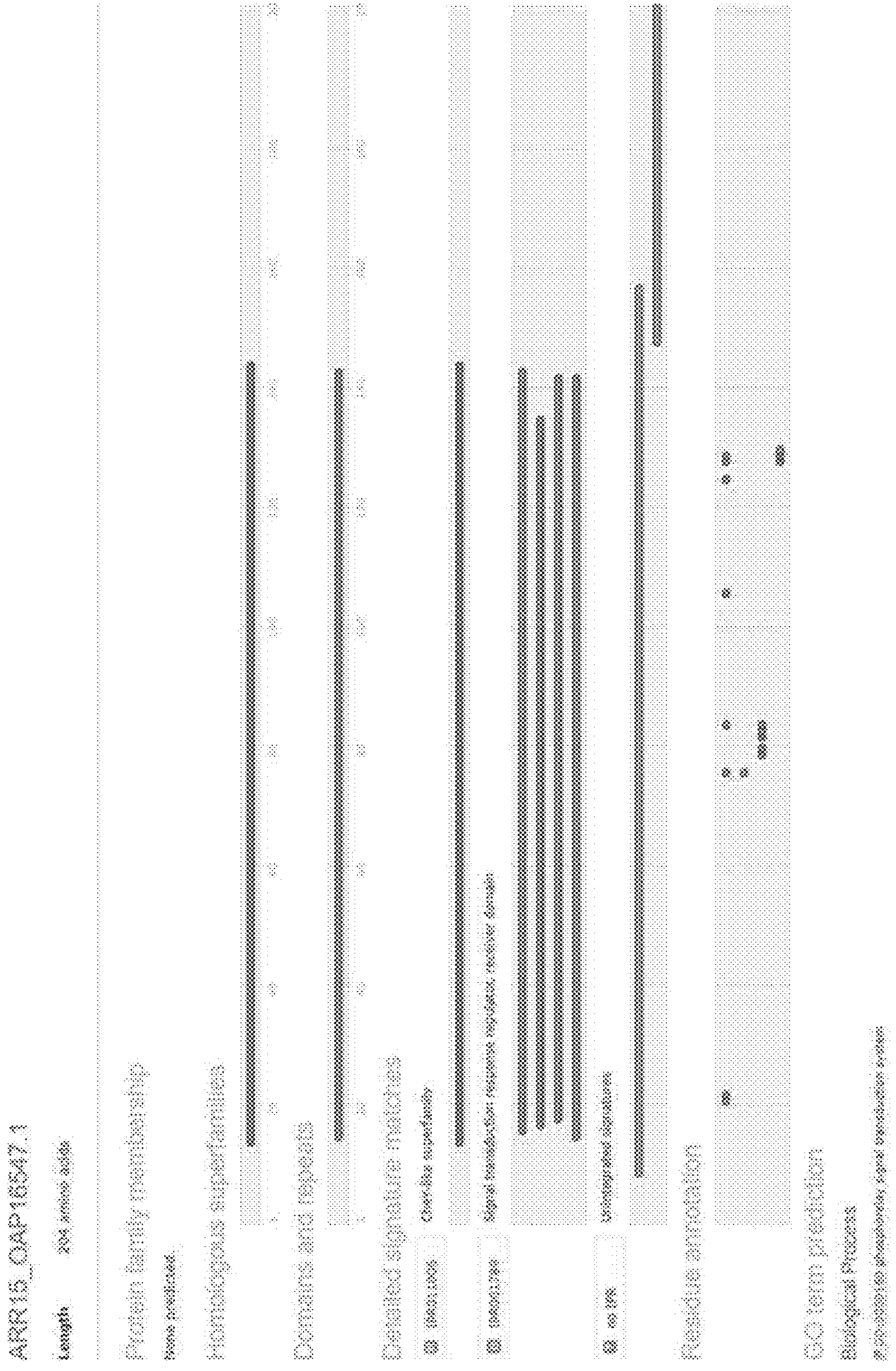
FIG. 9 shows an exemplary domain architecture analysis of *Arabidopsis thaliana* SGI2 protein.

A schematics of SGI1 gene is shown in FIG. 2A and the schematics of the corresponding protein in FIG. 2B.

An exemplary *Parachlorella* SGI2 gene sequence is provided as SEQ ID NO:4 was found to encode a polypeptide (SEQ ID NO:5) that comprises a response regulator domain (SEQ ID NO: 6).

Exemplary orthologous polypeptide sequences in various photosynthetic organisms are shown below in Table 3 below.

TABLE 3

| Orthologous SGI2 sequences in various photosynthetic organisms | |
|---|---|
| Photosynthetic Organism | Polypeptide Sequence |
| *Oocystis* sp. | SEQ ID NO: 40 |
| *Tetraselmis* sp. | SEQ ID NO: 41 |
| *Arabidopsis thaliana* | SEQ ID NO: 42 |
| *Arabidopsis thaliana* | SEQ ID NO: 43 |
| *Arabidopsis thaliana* | SEQ ID NO: 44 |
| *Arabidopsis thaliana* | SEQ ID NO: 45 |
| *Arabidopsis thaliana* | SEQ ID NO: 46 |
| *Glycine max* | SEQ ID NO: 47 |
| *Vitis vinifera* | SEQ ID NO: 48 |
| *Theobroma cacao* | SEQ ID NO: 49 |
| *Oryza sativa* | SEQ ID NO: 50 |
| *Zea mays* | SEQ ID NO: 51 |
| *Physcomitrella patens* | SEQ ID NO: 52 |
| *Volvox carteri* | SEQ ID NO: 53 |
| *Chlamydomonas reinhardtii* | SEQ ID NO: 54 |
| *Chlorella zofingiensis* | SEQ ID NO: 55 |
| *Coccomyxa subellipsoidea* C-169 | SEQ ID NO: 56 |

An exemplary *Parachlorella* SGI2 cDNA sequence is provided as SEQ ID NO: 7. Orthologous cDNA sequences of SGI2 gene in other photosynthetic organisms are shown in Table 4 below.

TABLE 4

| Orthologous cDNA sequences of SGI2 gene in other photosynthetic organisms | |
|---|---|
| Photosynthetic Organism | cDNA Sequence |
| *Oocystis* sp. | SEQ ID NO: 57 |
| *Tetraselmis* sp. | SEQ ID NO: 58 |
| *Glycine max* | SEQ ID NO: 59 |
| *Vitis vinifera* | SEQ ID NO: 60 |
| *Theobroma cacao* | SEQ ID NO: 61 |
| *Oryza sativa* | SEQ ID NO: 62 |
| *Zea mays* | SEQ ID NO: 63 |
| *Physcomitrella patens* | SEQ ID NO: 64 |
| *Volvox carteri* | SEQ ID NO: 65 |
| *Chlamydomonas reinhardtii* | SEQ ID NO: 66 |
| *Coccomyxa subellipsoidea* | SEQ ID NO: 67 |

In some embodiments, the SGI2 polypeptide of a photosynthetic organism comprise an amino acid sequence that is at least 35, 40, 45, 50, 55, 60, 65, 70, 75, 80, 85, 90, 95 percent identical to SEQ ID NO: 6. In some embodiments, the SGI2 polypeptide of a photosynthetic organism comprise an amino acid sequence that is at least 35, 40, 45, 50, 55, 60, 65, 70, 75, 80, 85, 90, 95 percent identical to at least 100, 150, 200, 250 amino acids or the entire length of SEQ ID NOs: 5, 40, 41, 42, 43, 44, 45, 46, 47, 48, 49, 50, 51, 52, 53, 54, 55, or 56.

In some embodiments, a photosynthetic organism comprise a polynucleotide encoding a SGI2 polypeptide in which the nucleic acid sequence of the polynucleotide is at least 35, 40, 45, 50, 55, 60, 65, 70, 75, 80, 85, 90, 95 percent identical to at least 100, 150, 200, 250 nucleotides or the entire length of SEQ ID NOs: 4, 7, 57, 58, 59, 60, 61, 62, 63, 64, 65, 66, or 67.

In some embodiments, the modulation of the SGI2 gene such as mutation, attenuation, or a knockout of the SGI2 gene in photosynthetic organisms such as algal species, increases the maximum quantum yield of photochemistry in photosystem II ($F_V/F_M$) (by about 10-14%), decreased chlorophyll/per total organic carbon (TOC), increased biomass.

SPR54 Gene

Modulation of the SPR54 gene has been described in US Patent Application Publication 2016/0304896, which is incorporated by reference in its entirety. An exemplary *Parachlorella* chloroplastic SRP54 (cpSRP54) cDNA sequence is provided as SEQ ID NO: 8 that encodes a polypeptide having SEQ ID NO: 68.

Other non-limiting exemplary cpSRP54 orthologus polypeptides include GenBank Accession Nos: EDP00260 for *Chlamydomonas reinhardtii* (SEQ ID NO: 75); EEH59526 for *Micromonas pusilla* (SEQ ID NO: 76); EEH59526 for *Micromonas* sp. (SEQ ID NO: 77); ACB42577 for *Paulinella chromatophora* (SEQ ID NO: 78); ABO94038 for *Ostreococcus lucimarinus* (SEQ ID NO: 79); Q01H03 for *Ostreococcus tauri* (SEQ ID NO: 80); EFJ41797 for *Volvox carteri* (SEQ ID NO: 81); EEC48599 for *Phaeodactylum tricornutum* (SEQ ID NO: 82); EED94755 for *Thalassiosira pseudonana*(SEQ ID NO: 83); EGB12501 for *Aureococcus anophagefferens* (SEQ ID NO: 84); CBN76263 for *Ectocarpus siliculosus* (SEQ ID NO: 85).

In some embodiments, cpSRP54 gene of a photosynthetic organism that encodes a polypeptide that is at least 55%, at least 60%, at least 65%, at least 70%, at least 75%, at least 80% or at least 85%, at least 90%, or at least 95% sequence identity to a cpSRP54 disclosed above.

Modulation of SGI2, a combination of SGI1 and SRP54, a combination of SGI2 and SRP54 genes, or a combination of SGI1, SGI2, and SRP54 genes of photosynthetic organisms Modulation of SGI2, a combination of SGI1 and SRP54, a combination of SGI2 and SRP54 genes, or a combination of SGI1, SGI2, and SRP54 genes of photosynthetic organisms results in mutant photosynthetic organisms. The SGI1, SGI2, SRP54 genes can be modulated by UV mutagenesis, gamma irradiation, or genetic engineering techniques. The gene sequences can be altered, gene sequences can be partially or completely deleted, the expression of the genes can be altered.

In some embodiments, the SGI1, SGI2, and/or SRP54 genes can operably linked to algal promoters and terminator sequences as described in US Application Publication 2017/0058303, which is incorporated by reference in its entirety.

In some embodiments, a mutant photosynthetic organism, e.g., plant, alga has at least a 20%, at least a 30%, at least a 40%, at least a 50%, at least a 55%, at least a 60%, at least a 65%, or at least a 70% reduction in total chlorophyll with respect to a control cell, optionally further wherein the mutant has a chlorophyll a to chlorophyll b ratio that is increased by at least with respect to a control cell, further optionally wherein the ratio of chlorophyll a to chlorophyll b is at least about 2.8:1, at least about 3:1, at least about 3.2:1, about 3.3:1, at least about 3.5:1, at least about 3.7:1, at least about 3.9:1, at least about 4:1, or at least about 4.3:1.

In some embodiments, the mutant photosynthetic organism, e.g., plant or alga exhibits: a) higher qP with respect to a control photosynthetic organism of the same species at all irradiances between about 100 and about 2800 μmol photons $m^{-2}$ $sec^{-1}$, between about 150 and about 2800 μmol photons m−2 sec−1, between about 75 and about 2800 μmol photons $m^{-2}$ $sec^{-1}$, between about 40 and about 2800 μmol photons $m^{-2}$ $sec^{-1}$, or between about 10 and about 2800 μmol photons m−2 sec−1;

(b) lower NPQ with respect to a control alga at all irradiances between about 100 and about 2800 μmol photons $m^{-2}$ $sec^{-1}$, between about 150 and about 2800 μmol photons m−2 sec−1, between about 75 and about 2800 μmol photons $m^{-2}$ $sec^{-1}$, between about 40 and about 2800 μmol photons $m^2$ $sec^{-1}$, or between about 10 and about 2800 μmol photons $m^{-2}$ $sec^{-1}$;

(c) higher Y(II) with respect to a photosynthetic organism, e.g., alga at all irradiances between about 100 and about 2800 μmol photons $m^{-2}$ $sec^{-1}$, between about 150 and about 2800 μmol photons $m^2$ $sec^{-1}$, between about 75 and about 2800 μmol photons $m^{-2}$ $sec^{-1}$, between about 40 and about 2800 μmol photons $m^{-2}$ $sec^{-1}$, or between about 10 and about 2800 μmol photons $m^{-2}$ $sec^{-1}$;

(d) higher $F_V/F_M$ with respect to a control alga between about 100 and about 2800 μmol photons $m^{-2}$ $sec^{-1}$, between about 150 and about 2800 μmol photons $m^{-2}$ $sec^{-1}$, between about 75 and about 2800 μmol photons $m^2$ $sec^{-1}$, between about 40 and about 2800 μmol photons $m^{-2}$ $sec^{-1}$, or between about 10 and about 2800 μmol photons $m^{-2}$ $sec^{-1}$;

(e) higher ESR(II) with respect to a control alga between about 250 and about 2800 μmol photons $m^{-2}$ $sec^{-1}$, between about 150 and about 2800 μmol photons $m^{-2}$ $sec^{-1}$, between about 75 and about 2800 μmol photons $m^{-2}$ $sec^{-1}$, between about 40 and about 2800 μmol photons $m^{-2}$ $sec^{-1}$, or between about 10 and about 2800 μmol photons $m^{-2}$ $sec^{-1}$;

(f) oxygen evolution on a per chlorophyll basis increased by at least 50%, at least 100% at least 200%, at least 300%, at least 350%, or at least 400% with respect to a control alga; and (g) carbon fixation on a per chlorophyll basis increased by at least 50%, at least 60% at least 70%, at least 80%, at least 90%, or at least 100% with respect to a control photosynthetic organism of the same species.

In some embodiments, the mutant photosynthetic organism demonstrates at least 5%, at least 6%, at least 8%, or at least 10%, at least 15%, at least 25%, or at least 30% greater biomass productivity than a control alga cultured under identical conditions.

In some embodiments, the mutant photosynthetic organism, e.g., plant, alga demonstrates greater productivity with respect to the control alga in a diel cycle culture having a variable light intensity mimicking natural daylight, optionally wherein the light intensity peaks at between about 1900 and about 2000 μmol photons $m^{-2}$ $sec^{-1}$.

In some embodiments, the mutant photosynthetic organism, e.g., plant or alga has higher lipid productivity, for example, at least 5%, at least 10%, at least 15%, at least 20%, or at least 25% higher lipid productivity with respect to a control photosynthetic organism of the same species that does not have an altered or attenuated gene(s).

Definitions

Unless defined otherwise, all technical and scientific terms used herein have the same meaning as commonly understood by one of ordinary skill in the art to which this invention belongs. In case of conflict, the present application including the definitions will control. Unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference.

As used in the present disclosure and claims, the singular forms “a,” “an,” and “the” also include plural forms unless the context clearly dictates otherwise.

All ranges provided within the application are inclusive of the values of the upper and lower ends of the range.

The term “and/or” as used in a phrase such as “A and/or B” herein is intended to include “A and B”, “A or B”, “A”, and “B”.

The term “gene” is used broadly to refer to any segment of a nucleic acid molecule (typically DNA, but optionally RNA) encoding a polypeptide or expressed RNA. Thus, genes include sequences encoding expressed RNA (which can include polypeptide coding sequences or, for example, functional RNAs, such as ribosomal RNAs, tRNAs, antisense RNAs, microRNAs, short hairpin RNAs, ribozymes, etc.). Genes may further comprise regulatory sequences required for or affecting their expression, as well as sequences associated with the protein or RNA-encoding sequence in its natural state, such as, for example, intron sequences, 5' or 3' untranslated sequences, etc. In some examples, “gene” may only refer to a protein-encoding portion of a DNA or RNA molecule, which may or may not include introns. A gene is preferably greater than 50 nucleotides in length, more preferably greater than 100 nucleotide in length, and can be, for example, between 50 nucleotides and 500,000 nucleotides in length, such as between 100 nucleotides and 100,000 nucleotides in length or between about 200 nucleotides and about 50,000 nucleotides in length, or about 200 nucleotides and about 20,000 nucleotides in length. Genes can be obtained from a variety of sources, including cloning from a source of interest or synthesizing from known or predicted sequence information.

The term “nucleic acid” or “nucleic acid molecule” refers to, a segment of DNA or RNA (e.g., mRNA), and also includes nucleic acids having modified backbones (e.g., peptide nucleic acids, locked nucleic acids) or modified or non-naturally-occurring nucleobases. The nucleic acid molecules can be double-stranded, partially double-stranded, or single-stranded; a single-stranded nucleic acid that comprises a gene or a portion thereof can be a coding (sense) strand or a non-coding (antisense) strand.

A nucleic acid molecule may be “derived from” an indicated source, which includes the isolation (in whole or in part) of a nucleic acid segment from an indicated source. A nucleic acid molecule may also be derived from an indicated source by, for example, direct cloning, PCR amplification, or artificial synthesis from the indicated polynucleotide source or based on a sequence associated with the indicated polynucleotide source. Genes or nucleic acid molecules derived from a particular source or species also include genes or nucleic acid molecules having sequence modifications with respect to the source nucleic acid molecules. For example, a gene or nucleic acid molecule derived from a source (e.g., a particular referenced gene) can include one or more mutations with respect to the source gene or nucleic acid molecule that are unintended or that are deliberately introduced, and if one or more mutations, including substitutions, deletions, or insertions, are deliberately introduced the sequence alterations can be introduced by random or targeted mutation of cells or nucleic acids, by amplification or other gene synthesis or molecular biology techniques, or by chemical synthesis, or any combination thereof. A gene or nucleic acid molecule that is derived from a referenced gene or nucleic acid molecule that encodes a functional RNA or polypeptide can encode a functional RNA or polypeptide having at least 75%, at least 80%, at least 85%, at least 90%, or at least 95%, sequence identity with the referenced or source functional RNA or polypeptide, or to a functional fragment thereof. For example, a gene or nucleic acid molecule that is derived from a referenced gene or nucleic acid molecule that encodes a functional RNA or polypeptide can encode a functional RNA or polypeptide having at least 85%, at least 90%, at least 95%, at least 96%, at least 97%, at least 98%, or at least 99% sequence identity with the referenced or source functional RNA or polypeptide, or to a functional fragment thereof.

As used herein, an “isolated” nucleic acid or protein is removed from its natural milieu or the context in which the nucleic acid or protein exists in nature. For example, an isolated protein or nucleic acid molecule is removed from the cell or organism with which it is associated in its native or natural environment. An isolated nucleic acid or protein can be, in some instances, partially or substantially purified, but no particular level of purification is required for isolation. Thus, for example, an isolated nucleic acid molecule can be a nucleic acid sequence that has been excised from the chromosome, genome, or episome that it is integrated into in nature.

A “purified” nucleic acid molecule or nucleotide sequence, or protein or polypeptide sequence, is substantially free of cellular material and cellular components. The purified nucleic acid molecule or protein may be substantially free of chemicals beyond buffer or solvent, for example “Substantially free” is not intended to mean that other components beyond the novel nucleic acid molecules are undetectable.

The terms “naturally-occurring” and “wild-type” refer to a form found in nature. For example, a naturally occurring or wild-type nucleic acid molecule, nucleotide sequence or protein may be present in an isolated from a natural source, and is not intentionally modified by human manipulation.

As used herein “attenuated” means reduced in amount, degree, intensity, or strength. Attenuated gene expression may refer to a significantly reduced amount and/or rate of transcription of the gene in question, or of translation, folding, or assembly of the encoded protein. As nonlimiting examples, an attenuated gene may be a mutated or disrupted gene (e.g., a gene disrupted by partial or total deletion, truncation, frameshifting, or insertional mutation), having decreased expression due to alteration or disruption of gene regulatory sequences, or may be a gene targeted by a construct that reduces expression of the gene, such as, for example, an antisense RNA, microRNA, RNAi molecule, or ribozyme.

“Exogenous nucleic acid molecule” or “exogenous gene” refers to a nucleic acid molecule or gene that has been introduced (“transformed”) into a cell. A transformed cell may be referred to as a recombinant cell, into which additional exogenous gene(s) may be introduced. A descendant of a cell transformed with a nucleic acid molecule is also referred to as “transformed” if it has inherited the exogenous nucleic acid molecule. The exogenous gene may be from a different species (and so “heterologous”), or from the same species (and so “homologous”), relative to the cell being transformed. An “endogenous” nucleic acid molecule, gene or protein is a native nucleic acid molecule, gene or protein as it occurs in, or is naturally produced by, the host.

The term “native” is used herein to refer to nucleic acid sequences or amino acid sequences as they naturally occur in the host. The term “non-native” is used herein to refer to nucleic acid sequences or amino acid sequences that do not occur naturally in the host. A nucleic acid sequence or amino acid sequence that has been removed from a cell, subjected to laboratory manipulation, and introduced or reintroduced into a host cell is considered "non-native." Synthetic or partially synthetic genes introduced into a host cell are "non-native." Non-native genes further include genes endogenous to the host microorganism operably linked to one or more heterologous regulatory sequences that have been recombined into the host genome.

A "recombinant" or "engineered" nucleic acid molecule is a nucleic acid molecule that has been altered through human manipulation. As non-limiting examples, a recombinant nucleic acid molecule includes any nucleic acid molecule that: 1) has been partially or fully synthesized or modified in vitro, for example, using chemical or enzymatic techniques (e.g., by use of chemical nucleic acid synthesis, or by use of enzymes for the replication, polymerization, digestion (exonucleolytic or endonucleolytic), ligation, reverse transcription, transcription, base modification (including, e.g., methylation), integration or recombination (including homologous and site-specific recombination) of nucleic acid molecules); 2) includes conjoined nucleotide sequences that are not conjoined in nature; 3) has been engineered using molecular cloning techniques such that it lacks one or more nucleotides with respect to the naturally occurring nucleic acid molecule sequence; and/or 4) has been manipulated using molecular cloning techniques such that it has one or more sequence changes or rearrangements with respect to the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector.

The term "recombinant protein" as used herein refers to a protein produced by genetic engineering.

When applied to organisms, the term recombinant, engineered, or genetically engineered refers to organisms that have been manipulated by introduction of a heterologous or exogenous recombinant nucleic acid sequence into the organism, and includes gene knockouts, targeted mutations, gene replacement, and promoter replacement, deletion, or insertion, as well as introduction of transgenes or synthetic genes into the organism. Recombinant or genetically engineered organisms can also be organisms into which constructs for gene "knock down" have been introduced. Such constructs include, but are not limited to, RNAi, microRNA, shRNA, siRNA, antisense, and ribozyme constructs. Also included are organisms whose genomes have been altered by the activity of meganucleases, zinc finger nucleases, TALENs, or Cas/CRISPR systems. An exogenous or recombinant nucleic acid molecule can be integrated into the recombinant/genetically engineered organism's genome or in other instances may not be integrated into the host genome. As used herein, "recombinant microorganism" or "recombinant host cell" includes progeny or derivatives of the recombinant microorganisms of the invention. Because certain modifications may occur in succeeding generations due to either mutation or environmental influences, such progeny or derivatives may not, in fact, be identical to the parent cell, but are still included within the scope of the term as used herein.

The term "promoter" refers to a nucleic acid sequence capable of binding RNA polymerase in a cell and initiating transcription of a downstream (3' direction) coding sequence. A promoter includes the minimum number of bases or elements necessary to initiate transcription at levels detectable above background. A promoter can include a transcription initiation site as well as protein binding domains (consensus sequences) responsible for the binding of RNA polymerase. Eukaryotic promoters often, but not always, contain "TATA" boxes and "CAT" boxes. Prokaryotic promoters may contain −10 and −35 prokaryotic promoter consensus sequences. A large number of promoters, including constitutive, inducible and repressible promoters, from a variety of different sources are well known in the art. Representative sources include for example, algal, viral, mammalian, insect, plant, yeast, and bacterial cell types, and suitable promoters from these sources are readily available, or can be made synthetically, based on sequences publicly available online or, for example, from depositories such as the ATCC as well as other commercial or individual sources. Promoters can be unidirectional (initiate transcription in one direction) or bi-directional (initiate transcription in either direction). A promoter may be a constitutive promoter, a repressible promoter, or an inducible promoter. A promoter region can include, in addition to the gene-proximal promoter where RNA polymerase binds to initiate transcription, additional sequences upstream of the gene that can be within 1 kb, 2 kb, 3 kb, 4 kb, 5 kb or more of the transcriptional start site of a gene, where the additional sequences can influence the rate of transcription of the downstream gene and optionally the responsiveness of the promoter to developmental, environmental, or biochemical (e.g., metabolic) conditions.

The term "heterologous" when used in reference to a polynucleotide, gene, nucleic acid, polypeptide, or enzyme refers to a polynucleotide, gene, nucleic acid, polypeptide, or enzyme that is from a source or derived from a source other than the host organism species. In contrast a "homologous" polynucleotide, gene, nucleic acid, polypeptide, or enzyme is used herein to denote a polynucleotide, gene, nucleic acid, polypeptide, or enzyme that is derived from the host organism species. When referring to a gene regulatory sequence or to an auxiliary nucleic acid sequence used for maintaining or manipulating a gene sequence (e.g. a promoter, a 5' untranslated region, 3' untranslated region, poly A addition sequence, intron sequence, splice site, ribosome binding site, internal ribosome entry sequence, genome homology region, recombination site, etc.), "heterologous" means that the regulatory sequence or auxiliary sequence is not naturally associated with the gene with which the regulatory or auxiliary nucleic acid sequence is juxtaposed in a construct, genome, chromosome, or episome. Thus, a promoter operably linked to a gene to which it is not operably linked to in its natural state (i.e. in the genome of a non-genetically engineered organism) is referred to herein as a "heterologous promoter," even though the promoter may be derived from the same species (or, in some cases, the same organism) as the gene to which it is linked.

As used herein, the term "protein" or "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of, or interchangeably with any of these terms.

Gene and protein Accession numbers, commonly provided herein in parenthesis after a gene or species name, are unique identifiers for a sequence record publicly available at the National Center for Biotechnology Information (NCBI) website (ncbi.nlm nih.gov) maintained by the United States National Institutes of Health. The "GenInfo Identifier" (GI) sequence identification number is specific to a nucleotide or amino acid sequence. If a sequence changes in any way, a new GI number is assigned. A Sequence Revision History tool is available to track the various GI numbers, version numbers, and update dates for sequences that appear in a specific GenBank record. Searching and obtaining nucleic acid or gene sequences or protein sequences based on Accession numbers and GI numbers is well known in the arts of, e.g., cell biology, biochemistry, molecular biology, and molecular genetics.

As used herein, the terms "percent identity" or "homology" with respect to nucleic acid or polypeptide sequences are defined as the percentage of nucleotide or amino acid residues in the candidate sequence that are identical with the known polypeptides, after aligning the sequences for maximum percent identity and introducing gaps, if necessary, to achieve the maximum percent homology. N-terminal or C-terminal insertion or deletions shall not be construed as affecting homology, and internal deletions and/or insertions into the polypeptide sequence of less than about 30, less than about 20, or less than about 10 amino acid residues shall not be construed as affecting homology. Homology or identity at the nucleotide or amino acid sequence level can be determined by BLAST (Basic Local Alignment Search Tool) analysis using the algorithm employed by the programs blastp, blastn, blastx, tblastn, and tblastx (Altschul (1997), Nucleic Acids Res. 25, 3389-3402, and Karlin (1990), Proc. Natl. Acad. Sci. USA 87, 2264-2268), which are tailored for sequence similarity searching. The approach used by the BLAST program is to first consider similar segments, with and without gaps, between a query sequence and a database sequence, then to evaluate the statistical significance of all matches that are identified, and finally to summarize only those matches which satisfy a preselected threshold of significance. For a discussion of basic issues in similarity searching of sequence databases, see Altschul (1994), Nature Genetics 6, 119-129. The search parameters for histogram, descriptions, alignments, expect (i.e., the statistical significance threshold for reporting matches against database sequences), cutoff, matrix, and filter (low complexity) can be at the default settings. The default scoring matrix used by blastp, blastx, tblastn, and tblastx is the BLOSUM62 matrix (Henikoff (1992), Proc. Natl. Acad. Sci. USA 89, 10915-10919), recommended for query sequences over 85 in length (nucleotide bases or amino acids).

For blastn, designed for comparing nucleotide sequences, the scoring matrix is set by the ratios of M (i.e., the reward score for a pair of matching residues) to N (i.e., the penalty score for mismatching residues), wherein the default values for M and N can be +5 and −4, respectively. Four blastn parameters can be adjusted as follows: Q=10 (gap creation penalty); R=10 (gap extension penalty); wink=1 (generates word hits at every winkth position along the query); and gapw=16 (sets the window width within which gapped alignments are generated). The equivalent Blastp parameter settings for comparison of amino acid sequences can be: Q=9; R=2; wink=1; and gapw=32. A Bestfit comparison between sequences, available in the GCG package version 10.0, can use DNA parameters GAP=50 (gap creation penalty) and LEN=3 (gap extension penalty), and the equivalent settings in protein comparisons can be GAP=8 and LEN=2.

Thus, when referring to the polypeptide or nucleic acid sequences of the present invention, included are sequence identities of at least 40%, at least 45%, at least 50%, at least 55%, of at least 70%, at least 65%, at least 70%, at least 75%, at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, at least 99%, or about 100% sequence identity with the full-length polypeptide or nucleic acid sequence, or to fragments thereof comprising a consecutive sequence of at least 50, at least 75, at least 100, at least 125, at least 150 or more amino acid residues of the entire protein; variants of such sequences, e.g., wherein at least one amino acid residue has been inserted N- and/or C-terminal to, and/or within, the disclosed sequence(s) which contain(s) the insertion and substitution. Contemplated variants can additionally or alternately include those containing predetermined mutations by, e.g., homologous recombination or site-directed or PCR mutagenesis, and the corresponding polypeptides or nucleic acids of other species, including, but not limited to, those described herein, the alleles or other naturally occurring variants of the family of polypeptides or nucleic acids which contain an insertion and substitution; and/or derivatives wherein the polypeptide has been covalently modified by substitution, chemical, enzymatic, or other appropriate means with a moiety other than a naturally occurring amino acid which contains the insertion and substitution (for example, a detectable moiety such as an enzyme).

As used herein, the phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz (1979) Principles of Protein Structure, Springer-Verlag). According to such analyses, groups of amino acids can be defined where amino acids within a group exchange preferentially with each other, and therefore resemble each other most in their impact on the overall protein structure (Schulz (1979) Principles of Protein Structure, Springer-Verlag). Examples of amino acid groups defined in this manner can include: a "charged/polar group" including Glu, Asp, Asn, Gln, Lys, Arg, and His; an "aromatic or cyclic group" including Pro, Phe, Tyr, and Trp; and an "aliphatic group" including Gly, Ala, Val, Leu, Ile, Met, Ser, Thr, and Cys. Within each group, subgroups can also be identified. For example, the group of charged/polar amino acids can be sub-divided into sub-groups including: the "positively-charged sub-group" comprising Lys, Arg and His; the "negatively-charged sub-group" comprising Glu and Asp; and the "polar sub-group" comprising Asn and Gln. In another example, the aromatic or cyclic group can be sub-divided into sub-groups including: the "nitrogen ring sub-group" comprising Pro, His, and Trp; and the "phenyl sub-group" comprising Phe and Tyr. In another further example, the aliphatic group can be sub-divided into sub-groups including: the "large aliphatic non-polar sub-group" comprising Val, Leu, and Ile; the "aliphatic slightly-polar sub-group" comprising Met, Ser, Thr, and Cys; and the "small-residue sub-group" comprising Gly and Ala. Examples of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free —NH2 can be maintained. A "conservative variant" is a polypeptide that includes one or more amino acids that have been substituted to replace one or more amino acids of the reference polypeptide (for example, a polypeptide whose sequence is disclosed in a publication or sequence database, or whose sequence has been determined by nucleic acid sequencing) with an amino acid having common properties, e.g., belonging to the same amino acid group or sub-group as delineated above.

As used herein the term "modulating" or "modulation" of a gene refers to altering the nucleic acid sequence of the gene, completely or partially deleting the gene, causing a fragmentation in the gene, altering the expression of the gene, inhibiting or silencing the expression of the gene. In some embodiments, altering the sequence of a gene is by insertion of one or more nucleotides, deletion of one or more nucleotides, substitution of the nucleotides. Altering the sequences can be achieved by UV radiation, gamma radiation, genetic engineering.

As used herein "attenuating expression of a gene" means reducing or eliminating expression of the gene in any manner that reduces production of the fully functional protein.

As used herein, "expression" includes the expression of a gene at least at the level of RNA production, and an "expression product" includes the resultant product, e.g., a polypeptide or functional RNA (e.g., a ribosomal RNA, a tRNA, an antisense RNA, a micro RNA, a shRNA, a ribozyme, etc.), of an expressed gene. The term "increased expression" includes an alteration in gene expression to facilitate increased mRNA production and/or increased polypeptide expression. "Increased production" includes an increase in the amount of polypeptide expression, in the level of the enzymatic activity of a polypeptide, or a combination of both, as compared to the native production or enzymatic activity of the polypeptide.

Some aspects of the present invention include the partial, substantial, or complete deletion, silencing, inactivation, or down-regulation of expression of particular polynucleotide sequences. The genes may be partially, substantially, or completely deleted, silenced, inactivated, or their expression may be down-regulated in order to affect the activity performed by the polypeptide they encode, such as the activity of an enzyme. Genes can be partially, substantially, or completely deleted, silenced, inactivated, or down-regulated by insertion of nucleic acid sequences that disrupt the function and/or expression of the gene (e.g., viral insertion, transposon mutagenesis, meganuclease engineering, homologous recombination, or other methods known in the art). The terms "eliminate," "elimination," and "knockout" can be used interchangeably with the terms "deletion," "partial deletion," "substantial deletion," or "complete deletion." In certain embodiments, a microorganism of interest may be engineered by site-directed homologous recombination to knockout a particular gene of interest. In still other embodiments, RNAi or antisense DNA (asDNA) constructs may be used to partially, substantially, or completely silence, inactivate, or down-regulate a particular gene of interest.

These insertions, deletions, or other modifications of certain nucleic acid molecules or particular polynucleotide sequences may be understood to encompass "genetic modification(s)" or "transformation(s)" such that the resulting strains of the microorganisms or host cells may be understood to be "genetically modified", "genetically engineered" or "transformed."

As used herein, "up-regulated" or "up-regulation" includes an increase in expression of a gene or nucleic acid molecule of interest or the activity of an enzyme, e.g., an increase in gene expression or enzymatic activity as compared to the expression or activity in an otherwise identical gene or enzyme that has not been up-regulated.

As used herein, "down-regulated" or "down-regulation" includes a decrease in expression of a gene or nucleic acid molecule of interest or the activity of an enzyme, e.g., a decrease in gene expression or enzymatic activity as compared to the expression or activity in an otherwise identical gene or enzyme that has not been down-regulated.

As used herein, "mutant" refers to an organism that is non-naturally occurring and has a mutation in a gene that has arisen as a result of classical mutagenesis, for example, using gamma irradiation, UV, or chemical mutagens. "Mutant" as used herein also refers to a recombinant cell that has altered structure or expression of a gene as a result of genetic engineering that may include, as non-limiting examples, overexpression, including expression of a gene under different temporal, biological, or environmental regulation and/or to a different degree than occurs naturally and/or expression of a gene that is not naturally expressed in the recombinant cell; homologous recombination, including knock-outs and knock-ins (for example, gene replacement with genes encoding polypeptides having greater or lesser activity than the wild-type polypeptide, and/or dominant negative polypeptides); gene attenuation via RNAi, antisense RNA, or ribozymes, or the like; and genome engineering using meganucleases, TALENs, and/or CRISPR technologies, and the like. A mutant organism of interest will typically have a phenotype different than that of the corresponding wild-type or progenitor strain that lacks the mutation, where the phenotype can be assessed by growth assays, product analysis, photosynthetic properties, biochemical assays, etc. When referring to a gene "mutant" means the gene has at least one base (nucleotide) change, deletion, or insertion with respect to a native or wild-type gene. The mutation (change, deletion, and/or insertion of one or more nucleotides) can be in the coding region of the gene or can be in an intron, 3' UTR, 5' UTR, or promoter region, e.g., within 2 kb of the transcriptional start site or within 3 kb or the translational start site. As nonlimiting examples, a mutant gene can be a gene that has an insertion within the promoter region that can either increase or decrease expression of the gene; can be a gene that has a deletion, resulting in production of a nonfunctional protein, truncated protein, dominant negative protein, or no protein; can be a gene that has one or more point mutations leading to a change in the amino acid of the encoded protein or results in aberrant splicing of the gene transcript, etc. As used herein, "mutant" refers to an organism that is non-naturally occurring and has a mutation in a gene that has arisen as a result of classical mutagenesis, for example, using gamma irradiation, UV, or chemical mutagens. "Mutant" as used herein also refers to a recombinant cell that has altered structure or expression of a gene as a result of genetic engineering that may include, as non-limiting examples, overexpression, including expression of a gene under different temporal, biological, or environmental regulation and/or to a different degree than occurs naturally and/or expression of a gene that is not naturally expressed in the recombinant cell.

The term "Pfam" refers to a large collection of protein domains and protein families maintained by the Pfam Consortium and available at Welcome Trust, Sanger Institute); pfam.sbc.su.se (Stockholm Bioinformatics Center; Janelia Farm, Howard Hughes Medical Institute; Institut national de la Recherche Agronomique. The latest release of Pfam is Pfam 27.0 (March 2013) based on the UniProt protein database release 2012_06. Pfam domains and families are identified using multiple sequence alignments and hidden Markov models (HMMs). Pfam-A family or domain assignments, are high-quality assignments generated by a curated seed alignment using representative members of a protein family and profile hidden Markov models based on the seed alignment. (Unless otherwise specified, matches of a queried protein to a Pfam domain or family are Pfam-A matches.) All identified sequences belonging to the family are then used to automatically generate a full alignment for the family (Sonnhammer (1998) Nucleic Acids Research 26, 320-322; Bateman (2000) Nucleic Acids Research 26, 263-266; Bateman (2004) Nucleic Acids Research 32, Database Issue, D138-D141; Finn (2006) Nucleic Acids Research Database Issue 34, D247-251; Finn (2010) Nucleic Acids Research Database Issue 38, D211-222). By accessing the Pfam database, for example, using any of the above-referenced websites, protein sequences can be queried against the HMMs using HMMER homology search software (e.g., HMMER2, HMMER3, or a higher version). Significant matches that identify a queried protein as being in a Pfam family (or as having a particular Pfam domain) are those in which the bit score is greater than or equal to the gathering threshold for the Pfam domain. Expectation values (e values) can also be used as a criterion for inclusion of a queried protein in a Pfam or for determining whether a queried protein has a particular Pfam domain, where low e values (much less than 1.0, for example less than 0.1, or less than or equal to 0.01) represent low probabilities that a match is due to chance.

As used herein, the term "photosynthetic organism" refers to an organism that can convert light energy into chemical energy. In some embodiments, the chemical energy can later be released to fuel the organisms' activities (energy transformation). In some embodiments, this chemical energy is stored in carbohydrate molecules, such as sugars, which are synthesized from carbon dioxide and water.

Non-limiting examples of photosynthetic organisms include plants, algae, and cyanobacteria. Non-limiting examples of algae belong to genus *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Gloeothamnion, Haematococcus, Halocafeteria, Heterosigma, Hymenomonas, Isochrysis, Lepocinclis, Micractinium, Monodus, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Skeletonema, Spyrogyra, Stichococcus, Tetraselmis, Thalassiosira, Tribonema, Vaucheria, Viridiella, Vischeria*, and *Volvox*.

Non-limiting examples of plants include *Arabidopsis arenicola, Arabidopsis arenosa, Arabidopsis cebennensis, Arabidopsis croatica, Arabidopsis halleri, Arabidopsis lyrata, Arabidopsis neglecta, Arabidopsis pedemontana, Arabidopsis suecica, Arabidopsis thaliana, Zea mays, Oryza sativa, Triticum aestivum, Solanum tuberosum, Allium cepa, Allium sativum, Glycine max, Solanum lycopersicum, Gossypium hirsutum, Gossypium herbaceum, Gossypium arboreum, Gossypium tomentosum, Brassica nigra*, and *Brassica* sp.

As used herein, the term "mutant photosynthetic organism" or "mutant algae" refer to a photosynthetic organism or algae in which at least the SGI1, SGI2, a combination of SGI1 and SRP54, a combination of SGI2 and SRP54, or a combination of SGI1, SGI2, and SRP54 is modulated. Such modulations may include a change in the nucleic acid sequence or alternation of the expression of the gene(s).

As used herein, modulation of a combination of SGI1 and SRP54 genes refer to modulation of SGI1 and modulation of SRP54 genes in the same photosynthetic organism. Similarly, modulation of a combination of SGI2 and SRP54 genes refer to modulation of SGI2 and modulation of SRP54 genes in the same photosynthetic organism. Likewise, modulation of a combination of SGI1, SGI2, and SRP54 genes refer to modulation of SGI1, modulation of SGI2, and modulation of SRP54 genes in the same photosynthetic organism.

As used herein, the term control photosynthetic organism refers to a photosynthetic organism that is genetically substantially identical in all relevant respects to the mutant photosynthetic organism with the exception that the control photosynthetic organism does not have a mutated or attenuated SRP54, SGI1, SGI2, or a combination of two or more of the genes. For example, a control photosynthetic organism is of the same species and, with the exception of alterations to the cpSRP54, cytosolic SRP54, SGI1, or SGI2 genes or constructs for attenuating the cpSRP54, cytosolic SRP54, SGI1, SGI2 genes present in the mutant, is genetically identical with the exception of small genome changes (e.g., "SNPs") that do not affect cell physiology that may be incurred during mutagenesis through normal propagation. In various embodiments, a control photosynthetic organism is a strain from which the mutant photosynthetic organism having attenuated expression of a cytosolic SRP54, cpSRP54, SGI1, SGI2, or a combination of at least two genes is derived.

When referring to a photosynthetic organism, such as an algal, the term "acclimated to low light" means having the increased chlorophyll and photosynthetic properties of the photosynthetic organism after being exposed to a low light intensity for a period of time that is sufficient for changes in chlorophyll and photosynthetic properties to stabilize at the low light condition. Low light can be for example, less than 200 $\mu E \cdot m^{-2} \cdot s^{-1}$ and preferably about 100 $\mu E \cdot m^{-2} \cdot s^{-1}$ or less or 50 $\mu E \cdot m^{-2} \cdot s^{-1}$ or less, and the period of time for acclimation can be for at least about four hours, at least about six hours, at least about eight hours, or at least about twelve hours, at least 24 hours, or at least 48 hours, and may be as long as 2, 3, 4, or 5 days.

A "cDNA" is a DNA molecule that comprises at least a portion of the nucleotide sequence of a mRNA molecule, with the exception that the DNA molecule substitutes the nucleobase thymine, or T, in place of uridine, or U, occurring in the mRNA sequence. A cDNA can be double-stranded or single stranded and can be, for example, the complement of the mRNA sequence. In preferred examples, a cDNA does not include one or more intron sequences that occur in the naturally-occurring gene that the cDNA corresponds to (i.e., the gene as it occurs in the genome of an organism). For example, a cDNA can have sequences from upstream of an intron of a naturally-occurring gene juxtaposed to sequences downstream of the intron of the naturally-occurring gene, where the upstream and downstream sequences are not juxtaposed in a DNA molecule in nature (i.e., the sequences are not juxtaposed in the naturally occurring gene). A cDNA can be produced by reverse transcription of mRNA molecules, or can be synthesized, for example, by chemical synthesis and/or by using one or more restriction enzymes, one or more ligases, one or more polymerases (including, but not limited to, high temperature tolerant polymerases that can be used in polymerase chain reactions (PCRs)), one or more recombinases, etc., based on knowledge of the cDNA sequence, where the knowledge of the cDNA sequence can optionally be based on the identification of coding regions from genome sequences or compiled from the sequences multiple partial cDNAs.

An algal mutant "deregulated in low light acclimation" (or a "Locked in High Light Acclimation" or LIHLA mutant) is a mutant that does not exhibit the changes in phenotype and gene expression that are characteristic of a low light acclimated wild type algal cell, including: a substantial increase in chlorophyll and a substantial increase in the expression of the majority of light harvesting complex protein (LHCP) genes. An algal mutant deregulated in low light acclimation, when acclimated to low light, has decreased expression with respect to low light acclimated wild type cells, of multiple genes (for example, at least ten, at least twenty, at least thirty, at least forty or at least fifty genes) that are upregulated during low light acclimation of wild-type cells. Further, an algal mutant deregulated in low light acclimation has increased expression of genes with respect to low light acclimated wild type cells (for example, at least five, at least six, at least seven, at least eight, at least nine, or at least ten genes) that are downregulated during low light acclimation of wild-type cells. Further, as disclosed herein, an algal mutant deregulated in low light acclimation may have photosynthetic properties that are significantly different than the photosynthetic properties of wild-type cells when both mutant and wild-type cells are acclimated to low light.

"Photosynthetic properties", "photosynthetic properties", "photophysiological properties", or photophysiological parameters" include, without limitation, maximal photosynthetic rate, Pmax (calculated on a per cell or per mg chlorophyll basis), the intensity at which photosynthesis saturates, Ek, as measured by oxygen evolution, and $\alpha$ ("alpha") the initial slope of the photosynthesis (oxygen evolution) versus irradiance intensity (P/I) curve. Additional photosynthetic properties include various parameters that can be measured using fluorescence detection, including, for example, maximum quantum yield of photochemistry in photosystem II, $F_V/F_M$; the photosynthetic quantum yield of photosystem II (PSII), ϕPSII; photochemical quenching, or the proportion of open PSII centers, qP; non-photochemical quenching, NPQ; PSII electron transport rate, ETRPSII; PSI electron transport rate, $ETR_{PSI}$; functional absorption cross-sectional size of PSI ($\sigma_{PSI}$), and functional absorption cross-section of PSII ($\sigma_{PSII}$). The listing here is not exhaustive, and the terms do not exclude other parameters that measure various aspects of photosynthesis.

Reference to properties that are "substantially the same" are intended to mean the properties are within 10%, and preferably within 5%, of the reference value.

Although methods and materials similar or equivalent to those described herein can be used in practice or testing of the present invention, suitable methods and materials are described below. The materials, methods, and examples are illustrative only and are not intended to be limiting. Other features and advantages of the invention will be apparent from the detailed description and from the claims.

Gene Attenuation

A mutant photosynthetic organism can be a mutant generated by any feasible method, including but not limited to UV irradiation, gamma irradiation, or chemical mutagenesis, and screening for low chlorophyll mutants having the photosynthetic properties disclosed herein. Methods for generating mutants of microbial strains are well-known. Mutants can be identified by methods known in the art, including, for example, genome sequencing, PCR, immunodetection of the cpSRP54 or cytoSRP54 protein, and expression analysis (e.g., reverse transcription/PCR).

A mutant photosynthetic organism as provided herein can also be a genetically engineered in the SGI1, SGI2, cpSRP54, cytoSRP54, a combination of SGI1 and cpSRP54 gene, or a combination of SGI2 and cpSRP54 for example, that has been targeted by homologous recombination for knock-out or gene replacement (for example with a mutated form of the gene that may encode a polypeptide having reduced activity with respect to the wild-type polypeptide). In additional examples, an algal strain of interest may be engineered by site-directed homologous recombination to insert a particular gene of interest with or without an expression control sequence such as a promoter, into a particular genomic locus, or to insert a promoter into a genetic locus of the host microorganism to affect the expression of a particular gene or set of genes at the locus.

For example, gene knockout or replacement by homologous recombination can be by transformation of a nucleic acid (e.g., DNA) fragment that includes a sequence homologous to the region of the genome to be altered, where the homologous sequence is interrupted by a foreign sequence, typically a selectable marker gene that allows selection for the integrated construct. The genome-homologous flanking sequences on either side of the foreign sequence or mutated gene sequence can be for example, at least 50, at least 100, at least 200, at least 300, at least 400, at least 500, at least 600, at least 700, at least 800, at least 900, at least 1,000, at least 1,200, at least 1,500, at least 1,750, or at least 2,000 nucleotides in length. A gene knockout or gene "knock in" construct in which a foreign sequence is flanked by target gene sequences, can be provided in a vector that can optionally be linearized, for example, outside of the region that is to undergo homologous recombination, or can be provided as a linear fragment that is not in the context of a vector, for example, the knock-out or knock-in construct can be an isolated or synthesized fragment, including but not limited to a PCR product. In some instances, a split marker system can be used to generate gene knock-outs by homologous recombination, where two DNA fragments can be introduced that can regenerate a selectable marker and disrupt the gene locus of interest via three crossover events (Jeong et al. (2007) FEMS Microbiol Lett 273: 157-163).

In one aspect the invention provides genetically modified organisms, e.g. microorganisms having one or more genetic modifications for attenuating expression of a SGI1, SGI2, cpSRP54, cytoSRP54, a combination of SGI1 and cpSRP54 gene, or a combination of SGI2 and cpSRP54 genes. As used herein "attenuating expression of a SGI1, SGI2, cpSRP54, cytoSRP54, a combination of SGI1 and cpSRP54 gene, or a combination of SGI2 and cpSRP54 gene" means reducing or eliminating expression of one or more above mentioned genes in any manner that reduces production of the fully functional protein.

For example, a recombinant photosynthetic organism engineered to have attenuated expression of a SGI1, SGI2, cpSRP54, cytoSRP54, a combination of SGI1 and cpSRP54 gene, or a combination of SGI2 and cpSRP54 gene can have a disrupted SGI1, SGI2, cpSRP54, cytoSRP54, a combination of SGI1 and cpSRP54 gene, or a combination of SGI2 and cpSRP54 gene, in which the recombinant microorganism can have a SGI1, SGI2, cpSRP54, cytoSRP54, a combination of SGI1 and cpSRP54 gene, or a combination of SGI2 and cpSRP54 gene that includes as least one insertion, mutation, or deletion that reduces or abolishes expression of the gene such that a fully functional SGI1, SGI2, cpSRP54, cytoSRP54, a combination of SGI1 and cpSRP54 gene, or a combination of SGI2 and cpSRP54 gene, or cytoSRP54 gene is not produced or is produced in lower amounts than is produced by a control photosynthetic organism of the same species. The disrupted SGI1, SGI2, cpSRP54, cytoSRP54, a combination of SGI1 and cpSRP54 gene, a combination of SGI2 and cpSRP54, or cytoSRP54 gene can be disrupted by, for example, an insertion or gene replacement mediated by homologous recombination and/or by the activity of a meganuclease, zinc finger nuclease (Perez-Pinera et al. (2012) Curr. Opin. Chem. Biol. 16: 268-277), TALEN (WO 2014/207043; WO 2014/076571), or an RNA-guided endonuclease such as a cas protein (e.g., a Cas9 protein) of a CRISPR system.

CRISPR systems, reviewed recently by Hsu et al. (Cell 157:1262-1278, 2014) include, in addition to the Cas nuclease polypeptide or complex, a targeting RNA, often denoted "crRNA", that interacts with the genome target site by complementarity with a target site sequence, a trans-activating ("tracr") RNA that complexes with the Cas polypeptide and also includes a region that binds (by complementarity) the targeting crRNA.

The invention contemplates the use of two RNA molecules (a "crRNA" and a "tracrRNA") that can be cotransformed into a host strain (or expressed in a host strain) that expresses or is transfected with a cas protein for genome editing, or the use of a single guide RNA that includes a sequence complementary to a target sequence as well as a sequence that interacts with a cas protein. That is, in some strategies a CRISPR system as used herein can comprise two separate RNA molecules (RNA polynucleotides: a "tracr-RNA" and a "targeter-RNA" or "crRNA", see below) and referred to herein as a "double-molecule DNA-targeting RNA" or a "two-molecule DNA-targeting RNA." Alternatively, as illustrated in the examples, the DNA-targeting RNA can also include the trans-activating sequence for interaction with the Cas protein (in addition to the target-homologous ("cr") sequences), that is, the DNA-targeting RNA can be a single RNA molecule (single RNA polynucleotide) and is referred to herein as a "chimeric guide RNA," a "single-guide RNA," or a "sgRNA." The terms "DNA-targeting RNA" and "gRNA" are inclusive, referring both to double-molecule DNA-targeting RNAs and to single-molecule DNA-targeting RNAs (i.e., sgRNAs). Both single-molecule guide RNAs and two RNA systems have been described in detail in the literature and for example, in U.S. Patent Application Publication No. US 2014/0068797, incorporated by reference herein in its entirety.

Any Cas protein can be used in the methods herein, e.g., Cast, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. In some embodiments, the Cas protein is a class II Cas protein. The Cas protein can be a Cas9 protein, such as a Cas9 protein of *Staphylococcus pyogenes, S. thermophilus, S. pneumonia, S. aureus*, or *Neisseria meningitidis*, as nonlimiting examples. Other Cas proteins of interest include, without limitation, the Cpf1 RNA-guided endonuclease (Zetsche et al. (2015) Cell 163: 1-13) as well as the C2c1, C2c2, C2c3 RNA-guided nucleases (Shmakov et al. (2015) Molecular Cell 60:1-13). Also considered are the Cas9 proteins provided as SEQ ID NOs:1-256 and 795-1346 in U.S. Patent Application Publication No. US 2014/0068797, and chimeric Cas9 proteins that may combine domains from more than one Cas9 protein, as well as variants and mutants of identified cas9 proteins. (For example, a Cas9 protein encoded by a nucleic acid molecule introduced into a host cell can comprise at least one mutation with respect to a wild-type Cas9 protein; for example, the Cas9 protein can be inactivated in one of the cleavage domains of the protein resulting in a "nickase" variant. Nonlimiting examples of mutations include D10A, H840A, N854A, and N863A.) The nucleic acid sequence encoding the Cas protein can be codon optimized for the host cell of interest.

Cas nuclease activity cleaves target DNA to produce double-strand breaks. These breaks are then repaired by the cell in one of two ways: non-homologous end joining or homology-directed repair. In non-homologous end joining (NHEJ), the double-strand breaks are repaired by direct ligation of the break ends to one another. In this case, no new nucleic acid material is inserted into the site, although some nucleic acid material may be lost, resulting in a deletion, or altered, often resulting in a mutation. In homology-directed repair, a donor polynucleotide (sometimes referred to as a "donor DNA" or "editing DNA") which may have homology to the cleaved target DNA sequence is used as a template for repair of the cleaved target DNA sequence, resulting in the transfer of genetic information from the donor polynucleotide to the target DNA. As such, new nucleic acid material may be inserted/copied into the site. The modifications of the target DNA due to NHEJ and/or homology-directed repair (for example using a donor DNA molecule) can lead to, for example, gene correction, gene replacement, gene tagging, transgene insertion, nucleotide deletion, gene disruption, gene mutation, etc.

In some instances, cleavage of DNA by a site-directed modifying polypeptide (e.g., a Cas nuclease, zinc finger nuclease, meganuclease, or TALEN) may be used to delete nucleic acid material from a target DNA sequence by cleaving the target DNA sequence and allowing the cell to repair the sequence in the absence of an exogenously provided donor polynucleotide. Such NHEJ events can result in mutations ("mis-repair") at the site of rejoining of the cleaved ends that can result in gene disruption.

Alternatively, if a DNA-targeting RNA is co-administered to cells that express a cas nuclease along with a donor DNA, the subject methods may be used to add, i.e. insert or replace, nucleic acid material to a target DNA sequence (e.g. "knock out" by insertional mutagenesis, or "knock-in" a nucleic acid that encodes a protein (e.g., a selectable marker and/or any protein of interest), an siRNA, an miRNA, etc., to modify a nucleic acid sequence (e.g., introduce a mutation), and the like.

A donor DNA can in particular embodiments include a gene regulatory sequence (e.g., a promoter) that can, using CRISPR targeting, be inserted upstream of the coding regions of the gene and upstream of the presumed proximal promoter region of the gene, for example, at least 50 bp, at least 100 bp, at least 120 bp, at least 150 bp, at least 200 bp, at least 250 bp, at least 300 bp, at least 350 bp, at least 400 bp, at least 450 bp, or at least 500 bp upstream of the initiating ATG of the coding region of the cpSRP54 gene.

The donor DNA can include a sequence, such as for example a selectable marker or any convenient sequence, that may interfere with the native promoter. The additional sequence inserted upstream of the initiating ATG of the SGI1, SGI2, cpSRP54, cytoSRP54, a combination of the genes, or a combination of the open reading frame (e.g., in the 5'UTR or upstream of the transcriptional start site of the cpSRP54 gene) can decrease or even eliminate expression of the endogenous SGI1, SGI2, cpSRP54, cytoSRP54, a combination of the genes. Alternatively or in addition, the native SGI1, SGI2, cpSRP54, cytoSRP54, or a combination of the genes, can have its endogenous promoter wholly or partially replaced by a weaker or differently regulated promoter, or a non-promoter sequence.

In some examples, a nucleic acid molecule introduced into a host cell for generating a high efficiency genome editing cell line encodes a Cas9 enzyme that is mutated to with respect to the corresponding wild-type enzyme such that the mutated Cas9 enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (an enzyme that cleaves a single strand). Other examples of mutations that render Cas9 a nickase include, without limitation, H840A, N854A, and N863A. In some embodiments, a Cas9 nickase may be used in combination with guide sequence(s), e.g., two guide sequences, which target respectively sense and antisense strands of the DNA target. This combination allows both strands to be nicked and used to induce NHEJ. Two nickase targets (within close proximity but targeting different strands of the DNA) can be used to inducing mutagenic NHEJ. Such targeting of a locus using enzymes that cleave opposite strains at staggered positions can also reduce nontarget cleavage, as both strands must be accurately and specifically cleaved to achieve genome mutation.

In additional examples, a mutant Cas9 enzyme that is impaired in its ability to cleave DNA can be expressed in the cell, where one or more guide RNAs that target a sequence upstream of the transcriptional or translational start site of the targeted gene are also introduced. In this case, the Cas enzyme may bind the target sequence and block transcription of the targeted gene (Qi et al. (2013) Cell 152:1173-1183).

In some cases, a Cas polypeptide such as a Cas9 polypeptide is a fusion polypeptide, comprising, e.g.: i) a Cas9 polypeptide (which can optionally be variant Cas9 polypeptide as described above); and b) a covalently linked heterologous polypeptide (also referred to as a "fusion partner"). A heterologous nucleic acid sequence may be linked to another nucleic acid sequence (e.g., by genetic engineering) to generate a chimeric nucleotide sequence encoding a chimeric polypeptide. In some embodiments, a Cas9 fusion polypeptide is generated by fusing a Cas9 polypeptide with a heterologous sequence that provides for subcellular localization (i.e., the heterologous sequence is a subcellular localization sequence, e.g., a nuclear localization signal (NLS) for targeting to the nucleus; a mitochondrial localization signal for targeting to the mitochondria; a chloroplast localization signal for targeting to a chloroplast; an ER retention signal; and the like). In some embodiments, the heterologous sequence can provide a tag (i.e., the heterologous sequence is a detectable label) for ease of tracking and/or purification (e.g., a fluorescent protein, e.g., green fluorescent protein (GFP), YFP, RFP, CFP, mCherry, tdTomato, and the like; a hemagglutinin (HA) tag; a FLAG tag; a Myc tag; and the like).

Host cells can be genetically engineered (e.g. transduced or transformed or transfected) with, for example, a vector construct that can be, for example, a vector for homologous recombination that includes nucleic acid sequences homologous to a portion of a SGI1, SGI2, cpSRP54, cytoSRP54, a combination of SGI1 and cpSRP54 gene, or a combination of SGI2 and cpSRP54 gene locus of the host cell or to regions adjacent thereto, or can be an expression vector for the expression of any or a combination of: a Cas protein (e.g., a Class II Cas protein), a CRISPR chimeric guide RNA, a crRNA, and/or a tracrRNA, an RNAi construct (e.g., a shRNA), an antisense RNA, or a ribozyme. The vector can be, for example, in the form of a plasmid, a viral particle, a phage, etc. A vector for expression of a polypeptide or RNA for genome editing can also be designed for integration into the host, e.g., by homologous recombination. A vector containing a polynucleotide sequence as described herein, e.g., sequences having homology to host SGI1, SGI2, cpSRP54, cytoSRP54, a combination of SGI1 and cpSRP54 gene, or a combination of SGI2 and cpSRP54 gene sequences (including sequences that are upstream and downstream of the cpSRP54 or cytoSRP54-encoding sequences), as well as, optionally, a selectable marker or reporter gene, can be employed to transform an appropriate host to cause attenuation of a SGI1, SGI2, cpSRP54, cytoSRP54, a combination of SGI1 and cpSRP54 gene, or a combination of SGI2 and cpSRP54 gene.

The recombinant photosynthetic organism in some examples can have reduced but not abolished expression of the SGI1, SGI2, cpSRP54, cytoSRP54, a combination of SGI1 and cpSRP54 genes, or a combination of SGI2 and cpSRP54 genes, and the recombinant photosynthetic organism can have a reduction in chlorophyll from about 10% to about 90%, for example, a reduction in total chlorophyll from about 20% to about 80%. A genetically modified microorganism as provided herein can in some examples include a nucleic acid construct for attenuating the expression of an SGI1, SGI2, cpSRP54, cytoSRP54, a combination of SGI1 and cpSRP54 genes, or a combination of SGI2 and cpSRP54 genes. For example, a host microorganism can include a construct for expressing an RNAi molecule, ribozyme, or antisense molecule that reduces expression of SGI1, SGI2, cpSRP54, cytoSRP54, a combination of SGI1 and cpSRP54 gene, or a combination of SGI2 and cpSRP54 genes. In some examples, a recombinant microorganism as provided herein can include at least one introduced (exogenous or non-native) construct for reducing expression of an SGI1, SGI2, cpSRP54, cytoSRP54, a combination of SGI1 and cpSRP54 gene, or a combination of SGI2 and cpSRP54 genes.

Engineered strains can be selected for expression of an SGI1, SGI2, cpSRP54, cytoSRP54, a combination of SGI1 and cpSRP54 gene, or a combination of SGI2 and cpSRP54 genes that is decreased with respect to a control cell that does not include a genetic modification for attenuating SGI1, SGI2, cpSRP54, cytoSRP54, a combination of SGI1 and cpSRP54 gene, or a combination of SGI2 and cpSRP54 gene expression, but not eliminated, using methods known in the art, such as, for example, RNA-Seq or reverse transcription-PCR (RT-PCR).

A genetically engineered strain as provided herein can be engineered to include a construct for attenuating gene expression by reducing the amount, stability, or translatability of mRNA of a gene encoding an SGI1, SGI2, cpSRP54, cytoSRP54, a combination of SGI1 and cpSRP54 genes, or a combination of SGI2 and cpSRP54 genes. For example, a photosynthetic organism such as a plant or an algal or heterokont strain can be transformed with an antisense RNA, RNAi, or ribozyme construct targeting a mRNA of an SGI1, SGI2, cpSRP54, cytoSRP54, a combination of SGI1 and cpSRP54 genes, or a combination of SGI2 and cpSRP54 genes using methods known in the art. For example, an antisense RNA construct that includes all or a portion of the transcribed region of a gene can be introduced into a microorganism to decrease gene expression (Shroda et al. (1999) The Plant Cell 11:1165-78; Ngiam et al. (2000) Appl. Environ. Microbiol. 66: 775-782; Ohnuma et al. (2009) Protoplasma 236: 107-112; Lavaud et al. (2012) PLoS One 7:e36806). Alternatively or in addition, an RNAi construct (for example, a construct encoding a short hairpin RNA) targeting a cpSRP54 or cytoSRP54 gene can be introduced into a microorganism such as an alga or heterokont for reducing expression of the cpSRP54 or cytoSRP54 gene (see, for example, Cerruti et al. (2011) Eukaryotic Cell (2011) 10: 1164-1172; Shroda et al. (2006) Curr. Genet. 49:69-84).

Ribozymes are RNA-protein complexes that cleave nucleic acids in a site-specific fashion. Ribozymes have specific catalytic domains that possess endonuclease activity. For example, U.S. Pat. No. 5,354,855 reports that certain ribozymes can act as endonucleases with a sequence specificity greater than that of known ribonucleases and approaching that of the DNA restriction enzymes. Catalytic RNA constructs (ribozymes) can be designed to base pair with a mRNA encoding a gene as provided herein to cleave the mRNA target. In some examples, ribozyme sequences can be integrated within an antisense RNA construct to mediate cleavage of the target. Various types of ribozymes can be considered, their design and use is known in the art and described, for example, in Haseloff et al. (1988) Nature 334:585-591.

Ribozymes are targeted to a given sequence by virtue of annealing to a site by complementary base pair interactions. Two stretches of homology are required for this targeting. These stretches of homologous sequences flank the catalytic ribozyme structure defined above. Each stretch of the homologous sequence can vary in length from 7 to 15 nucleotides. The only requirement for defining the homologous sequences is that, on the target RNA, they are separated by a specific sequence which is the cleavage site. For hammerhead ribozyme, the cleavage site is a dinucleotide sequence on the target RNA is a uracil (U) followed by either an adenine, cytosine or uracil (A, C, or U) (Thompson et al., (1995) Nucl Acids Res 23:2250-68). The frequency of this dinucleotide occurring in any given RNA is statistically 3 out of 16. Therefore, for a given target messenger RNA of 1,000 bases, 187 dinucleotide cleavage sites are statistically possible.

The general design and optimization of ribozyme directed RNA cleavage activity has been discussed in detail (Haseloff and Gerlach (1988) Nature 334:585-591; Symons (1992) Ann Rev Biochem 61: 641-71; Chowrira et al. (1994) J Biol Chem 269:25856-64; Thompson et al. (1995) supra). Designing and testing ribozymes for efficient cleavage of a target RNA is a process well known to those skilled in the art. Examples of scientific methods for designing and testing ribozymes are described by Chowrira et al., (1994) supra and Lieber and Strauss (1995) Mol Cell Biol. 15: 540-51, each incorporated by reference. The identification of operative and preferred sequences for use in down-regulating a given gene is a matter of preparing and testing a given sequence, and is a routinely practiced "screening" method known to those of skill in the art.

The use of RNAi constructs is described in the literature cited above as well as in US2005/0166289 and WO 2013/016267, for example A double-stranded RNA with homology to the target gene is delivered to the cell or produced in the cell by expression of an RNAi construct, for example, an RNAi short hairpin (sh) construct. The construct can include a sequence that is identical to the target gene, or at least 70%, 80%, 90%, 95%, or between 95% and 100% identical to a sequence of the target gene. The construct can have at least 20, at least 30, at least 40, at least 50, at least 100, at least 200, at least 300, at least 400, at least 500, at least 600, at least 700, at least 800, at least 900, or at least 1 kb of sequence homologous to the target gene. Expression vectors can be engineered using promoters selected for continuous or inducible expression of an RNAi construct, such as a construct that produces a shRNA.

A nucleic acid construct for gene attenuation, e.g., a ribozyme, RNAi, or antisense construct can include at least fifteen, at least twenty, at least thirty, at least forty, at least fifty, or at least sixty nucleotides having at least 80% identity, such as at least 85%, at least 90%, at least 95%, or at least 99% or complementarity to at least a portion of the sequence of an endogenous SGI1, SGI2, cpSRP54, cytoSRP54, a combination of SGI1 and cpSRP54 genes, or a combination of SGI2 and cpSRP54 genes of the microorganism to be engineered. A nucleic acid construct for gene attenuation, e.g., a ribozyme, RNAi, or antisense construct can include at least fifteen, at least twenty, at least thirty, at least forty, at least fifty, or at least sixty nucleotides having at least 80%, such as at least 95% or about 100%, identity or complementarity to the sequence of a naturally-occurring gene, such as a gene having encoding a polypeptide having at least 50%, at least 55%, at least 60%, at least 65%, at least 70%, at least 75%, at least 80% or at least 85%, at least 90%, or at least 95% sequence identity to an endogenous SGI1, SGI2, cpSRP54, cytoSRP54, a combination of SGI1 and cpSRP54 genes, or a combination of SGI2 and cpSRP54 genes. For example, a nucleic acid construct for gene attenuation, e.g., a ribozyme, RNAi, or antisense construct can include at least fifteen, at least twenty, at least thirty, at least forty, at least fifty, or at least sixty nucleotides having at least 80% identity or complementarity to the sequence of a naturally-occurring cpSRP54 gene, such as any provided herein. The nucleotide sequence can be, for example, from about 30 nucleotides to about 3 kilobases or greater, for example, from 30-50 nucleotides in length, from 50 to 100 nucleotides in length, from 100 to 500 nucleotides in length, from 500 nucleotides to 1 kb in length, from 1 kb to 2 kb in length, or from 2 to 5 kb. For example, an antisense sequence can be from about 100 nucleotides to about 1 kb in length. For example, a nucleic acid construct for gene attenuation, e.g., a ribozyme, RNAi, or antisense construct can include at least fifteen, at least twenty, at least thirty, at least forty, at least fifty, at least sixty, or at least 100 nucleotides having at least 50%, at least 55%, at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, or at least 95% identity or complementarity to an endogenous SGI1, SGI2, cpSRP54, cytoSRP54, a combination of SGI1 and cpSRP54 genes, or a combination of SGI2 and cpSRP54 genes or a portion thereof.

Promoters used in antisense, RNAi, or ribozyme constructs can be any that are functional in the host organism and that are suitable for the levels of expression required for reducing expression of the target gene to a desired amount. Promoters functional in algae and heterokonts are known in the art and disclosed herein. The construct can be transformed into algae using any feasible method, include any disclosed herein. A recombinant organism or microorganism transformed with a nucleic acid molecule for attenuating SGI1, SGI2, cpSRP54, cytoSRP54, a combination of SGI1 and cpSRP54 gene, or a combination of SGI2 and cpSRP54 gene expression, such as but not limited to an antisense, RNAi, or ribozyme construct, can have the properties of a SGI1, SGI2, cpSRP54, cytoSRP54, a combination of SGI1 and cpSRP54 gene, or a combination of SGI2 and cpSRP54 mutant as described herein, including, for example, reduced chlorophyll, increased photosynthetic efficiency, and increased productivity in culture, with respect to a host organism or microorganism that does not include the exogenous nucleic acid molecule that results in attenuated gene expression.

Nucleic Acid Molecules and Constructs

One skilled in the art will appreciate that a number of transformation methods can be used for genetic transformation of microorganisms and, therefore, can be deployed for the methods of the present invention. "Stable transformation" is intended to mean that the nucleic acid construct introduced into an organism integrates into the genome of the organism or is part of a stable episomal construct and is capable of being inherited by the progeny thereof. "Transient transformation" is intended to mean that a polynucleotide is introduced into the organism and does not integrate into the genome or otherwise become established and stably inherited by successive generations.

Genetic transformation can result in stable insertion and/or expression of transgenes, constructs from either the nucleus or the plastid, and in some cases can result in transient expression of transgenes. The transformation methods can also be used for the introduction of guide RNAs or editing DNAs. Genetic transformation of microalgae has been reported successful for more than 30 different strains of microalgae, which belong to at least ~22 species of green, red, and brown algae, diatoms, euglenids, and dianoflagellates (see, e.g., Radakovits et al., Eukaryotic Cell, 2010; and Gong et al., J. Ind. Microbiol. Biotechnol., 2011). Non-limiting examples of such useful transformation methods include agitation of cells in the presence of glass beads or silicon carbide whiskers as reported by, for example, Dunahay, Biotechniques, 15(3):452-460, 1993; Kindle, Proc. Natl. Acad. Sci. U.S.A., 1990; Michael and Miller, Plant J., 13, 427-435, 1998. Electroporation techniques have been successfully used for genetic transformation of several microalgal species including *Nannochloropsis* sp. (see, e.g., Chen et al., J. Phycol., 44:768-76, 2008), *Chlorella* sp. (see, e.g., Chen et al., Curr. Genet., 39:365-370, 2001; Chow and Tung, Plant Cell Rep. Vol. 18, No. 9, 778-780, 1999), *Chlamydomonas* (Shimogawara et al., Genetics, 148: 1821-1828, 1998), *Dunaliella* (Sun et al., Mol. Biotechnol., 30(3): 185-192, 2005). Micro-projectile bombardment, also referred to as microparticle bombardment, gene gun transformation, or biolistic bombardment, has been used successfully for several algal species including, for example, diatoms species such as *Phaeodactylum* (Apt et al., Mol. Gen. Genet., 252:572-579, 1996), Cyclotella and Navicula (Dunahay et al., J. Phycol., 31:1004-1012, 1995), Cylindrotheca (Fischer et al., J. Phycol., 35:113-120, 1999), and Chaetoceros sp. (Miyagawa-Yamaguchi et al., Phycol. Res. 59: 113-119, 2011), as well as green algal species such as *Chlorella* (El-Sheekh, Biologia Plantarum, Vol. 42, No. 2: 209-216, 1999), and *Volvox* species (Jakobiak et al., Protist, 155:381-93, 2004). Additionally, *Agrobacterium*-mediated gene transfer techniques can also be useful for the genetic transformation of microalgae, as has been reported by, for example, Kumar, Plant Sci., 166(3):731-738, 2004, and Cheney et al., J. Phycol., Vol. 37, Suppl. 11, 2001.

A transformation vector or construct as described herein will typically comprise a marker gene that confers a selectable or scorable phenotype on target host cells, e.g., algal cells or may be co-transformed with a construct that includes a marker. A number of selectable markers have been successfully developed for efficient isolation of genetic transformants of algae. Common selectable markers include antibiotic resistance, fluorescent markers, and biochemical markers. Several different antibiotic resistance genes have been used successfully for selection of microalgal transformants, including blastocydin, bleomycin (see, for example, Apt et al., 1996, supra; Fischer et al., 1999, supra; Fuhrmann et al., Plant J., 19, 353-61, 1999, Lumbreras et al., Plant J., 14(4):441-447, 1998; Zaslayskaia et al., J. Phycol., 36:379-386, 2000), spectinomycin (Cerutti et al., Genetics, 145: 97-110, 1997; Doetsch et al., Curr. Genet., 39, 49-60, 2001; Fargo, Mol. Cell. Biol., 19:6980-90, 1999), streptomycin (Berthold et al., Protist, 153:401-412, 2002), paromomycin (Jakobiak et al., Protist, supra.; Sizova et al., Gene, 277: 221-229, 2001), nourseothricin (Zaslayskaia et al., 2000, supra), G418 (Dunahay et al., 1995, supra; Poulsen and Kroger, FEBS Lett., 272:3413-3423, 2005, Zaslayskaia et al., 2000, supra), hygromycin (Berthold et al., 2002, supra), chloramphenicol (Poulsen and Kroger, 2005, supra), and many others. Additional selectable markers for use in microalgae such as *Chlamydomonas* can be markers that provide resistance to kanamycin and amikacin resistance (Bateman, Mol. Gen. Genet. 263:404-10, 2000), zeomycin and phleomycin (e.g., ZEOCIN™ pheomycin D1) resistance (Stevens, Mol. Gen. Genet. 251:23-30, 1996), and paramomycin and neomycin resistance (Sizova et al., 2001, supra). Other fluorescent or chromogenic markers that have been used include luciferase (Falciatore et al., J. Mar. Biotechnol., 1: 239-251, 1999; Fuhrmann et al., Plant Mol. Biol., 2004; Jarvis and Brown, Curr. Genet., 19: 317-322, 1991), β-glucuronidase (Chen et al., 2001, supra; Cheney et al., 2001, supra; Chow and Tung, 1999, supra; El-Sheekh, 1999, supra; Falciatore et al., 1999, supra; Kubler et al., J. Mar. Biotechnol., 1:165-169, 1994), β-galactosidase (Gan et al., J. Appl. Phycol., 15:345-349, 2003; Jiang et al., Plant Cell Rep., 21:1211-1216, 2003; Qin et al., High Technol. Lett., 13:87-89, 2003), and green fluorescent protein (GFP) (Cheney et al., 2001, supra; Ender et al., Plant Cell, 2002, Franklin et al., Plant J., 2002; 56, 148, 210).

One skilled in the art will readily appreciate that a variety of known promoter sequences can be usefully deployed for transformation systems of microalgal species in accordance with the present invention. For example, the promoters commonly used to drive transgene expression in microalgae include various versions of the of cauliflower mosaic virus promoter 35S (CaMV35S), which has been used in both dinoflagellates and *Chlorophyta* (Chow et al, Plant Cell Rep., 18:778-780, 1999; Jarvis and Brown, Curr. Genet., 317-321, 1991; Lohuis and Miller, Plant J., 13:427-435, 1998). The SV40 promoter from the simian virus has also reported being active in several algae (Gan et al., J. Appl. Phycol., 151 345-349, 2003; Qin et al., Hydrobiologia 398-399, 469-472, 1999). The promoters of RBCS2 (ribulose bisphosphate carboxylase, small subunit) (Fuhrmann et al., Plant J., 19:353-361, 1999) and PsaD (abundant protein of photosystem I complex; Fischer and Rochaix, FEBS Lett.

581:5555-5560, 2001) from *Chlamydomonas* can also be useful. The fusion promoters of HSP70A/RBCS2 and HSP70A/β2TUB (tubulin) (Schroda et al., Plant J., 21:121-131, 2000) can also be useful for an improved expression of transgenes, in which HSP70A promoter may serve as a transcriptional activator when placed upstream of other promoters. High-level expression of a gene of interest can also be achieved in, for example diatoms species, under the control of a promoter of an fcp gene encoding a diatom fucoxanthin-chlorophyll a/b binding protein (Falciatore et al., Mar. Biotechnol., 1:239-251, 1999; Zaslayskaia et al., J. Phycol. 36:379-386, 2000) or the vcp gene encoding a eustigmatophyte violaxanthin-chlorophyll a/b binding protein (see U.S. Pat. No. 8,318,482). If so desired, inducible promoters can provide rapid and tightly controlled expression of genes in transgenic microalgae. For example, promoter regions of the NR genes encoding nitrate reductase can be used as such inducible promoters. The NR promoter activity is typically suppressed by ammonium and induced when ammonium is replaced by nitrate (Poulsen and Kroger, FEBS Lett 272:3413-3423, 2005), thus gene expression can be switched off or on when microalgal cells are grown in the presence of ammonium/nitrate. Additional algal promoters that can find use in the constructs and transformation systems provided herein include those disclosed in U.S. Pat. No. 8,883,993; U.S. Patent Appl. Pub. No. US 2013/0023035; U.S. Patent Application Pub. No. US 2013/0323780; and U.S. Patent Application Pub. No. US 2014/0363892.

Host cells can be either untransformed cells or cells that are already transfected with at least one nucleic acid molecule. For example, an algal host cell that is engineered to have attenuated expression of a cpSRP54 gene can further include one or more genes that may confer any desirable trait, such as, but not limited to, increased production of biomolecules of interest, such as one or more proteins, pigments, alcohols, or lipids.

Methods of Producing Products from Photosynthetic Organisms

Also provided herein are methods of producing products from photosynthetic organisms, such as algae by culturing the photosynthetic organism having increased photosynthetic efficiency, such as the SGI1, SGI2, cpSRP54, cytoSRP54, a combination of SGI1 and cpSRP54 gene, or a combination of SGI2 and cpSRP54 mutants disclosed herein. The methods include culturing a photosynthetic organism mutant SGI1, SGI2, cpSRP54, cytoSRP54, a combination of SGI1 and cpSRP54 gene, or a combination of SGI2 and cpSRP54 in a suitable medium to provide a photosynthetic organism culture and recovering biomass or at least one product from the culture. In some embodiments the product is a lipid. The culture comprising photosynthetic organism is preferably a photoautotrophic culture, and the culture medium preferably does not include a substantial amount of reduced carbon, that is, the culture does not include reduced carbon in a form or at a level that can be used by the algae for growth.

In some embodiments, the photosynthetic organism may be cultured in any suitable vessel, including flasks or bioreactors, where the photosynthetic organism may be exposed to artificial or natural light. The culture comprising mutant photosynthetic organism may be cultured on a light/dark cycle that may be, for example, a natural or programmed light/dark cycle, and as illustrative examples, may provide twelve hours of light to twelve hours of darkness, fourteen hours of light to ten hours of darkness, sixteen hours of light to eight hours of darkness, etc.

Culturing refers to the intentional fostering of growth (e.g., increases in cell size, cellular contents, and/or cellular activity) and/or propagation (e.g., increases in cell numbers via mitosis) of one or more cells by use of selected and/or controlled conditions. The combination of both growth and propagation may be termed proliferation. As demonstrated in the examples herein, the mutants provided herein exhibiting deregulated adaptation to low light intensity can achieve higher cell density of the culture over time, for example, over a period of a week or more, with respect to a culture wild type algal cells of the same strain that are not deregulated in low light acclimation. For example, a cpSRP54 mutant may be cultured for at least five, at least six, at least seven at least eight, at least nine, at least ten, at least eleven at least twelve, at least thirteen, at least fourteen, or at least fifteen days, or at least one, two three, four, five, six, seven, eight, nine, or ten weeks, or longer.

Non-limiting examples of selected and/or controlled conditions that can be used for culturing the recombinant microorganism can include the use of a defined medium (with known characteristics such as pH, ionic strength, and/or carbon source), specified temperature, oxygen tension, carbon dioxide levels, growth in a bioreactor, or the like, or combinations thereof. In some embodiments, the microorganism or host cell can be grown mixotrophically, using both light and a reduced carbon source. Alternatively, the microorganism or host cell can be cultured phototrophically. When growing phototrophically, the algal strain can advantageously use light as an energy source. An inorganic carbon source, such as $CO_2$ or bicarbonate can be used for the synthesis of biomolecules by the microorganism. "Inorganic carbon", as used herein, includes carbon-containing compounds or molecules that cannot be used as a sustainable energy source by an organism. Typically "inorganic carbon" can be in the form of $CO_2$ (carbon dioxide), carbonic acid, bicarbonate salts, carbonate salts, hydrogen carbonate salts, or the like, or combinations thereof, which cannot be further oxidized for sustainable energy nor used as a source of reducing power by organisms. A microorganism grown photoautotrophically can be grown on a culture medium in which inorganic carbon is substantially the sole source of carbon. For example, in a culture in which inorganic carbon is substantially the sole source of carbon, any organic (reduced) carbon molecule or organic carbon compound that may be provided in the culture medium either cannot be taken up and/or metabolized by the cell for energy and/or is not present in an amount sufficient to provide sustainable energy for the growth and proliferation of the cell culture.

Microorganisms and host cells that can be useful in accordance with the methods of the present invention can be found in various locations and environments throughout the world. The particular growth medium for optimal propagation and generation of lipid and/or other products can vary and may be optimized to promote growth, propagation, or production of biomass or a product such as a lipid, protein, pigment, antioxidant, etc. Solid and liquid growth media are generally available from a wide variety of sources, as are instructions for the preparation of particular media suitable for a wide variety of strains of microorganisms. For example, various fresh water and salt water media can include those described in Barsanti (2005) Algae: Anatomy, Biochemistry & Biotechnology, CRC Press for media and methods for culturing algae. Algal media recipes can also be found at the websites of various algal culture collections, including, as nonlimiting examples, the UTEX Culture Collection of Algae (www.sbs.utexas.edu/utex/media.aspx);

Culture Collection of Algae and Protozoa (www.ccap.ac.uk); and Katedra Botaniky (botany.natur.cuni.cz/algo/caup-media.html).

The culture methods can optionally include inducing expression of one or more genes for the production of a product, such a but not limited to a protein that participates in the production of a lipid, one or more proteins, antioxidants, or pigments, and/or regulating a metabolic pathway in the microorganism. Inducing expression can include adding a nutrient or compound to the culture, removing one or more components from the culture medium, increasing or decreasing light and/or temperature, and/or other manipulations that promote expression of the gene of interest. Such manipulations can largely depend on the nature of the (heterologous) promoter operably linked to the gene of interest.

In some embodiments of the present invention, the microorganisms deregulated in acclimation to low light intensity can be cultured in a "photobioreactor" equipped with an artificial light source, and/or having one or more walls that is transparent enough to light, including sunlight, to enable, facilitate, and/or maintain acceptable microorganism growth and proliferation. For the production of fatty acid products or triglycerides, photosynthetic microorganisms or host cells can additionally or alternatively be cultured in shake flasks, test tubes, vials, microtiter dishes, Petri dishes, or the like, or combinations thereof.

Additionally or alternatively, recombinant photosynthetic microorganisms or host cells may be grown in ponds, canals, sea-based growth containers, trenches, raceways, channels, or the like, or combinations thereof. In such systems, the temperature may be unregulated, or various heating or cooling method or devices may be employed. As with standard bioreactors, a source of inorganic carbon (such as, but not limited to, $CO_2$, bicarbonate, carbonate salts, and the like), including, but not limited to, air, $CO_2$-enriched air, flue gas, or the like, or combinations thereof, can be supplied to the culture. When supplying flue gas and/or other sources of inorganic that may contain CO in addition to $CO_2$, it may be necessary to pre-treat such sources such that the CO level introduced into the (photo)bioreactor do not constitute a dangerous and/or lethal dose with respect to the growth, proliferation, and/or survival of the microorganisms.

The mutant photosynthetic organism can include one or more non-native genes encoding a polypeptide for the production of a product, such as, but limited to, a lipid, a colorant or pigment, an antioxidant, a vitamin, a nucleotide, a nucleic acid, an amino acid, a hormone, a cytokine, a peptide, a protein, or a polymer. For example, the encoded polypeptide can be an enzyme, metabolic regulator, cofactor, carrier protein, or transporter. The methods include culturing a cpSRP54 mutant or cytoSRP54 mutant that includes at least one non-native gene encoding a polypeptide that participates in the production of a product, to produce biomass or at least one algal product. Products such as lipids and proteins can be recovered from the culture by the recovery means known to those of ordinary skill in the art, such as by whole culture extraction, for example, using organic solvents. In some cases, recovery of fatty acid products can be enhanced by homogenization of the cells. For example, lipids such as fatty acids, fatty acid derivatives, and/or triglycerides can be isolated from algae by extraction of the algae with a solvent at elevated temperature and/or pressure, as described in the co-pending, commonly-assigned U.S. Patent Application Publication No. US 2013/0225846, which is incorporated herein by reference in its entirety.

Other alternative embodiments and methods will be apparent to those of skill in the art upon review of this disclosure. The discussion of the general methods given herein is intended for illustrative purposes only. The following non-limiting examples are provided below.

EXAMPLES

Example 1

Generation of *Parachlorella* Strains Overexpressing Cas9

Generation of *Parachlorella* strains overexpressing Cas9 was described in US Patent Application Publication 2016/0304896, which is incorporated by reference in its entirety.

Briefly, a vector, pSGE-6709, was engineered for the expression of the *Streptococcus pyogenes* Cas9 gene in *Parachlorella*. The vector included the following three elements: 1) a Cas9 expression cassette which contained an engineered Cas9 gene codon optimized for *Parachlorella* and containing introns from *Parachlorella*, that also included an N-terminal FLAG tag, nuclear localization signal, and peptide linker operably linked to the *Parachlorella* RPS17 promoter and terminated by the *Parachlorella* RPS17 terminator a selectable marker expression cassette, which contained the blasticidin resistance gene from *Aspergillus terreus* codon optimized for *Parachlorella* and containing *Parachlorella* introns, operably linked to the *Parachlorella* RPS4 promoter and terminated by the *Parachlorella* RPS4 terminator, a GFP reporter expression cassette, which contained the TurboGFP gene (Evrogen, Moscow, Russia), driven by the *Parachlorella* ACP1 promoter and terminated by the *Parachlorella* ACP1 terminator.

The vector was transformed into *Parachlorella* by biolistics. Transformation of *Parachlorella* wild-type strain WT-1185 was accomplished using the BioRad Helios® Gene Gun System essentially as described in US Patent Publication No. 2014/0154806, incorporated herein by reference. DNA for transformation was precipitated onto gold particles, the gold particles adhered to the inside of lengths of tubing, and a burst of helium gas was fired through the tubing positioned within the Gene Gun to propel the DNA-coated gold particles into *Parachlorella* strain WT-1185 cells which were adhered on solid non-selective media (2% agar plates containing PM074 algal growth medium). The Helios® Gene Gun was used to fire two bullets per cell circle at 600 psi from a distance of 3-6 cm from the plate. The following day, cells were transferred onto a selective medium for growth of transformed colonies.

Colonies were screened for full GFP penetrance by flow cytometry and identification of transformed strains that had a single fluorescence peak shifted to a higher value than the wild-type fluorescence peak. Fully penetrant Cas9 strains demonstrating a clearly shifted fluorescence peak with respect to nontransformed cells were tested for Cas9 expression by anti-Cas9 western blotting for evidence of Cas9 expression. Based on these screens, isolate 6709-2 was carried forward and given strain identifier GE-15699.

Example 2

Knockout of CPSRP54 Using Fully Penetrant *Parachlorella* Cas9 Editor Line

Knockout of cpSRP54 using fully penetrant *Parachlorella* Cas9 editor line was described in US Patent Application Publication 2016/0304896, which is incorporated by reference in its entirety. Briefly, a chimeric gRNA (SEQ ID NO:103) was designed, the last three nucleotides represent the PAM, and synthesized in vitro to target the chloroplastic SRP54 gene in *Parachlorella* coding sequence.

GE-15699 was transformed by electroporation with 1-2 μg of purified chimeric guide RNA, and 1 μg of selectable marker DNA which contained a bleomycin resistance “BleR” gene codon-optimized for *Parachlorella* and containing introns from *Parachlorella* (SEQ ID:70). The BleR gene was operably linked to the *Parachlorella* RPS4 promoter (SEQ ID:71) and terminated by the *Parachlorella* RPS4 terminator (SEQ ID:72).

Electroporation was performed by inoculating a 100 mL seed culture inoculated to $1\times10^6$ cells/mL six days before the transformation was used to inoculate a 1 L culture to $1\times10^6$ cells/mL two days before transformation. On the day of transformation, cells were pelleted by centrifugation at 5000×g for 20 minutes, washed three times with 0.1 um filtered 385 mM sorbitol, and resuspended to $5\times10^9$ cells/mL in 385 mM sorbitol. Electroporation of 100 μL concentrated cells was performed in 0.2 cm cuvettes in a BioRad Gene Pulser Xcell™ under varied conditions. The DNA used for optimization of electroporation was linearized pSG6640 including the bleR and TurboGFP expression cassettes. The TurboGFP cassette included the *Parachlorella* ACP1 promoter (SEQ ID NO:67) operably linked to the TurboGFP gene (SEQ ID NO:24) and the *Parachlorella* ACP1 terminator (SEQ ID NO:68). Immediately after electroporating pre-chilled cells and cuvettes, 1 mL cold sorbitol was added and used to transfer cells into 10 mL PM074. After overnight recovery, cells were concentrated and spread onto 13 cm-diameter PM074 media containing zeocin at 250 mg/L and grown under the conditions listed in the biolistics section.

Electroporation conditions were 1.0-1.2 kV (5000-6000 V/cm), 200-300 ohms, and 25-50 μF. Use of larger quantities of DNA increased the resulting number of zeocin-resistant colonies, though the effect plateaued at amounts larger than 4 μg. Following electroporation, cells were plated on agar medium (PM130) containing 250 μg/ml zeocin to select for transformants that incorporated the ble cassette. Transformants were screened by colony PCR using primers designed to amplify across the native targeted locus (oligo-AE596 and oligo-AE597). The primers were designed to produce a 700 bp band in the absence of integration (e.g., “knock-in” of the BleR cassette) into the locus, or a 4.3 kb band if there was the integration of a single ble cassette into the targeted locus. In addition, colony PCR was also performed using primers designed to amplify a fragment extending from the cpSRP54 gene (oligo-AE597) into the selectable marker. Depending on the orientation of the integrated ble cassette, a 1.2 kb band would result from either amplification by primers 405/597 or primers 406/597 spanning from within the ble cassette out into the cpSRP54 gene. The results showed a high frequency (between 40 and 45% in this sample) of knock-in of the BleR cassette into the targeted locus in the absence of homology arms. The cpSRP54 knockouts resulted in a pale green phenotype.

Example 3

Knockout of SGI2 Using Fully Penetrant *Parachlorella* Cas9 Editor Line

The knockout of SGI2 using fully penetrant *Parachlorella* Cas9 editor Line was done essentially as described for cpSRP54 above. Briefly, a chimeric gRNA (SEQ ID NO:104) was designed, the last three nucleotides represent the PAM, and synthesized in vitro to target the chloroplastic SGI2 gene in *Parachlorella* coding sequence.

GE-15699 was transformed by electroporation with 1-2 μg of purified chimeric guide RNA, and 1 μg of selectable marker DNA which contained a bleomycin resistance “BleR” gene codon-optimized for *Parachlorella* and containing introns from *Parachlorella* (SEQ ID:70). The BleR gene was operably linked to the *Parachlorella* RPS4 promoter (SEQ ID:71) and terminated by the *Parachlorella* RPS4 terminator (SEQ ID:72).

The Ble-resistant colonies were selected and the knockout is confirmed by PCR.

Example 4

Knockout of SGI1 Using Fully Penetrant *Parachlorella* Cas9 Editor Line

Figure 10:
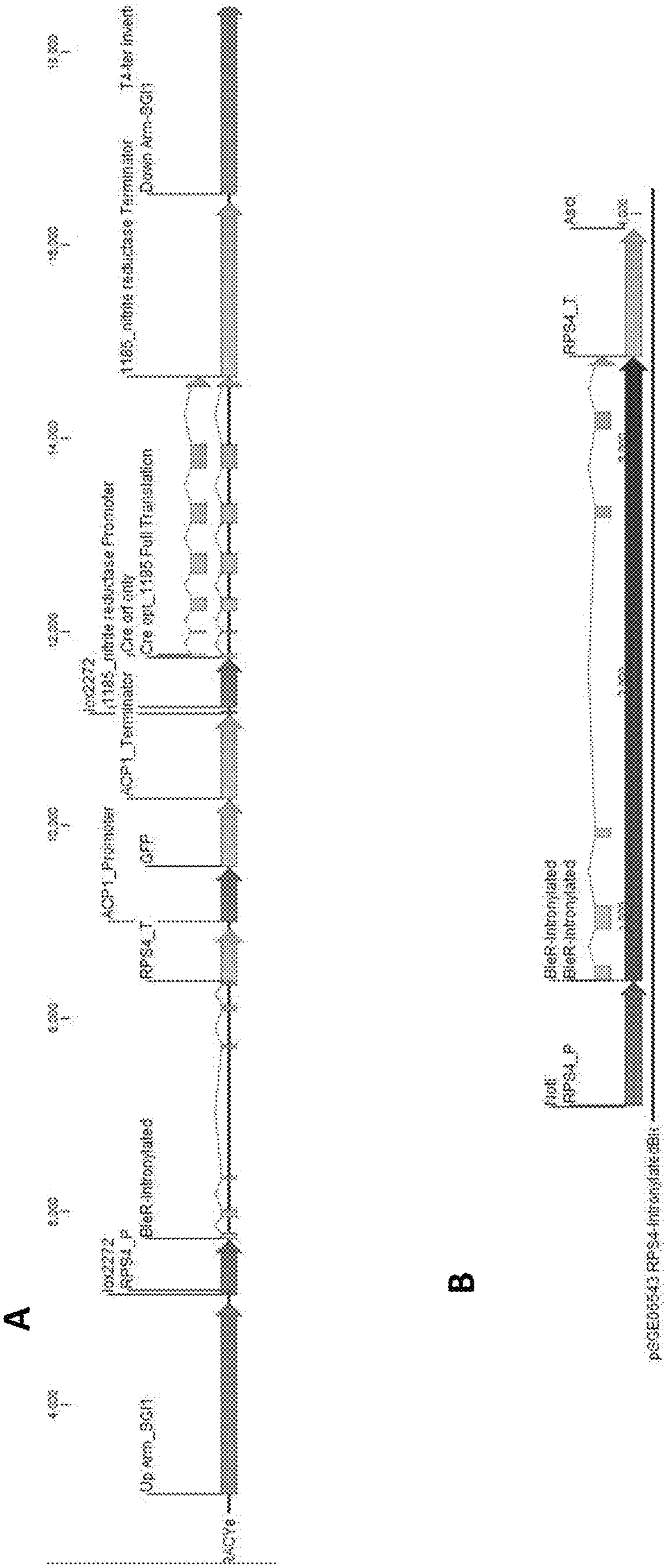
FIG. 10A shows a schematic of a DNA cassette containing a codon optimized Cre gene flanked by nitrite reductase promoter and terminators.
FIG. 10B shows a schematic of a DNA cassette comprising bleR and GFP sequences.

SGI1 knockout strain 24183 was created starting with the Cas9 expressing mother-strain, GE-15699. The GE-15699 cells were electroporated a chimeric gRNA (SEQ ID NO:105, the last three nucleotides of SEQ ID NO: 105 represent the PAM), and a DNA cassette containing a codon optimized Cre gene flanked by nitrite reductase promoter and terminators and shown in FIG. 10A. The cassette also contained ble and GFP genes that have been previously used. Ble and GFP were flanked by lox2272 sites. When Cre is expressed, the lox sites recombine, looping out the DNA between these sequences. Homologous sequences to the SGI1 gene surrounding the CRISPR target were also on the ends of the cassette, to enhance single copy integration. The sequence was confirmed by DNA sequencing for the presence of the cassette in the SGI1 locus. The copy number was confirmed to be a single copy integrant using ddPCR. We then cultured the strain in non-ammonium containing media, to express Cre. When Cre is expressed, the lox sites recombine, looping out the DNA between these sequences.

Example 5

Double Knockout of SGI2 and CPSRP54 Using Fully Penetrant *Parachlorella* Cas9 Editor Line The double knockout of SGI2 and SRP54 using fully penetrant *Parachlorella* Cas9 editor Line was done essentially as described for cpSRP54 above. Briefly, two chimeric gRNAs, one for cpSRP54 (SEQ ID NO:69) and another for SGI2 (SEQ ID NO: 73) was designed, the last three nucleotides represent the PAM, and synthesized in vitro to target the chloroplastic SGI1 gene in *Parachlorella* coding sequence.

GE-15699 was transformed by electroporation with 1-2 μg of purified chimeric guide RNAs, and 1 μg of selectable marker DNA which contained a bleomycin resistance “BleR” gene codon-optimized for *Parachlorella* and containing introns from *Parachlorella* (SEQ ID:70). The BleR gene was operably linked to the *Parachlorella* RPS4 promoter (SEQ ID:71) and terminated by the *Parachlorella* RPS4 terminator (SEQ ID:72).

The Ble-resistant colonies were selected and the knockout is confirmed by PCR.

Example 6

Double Knockout of SGI1 and CPSRP54 Using Fully Penetrant *Parachlorella* Cas9 Editor Line The *Parachlorella* SGI1 knockout strain 24183 as described above was electroporated with chimeric gRNA targeting cpSRP54 (SEQ ID NO: 69) with a DNA cassette comprising ble and GFP sequences (FIG. 10B) to generate the double knockout of SGI1 and cpSRP54. The Ble-resistant colonies were selected and the knockout is confirmed by PCR. Three double knockout strains were generated: STR24538, STR24540, and STR24541 which were identical in their photophysiological properties and physical phenotypes.

Example 7

Figure 17:
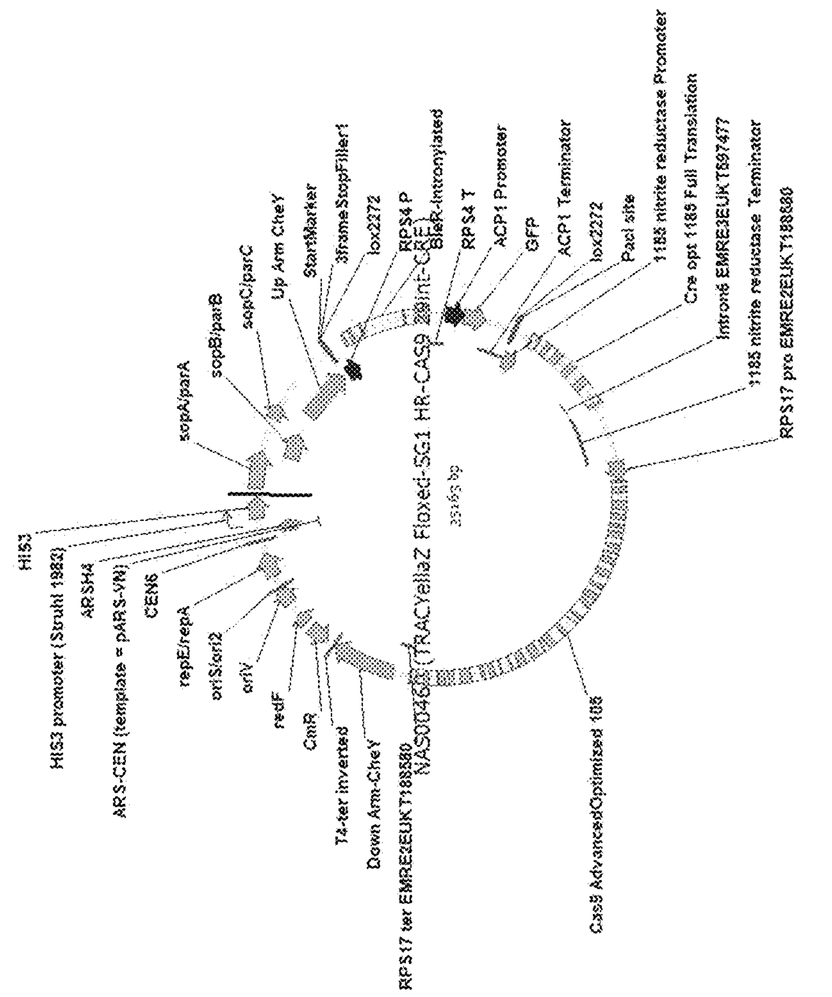
FIG. 17 shows a schematic diagram of the recombinant pCC1BAC vector comprising Cas9, GFP, BleR, Cre genes, and a lox site.

Generation of a *Parachlorella* SGI1 Knockout Strain Comprising a Single Copy Cas9 Gene A bleomycin resistance "BleR" gene codon-optimized for *Parachlorella* and comprising the introns from *Parachlorella* (SEQ ID:70), GFP gene, Cre gene, a lox site, and Cas9 gene were cloned into a pCC1BAC vector. The Cas9 gene was operably linked to the *Parachlorella* RPS17 promoter and comprises 29 native PBP introns and was outside of the lox2272 sites. The Cas9 gene was terminated by the *Parachlorella* RPS17 terminator. The BleR gene was operably linked to the *Parachlorella* RPS4 promoter (SEQ ID:71) and terminated by the *Parachlorella* RPS4 terminator (SEQ ID:72). The GFP gene was operably linked to the *Parachlorella* ACP1 promoter and terminated by the *Parachlorella* ACP1 terminator. The Cre gene was operably linked to the *Parachlorella* nitrite reductase promoter and *Parachlorella* nitrite reductase terminator. These genes are flanked by portions of SGI1 (CheY) sequences which serves as homologous recombination sites. A schematic diagram of the recombinant pCC1BAC vector is shown in FIG. 17.

Transformation WT *Parachlorella* host strain: STR00010

A Cas9 gene, WT *Parachlorella* host strain was co-transformed with gRNA targeting SGI1 gene (SEQ ID NO: 74) and a PvuI-digested and spin-purified selection cassette (NAS00460, SEQ ID NO: 86).

The selection cassette (NAS00460) comprises a fragment that includes 1.7 kb of the vector backbone (corresponding to sequences 1-1761 of SEQ ID NO: 86) upstream of the SGI1 homologous recombination (HR) up arm and no portion of the vector downstream of the SGI1 HR down arm, bleomycin resistance "BleR" gene codon-optimized for *Parachlorella* and containing introns from *Parachlorella* (SEQ ID:70), GFP gene (corresponding to sequences 8260-8961 of SEQ ID NO: 86), and Cas9 gene. Selection cassette contains ble and GFP within lox sites. The CRE gene (corresponding to sequences 10418-13326 of SEQ ID NO: 86) comprises 6 Nitrite reductase codon optimized *Parachlorella* introns. was under the nitrite reductase inducible promoter (corresponding to sequences 9906-10417 of SEQ ID NO: 86). The Cre gene is terminated by Nitrite reductase terminator (corresponding to sequences 13327-15140 of SEQ ID NO: 86). The Cas9 gene including the 29 native PBP introns corresponds to sequence 15754 to sequence 25918 of SEQ ID NO: 86. The Cas9 gene was under the *Parachlorella* RPS17 promoter (corresponding to sequences 15166-15753 of SEQ ID NO: 86) and containing 29 native PBP introns and was outside of the lox sites. The Cas9 gene was terminated by the *Parachlorella* RPS17 terminator (corresponding to sequences 25919-26373 of SEQ ID NO: 86).

The BleR gene was operably linked to the *Parachlorella* RPS4 promoter (SEQ ID:71) and terminated by the *Parachlorella* RPS4 terminator (SEQ ID:72). The GFP gene was operably linked to the *Parachlorella* ACP1 promoter (corresponding to sequences 7688 to 8259 of SEQ ID NO: 86) and terminated by the *Parachlorella* ACP1 terminator (corresponding to sequences 8692-9830 of SEQ ID NO: 86). The SGI1 homologous recombination (HR) up arm corresponds to sequences 1762-3578 of SEQ ID NO: 86. The SGI1 homologous recombination (HR) downstream arm corresponds to sequences 26448-28447 of SEQ ID NO: 86. The 5' lox2272 site corresponds to sequences 3831-3864 of SEQ ID NO: 86 and the 3' lox2272 corresponds to sequences 9839-9872 of SEQ ID NO: 86. All the sequences are within 2 kb homologous regions upstream and downstream of the SGI1 CRISPR target.

Upon co-transformation of the SGI1 gRNA (SEQ ID NO: 105) and selection cassette (SEQ ID NO: 86), the SGI1 gene is knocked out and a selection cassette comprising the Cas9, BleR, and GFP genes is inserted into the SGI1 site by homologous recombination. The BleR, and GFP genes are flanked by lox2272 sites, while the Cas9 and the Cre genes of the selection cassette are outside the lox2272 sites but within the portions of the SGI1 sequences that serve as homologous recombination sites.

Once the selection cassette is inserted into the SGI1 locus, the Cre gene is operably linked to an inducible nitrite reductase promoter. Thus, when the microorganism is grown in a growth media comprising nitrite, the Cre gene expression is induced. Upon the expression of the Cre gene, the Cre enzyme acts on the lox2272 sites and removes the BleR and GFP sequences that are flanked within the lox sites. This results in a system where the selectable markers (e.g., GFP, other antibiotic markers, e.g., BleR) can be reintroduced during subsequence transformation of other sequences.

Screening of Transformed *Parachlorella* Strains for Cas9 Insertion

The transformed *Parachlorella* cells were plated to single colonies on selective plates containing ammonium to repress CRE expression, patched colonies again on selective repressive plates, and screened for knockouts using PCR and GFP shifts. PCR primers used for confirming the knockout are shown below:

```
AE803:
                                        (SEQ ID NO: 87)
AGGCTACTCTCAGACATGACGGTGGCTCTG

ST815:
                                        (SEQ ID NO: 88)
GCCACAAATGAAGGTTGGCAGGGTCAGTGC
```

PCR positive reactions were sent for sequencing to confirm knockouts (insertion of the cassette) and perfect HR. Inventors of the present application surprisingly and unexpectedly found that a single copy was Cas9 gene was inserted in the SGI1 locus.

Example 8

Triple Knockout of SGI1, SGI2, and CPSRP54 Using Fully Penetrant *Parachlorella* Single Copy Cas9 Editor Line A *Parachlorella* SGI1 knockout strain STR24129 as described above was created, which has a single copy of Cas9 and Cre inserted into SGI1 locus, with markers (ble/GFP) foxed out using an SGI1 knockout guide sequence:

```
                                        (SEQ ID NO: 89)
ACACCACCTTAAGGCACATGAGG.
```

SGI1 knockout strain STR24129 was used as a transformation host for knocking out SGI2 and SRP54 genes. Host strain STR24129 was co-transformed with gRNA targeting SGI2 and SRP54 genes and Selection cassette (pSGE06866) comprising Ultramers comprising homologous recombination (HR) arms for each target (e.g., SRP54 and SGI2). The BleR gene was operably linked to the *Parachlorella* RPS4 promoter (SEQ ID:71) and terminated by the *Parachlorella* RPS4 terminator (SEQ ID:72). The GFP gene was operably linked to the *Parachlorella* ACP1 promoter and terminated by the *Parachlorella* ACP1 terminator. Selection cassette comprises ble and GFP markers surrounded by lox sites for potential marker recycling. When Cre is expressed, the lox sites recombine, looping out the DNA between these sequences.

Transformed host cells were plated on selective plates, patched colonies and single colonies were picked, and screened for knockouts using PCR. PCR positive reactions were sent for sequencing to confirm knockout (insertion of the cassette) of each target.

Figure 16:
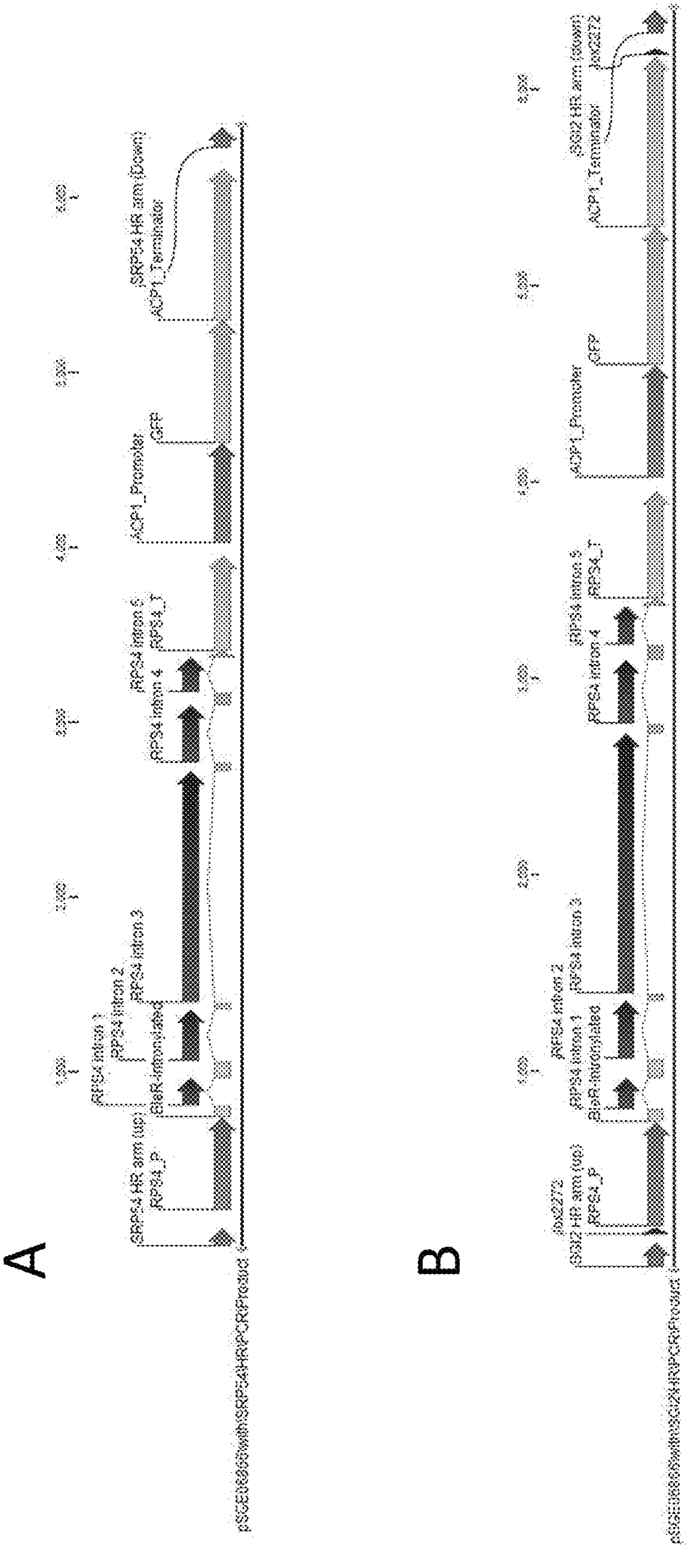
FIG. 16A shows the schematics of the selection cassette for knocking out *Parachlorella* SPR54.
FIG. 16B shows the schematics of the selection cassette for knocking out *Parachlorella* SGI2.

FIGS. 16A and 16B shows the schematics of the selection cassettes for knocking out *Parachlorella* SRP54 and *Parachlorella* SGI2. The sequences of the gRNA, Ultramers with HR arms are shown below.

```
SRP54-EMRE3EUKT592650
gRNA sequence:
                                    (SEQ ID NO: 90)
GGCGTGGGACATGGTGCGCAAGG

Ultramers with HR-arms to amplify pSGE06866:
ST938_HR_SRP54-UP
                                    (SEQ ID NO: 91)
TGAAGCACCCCCCGGCCTCTCCCCCCGCAGGGCCGCCCCTCCCGCCTCG

TCGTGC

ST939_HR_SRP54-DOWN
                                    (SEQ ID NO: 92)
CGCAACGCTCTCCCTCCCCACCCCCCAGCCTCACATCCGCCTCAAGCAG

CGCCCTG

Primer sequences:
ST949_CasPipe9GT_SRP54-fwd:
                                    (SEQ ID NO: 93)
caagctatgcgaggaagggagggtc

ST950_CasPipe9GT_SRP54-rev:
                                    (SEQ ID NO: 94)
ctgccgcaagtgagtgtgctgtc

Other Primers used for screening-located in
selection cassette:
JV946-Linker5-For:
                                    (SEQ ID NO: 95)
caccagatataggtgacccgataac

AE608 ble rev:
                                    (SEQ ID NO: 96)
AAAACTCCACTGCACCTGCAACAT

SGI2-EMRE3EUKT590485
gRNA sequence:
ST937_crRNA_064_EMRE3EUKT590485:
                                    (SEQ ID NO: 97)
TGCGGTGAAGCTTGGAGCTG

Ultramer sequences to put HR arms onto PSGE06866
ST940_HR_SGI2-UP
                                    (SEQ ID NO: 98)
TTGCCGTCGACGAGACTTCGGGGCGCGCATTTATCGACTCTCTTGAAGA

TACACCGGTT

ST941_HR_SGI2-DOWN
```

-continued

```
                                    (SEQ ID NO: 99)
TCCAATTGTAGATATCATATTGTTTCCGGACCTACCTTACGCACTGAGT

GCTGCCAGATGTTCTT

Primers sequences:
ST046CasPipe9GT-064-fwd:
                                    (SEQ ID NO: 100)
gaggtgggtggtagtgcttcgcgaggtg

ST047CasPipe9GT-064-rev:
                                    (SEQ ID NO: 101)
atcacagctcacagggcagacactgcgtc
```

Primers Sequences:

Primers JV946 and AE608 were also used as screening primers.

Example 9

Bioinformatic Analysis of the Domain Architecture of SGI2 Proteins

Domain architecture of exemplary SGI2 proteins from *Parachlorella* sp., *Oocystis* sp., *Tetraselmis* sp., *Arabidopsis thaliana* were analyzed using an online tool InterProScan (tool version 5.27, database version 66.0, from EMBL-EBI, Hinxton, Cambridgeshire, CB10 1SD, UK.)

A single conserved response receiver domain was identified in the N-terminus of the SGI2 proteins as shown in FIGS. 3-9.

Example 10

Bioinformatic Analysis of Response Receiver Domains of Various SGI2 Proteins Local alignment of *Parachlorella* response receiver domain (SEQ ID NO: 6) was performed with other orthologous proteins from other algal species and various plants using BLOSUM62 Matrix, Gap penalty of 10 and Extend penalty of 0.5. Local alignment of *Parachlorella* response receiver domain (SEQ ID NO: 6) with various photosynthetic organisms are shown below in Table 5.

TABLE 5

Results of local alignments of *Parachlorella* response receiver domain with various orthologous proteins.

| Species | SEQ ID NO: | Alignment Result |
|---|---|---|
| *Arabidopsis thaliana* | 42 | Length: 121<br>Identity: 39/121 (32.2%)<br>Similarity: 61/121 (50.4%)<br>Gaps: 9/121 (7.4%)<br>Score: 149.5 |
| *Arabidopsis thaliana* | 43 | Length: 128<br>Identity: 30/128 (23.4%)<br>Similarity: 60/128 (46.9%)<br>Gaps: 20/128 (15.6%)<br>Score: 84.5 |
| *Arabidopsis thaliana* | 44 | Length: 121<br>Identity: 37/121 (30.6%)<br>Similarity: 59/121 (48.8%)<br>Gaps: 9/121 (7.4%)<br>Score: 133.5 |
| *Arabidopsis thaliana* | 45 | Length: 121<br>Identity: 37/121 (30.6%)<br>Similarity: 60/121 (49.6%)<br>Gaps: 9/121 (7.4%)<br>Score: 136.5 |

TABLE 5-continued

Results of local alignments of *Parachlorella* response receiver domain with various orthologous proteins.

| Species | SEQ ID NO: | Alignment Result |
|---|---|---|
| *Arabidopsis thaliana* | 46 | Length: 129<br>Identity: 29/129 (22.5%)<br>Similarity: 54/129 (41.9%)<br>Gaps: 22/129 (17.1%)<br>Score: 66.0 |
| *Oocystis* sp. | 40 | Length: 120<br>Identity: 53/120 (44.2%)<br>Similarity: 77/120 (64.2%)<br>Gaps: 4/120 (3.3%)<br>Score: 242.5 |
| *Tetraselmis* sp. | 41 | Length: 125<br>Identity: 45/125 (36.0%)<br>Similarity: 69/125 (55.2%)<br>Gaps: 16/125 (12.8%)<br>Score: 167.5 |
| *Glycine max* | 47 | Length: 121<br>Identity: 36/121 (29.8%)<br>Similarity: 61/121 (50.4%)<br>Gaps: 9/121 (7.4%)<br>Score: 140.5 |
| *Vitis vinifera* | 48 | Length: 121<br>Identity: 37/121 (30.6%)<br>Similarity: 62/121 (51.2%)<br>Gaps: 9/121 (7.4%)<br>Score: 143.5 |
| *Theobroma cacao* | 49 | Length: 121<br>Identity: 38/121 (31.4%)<br>Similarity: 60/121 (49.6%)<br>Gaps: 9/121 (7.4%)<br>Score: 148.5 |
| *Oryza sativa* | 50 | Length: 121<br>Identity: 40/121 (33.1%)<br>Similarity: 64/121 (52.9%)<br>Gaps: 9/121 (7.4%)<br>Score: 169.5 |
| *Zea mays* | 51 | Length: 121<br>Identity: 41/121 (33.9%)<br>Similarity: 61/121 (50.4%)<br>Gaps: 9/121 (7.4%)<br>Score: 153.5 |
| *Physcomitrella patens* | 52 | Length: 121<br>Identity: 39/121 (32.2%)<br>Similarity: 64/121 (52.9%)<br>Gaps: 9/121 (7.4%)<br>Score: 164.5 |
| *Volvox carteri* | 53 | Length: 123<br>Identity: 39/123 (31.7%)<br>Similarity: 63/123 (51.2%)<br>Gaps: 14/123 (11.4%)<br>Score: 143.0 |
| *Chlamydomonas reinhardtii* | 54 | Length: 125<br>Identity: 35/125 (28.0%)<br>Similarity: 61/125 (48.8%)<br>Gaps: 12/125 (9.6%)<br>Score: 135.5 |
| *Chlorella zofingiensis* | 55 | Length: 121<br>Identity: 38/121 (31.4%)<br>Similarity: 60/121 (49.6%)<br>Gaps: 11/121(9.1%)<br>Score: 138.0 |
| *Coccomyxa subellipsoidea* C-169 | 56 | Length: 120<br>Identity: 57/120 (47.5%)<br>Similarity: 79/120 (65.8%)<br>Gaps: 1/120 (0.8%)<br>Score: 256.0 |

The response receiver domain of *Parachlorella* sp. showed higher percent of identity with other algal species and a high degree of similarity with various plant species.

Example 11

Screens for Low Chlorophyll *Parachlorella* sp. Strain Wt-1185 Mutants

Following knockout of SGI1, SGI2, double knockout of SGI1 and cpSRP54, or double knockout of SGI2 and cpSRP54 of *Parachlorella* sp. genes, as described above, cells from pale-colored colonies were selected and allowed to grow from between one and five days in low (100 μmol photons $m^{-2}$ $sec^{-1}$) light, after which they were sorted by flow cytometry using a BD FACSAria II flow cytometer (BD Biosciences, San Jose, Calif.) to select cells having low chlorophyll fluorescence. In general, the portion of cells with the lowest approximately 0.5 to 2% of chlorophyll fluorescence compared to the total population of cells was selected. Further primary screening of antenna-reduced lines isolated through flow cytometry was conducted through the selection of pale green or yellow colonies visually after sorted cells were plated. In order to screen putative antenna-reduced lines from other reduced pigment mutants and false positives, selected colonies were subjected to a medium-throughput secondary cultivation screen to acclimate the isolates to low light conditions prior to photo-physiological measurements. Chlorophyll fluorescence was monitored during low light acclimation to select clones that retained the reduced chlorophyll fluorescence characteristic of the high light acclimated state. Clones that were selected demonstrated only small increases in chlorophyll (relative to wild-type cells) when transferred from high to low light.

Semicontinuous culture assays in constant high light (approximately 1,700 μmol photons $m^{-2}$ $sec^{-1}$) using 165 ml cultures in 75 $cm^2$ tissue culture flasks were performed to identify strains having increased productivity (increased rate of biomass production, measured as Total Organic Carbon (TOC) accumulation) with respect to the wild-type progenitor strain WT-1185. Two 75 $cm^2$ flasks were inoculated with seed culture of a given mutant strain. The flasks had stoppers having tubing connected with syringe filters for delivering $CO_2$-enriched air (1% $CO_2$) that was bubbled through the cultures. The flasks were aligned with the width (narrowest dimension) against an LED light bank. The depth of the cultures (the distance from the wall of the flask nearest the light source to the wall at the back of the flask) was approximately 8.0 cm. The cultures were diluted daily at the beginning of the light period by removing 65% of the culture volume and replacing it with fresh PM119 media diluted to adjust for the increase in salinity due to evaporation occurring in the cultures (212 ml di $H_2O$ to 1 L PM119 medium). Samples for TOC analysis were taken from the culture removed for the dilution.

Example 12

Semi-Continuous Productivity Assays of *Parachlorella* sp. Mutants

Among the *Parachlorella* strains that were found to have reduced chlorophyll under low light conditions were analyzed for increased productivity. In the productivity assay, photoautotrophic cultures of the mutants were grown over several days in constant light semi-continuous mode (CL-SCPA) with culture samples removed daily for biomass determination. The light was kept at a constant 1900-2000 μmol photons $m^{-2}$ $sec^{-1}$ for 24 hours per day. In this assay PM119 culture medium in a 225 $cm^2$ flask was inoculated with seed culture of a given mutant strain. Three cultures were initiated per strain. The flasks included stir bars and had stoppers having tubing connected with syringe filters for delivering $CO_2$ enriched air (1% $CO_2$) that was bubbled through the cultures. The flasks were aligned with the width (narrowest dimension) against an LED light bank. The "depth" dimension of the flasks, extending back from the light source, was 13.7 cm. Taking into account the positioning of the flasks the farthest distance of the cells in the flasks from the surface of the light source was approximately 15.5 cm. The cultures were diluted daily by removing 65% of the culture volume and replacing it with fresh PM119 culture medium diluted to adjust for the increase in salinity due to evaporation occurring in the cultures. Samples for TOC analysis were taken from the culture removed for the dilution. The semi-continuous productivity assay was run for 12 days once the cultures had reached steady state.

Productivity for the assay was assessed by measuring total organic carbon (TOC) from the samples that were removed daily. Total organic carbon (TOC) was determined by diluting 2 mL of cell culture to a total volume of 20 mL with DI water. Three injections per measurement were injected into a Shimadzu TOC-Vcsj Analyzer for determination of Total Carbon (TC) and Total Inorganic Carbon (TIC). The combustion furnace was set to 720° C., and TOC was determined by subtracting TIC from TC. The 4 point calibration range was from 2 ppm to 200 ppm corresponding to 20-2000 ppm for non-diluted cultures with a correlation coefficient of r2>0.999.

A number of embodiments of the invention have been described. Nevertheless, it will be understood that elements of the embodiments described herein can be combined to make additional embodiments and various modifications may be made without departing from the spirit and scope of the invention. Accordingly, other embodiments, alternatives and equivalents are within the scope of the invention as described and claimed herein.

Example 13

Semi-Continuous Urea Batch Assay of *Parachlorella* sp. Mutants

In the SCUBA (Semi-Continuous Urea Batch Assay), photoautotrophic cultures of the mutants were grown over several days in diel light nitrogen replete semi-continuous mode followed by a nitrogen deplete batch mode. The light was programmed to mimic an average May 4th day in the Imperial Valley, Ca ranging from darkness to 2000 μmol photons $m^{-2}$ $sec^{-1}$ at noon. Samples were taken at "dusk" each day. In this assay 420 ml of urea based PM153 culture medium in a 500 ml square flask was inoculated with seed culture of a given mutant strain.

The PM152 is a nutrient deplete medium that is based on PM074 but includes urea instead of nitrate as the nitrogen source. It is made by adding 1.3 ml PROLINE® F/2 Algae Feed Part A (Aquatic Eco-Systems) and 1.3 ml 'Solution C' to a final volume of 1 liter of a solution of Instant Ocean salts (17.5 g/L) (Aquatic Eco Systems, Apopka, Fla.). Solution C is 38.75 g/L NaH2PO4 H2O, 758 mg/L Thiamine HCl, 3.88 mg/L vitamin B12, and 3.84 mg/L biotin.

Three cultures were initiated per strain. The flasks included stir bars and had stoppers having tubing connected with syringe filters for delivering $CO_2$ enriched air (1% $CO_2$) that was bubbled through the cultures. The flasks were aligned with an aperture towards the light of 0.0875 $m^2$ and "depth" dimension of the flasks, extending back from the light source, was 8 cm. For semi-continuous biomass determination the cultures were diluted daily by removing 40% of the culture volume and replacing it with fresh PM153 culture medium diluted to adjust for the increase in salinity due to evaporation occurring in the cultures. Samples for TOC analysis were taken from the culture removed for the dilution. The semi-continuous productivity assay was run until the cultures had reached steady state. Following semi-continuous, cultures were removed from the assay, pelleted in using centrifugation and resuspended in 420 ml of nitrogen deplete PM152 media. Cultures were grown in batch for 4-5 days using the same growth conditions as the semi-continuous mode. During the batch mode, FAME samples were taken to determine lipid productivity and TOC samples were taken to determine FAME/TOC.

Example 14

Chlorophyll Content, Antenna Size, and Photophysiology of *Parachlorella* Knockout Mutants of SGI1, SGI2 Genes, Double Knockout of SGI1 and SRP54 and SGI2 and SRP54 Genes Chlorophyll content of the high productivity mutants was determined by extracting cells with methanol and analyzing the supernatant by spectrophotometry. Briefly, 500 μl aliquots of culture were pipetted into 2.0 ml twist top tubes and pelleted using a table top microcentrifuge at 15,000 rpm for 10 minutes. The supernatants were aspirated from the pellets, and each pellet was resuspended in 1.5 ml 99.8% methanol (previously neutralized with magnesium carbonate). 0.2 ml of glass beads (0.1 mm diameter) were added to each vial and bead beat for 3 min 1.0 ml of supernatant was transferred to new 1.7 ml flip-top tubes and were centrifuged in a table top microcentrifuge at 15,000 rpm for 10 minutes. The resulting pellets were white indicating that a complete extraction had been performed. 0.8 ml of each supernatant was pipetted into an optical glass cuvette and absorption wavelengths were read immediately at 720 nm, 665 nm and 652 nm wavelengths. Spectrophotometric measurements were carried out in a dual-beam mode using a 99.8% methanol blank. The following equations were used to calculate the concentration of chlorophyll: Chlorophyll a [g $m^{-3}$]=16.72 (A665-A720)+9.16 (A652-A720) and Chlorophyll b [g $m^{-3}$]=34.09 (A652-A720)−15.28(A665-A720). The amount of chlorophylls a and b were standardized on a per cell and per TOC basis. While the amount of total chlorophyll per cell varied somewhat among the SGI1-2261 mutants, it was universally decreased with respect to wild-type cells by an amount ranging from about 30% to about 65%, consistent with the observed reduction in antenna size. On a per TOC basis, the reduction in total chlorophyll in SGI1 mutants with respect to wild-type cells ranged from about 30% to about 50%.

In addition to chlorophyll content, SGI1 and SGI2 knockout mutants and the double knockout of SGI1 and SRP54 and SGI2 and SRP54 were analyzed for functional absorption cross-section of PSII, functional absorption cross-section of PSI, $1/\tau'_{Qa}$ (the light saturated rate of electron transport on the acceptor side of photosystem II at light saturation, a measure of the efficiency of linear photosynthetic electron transport) as well as maximal rate of carbon fixation, Pmax. Cells of the wild-type and mutant strains were cultured in the constant light semicontinuous culture assay (CL-SCPA) described above.

Analysis of various photosynthetic parameters was performed using the Fluorescence Induction and Relaxation (FIRe) technique developed to measure a comprehensive series of photosynthetic and physiological characteristics of photosynthetic organisms (Gorbunov and Falkowski (2005) "Fluorescence Induction and Relaxation (FIRe) Technique and Instrumentation for Monitoring Photosynthetic Processes and Primary Production in Aquatic Ecosystems" in: Photosynthesis: Fundamental Aspects to Global Perspectives, Proc. 13th International Congress of Photosynthesis, Montreal, Aug. 29-Sep. 3, 2004. (Eds: A. van der Est and D. Bruce), Allen Press, V.2, pp. 1029-1031). The FIRe technique relies on measurement and analysis of chlorophyll "variable fluorescence" profiles (reviewed by Falkowski et. al., 2004 "Development and Application of Variable Chlorophyll Fluorescence Techniques in Marine Ecosystems" in: Chlorophyll a Fluorescence: A Signature of Photosynthesis (C. Papageorgiou and Govingjee, eds), Springer, pp. 757-778) which depend on the relationship between chlorophyll fluorescence and the efficiency of photosynthetic processes. This technique provides a set of parameters that characterize photosynthetic light-harvesting processes, the photochemistry in Photosystem II (PSII), and photosynthetic electron transport down to carbon fixation. The measurements performed herein used a mini-FIRe device produced by Maxim Gorbunov of Rutgers University, East Brunswick, N.J. A commercially available FIRe device is available from Sea-Bird Scientific (Halifax, Canada, satlantic.com and planet-ocean.co.uk). Further information regarding the use of the FIRe device is available in company manuals. All measurements were taken using constant light (2000 μmol photons·$m^{-2}$·$sec^{-1}$) semicontinuous cultures (CL-SCPA) cultures (see Example 3). To obtain FV/FM and σPSII measurements of Fluorescence Induction and Relaxation (FIRe) kinetics were performed in the dark. The values for $F_V/F_M$ and $\sigma_{PSII}$ presented in Table 6 were calculated as an average of 6 measurements (3 measurements of each of the 2 biological replicates), errors for these parameters did not exceed 5%.

Measurements of PSI cross-section were performed using a modified JTS-10 spectrometer with a filter set to measure the electrochromic shift (ECS) at 520 nm equipped with a custom-built single turnover flasher (STF). The peak power density in the sample chamber was high enough to ensure full closure of reaction centers within approximately 10 μs. The resulting excitation rate was ~1 to 3 hits per reaction center per 10 μs (depending on the functional absorption cross-section of the photosystem). The STF generated short ultra-bright pulses of blue light (455 nm, with 30 nm half bandwidth), and the pulse timing was controlled by the trigger from the JTS-10 Spectrometer. The pulse duration was controlled by the STF Pulse Control Box and was adjustable in the range from 1 μs to 50 μs using the potentiometer on the front panel. To measure the PSI cross-section, we diluted cultures to an OD of about 0.2 at the chlorophyll maximum (~440 nm) based on measurement of absorption spectra of cell suspension using a Perkin Elmer Lambda 650 spectrophotometer equipped with an integrating sphere. The ECS was measured using 10 μs flashes with intensities ranging from 4000 to 120,000 μmol photons m−2 s−1 in the presence of DCMU and hydroxylamine. The experimental curve was fitted with a simple exponential function $$ECS=ECS_M\times(1-e^{It\times\sigma PSI})$$

where $ECS_M ECS_M$ is the maximal ECS signal; ItIt is photon density in photons/m2; and $\sigma_{PSI}\sigma_{PSI}$ is a functional cross-section of PSI. Obtained values for a functional cross-section of PSI for the wild type of *Parachlorella* (WT-1185) was $(4.0\pm0.5)\times10^{-18}(4.0\pm0.5)\times10^{-18}$ $m^2$. These values are close to those obtained for the functional cross-section of PSII grown under the same conditions ($\sigma_{PSII}$=$(4.3\pm0.1)\times10^{-18}\sigma_{PSII}$=$(4.3\pm0.1)\times10^{-18}$ m2). Errors for these parameters were estimated not to exceed 20%.

Carbon fixation rates ($C^{14}$ Pmax) were measured using cultures normalized to 5 μg chl ml-1 in media containing 0.5 g l-1 (5.95 mM) sodium bicarbonate. 20.4 μCi ml-1 C14 labeled sodium bicarbonate was added to each culture and exposed to 2500 μE for a duration of 10 minutes. Samples were immediately acidified with 2N HCl and allowed to off-gas overnight. The following day samples were measured using a Beckman LS6500 scintillation counter and quantified.

$\tau'_{Qa}$ (the time of electron transport on the acceptor side of PSII measured under saturating light conditions—effectively determined by the slowest step of linear photosynthetic electron transport) was measured from FIRe light curves and dark induced relaxation kinetics (DIRK) profiles. Volumetric PSII concentration relative to wild-type was estimated as ($Fv/\sigma_{530PSII}$). Errors for these parameters were estimated not to exceed 15%. Optical absorption cross section (averaged over emission spectrum of a light source) was estimated using the following equation:

$$a_{chl/TOC} = \frac{1}{[Chl/TOC]}\int_{400}^{700} \ln(10)\times\frac{OD(\lambda)}{\Delta l}\times\frac{I(\lambda)}{\int_{400}^{700} I(\lambda)d\lambda}d\lambda$$

where [Chl/TOC] is the chlorophyll/TOC of the sample, OD(λ)OD(λ) is the measured optical density of the sample at a wavelength λλ, ΔlΔl is the measuring beam pathlength in the cuvette (1 cm), I(λ)I(λ) is the intensity of the light source used to grow algae at the wavelength λλ.

TABLE 6

Fluorescent and Photosynthetic Parameters Measured with the FIReTechnique

| FIRe, JTS-10 retrieved parameters | Description |
|---|---|
| $F_V/F_M$ | Maximum quantum yield of photochemistry in PSII, measured in a dark- adapted state (dimensionless). This parameter characterizes the efficiency of primary photosynthetic reactions. |
| $\sigma_{PSII}$ | Functional absorption cross section of PSII ($Å^2$) in a dark-adapted state. The parameter is the product of the optical absorption cross section of PSII (i.e., the physical size of the PSII unit) and the quantum yield of photochemistry in PSII. Could be measured using different excitation wavelengths, e.g., 450 nm, 530 nm, or 590 nm |
| $\sigma_{PSI}$ | Functional absorption cross section of PSI ($Å^2$) in a dark-adapted state. The parameter is the product of the optical absorption cross section of PSII (i.e., the physical size of the PSI unit) and the quantum yield of photochemistry in PSI. |
| $1/\tau'_{Qa}$ | Light saturated rate of electron transport on the acceptor side of photosystem II. This parameter indicates the efficiency of linear photosynthetic electron transport |

The photophysiological data, the chlorophyll content and the productivity data of the wild-type *Parachlorella* strain WT-1185, single knockout of SRP54 and SGI2 genes, and the double knockout of SGI2 and SRP54 genes in *Parachlorella* are summarized were evaluated. All measurements were taken using CL-SCPA cultures. To obtain FV/FM and PSII measurements of Fluorescence Induction and Relaxation (FIRe) kinetics were performed in the dark. Presented values for Fv/Fm and σPSII were calculated as an average of 6 measurements (3 measurements of each of the 2 biological replicates)—errors for these parameters did not exceed 5%. τ'Qa (time of electron transport on the acceptor side of PSII measured under saturating light conditions—effectively determined by the slowest step of linear photosynthetic electron transport) were measured from FIRe light curves and DIRK profile. Measurements of PSI cross-section were performed as described above. The results are summarized below in Table 7.

TABLE 7

Photophysiology, Chlorophyll, and Productivity Data

| Strain | FIRe $F_V/F_M$ | FIRe $\sigma_{PSII}$ ($Å^2$, 530 nm) | FIRe $\tau'_{Qa}$ (ms) | FIRe [PSII]/TOC (relative) | Chlorophyll (Chl/TOC) | Chlorophyll Chl b:a | $^{14}C$ $P_{max}$ nmol $^{14}C$/μg TOC/h | Productivity g $m^{-2}day^{-1}$ |
|---|---|---|---|---|---|---|---|---|
| WT-1185 | 0.62 | 152 | 12.7 | 20 | 6.8% | 0.35 | 9.4 | 31.4 |
| SGI2/SRP54 | 0.67 | 76 | 5.9 | 14 | 3.3% | 0.21 | 11.9 | 41.4 |
| SRP54 | 0.65 | 91 | 7.0 | 8 | 3.7% | 0.24 | 10.5 | 36.6 |
| SGI2 | 0.64 | 120 | 7.0 | 8 | 5.0% | 0.31 | 11.4 | 36.7 |

Figure 11:
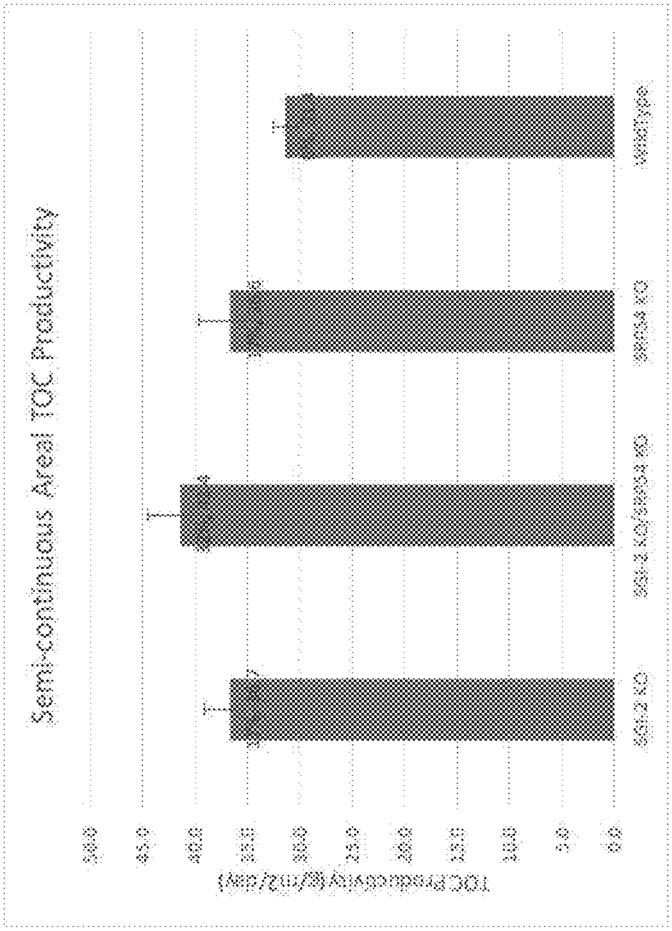
FIG. 11 shows the results of the productivity assay for *Parachorella* wild-type strain, SRP54 knockout strain, SGI2 knockout strain, and the double knockout strain of SGI2 and SRP54.

There is a substantial decrease in the functional absorption cross-section of PSII (50%) and some decrease in the number of functional PSII complexes. The cells have improved carbon fixation capacity (26% increase in Pmax). Single knockout of SGI2 or SRP54 showed at least 17% increase TOC productivity as compared to wildtype strain. Overall, the double SGI2/SRP54 knockout strain showed a 32% improvement in TOC productivity (both times the double SGI2/SRP54 knockout strain was run on the CL-SCPA assay it showed productivities>40 $g/m^2$/day), among the highest increases in productivity observed for *Parachlorella* and higher than the average improvements of the single knockout of either SRP54 or SGI2 as shown in FIG. 11. The results demonstrate that there appears to be a synergistic effect on productivity when both SGI2 and SRP54 genes are knocked out.

The photophysiological data, of the wild-type *Parachlorella* strain WT-1185, single knockout of SRP54 and SGI1 genes, and three strain with the double knockout of SGI1 and SRP54 genes in *Parachlorella* were evaluated. All measurements were taken using CL-SCPA cultures. To obtain FV/FM and σPSII measurements of Fluorescence Induction and Relaxation (FIRe) kinetics were performed in the dark. Presented values for $F_V/F_M$ and $\sigma_{PSII}$ were calculated as an average of 6 measurements (3 measurements of each of the 2 biological replicates)—errors for these parameters did not exceed 5%. $\tau'_{Qa}$ (time of electron transport on the acceptor side of PSII measured under saturating light conditions—effectively determined by the slowest step of linear photosynthetic electron transport) were measured from FIRe light curves and DIRK profiles. The results are summarized in Table 8 below.

TABLE 8

Photophysiology of *Parachlorella* strains

| Strain | FIRe $F_V/F_M$ | FIRe $\sigma_{PSII}$ ($A^2$, 530 nm) | FIRe $\tau'_{Qa}$ (ms) | FIRe [PSII]/TOC (relative) |
|---|---|---|---|---|
| STR24538 (SRP54/SGI1 KO) | 0.707 | 64 | 4.5 | 19.3 |
| STR24540 (SRP54/SGI1 KO) | 0.699 | 61 | 4.6 | 18.6 |
| STR24541 (SRP54/SGI1 KO) | 0.694 | 61 | 4.7 | 19.4 |
| GE-17407 (SRP54 KO) | 0.646 | 85 | 5.5 | 16.4 |
| STR24183 (SGI1 KO) | 0.637 | 102 | 6.2 | 18.2 |

There is a substantial decrease in the functional cross-section of PSII of the SGI1/SRP54 double knockout strain as compared to single SGI1 or SRP54 genes knockouts, as well as a decrease in light saturated rate of electron transport, indicating improved rates of photosynthesis. There is also some increase in the number of functional PSII complexes. There is an improved maximum quantum yield of photochemistry in photosystem II ($F_V/F_M$) in the double knockout strain as compared to single knock of SRP54 or SGI1 alone.

Example 15

Microproximate Analysis of SGI1/SGI2, SGI1/SRP54, and SGI1/SGI2/SRP54 Knockout Mutants To determine the overall biomass composition of the SGI1/SGI2, SGI1/SRP54, and SGI1/SGI2/SRP54 knockout mutants, quantitative analysis of samples from cultures grown in semicontinuous mode with 40% daily dilution was performed to determine the total organic carbon (TOC) and lipid content of the cells in semi-continuous culture. After the cultures reached steady state, aliquots of the culture removed for daily dilution was used for analysis of lipid, protein, and carbohydrate. Total organic carbon (TOC) of the algal culture samples was determined by diluting 2 mL of cell culture to a total volume of 20 mL with DI water.

Three injections per measurement were injected into a Shimadzu TOC-Vcsj Analyzer for determination of Total Carbon (TC) and Total Inorganic Carbon (TIC). The combustion furnace was set to 720° C., and TOC was determined by subtracting TIC from TC. The 4 point calibration range was from 2 ppm to 200 ppm corresponding to 20-2000 ppm for non-diluted cultures with a correlation coefficient of r2>0.999.

To determine lipid content, FAME analysis was performed on 2 mL samples that were dried using a GeneVac HT-4X. To the dried pellets the following was added: 500 μL of 500 mM KOH in methanol, 200 μL of tetrahydrofuran containing 0.05% butylated hydroxyl toluene, 40 μL of a 2 mg/ml C11:0 free fatty acid/C13:0 triglyceride/C23:0 fatty acid methyl ester internal standard mix and 500 μL of glass beads (425-600 μm diameter). The vials were capped with open top PTFE septa-lined caps and placed in an SPEX GenoGrinder at 1.65 krpm for 7.5 minutes. The samples were then heated at 80° C. for five minutes and allowed to cool. For derivatization, 500 μL of 10% boron trifluoride in methanol was added to the samples prior to heating at 80° C. for 30 minutes. The tubes were allowed to cool prior to adding 2 mL of heptane and 500 μL of 5 M NaCl. The samples were then vortexed for five minutes at 2 krpm and finally centrifuged for three minutes at 1 krpm. The heptane layer was sampled using a Gerstel MPS Autosampler. Quantitation used the 80 μg of C23:0 FAME internal standard.

Figure 12:
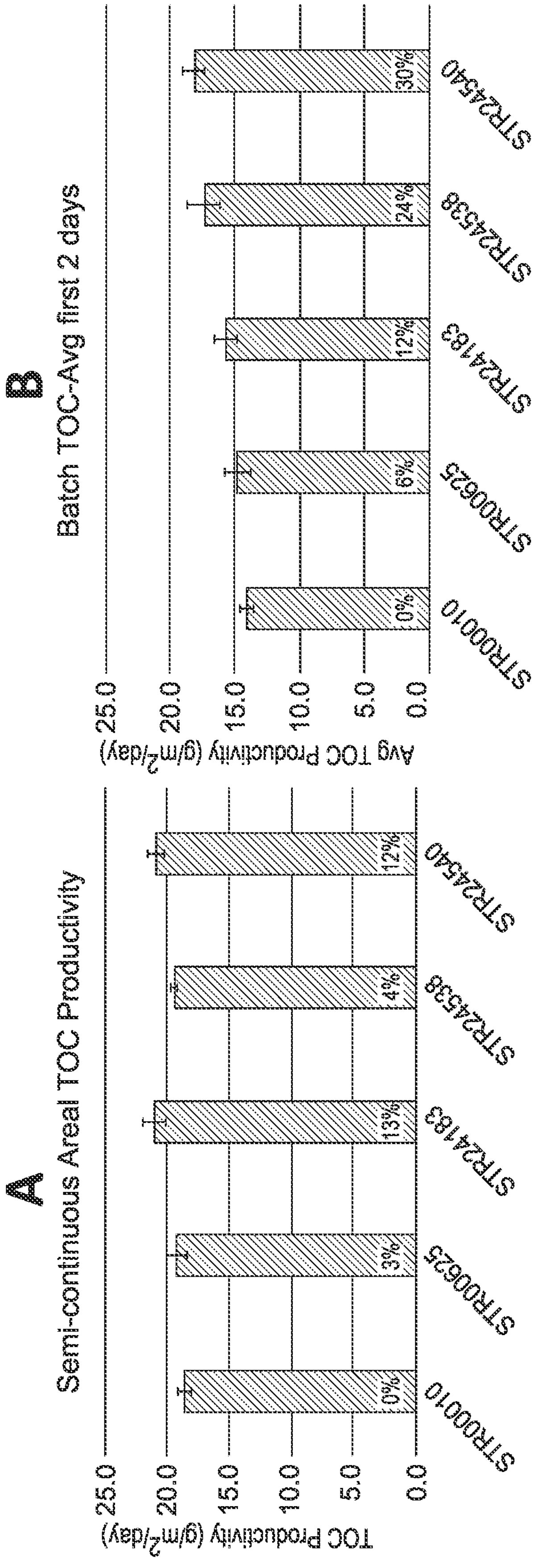
FIG. 12A shows the results of the Semi continuous areal TOC productivity assay for *Parachorella* wild-type strain (STR00010), SRP54 knockout mutant (STR00625), SGI1 knockout mutant (STR24183), SGI1/SRP54 double knockout mutants (STR24538 and STR24550).
FIG. 12B shows the results of the batch TOC productivity assay for *Parachorella* wild-type strain (STR00010), SRP54 knockout mutant (STR00625), SGI1 knockout mutant (STR24183), SGI1/SRP54 double knockout mutants (STR24538 and STR24550).

The results of the assays indicating semi-continuous areal TOC productivity and batch TOC for the *Parachorella* wild-type strain (STR00010), SRP54 knockout mutant (STR00625), SGI1 knockout mutant (STR24183), SGI1/SRP54 double knockout mutants (STR24538 and STR24540) are shown in FIGS. 12A and 12B, respectively. SRP54 knockout mutant, SGI1 knockout mutant, SGI1/SRP54 double knockout mutants showed increased TOC productivity over the *Parachorella* wild-type strain.

Figure 13:
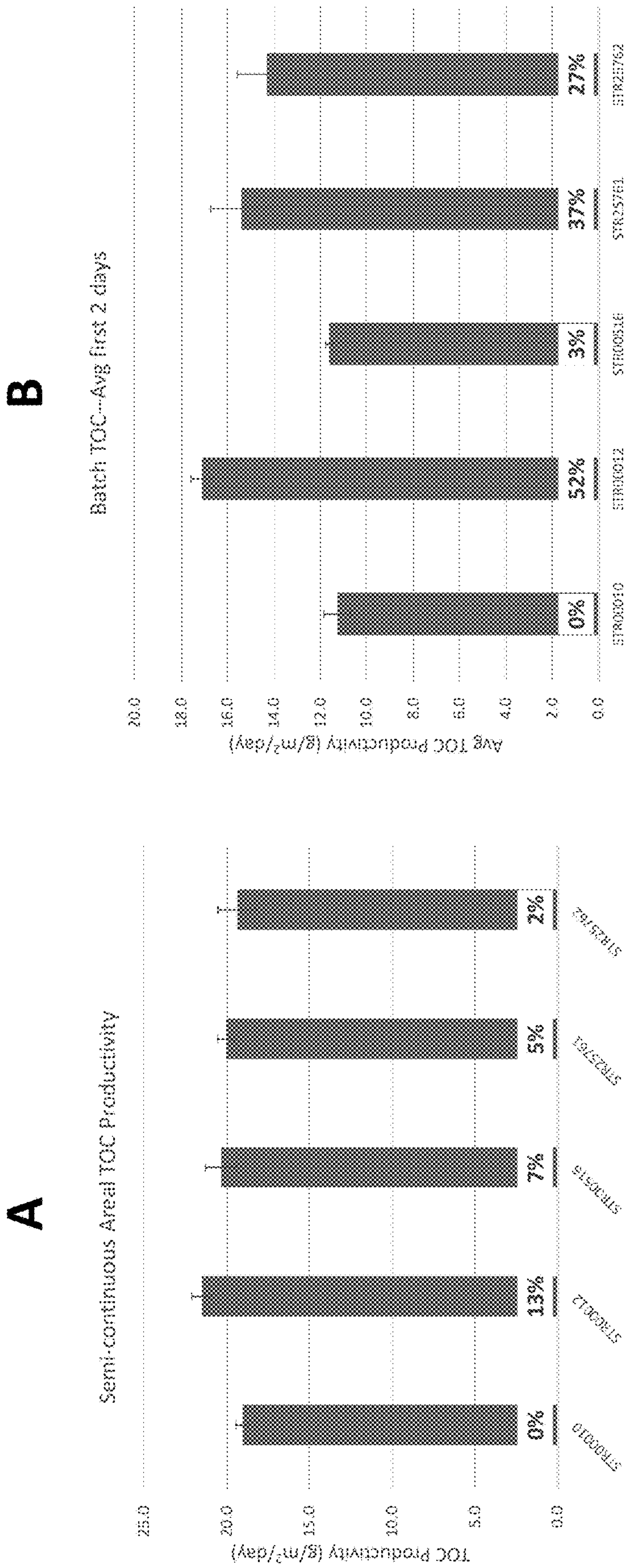
FIG. 13A shows the results of the assays indicating semi-continuous areal TOC productivity for the *Parachorella* wild-type strain (STR00010), SRP54 knockout mutant (STR00625), SGI1 knockout mutant (STR00012), SGI2/SRP54 double knockout mutant (STR25761), and SGI1/SGI2/SRP54 triple knockout mutants (STR25761 and STR25762).
FIG. 13B shows the results of the assays indicating batch TOC productivity for the *Parachorella* wild-type strain (STR00010), SRP54 knockout mutant (STR00625), SGI1 knockout mutant (STR00012), SGI2/SRP54 double knockout mutant (STR25761), and SGI1/SGI2/SRP54 triple knockout mutants (STR25761 and STR25762).

The results of the assays indicating semi-continuous areal TOC productivity and batch TOC for the *Parachorella* wild-type strain (STR00010), SRP54 knockout mutant (STR00625), SGI1 knockout mutant (STR00012), SGI2/SRP54 double knockout mutant (STR00516), and SGI1/SGI2/SRP54 triple knockout mutants (STR25761 and STR25762) are shown in FIGS. 13A and 13B, respectively. SGI1 knockout mutant, SGI2/SRP54 double knockout mutant and SGI1/SGI2/SRP54 triple knockout mutants showed increased TOC productivity over the *Parachorella* wild-type strain.

Figure 14:
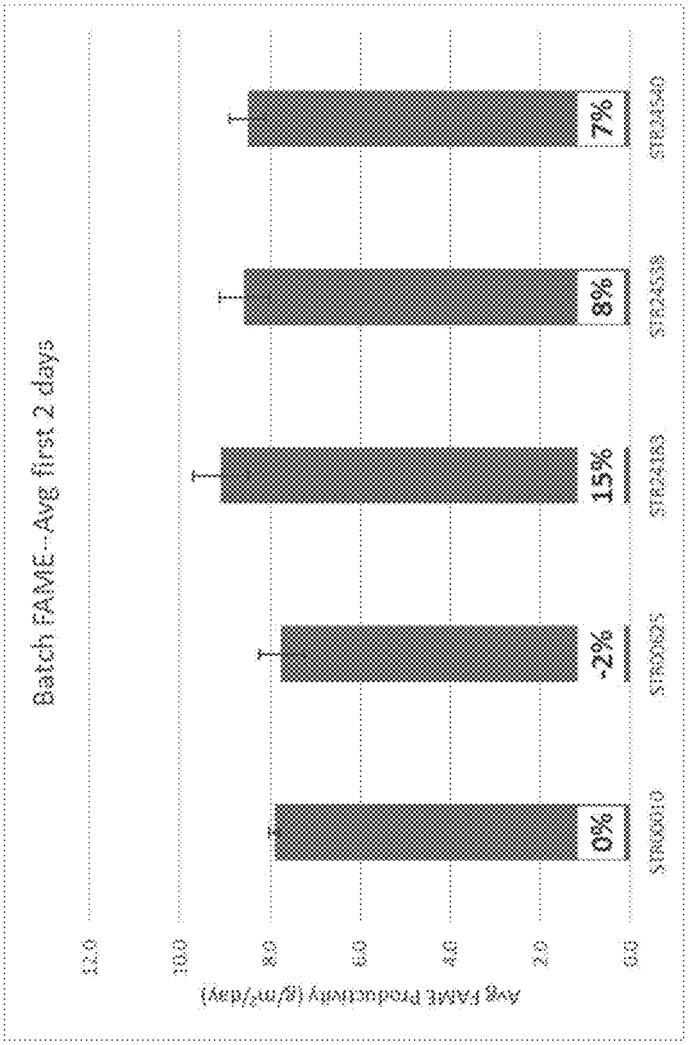
FIG. 14 shows the results of the batch FAME productivity assay for *Parachorella* wild-type strain (STR00010), SRP54 knockout mutant (STR00625), SGI1 knockout mutant (STR24183), SGI1/SRP54 double knockout mutants (STR24538 and STR24540).

The results of the batch FAME productivity assay for *Parachorella* wild-type strain (STR00010), SRP54 knockout mutant (STR00625), SGI1 knockout mutant (STR24183), SGI1/SRP54 double knockout mutants (STR24538 and STR24540) are shown in FIG. 14. SGI1 knockout mutant and SGI/SRP54 knockout mutants showed increased FAME productivity over the *Parachorella* wild-type strain.

Figure 15:
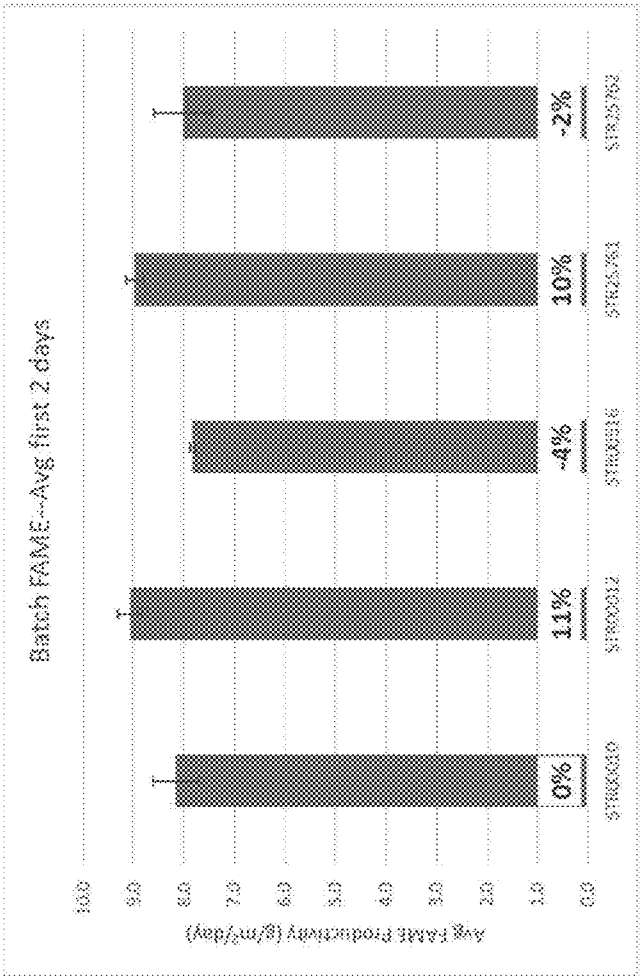
FIG. 15 shows the results of the batch FAME productivity assay for *Parachorella* wild-type strain (STR00010), SGI1 knockout mutant (STR00012), SGI2/SRP54 double knockout mutant (STR00516), and SGI1/SGI2/SRP54 triple knockout mutants (STR25761 and STR25762).

The results of the batch FAME productivity assay for *Parachorella* wild-type strain (STR00010), SGI1 knockout mutant (STR00012), SGI2/SRP54 double knockout mutant (STR00516), and SGI1/SGI2/SRP54 triple knockout mutants (STR25761 and STR25762) are shown in FIG. 15.

Headings within the application are solely for the convenience of the reader, and do not limit in any way the scope of the invention or its embodiments.

All publications and patent applications mentioned in this specification are herein incorporated by reference to the same extent as if each individual publication or patent application was specifically and individually indicated to be incorporated by reference.

We claim:

1. A mutant Chlorophyte alga comprising a complete knockout of a gene encoding a chloroplastic signal recognition protein 54 (cpSRP54) having at least 90% sequence identity to SEQ ID NO: 68, and a complete knockout of a gene encoding a significant growth improvement gene 2 (SGI2) polypeptide having at least 90% sequence identity to SEQ ID NO: 5.

2. A mutant Chlorophyte alga comprising a complete knockout of a gene encoding a significant growth improvement gene 2 (SGI2) having at least 90% sequence identity to SEQ ID NO: 5.

3. The mutant Chlorophyte alga of claim 1, further comprising a complete knockout of a gene encoding a significant growth improvement gene 1 (SGI1) gene having at least 90% sequence identity to SEQ ID NO: 3.

4. The mutant Chlorophyte alga according to claim 1, wherein the mutant comprises a complete knockout of a gene encoding a chloroplastic signal recognition protein 54 (cpSRP54) having at least 95% sequence identity to SEQ ID NO: 68, and exhibits a reduction in chlorophyll under low light conditions of at least 30% and a higher maximum quantum yield of photochemistry in photosystem II (Fv/FM) at all physiologically relevant irradiances above 100 μE m−2s−1 with respect to a control photosynthetic organism of the same species.

5. The mutant Chlorophyte alga according to claim 4, wherein the mutant comprises a complete knockout of a gene encoding a chloroplastic signal recognition protein 54 (cpSRP54) having at least 95% sequence identity to SEQ ID NO: 68, and exhibits a reduction in chlorophyll of at least 30% reduction with respect to a control photosynthetic organism of the same species.

6. The mutant Chlorophyte alga of claim 1, wherein the mutant comprises a complete knockout of a gene encoding a chloroplastic signal recognition protein 54 (cpSRP54) having at least 95% sequence identity to SEQ ID NO: 68, and exhibits lower nonphotochemical quenching (NPQ) at all physiologically relevant irradiances above 100 μE m−2 s−1 with respect to a control photosynthetic organism of the same species.

7. The mutant Chlorophyte alga of claim 1, wherein the mutant comprises a complete knockout of a gene encoding a chloroplastic signal recognition protein 54 (cpSRP54) having at least 95% sequence identity to SEQ ID NO: 68, and demonstrates a higher rate of carbon fixation on a per chlorophyll basis than does a control photosynthetic organism of the same species.

8. The mutant Chlorophyte alga according to claim 7, wherein the mutant comprises a complete knockout of a gene encoding a chloroplastic signal recognition protein 54 (cpSRP54) having at least 95% sequence identity to SEQ ID NO: 68, and has a rate of carbon fixation at least 50% higher than a control photosynthetic organism of the same species.

9. The mutant Chlorophyte alga according of claim 1, wherein the mutant comprises a complete knockout of a gene encoding a chloroplastic signal recognition protein 54 (cpSRP54) having at least 95% sequence identity to SEQ ID NO: 68, and has a rate of oxygen evolution is at least 100% higher than a control photosynthetic organism of the same species.

10. The mutant Chlorophyte alga of claims 1, wherein the mutant comprises a complete knockout of a gene encoding a chloroplastic signal recognition protein 54 (cpSRP54) having at least 95% sequence identity to SEQ ID NO: 68, and demonstrates greater biomass productivity than does a culture of a control photosynthetic organism of the same species.

11. The mutant Chlorophyte alga according to claim 10, wherein the mutant demonstrates greater biomass productivity in photoautotrophic culture.

12. The mutant Chlorophyte alga according to claim 11, wherein the mutant demonstrates greater biomass activity under continuous light conditions.

13. The mutant Chlorophyte alga according to claim 11, wherein the mutant demonstrates greater biomass activity under diel cycle conditions.

14. The mutant Chlorophyte alga of claim 1, wherein the mutant algae belongs to a genus selected from the group consisting of *Oocystis, Parachlorella, Picochlorum* and *Tetraselmis.*

15. A biomass comprising a mutant Chlorophyte alga of claim 1.

16. A method of producing a biological product, comprising culturing mutant Chlorophyte alga of claim 1 and isolating at least one product from the culture.

17. The method according to claim 16, wherein the biological product is a lipid.

18. The method according to claim 17, wherein the mutant Chlorophyte alga is engineered to include at least one exogenous gene encoding a polypeptide that participates in the production of a lipid.

19. The method according to claim 16, wherein the mutant Chlorophyte alga is cultured phototrophically.

20. The mutant Chlorophyte alga of claim 2 wherein the mutant comprises a complete knockout of a gene encoding a significant growth improvement gene 2 (SGI2) having at least 95% sequence identity to SEQ ID NO: 5, and has increased maximum quantum yield of photochemistry in photosystem II ($F_V/F_M$) compared to a control photosynthetic organism of the same species.

21. The mutant Chlorophyte alga of claim 2 wherein the mutant comprises a complete knockout of a gene encoding a significant growth improvement gene 2 (SGI2) having at least 95% sequence identity to SEQ ID NO: 5, and has decreased chlorophyll per total organic carbon compared to a control photosynthetic organism of the same species.

22. The mutant Chlorophyte alga of claim 2 wherein the mutant comprises a complete knockout of a gene encoding a significant growth improvement gene 2 (SGI2) having at least 95% sequence identity to SEQ ID NO: 5, and has increased biomass productivity compared to a control photosynthetic organism of the same species.

23. The mutant Chlorophyte alga of claim 1, wherein the mutant alga belongs to the genus *Parachlorella.*

24. The mutant Chlorophyte alga of claim 2, wherein the mutant alga belongs to the genus *Parachlorella.*

25. The mutant Chlorophyte alga of claim 3, wherein the mutant alga belongs to the genus *Parachlorella*.

* * * * *

SEQUENCE LISTING

```
<160> NUMBER OF SEQ ID NOS: 105

<210> SEQ ID NO 1
<211> LENGTH: 4531
<212> TYPE: DNA
<213> ORGANISM: Parachlorella sp.

<400> SEQUENCE: 1

atgtctggtt cagctggatc gggccaggct actctcagac atgacggtgg ctctgctggc     60

ggcagtgggc ctgtctcaga cggtttttca ccggccggcc tgaaggtaaa gtagaaagac    120

actcatacac atcttggttc ggcgttgaaa gtaggtcatt aacatactct ataaccaata    180

tttgtaggtt ctggtcgtgg acgacgacct catgtgcctt aaggtggtgt cagccatgtt    240

gaagaggtgc agctatcaag gtgaggtctt tactggtgtc tgttattgct gtaacatcat    300

ttcgctgttg cacaatttaa acatttgtaa tttactgttg ttattgcagt ggccacttgt    360

agcagtggca gcgaggcact gacacttcta cgtgaacgca acgaggacgg atcctccgac    420

cagttcgacc tcgtactgtc agatgtttac atgccgggta tgtcgtattc ctttgtaaac    480

tttacaatat gcgtctagtt tgacgcgtac actttgtaca ctttgcaaaa acgcaccctg    540

cgaggtctgc catttggtca ctacaacttg gccaccttgg ttgcaagttt gcaagttcgc    600

tctacgtcaa cgctgcaaaa tgaaccaatt gttttgcact gaccctgcca accttcattt    660

gtggctgcag acatggacgg tttcaagctg cttgaacaca tcggtctaga gttggagctt    720

cccgttatca gtaagttgat cgagccgagt ccagagcgaa gcctgcttct atactattag    780
```

-continued

```
cagctgtctt ttgatatttg acagcttgac ttgatatggt cacagagcat acttgcaacc    840
aggttacctg ttgaactagc aactgtgccc aagcatctct tcaagcacct ccgtcagtcc    900
atagggtact gttgatttgt actctgcaat actgcactgt aatgcgctgt gaatcactgc    960
ccttcacctc tagatggtgc ttccctggag ccctccccca cctccgcctc aagcccctca   1020
catgcctctc cccccctgc agtgatgtca tccaacgggg acacgaatgt cgtgctgcgg   1080
ggggtcaccc acggggctgt ggactttctg atcaagcccg ttcgaattga ggagctgcgg   1140
aacgtgtggc agcacgtggt gcgtcgtcgt tccatggcgc tggccaggac gccagacgag   1200
gggggacact cggacgagga ctctcaggtg cccttggcag cttctgggcg gcttgctgtg   1260
tcggatgcca cttggactgg ggatgcacga ggggtggggg gacaatggga gatgggccat   1320
agtaggccag agttgatggc agtggtggtg ggggggagta ggcgggagag aagcagccat   1380
cctggtgttg gttttgatga ttgagtgcat ggggatgatg cacaggtgag ctgactggat   1440
gccttgtctt gctgtgctgc gctgcagcgg cacagtgtga aacgcaagga gtcggagcag   1500
agcccgctgc agctcagcac agagcagggc gggaacaaga agccaagagt ggtgtggtcg   1560
gtggagatgc accaacaggt gtgcttgcgg gcgggtgtat acgggggagg ggggccagct   1620
gctggctgac ctggcgtgcg cggtgcattg cacttggcga tgaggggcgt gcttcagtat   1680
gtagctggga cgcaattggt tgtgctgtgt gaccagtgca caaaatacat ccctgaattc   1740
cagtgggttg aacagagttg tcctggaggt gggaagcaaa cgcgcacgtg gtagagggga   1800
gcagggtgca gaacagccgc agcaggggtg ttgcgcagtg tgcaggtatc ctgcctccat   1860
gccccgggcc atgggcatac tacgctggta ccgtcaggat gggcgttgag cctggcttgg   1920
ggggcagggg gcgagcgaat gcggaatggg agcggcaggt gctgggaggg tggctgactg   1980
gcttgcagga gcgcaagtcc tgtcgggggc gtcgtcctgt tccctcctgc ccgcttcacc   2040
cacgttcact ctcatgcctc cacactcctg ctgctgacac acctgtcgcc acctccgctg   2100
cagtttgtga acgcggtcaa ctccctgggc attgacaagg cggtgcccaa gcggattctg   2160
gacctgatga acgtggaggg gctgacgcgc gagaacgtgg ccagccatct gcaggtgcct   2220
gccatgaccc ctcccaccag ggacctggtg ttttgacacc ctggaactcc tctttgacgg   2280
agcctccagt tcaattccag caatcgaatt gaatcaaaaa gcatgtgcac ccacgtgctg   2340
tttgaatgtc ccatgtggta ggaaacacaa ctgccccctt gccatttgct ggagggtgcc   2400
cgctgcgcca tgcccgagtg cgctgtgctc agcgttgtgc tgcgcccccc gctgactgaa   2460
gctgacagcg tgcggctgag gagggtactg ggggaggggg ggtgggaggc ggccgctggc   2520
ggcggaaggg agggtgtgca cgcatggaca cagggccttt ccgccctgca cggcctctac   2580
tgcaccctgc cacgtgatgt atcgacatgg tgggccatgc tgtgctgtgc cgctgcagaa   2640
gtaccgcctg tacctgaagc gggtggaggg agtgcaatcg ggtgcggcag cctccaagca   2700
gcaccagcac ccgcagtatc accagcagca gcagcagcag caagcgcaac ctcgtgcagc   2760
tgtctcccct gcagcagctt cctttggtgc cctttccttg ggagccccgc agcaggcgca   2820
gcagggcatg ccgcagctgg ggatgcctgt gcaggtgaag actgcccccc cccccctccc   2880
cctttccatc ttccctccat cagcctgctg ttccttaccc ttgtcaaccc gtctctcctt   2940
tttcgcaagc agcgcaccac cccccatgca cgccttgcct ggcactgttg tcagctgccc   3000
ccctagaaat acacaaggtg tgggtgcaac tggtgggacc ccctcccccc cccccctggg   3060
gctgcagggt ctccctccaa acttggcagc catgggatcc cagccgccgc acatcccctt   3120
ccagcaggcc ctggccatgc aggcggcggc tgcggcggct gcagccagcg gcgcgctccc   3180
```

```
cgggagtctg cccccctaca tgccaccccc ggggatgatg ccccccggca tgccgggggg   3240
ggtccccggt atgggagggg tggtggggca tcctcaggta cgggcagcac atgagtgggc   3300
aggggtattg gagaggggaa gggcagggag gttgcatgtg aggggctgca tggcaaagag   3360
gctgcagcgc aggtgttgct tgcagcactt cccctcggtg gcgcttgcat caaattttga   3420
atcctccccc gatgggcacg cccgtgtgtg gggggggtg ggatggggga tgggggtggt    3480
tttgtggcat gtcgggcgct ttcatctacc cgggcccctg cccctgcctg tacgcgtgcg   3540
catgtgtgca gatgcccgcc ccagggatgg actttgcggg tttcaacggg tatggcaacg   3600
ctgcgggggg gctgatgttt ggcgggcagc agcaggcgca gcacgcgcag cagcacgcgt   3660
cagcgcaagc gggctcgctg gcgcagcagc aggcgcagca agtatccatg ggcttgggcc   3720
ttatgccccc cccgttgggg ttcccgccca cctcgctcgc cgcgccagcc ccgcgctccg   3780
cagcaactga gcccgccgca gccccactcc ccctgacgtc ctcgccgcca gctgcttcag   3840
caggcggcag cggcggccca gcagcagctg ctccgcagca cagcagcggc gccgcagcag   3900
cccaagcccc ccatcaccac ccacagtgct cggagcaggg agcggggggg ctcccgcccc   3960
cgctgcccgc gtccagcgcc ccgcagtcct atcccctccc tccccccctcc tcgcaggccg  4020
ctttgcatga cccggacgaa cactaccccc caggctcggc agaggtgagc acgtcccccc   4080
gccccctccc cccccccccc ccccctcccc ttcaccctgg cttggcgtgc aatgaaaccc   4140
taaataaccc taaaacctca ttatcagttg caaattggac ccgtgaagcg ggcgggggca   4200
actgcgctct gctggtgtca gcgctgtctc tgccggttcc tgcccagcgt gcgcctgcat   4260
gcaagggggg atgggggggg ggaggcattt aacaataggc cagtcatctc caatccaccg   4320
tcaatttcag ccccctcccc ccccctccct catccccttg cagatgcacc accagcacct   4380
cccagggctg tgtggcttta acccggacga cctgctgggg gggcagctgg gggacatggg   4440
gttcctgggg gagctggggg gggcggtggg aggaaagcac gaacaggacg acttcctgga   4500
cctgctgctg aagggggagg aggagctgtg a                                  4531
```

<210> SEQ ID NO 2
<211> LENGTH: 1860
<212> TYPE: DNA
<213> ORGANISM: Parachlorella sp.

<400> SEQUENCE: 2

```
atgtctggtt cagctggatc gggccaggct actctcagac atgacggtgg ctctgctggc     60
ggcagtgggc ctgtctcaga cggtttttca ccggccggcc tgaaggttct ggtcgtggac    120
gacgacctca tgtgccttaa ggtggtgtca gccatgttga agaggtgcag ctatcaagtg    180
gccacttgta gcagtggcag cgaggcactg acacttctac gtgaacgcaa cgaggacgga    240
tcctccgacc agttcgacct cgtactgtca gatgtttaca tgccggacat ggacggtttc    300
aagctgcttg aacacatcgg tctagagttg gagcttcccg ttatcatgat gtcatccaac    360
ggggacacga atgtcgtgct gcgggggtc acccacgggg ctgtggactt tctgatcaag     420
cccgttcgaa ttgaggagct gcggaacgtg tggcagcacg tggtgcgtcg tcgttccatg    480
gcgctggcca ggacgccaga cgagggggga cactcggacg aggactctca gcggcacagt    540
gtgaaacgca aggagtcgga gcagagcccg ctgcagctca gcacagagca gggcgggaac    600
aagaagccaa gagtggtgtg gtcggtggag atgcaccaac agtttgtgaa cgcggtcaac    660
tccctgggca ttgacaaggc ggtgcccaag cggattctgg acctgatgaa cgtggagggg    720
```

```
ctgacgcgcg agaacgtggc cagccatctg cagaagtacc gcctgtacct gaagcgggtg    780
gagggagtgc aatcgggtgc ggcagcctcc aagcagcacc agcacccgca gtatcaccag    840
cagcagcagc agcagcaagc gcaacctcgt gcagctgtct cccctgcagc agcttccttt    900
ggtgcccttt ccttgggagc cccgcagcag gcgcagcagg gcatgccgca gctggggatg    960
cctgtgcagg gtctccctcc aaacttggca gccatgggat cccagccgcc gcacatcccc   1020
ttccagcagg ccctggccat gcaggcggcg gctgcggcgg ctgcagccag cggcgcgctc   1080
cccgggagtc tgccccccta catgccaccc ccggggatga tgccccccgg catgccgggg   1140
ggggtccccg gtatgggagg ggtggtgggg catcctcaga tgcccgcccc agggatggac   1200
tttgcgggtt tcaacgggta tggcaacgct gcgggggggc tgatgtttgg cgggcagcag   1260
caggcgcagc acgcgcagca gcacgcgtca gcgcaagcgg gctcgctggc gcagcagcag   1320
gcgcagcaag tatccatggg cttgggcctt atgccccccc cgttggggtt cccgcccacc   1380
tcgctcgccg cgccagcccc gcgctccgca gcaactgagc ccgccgcagc cccactcccc   1440
ctgacgtcct cgccgccagc tgcttcagca ggcggcagcg gcggcccagc agcagctgct   1500
ccgcagcaca gcagcggcgc cgcagcagcc caagcccccc atcaccaccc acagtgctcg   1560
gagcagggag cggggggggct cccgcccccg ctgcccgcgt ccagcgcccc gcagtcctat   1620
cccctccctc ccccctcctc gcaggccgct ttgcatgacc cggacgaaca ctacccccca   1680
ggctcggcag agatgcacca ccagcacctc ccagggctgt gtggctttaa cccggacgac   1740
ctgctggggg ggcagctggg ggacatgggg ttcctggggg agctgggggg ggcggtggga   1800
ggaaagcacg aacaggacga cttcctggac ctgctgctga agggggagga ggagctgtga   1860
```

```
<210> SEQ ID NO 3
<211> LENGTH: 619
<212> TYPE: PRT
<213> ORGANISM: Parachlorella sp.

<400> SEQUENCE: 3

Met Ser Gly Ser Ala Gly Ser Gly Gln Ala Thr Leu Arg His Asp Gly
1               5                   10                  15

Gly Ser Ala Gly Gly Ser Gly Pro Val Ser Asp Gly Phe Ser Pro Ala
            20                  25                  30

Gly Leu Lys Val Leu Val Val Asp Asp Asp Leu Met Cys Leu Lys Val
        35                  40                  45

Val Ser Ala Met Leu Lys Arg Cys Ser Tyr Gln Val Ala Thr Cys Ser
    50                  55                  60

Ser Gly Ser Glu Ala Leu Thr Leu Leu Arg Glu Arg Asn Glu Asp Gly
65                  70                  75                  80

Ser Ser Asp Gln Phe Asp Leu Val Leu Ser Asp Val Tyr Met Pro Asp
                85                  90                  95

Met Asp Gly Phe Lys Leu Leu Glu His Ile Gly Leu Glu Leu Glu Leu
            100                 105                 110

Pro Val Ile Met Met Ser Ser Asn Gly Asp Thr Asn Val Val Leu Arg
        115                 120                 125

Gly Val Thr His Gly Ala Val Asp Phe Leu Ile Lys Pro Val Arg Ile
    130                 135                 140

Glu Glu Leu Arg Asn Val Trp Gln His Val Val Arg Arg Arg Ser Met
145                 150                 155                 160

Ala Leu Ala Arg Thr Pro Asp Glu Gly Gly His Ser Asp Glu Asp Ser
                165                 170                 175
```

-continued

```
Gln Arg His Ser Val Lys Arg Lys Glu Ser Glu Gln Ser Pro Leu Gln
            180                 185                 190

Leu Ser Thr Glu Gln Gly Gly Asn Lys Lys Pro Arg Val Val Trp Ser
        195                 200                 205

Val Glu Met His Gln Gln Phe Val Asn Ala Val Asn Ser Leu Gly Ile
    210                 215                 220

Asp Lys Ala Val Pro Lys Arg Ile Leu Asp Leu Met Asn Val Glu Gly
225                 230                 235                 240

Leu Thr Arg Glu Asn Val Ala Ser His Leu Gln Lys Tyr Arg Leu Tyr
                245                 250                 255

Leu Lys Arg Val Glu Gly Val Gln Ser Gly Ala Ala Ala Ser Lys Gln
            260                 265                 270

His Gln His Pro Gln Tyr His Gln Gln Gln Gln Gln Gln Gln Ala Gln
        275                 280                 285

Pro Arg Ala Ala Val Ser Pro Ala Ala Ala Ser Phe Gly Ala Leu Ser
    290                 295                 300

Leu Gly Ala Pro Gln Gln Ala Gln Gln Gly Met Pro Gln Leu Gly Met
305                 310                 315                 320

Pro Val Gln Gly Leu Pro Pro Asn Leu Ala Ala Met Gly Ser Gln Pro
                325                 330                 335

Pro His Ile Pro Phe Gln Gln Ala Leu Ala Met Gln Ala Ala Ala Ala
            340                 345                 350

Ala Ala Ala Ala Ser Gly Ala Leu Pro Gly Ser Leu Pro Pro Tyr Met
        355                 360                 365

Pro Pro Pro Gly Met Met Pro Pro Gly Met Pro Gly Gly Val Pro Gly
    370                 375                 380

Met Gly Gly Val Val Gly His Pro Gln Met Pro Ala Pro Gly Met Asp
385                 390                 395                 400

Phe Ala Gly Phe Asn Gly Tyr Gly Asn Ala Ala Gly Gly Leu Met Phe
                405                 410                 415

Gly Gly Gln Gln Gln Ala Gln His Ala Gln Gln His Ala Ser Ala Gln
            420                 425                 430

Ala Gly Ser Leu Ala Gln Gln Gln Ala Gln Gln Val Ser Met Gly Leu
        435                 440                 445

Gly Leu Met Pro Pro Pro Leu Gly Phe Pro Pro Thr Ser Leu Ala Ala
    450                 455                 460

Pro Ala Pro Arg Ser Ala Ala Thr Glu Pro Ala Ala Ala Pro Leu Pro
465                 470                 475                 480

Leu Thr Ser Ser Pro Pro Ala Ala Ser Ala Gly Gly Ser Gly Gly Pro
                485                 490                 495

Ala Ala Ala Ala Pro Gln His Ser Ser Gly Ala Ala Ala Ala Gln Ala
            500                 505                 510

Pro His His His Pro Gln Cys Ser Glu Gln Gly Ala Gly Gly Leu Pro
        515                 520                 525

Pro Pro Leu Pro Ala Ser Ser Ala Pro Gln Ser Tyr Pro Leu Pro Pro
    530                 535                 540

Pro Ser Ser Gln Ala Ala Leu His Asp Pro Asp Glu His Tyr Pro Pro
545                 550                 555                 560

Gly Ser Ala Glu Met His His Gln His Leu Pro Gly Leu Cys Gly Phe
                565                 570                 575

Asn Pro Asp Asp Leu Leu Gly Gly Gln Leu Gly Asp Met Gly Phe Leu
            580                 585                 590

Gly Glu Leu Gly Gly Ala Val Gly Gly Lys His Glu Gln Asp Asp Phe
```

```
        595                 600                 605

Leu Asp Leu Leu Leu Lys Gly Glu Glu Glu Leu
    610                 615


<210> SEQ ID NO 4
<211> LENGTH: 2802
<212> TYPE: DNA
<213> ORGANISM: Parachlorella sp.

<400> SEQUENCE: 4

atggctgccc ccccagtatc tatctcttcc aattttccaa aggttagtat ttacgtaaca     60

tttgccgaca gttgggcaat aacgctgagt tggagtgttg ccaacaagct tttgtgccgt    120

ttccagggtt tgcgggttct cttggtcgat caacagccaa gtaggagcca tattgaagcg    180

cagctgatgc agccggatct taattacaca ggtttgctgc agttttgcac attccaagct    240

tggcctttct ccgtgccaaa cccagcgcgc tgagctcttg ttgtttgttg cagttactgg    300

ttgcgagagc gtttctgaag ctctttcata ttgccgctcg ggagtaagca gctttgacgt    360

ggtgcttgcg gaggtgggtg gtagtgcttc gcgaggtgca cagtgcgcac cgggaaaaac    420

ttgaaaagta tttgtaaaat taattttgaa acttctgtat tattttacac ctcttaacaa    480

tgcacccaat gtttgttatg agcgccacgt taccggacgt ttgttgcagg caaggatcgt    540

tgccgtcgac gagacttcgg ggcgcgcatt tatcgactct cttgaagata caccggttat    600

tcttatgtcg gagggaagca cgacgggcga cgttcttcgt gcggtgaagc ttggagctgt    660

ggactggctg gataagcctc tctccgtcct gaagctcaag aacatctggc agcactcagt    720

gcgtaaggta ggtccggaaa caatatgata tctacaattg gaaagttacc agtgtcaact    780

atggaaaacg ttgtactggg tgctagtttc agttgagcca gttgcctgta tatgcatata    840

aggggcagtg acgcagtgtc tgccctgtga gctgtgatgc atcagggtgc acctgaagct    900

ggcagtggat cactccaccc aagatgttgt tgcaatccaa tgtgttgctg atgccttgct    960

tttctgactt gcaaacatgg tgtgggataa aagcgttgct agacagccac cgtgctccac   1020

gttgtcttct gcatgcaaaa ctgcagatga tgcagcgcac cacgttttac gacacttgct   1080

ccgagcagcc aacccagccg gcgcgcagca agctttcttc aggaatcgaa tcgccgagca   1140

cacccacgct gggagactct gtggacttgg acgccatctc ggcggcttcc ttcggcagca   1200

tcaaggactt gaccgatttt tcattttcca gcggagctga ggtgggcatc gctggttgtc   1260

cagcactgca gcatttccca ccagcttggt tggttgcctg tgttttagtg cagagcagag   1320

gccgaggcta ctggttcaac cagcctagtt actcaaaaca attttggcaa cctgctgact   1380

tctctcttaa cctgcagagc gtttcacagc atgtacactt ttcagtgggt ttcgtaattt   1440

cgtagcgcac ccgctggctt ttttctgcag gtcctgagag cctcctttga cagctgtgac   1500

ggctccgagg tcaacctagg cagcgctttg ggccagcctc gcccccctct ggcagtcaag   1560

cccagctcct ttggcccccct ggtgagtggc atagctcagc aggagaccca caagtggctg   1620

gaacccacca tgttggcgcg caccctgccc tcgcacgcgc ggctgccgtc tgcgcagcgc   1680

gccgcggtgc gccgctgtgg agttgtggtg ttgcggagtc actcgcgggc cagtgcttca   1740

cagcccattc tcgccgcaca caccctgccc gcacaaatgg ctgccacccc cctaaagcgg   1800

tcctcaggcc acccggatgt gctcaggatg gatccgccga atctcgcacc cctcctccct   1860

caatcccggt tgttcagacg gtttggaacc cctccggctc tctacccctc tgcaggtacc   1920

cgtccctccc acctcccagt ggccccagct gcaggctggc tgcgtgtggg gcactcccgt   1980
```

-continued

```
gggcggcccg ctggcgcccc cctccatgac caacgcccag catggtgccc cccacagcgt   2040

gcccctggca gacgcacact tggccggcag cgccagttac atgtccctct cctctgtgag   2100

tctcctcccc tccacccta catcttccaa tcgaacatgc gacgcacgca cacccatagt   2160

ccctaaacaa gtgctttggt gttttttcac ttgcaaaccc caaccctgac acctgaagcg   2220

tgacacaggc gactgcgctg ctccccgccc ccacacgccc ttggttgttt gtgccctgca   2280

cttctgccac gacatgcatg tcatgtcttt tcacgcctgc gatgtcgctg cttaaacttg   2340

aaactcattg tggccggggt gcagctcatg gaggaggaca ccccctgtcc cttggacatg   2400

gatgcaccag aggacgggat gcagcttcct gttgacttcc tgtctgttgc caacgtcagc   2460

agcaatggta ggtccagcac cagacgcctc tgtctgctat gagacgcacc tccagccgcc   2520

ccctctggac agacagcgcg ctgcacgctc tgcgcgctgg accttgccgc acacgcgcgc   2580

gacaaggcct ggtgtgatgc ttggatgtgg aaggttccag catggttgga caagatggta   2640

tcctggcaca catattggta tgcagcatac acccaggctg ccccttacc ctcgcacgcc    2700

ctacccctta ctgcaggcag cggtcccatt gggttgaagc tgaagaaaag caacagcctg   2760

ctgaacatga tcaacgcagc gctgatgtct ggtggtcagt ga                      2802
```

```
<210> SEQ ID NO 5
<211> LENGTH: 359
<212> TYPE: PRT
<213> ORGANISM: Parachlorella sp.

<400> SEQUENCE: 5

Met Ala Ala Pro Pro Val Ser Ile Ser Ser Asn Phe Pro Lys Gly Leu
1               5                   10                  15

Arg Val Leu Leu Val Asp Gln Gln Pro Ser Arg Ser His Ile Glu Ala
            20                  25                  30

Gln Leu Met Gln Pro Asp Leu Asn Tyr Thr Val Thr Gly Cys Glu Ser
        35                  40                  45

Val Ser Glu Ala Leu Ser Tyr Cys Arg Ser Gly Val Ser Ser Phe Asp
    50                  55                  60

Val Val Leu Ala Glu Ala Arg Ile Val Ala Val Asp Glu Thr Ser Gly
65                  70                  75                  80

Arg Ala Phe Ile Asp Ser Leu Glu Asp Thr Pro Val Ile Leu Met Ser
                85                  90                  95

Glu Gly Ser Thr Thr Gly Asp Val Leu Arg Ala Val Lys Leu Gly Ala
            100                 105                 110

Val Asp Trp Leu Asp Lys Pro Leu Ser Val Leu Lys Leu Lys Asn Ile
        115                 120                 125

Trp Gln His Ser Val Arg Lys Met Met Gln Arg Thr Thr Phe Tyr Asp
    130                 135                 140

Thr Cys Ser Glu Gln Pro Thr Gln Pro Ala Arg Ser Lys Leu Ser Ser
145                 150                 155                 160

Gly Ile Glu Ser Pro Ser Thr Pro Thr Leu Gly Asp Ser Val Asp Leu
                165                 170                 175

Asp Ala Ile Ser Ala Ala Ser Phe Gly Ser Ile Lys Asp Leu Thr Asp
            180                 185                 190

Phe Ser Phe Ser Ser Gly Ala Glu Val Leu Arg Ala Ser Phe Asp Ser
        195                 200                 205

Cys Asp Gly Ser Glu Val Asn Leu Gly Ser Ala Leu Gly Gln Pro Arg
    210                 215                 220

Pro Pro Leu Ala Val Lys Pro Ser Ser Phe Gly Pro Leu Val Pro Val
```

-continued 225 230 235 240

Pro Pro Thr Ser Gln Trp Pro Gln Leu Gln Ala Gly Cys Val Trp Gly
245 250 255

Thr Pro Val Gly Gly Pro Leu Ala Pro Pro Ser Met Thr Asn Ala Gln
260 265 270

His Gly Ala Pro His Ser Val Pro Leu Ala Asp Ala His Leu Ala Gly
275 280 285

Ser Ala Ser Tyr Met Ser Leu Ser Ser Leu Met Glu Glu Asp Thr Pro
290 295 300

Cys Pro Leu Asp Met Asp Ala Pro Glu Asp Gly Met Gln Leu Pro Val
305 310 315 320

Asp Phe Leu Ser Val Ala Asn Val Ser Ser Asn Gly Ser Gly Pro Ile
325 330 335

Gly Leu Lys Leu Lys Lys Ser Asn Ser Leu Leu Asn Met Ile Asn Ala
340 345 350

Ala Leu Met Ser Gly Gly Gln
355

<210> SEQ ID NO 6
<211> LENGTH: 119
<212> TYPE: PRT
<213> ORGANISM: Parachlorella sp.

<400> SEQUENCE: 6

Gly Leu Arg Val Leu Leu Val Asp Gln Gln Pro Ser Arg Ser His Ile
1 5 10 15

Glu Ala Gln Leu Met Gln Asp Leu Asn Tyr Thr Val Thr Gly Cys Glu
20 25 30

Ser Val Ser Glu Ala Leu Ser Tyr Cys Arg Ser Gly Val Ser Ser Phe
35 40 45

Asp Val Val Leu Ala Glu Ala Arg Ile Val Ala Val Asp Glu Thr Ser
50 55 60

Gly Arg Ala Phe Ile Asp Ser Leu Glu Asp Thr Pro Val Ile Leu Met
65 70 75 80

Ser Glu Gly Ser Thr Thr Gly Asp Val Leu Arg Ala Val Lys Leu Gly
85 90 95

Ala Val Asp Trp Leu Asp Lys Pro Leu Ser Val Leu Lys Leu Lys Asn
100 105 110

Ile Trp Gln His Ser Val Arg
115

<210> SEQ ID NO 7
<211> LENGTH: 1080
<212> TYPE: DNA
<213> ORGANISM: Parachlorella sp.

<400> SEQUENCE: 7
atggctgccc ccccagtatc tatctcttcc aattttccaa agggtttgcg ggttctcttg 60
gtcgatcaac agccaagtag gagccatatt gaagcgcagc tgatgcagcc ggatcttaat 120
tacacagtta ctggttgcga gagcgtttct gaagctcttt catattgccg ctcgggagta 180
agcagctttg acgtggtgct tgcggaggca aggatcgttg ccgtcgacga gacttcgggg 240
cgcgcattta tcgactctct tgaagataca ccggttattc ttatgtcgga gggaagcacg 300
acgggcgacg ttcttcgtgc ggtgaagctt ggagctgtgg actggctgga taagcctctc 360
tccgtcctga agctcaagaa catctggcag cactcagtgc gtaagatgat gcagcgcacc 420
acgttttacg acacttgctc cgagcagcca acccagccgg cgcgcagcaa gctttcttca 480
ggaatcgaat cgccgagcac acccacgctg ggagactctg tggacttgga cgccatctcg 540
gcggcttcct tcggcagcat caaggacttg accgattttt cattttccag cggagctgag 600
gtcctgagag cctcctttga cagctgtgac ggctccgagg tcaacctagg cagcgctttg 660
ggccagcctc gcccccctct ggcagtcaag cccagctcct ttggccccct ggtacccgtc 720
cctcccacct cccagtggcc ccagctgcag gctggctgcg tgtggggcac tcccgtgggc 780
ggcccgctgg cgcccccctc catgaccaac gcccagcatg gtgcccccca cagcgtgccc 840
ctggcagacg cacacttggc cggcagcgcc agttacatgt ccctctcctc tctcatggag 900
gaggacaccc cctgtccctt ggacatggat gcaccagagg acgggatgca gcttcctgtt 960
gacttcctgt ctgttgccaa cgtcagcagc aatggcagcg gtcccattgg gttgaagctg 1020
aagaaaagca acagcctgct gaacatgatc aacgcagcgc tgatgtctgg tggtcagtga 1080

<210> SEQ ID NO 8
<211> LENGTH: 1707
<212> TYPE: DNA
<213> ORGANISM: Parachlorella sp.

<400> SEQUENCE: 8
atgcttcggc agcagctgtt gcacagcggc aggcagccgg gtgcgacatg cagcttacta 60
acctgctcga catggcgacc gtctgccttg ttcggccgtc ctaagcccca aaaactgcac 120
agccagcgct tgcagcatca gggccgcccc tcccgcctcg tcgtgcgcag cgcaatgttc 180
gacaacctga gccgcagcct ggagagggcg tgggacatgg tgcgcaagga cgggcggcta 240
acggcggaca acatcaagga gcccatgcgg gagattcgca gggcgctgct tgaggcggat 300
gtgaggctgg gggcgccgct gatcagattc ttggtatcta cccccccccc ctcccaggtc 360
tccctccccg tggtgcgcaa gtttgtgaag gcggtggagg agaaggcgct gggttctgca 420
gtgaccaagg gtgtcacccc cgaccagcag ctggtgaagg tggtgtacga ccagctgcgg 480
gagctgatgg gggggcagca ggaagggctg gtgcccactt cgccagagga gccgcaggtg 540
atcttgatgg cggggctgca gggcacgggg aagacgacag ctgcggggaa gctggccttg 600
ttcctgcaga agaaggggca gaaggtgctg ctggtggcca ccgacatcta ccgccccgcc 660
gccatcgacc agctggtgaa gctgggcgac aggatagggg tgccggtgtt ccagctggga 720
acccaggtgc agccgccgga gattgcaagg caggggctgg agaaggcgcg agcagagggg 780
tttgacgccg tcatcgtcga cacggcgggg cggctgcaga tcgaccagag catgatggag 840
gagctggtgc agatcaagtc cacggtgaag ccctccgaca cgctgctagt ggtcgatgcg 900
atgacggggc aggaggcagc cgggctggtg aaggcgttca atgatgccgt ggacatcaca 960
ggcgccgtgc tgaccaagct tgacggggac agccgcggcg gcgccgcgct gagcgtgcgc 1020
caggtcagcg ggcggcccat caagtttgtg ggcatggggg agggcatgga ggcgctggag 1080
cccttctacc ccgagcgcat ggccagcagg attctgggca tgggtgacgt ggtcaccctg 1140
gtggagaagg ctgaggagag catcaaggaa gaggaggcgc aggagatatc gcggaagatg 1200
ctgtcggcca aatttgactt tgacgacttc ctgaagcagt acaagatggt ggcggggatg 1260
gggaacatgg cccaaatcat gaagatgctg ccaggcatga acaagtttac ggagaagcag 1320
ctggcgggcg ttgagaagca gtacaaggtg tacgagagca tgatccagag catgacggtg 1380
aaggagcgca agcagccgga gctgttggtg aagtcgccct ccaggaggcg gcgcatagcg 1440

-continued

```
cgcgggtcgg ggcgctcgga gcgggaggtc acagagctgc tgggggtgtt caccaacctg   1500

cggacgcaga tgcagagctt ctccaaaatg atggccatgg gggggatggg catgggctcc   1560

atgatgagcg acgaggagat gatgcaggcc acgctggcag gcgccggccc ccgccccgtg   1620

ccagctggca aggtgcggcg gaagaagctg gccgcggcgg gcgggtcgcg gggcatggct   1680

gagctggcat ccctgaaggc agaatga                                       1707
```

<210> SEQ ID NO 9
<211> LENGTH: 302
<212> TYPE: PRT
<213> ORGANISM: Coccomyxa subellipsoidea

<400> SEQUENCE: 9

```
Met Gly Leu Lys Ala Arg Ala Ala Ser Val Ser Val His Ser Ser Ala
1               5                   10                  15

Asn Asn Thr Ala Ser Pro Leu Ser Ser Gly Arg Arg Gly Phe Pro His
            20                  25                  30

Ser Gly Glu Met Ser Gly Glu Asp Leu Ala Arg Ser Asp Ser Trp Glu
        35                  40                  45

Met Phe Pro Ala Gly Leu Lys Val Leu Val Val Asp Asp Asp Pro Leu
    50                  55                  60

Cys Leu Lys Val Val Glu His Met Leu Arg Arg Cys Asn Tyr Gln Val
65                  70                  75                  80

Thr Thr Cys Pro Asn Gly Lys Ala Ala Leu Glu Lys Leu Arg Asp Arg
                85                  90                  95

Ser Val His Phe Asp Leu Val Leu Ser Asp Val Tyr Met Pro Asp Met
            100                 105                 110

Asp Gly Phe Lys Leu Leu Glu His Ile Gly Leu Glu Leu Asp Leu Pro
        115                 120                 125

Val Ile Met Met Ser Ser Asn Gly Glu Thr Asn Val Val Leu Arg Gly
    130                 135                 140

Val Thr His Gly Ala Val Asp Phe Leu Ile Lys Pro Val Arg Val Glu
145                 150                 155                 160

Glu Leu Arg Asn Val Trp Gln His Val Val Arg Arg Lys Arg Asp Gln
                165                 170                 175

Ala Val Ser Gln Ala Arg Asp Ser Arg Asp Ile Ser Asp Glu Glu Gly
            180                 185                 190

Thr Asp Asp Gly Lys Pro Arg Asp Lys Lys Arg Lys Glu Val Ile Leu
        195                 200                 205

Val Leu Trp Trp Asp Met Gln Arg Arg Asp Ser Asp Asp Gly Val Ser
    210                 215                 220

Ala Lys Lys Ala Arg Val Val Trp Ser Val Glu Met His Gln Gln Phe
225                 230                 235                 240

Val Gln Ala Val Asn Gln Leu Gly Ile Asp Lys Ala Val Pro Lys Arg
                245                 250                 255

Ile Leu Asp Leu Met Asn Val Asp Gly Leu Thr Arg Glu Asn Val Ala
            260                 265                 270

Ser His Leu Gln Val Pro His Leu Ser Ile Phe Ser Pro Leu Phe Ala
        275                 280                 285

Glu Leu Met Ser Thr Leu Pro Arg Arg Cys Phe Tyr Asp Phe
    290                 295                 300
```

<210> SEQ ID NO 10
<211> LENGTH: 269
<212> TYPE: PRT

<213> ORGANISM: Ostreococcus lucimarinus

<400> SEQUENCE: 10

```
Phe Pro Ala Gly Leu Gly Val Leu Val Val Asp Asp Asp Leu Leu Cys
1               5                   10                  15

Leu Lys Val Val Glu Lys Met Leu Lys Ala Cys Lys Tyr Lys Val Thr
            20                  25                  30

Ala Cys Ser Thr Ala Lys Thr Ala Leu Glu Ile Leu Arg Thr Arg Lys
        35                  40                  45

Glu Glu Phe Asp Ile Val Leu Ser Asp Val His Met Pro Asp Met Asp
    50                  55                  60

Gly Phe Lys Leu Leu Glu Ile Ile Gln Phe Glu Leu Ala Leu Pro Val
65                  70                  75                  80

Leu Met Met Ser Ala Asn Ser Asp Ser Ser Val Val Leu Arg Gly Ile
                85                  90                  95

Ile His Gly Ala Val Asp Tyr Leu Leu Lys Pro Val Arg Ile Glu Glu
            100                 105                 110

Leu Arg Asn Ile Trp Gln His Val Val Arg Arg Asp Tyr Ser Ser Ala
        115                 120                 125

Lys Ser Ser Gly Ser Glu Asp Val Glu Ala Ser Ser Pro Ser Lys Arg
    130                 135                 140

Ala Lys Thr Ser Gly Ser Asn Ser Lys Ser Glu Glu Val Asp Arg Thr
145                 150                 155                 160

Ala Ser Glu Met Ser Ser Gly Lys Ala Arg Lys Lys Pro Thr Gly Lys
                165                 170                 175

Lys Gly Gly Lys Ser Val Lys Glu Ala Glu Lys Lys Asp Val Val Asp
            180                 185                 190

Asn Ser Asn Ser Lys Lys Pro Arg Val Val Trp Ser Ala Glu Leu His
        195                 200                 205

Ala Gln Phe Val Thr Ala Val Asn Gln Leu Gly Ile Asp Lys Ala Val
    210                 215                 220

Pro Lys Arg Ile Leu Asp Leu Met Gly Val Gln Gly Leu Thr Glu Asn
225                 230                 235                 240

Val Ala Ser His Leu Gln Lys Tyr Arg Leu Tyr Leu Lys Arg Leu Gln
                245                 250                 255

Gly Asn Asp Ala Arg Gly Gly Gly Asn Ala Ser Ser Thr
            260                 265
```

<210> SEQ ID NO 11
<211> LENGTH: 941
<212> TYPE: PRT
<213> ORGANISM: Chlamydomonas reinhardtii

<400> SEQUENCE: 11

```
Met Asp Ser Gln Gly Val Lys Leu Glu Glu His Pro Gly His Thr Gly
1               5                   10                  15

Gly His Trp Gln Gly Phe Pro Ala Gly Leu Arg Leu Leu Val Val Asp
            20                  25                  30

Asp Asp Pro Leu Cys Leu Lys Val Val Glu Gln Met Leu Arg Lys Cys
        35                  40                  45

Ser Tyr Glu Val Thr Val Cys Ser Asn Ala Thr Thr Ala Leu Asn Ile
    50                  55                  60

Leu Arg Asp Lys Asn Thr Glu Tyr Asp Leu Val Leu Ser Asp Val Tyr
65                  70                  75                  80

Met Pro Asp Met Asp Gly Phe Arg Leu Leu Glu Leu Val Gly Leu Glu
```

-continued

```
                85                  90                  95

Met Asp Leu Pro Val Ile Met Met Ser Ser Asn Gly Asp Thr Ser Asn
            100                 105                 110

Val Leu Arg Gly Val Thr His Gly Ala Cys Asp Tyr Leu Ile Lys Pro
        115                 120                 125

Val Arg Leu Glu Glu Leu Arg Asn Leu Trp Gln His Val Val Arg Arg
    130                 135                 140

Arg Arg Gln His Ala Gln Glu Ile Asp Ser Asp Glu Gln Ser Gln Glu
145                 150                 155                 160

Arg Asp Glu Asp Gln Thr Arg Asn Lys Arg Lys Ala Asp Ala Ala Gly
                165                 170                 175

Val Thr Gly Asp Gln Cys Arg Leu Asn Gly Ser Gly Ser Gly Gly Ala
            180                 185                 190

Ala Gly Pro Gly Ser Gly Gly Gly Ala Gly Gly Met Thr Asp Glu Met
        195                 200                 205

Leu Met Met Ser Gly Gly Glu Asn Gly Ser Asn Lys Lys Ala Arg Val
    210                 215                 220

Val Trp Ser Val Glu Met His Gln Gln Phe Val Asn Ala Val Asn Gln
225                 230                 235                 240

Leu Gly Ile Asp Lys Ala Val Pro Lys Lys Ile Leu Glu Ile Met Gly
                245                 250                 255

Val Asp Gly Ser Ala Gly Arg Leu Ala Asp Thr Ser Gly Arg Asp Val
            260                 265                 270

Cys Gly Thr Val Tyr Arg Leu Tyr Leu Lys Arg Val Ser Gly Val Thr
        275                 280                 285

Pro Ser Gly His His His Asn Ala Ala His Lys Ser Asn Lys Pro Ser
    290                 295                 300

Pro His Thr Thr Pro Pro Pro Pro Ala Leu Pro Gly Gln Ala Gly Thr
305                 310                 315                 320

His Pro Ala Asn Gln Ala Thr Ala Ile Pro Pro Pro Pro Gln Pro Gly
                325                 330                 335

Ser Gly Thr Ala Ala Gly Ala Gly Ala Ala Ala Ala Gly Thr Gly Gly
            340                 345                 350

Gly Ala Ala Ala Ala Asn Gly His Ala Ala Thr Thr Gly Ala Gly Thr
        355                 360                 365

Pro Gly Ala Ala Pro Gly Ala Gly Gly Gly Val Gly Gly Thr Gly Ala
    370                 375                 380

Gly Gly Leu Gly Ser Gly Pro Asp Gly Ala Ala Ala Ala Ala Gly Pro
385                 390                 395                 400

Gly Pro Gly Ala Ala Val Pro Gly Gly Leu Gly Gly Leu Pro Leu Pro
                405                 410                 415

Pro Gly Ala Gly Pro Gly Pro Gly Pro Gly Gly Phe Gly Gly Pro Ser
            420                 425                 430

Pro Pro Pro Pro Pro His Pro Ala Ala Leu Leu Ala Asn Pro Met Ala
        435                 440                 445

Ala Ala Val Ala Gly Leu Asn Gln Ser Leu Leu Asn Ala Met Gly Ser
    450                 455                 460

Leu Gly Val Gly Val Gly Gly Met Ser Pro Leu Gly Pro Val Gly Pro
465                 470                 475                 480

Leu Gly Pro Leu Gly Gly Leu Pro Gly Leu Pro Gly Met Gln Pro Pro
                485                 490                 495

Pro Leu Gly Met Gly Gly Leu Gln Pro Gly Met Gly Pro Leu Gly Pro
            500                 505                 510
```

-continued

```
Leu Gly Leu Pro Gly Met Gly Gly Leu Pro Gly Leu Pro Gly Met Asn
        515                 520                 525

Pro Met Ala Asn Leu Met Gln Gly Met Ala Ala Gly Met Ala Ala Ala
    530                 535                 540

Asn Gln Met Asn Gly Met Gly Gly His Met Gly Gly His Met Gly Gly
545                 550                 555                 560

Met Asn Gly Pro Met Gly Ala Leu Ala Gly Met Asn Gly Leu Asn Gly
                565                 570                 575

Ala Met Met Gly Gly Leu Pro Gly Met Gly Gly Pro Gln Asn Met Phe
            580                 585                 590

Gln Ala Ala Ala Ala Ala Ala Ala Gln Gln Gln Gln Gln Gln Gln Glu
        595                 600                 605

Gln Gln His Ala Met Met Gln Gln Ala Ala Ala Gly Leu Leu Ala Ser
    610                 615                 620

Gln Gln Gln Gln Gln Gln Gln Gln Gln Gln Gln Gln Gln Gln Gln Ala
625                 630                 635                 640

Leu Gln Gln Gln Gln Gln Gln Gly Met Ala Val Ser Pro Pro Gly Pro
                645                 650                 655

His Asn Ala Thr Pro Asn Gly Gln Leu His Thr His Pro Gln Ala His
            660                 665                 670

His Pro His Gln His Gly Leu His Ala His Ala His Pro His Gln His
        675                 680                 685

Leu Asn Thr Ala Pro Ala Gly Ala Leu Gly Leu Ser Pro Pro Gln Pro
    690                 695                 700

Pro Ala Gly Leu Leu Ser Ala Ser Gly Leu Ser Ser Gly Pro Asp Gly
705                 710                 715                 720

Ser Gly Leu Gly Ser Gly Val Gly Gly Leu Leu Asp Gly Leu Gln Gln
                725                 730                 735

His Pro His His Pro Gln Leu Gln Leu Ala Gly Ser Leu Gly Thr Gly
            740                 745                 750

Gly Thr Gly Arg Ser Ser Gly Ala Ala Gly Arg Gly Ser Leu Asp Leu
        755                 760                 765

Pro Ala Asp Leu Met Gly Met Ala Leu Leu Asp Phe Pro Pro Val Pro
    770                 775                 780

Val Pro Gly Gly Ala Asp Val Gly Met Ala Gly Ala Gly Gly Gly Ala
785                 790                 795                 800

Ala Gly Ala His His His Gly His Gln Gly His Gln Gly Ile Gly Gly
                805                 810                 815

Gly Ala Gly Val Gly Ile Ala Gly Gly Val Gly Cys Gly Val Pro Ala
            820                 825                 830

Ala Ala His Gly Leu Glu Pro Ala Ile Leu Met Asp Asp Pro Ala Asp
        835                 840                 845

Leu Gly Ala Val Phe Ser Asp Val Met Tyr Gly Thr Pro Gly Gly Gly
    850                 855                 860

Gly Val Pro Gly Gly Val Pro Gly Gly Gly Val Gly Leu Gly Leu Gly
865                 870                 875                 880

Ala Gly Gln Val Pro Ser Gly Pro Ala Gly Ala Gly Gly Leu His Ser
                885                 890                 895

His His His Gln His His His His Gln His His Leu Gly His Val Val
            900                 905                 910

Pro Val Gly Gly Val Asp Pro Leu Ala Gly Asp Ala Ala Lys Met Ala
        915                 920                 925
```

Met Asn Asp Asp Asp Phe Phe Asn Phe Leu Leu Lys Asn
    930                 935                 940

<210> SEQ ID NO 12
<211> LENGTH: 523
<212> TYPE: PRT
<213> ORGANISM: Chromochloris zofingiensis

<400> SEQUENCE: 12

Met Asp Gly Phe Lys Leu Leu Glu Thr Val Gly Leu Glu Leu Asp Leu
1               5                   10                  15

Pro Val Ile Met Met Ser Ser Asn Gly Glu His Thr Thr Val Met Arg
            20                  25                  30

Gly Val Thr His Gly Ala Cys Asp Phe Leu Ile Lys Pro Val Arg Ile
        35                  40                  45

Glu Glu Leu Arg Asn Ile Trp Gln His Val Ile Arg Arg Thr Arg His
    50                  55                  60

Pro Val Phe Arg Asp Leu Glu Pro Asp Asp His Glu Gly Gly Asp Tyr
65                  70                  75                  80

Glu Ala Ser Lys Lys Arg Lys Asp Leu Tyr Arg Gly Glu Asn Ser Ser
                85                  90                  95

Gly Ser Gly Gly Ala Gly Gly Leu Glu Arg Asp Asp Asp Gly Ser Ala
            100                 105                 110

Ser Lys Lys Pro Arg Val Val Trp Ser Val Glu Met His Gln Gln Phe
        115                 120                 125

Val Gln Ala Val Asn Gln Leu Gly Ile Asp Lys Ala Val Pro Lys Lys
    130                 135                 140

Ile Leu Glu Leu Met Asn Val Asp Gly Leu Thr Arg Glu Asn Val Ala
145                 150                 155                 160

Ser His Leu Gln Lys Tyr Arg Leu Tyr Leu Lys Arg Val Gln Gly Val
                165                 170                 175

Gln Ala Pro Phe Gly Leu Pro Asn Ile Gln Leu Pro Arg Gln Thr Ser
            180                 185                 190

Ser Lys Gly Ala Gly Ser Ser Ser Gln Gln Gln His His Gln Gln Gln
        195                 200                 205

Gln His Gln Gln Gln His Gln His Gln His Gln Thr Ala Leu Gly Thr
    210                 215                 220

Gly Gln Gln Gln Ser His Gln Leu Gln Pro Cys Pro Val Ser Thr Ala
225                 230                 235                 240

Thr Pro Val Met Pro Ser Pro Asp Ala Met Val Ala Ala Ser Met Met
                245                 250                 255

Ser Ser Gln Ala Met Ala Ala Met Ala Pro Gly Val Met Asn Pro Met
            260                 265                 270

Thr Ala Met Asn Ser Met Met Ala Gly Leu Asn Pro Asn Met Met Gly
        275                 280                 285

Met Ala Ala Gly Leu Gly Leu Ala Gly Leu Gly Ile Gly Gly Met Ala
    290                 295                 300

Gly His Pro Val Pro Asn Pro Met Leu Ala Gly Met Gly Pro Met Gly
305                 310                 315                 320

Leu Gly Leu Pro Pro Pro Pro Gly Met Pro Pro Pro Pro Pro Gly Met
                325                 330                 335

Pro Pro Gly Met Pro Pro Gly Met Pro Pro Gly Met Pro Ala Met Met
            340                 345                 350

Gln Gly Leu Ser Met Ala Gly Met Ser His Leu Ala Ala Ala Gly Met
        355                 360                 365

```
Arg Pro Pro Pro Gly Ala Leu Gly Gly His Leu Gly Gly Pro Gly Leu
    370                 375                 380

Ser Pro Phe Gly Pro Pro Pro Pro Pro Gly Ala Asp Pro Ala Asn Met
385                 390                 395                 400

Met Ala Asn Met Ser Ser Met Met Ala Asn Met Gln Ala Ala Leu Ala
                405                 410                 415

Phe Gln Ala Asp Ala Ala Ala Ala Ala Gln His Gln Ala Ala Ser Thr
            420                 425                 430

Gly Ser Val Ala Pro Gly Arg Gln Gln Gln Val His Gln His Gln Gln
        435                 440                 445

Ala Val Gly Met Ala Val Asp Asp Ala Ala Ala Phe Pro Ser Pro Gly
    450                 455                 460

Cys Arg Pro Asn Gly Ser Ala Asp Ala Gly Ala Gln Ser Ala Ala Glu
465                 470                 475                 480

Pro Asn Asp Phe Ser Arg Val Phe Asp Asp Pro Phe Ala Gln Pro Ala
                485                 490                 495

Ala Ser Pro Ser Gly Ala Ala Ala Ala Gly Ser Asn Glu Ala Pro Gly
            500                 505                 510

Met Asp Asp Phe Leu Asp Phe Phe Leu Lys Ser
        515                 520


<210> SEQ ID NO 13
<211> LENGTH: 834
<212> TYPE: PRT
<213> ORGANISM: Volvox carteri

<400> SEQUENCE: 13

Met Asp Gly Arg Ala Glu Gly Thr Val Ala Ile Lys Gln Glu Asp His
1               5                   10                  15

Ala Ser Gly His Trp His Asn Phe Pro Ala Gly Leu Arg Leu Leu Val
            20                  25                  30

Val Asp Asp Asp Pro Leu Cys Leu Lys Val Val Glu Gln Met Leu Arg
        35                  40                  45

Lys Cys Ser Tyr Asp Val Thr Thr Cys Thr Asn Ala Thr Met Ala Leu
    50                  55                  60

Asn Leu Leu Arg Asp Lys Ser Thr Glu Tyr Asp Leu Val Leu Ser Asp
65                  70                  75                  80

Val Tyr Met Pro Asp Met Asp Gly Phe Lys Leu Leu Glu Val Val Gly
                85                  90                  95

Leu Glu Met Asp Leu Pro Val Ile Met Met Ser Ser Asn Gly Asp Thr
            100                 105                 110

Ser Asn Val Leu Arg Gly Val Thr His Gly Ala Cys Asp Tyr Leu Ile
        115                 120                 125

Lys Pro Val Arg Leu Glu Glu Leu Arg Asn Leu Trp Gln His Val Val
    130                 135                 140

Arg Arg Arg Arg Gln Leu Asn Leu Asp Met Asp Ser Asp Glu His Ser
145                 150                 155                 160

Gln Glu Arg Asp Asp Asp Gln Gly Arg Lys Arg Lys Ala Asp Thr Ala
                165                 170                 175

Gly Cys Ile Gly Asp Gln Leu Arg Met Met Gly Ala Gly Cys Ser Gly
            180                 185                 190

Gly Ala Asn Gly Leu Gly Ser Thr Gly Asn Leu Gly Ala Val Ala Thr
        195                 200                 205

Gly Ser Ala Gly Leu Gly Leu Gly Leu Gly Thr Ala Ala Asp Glu Leu
```

-continued

```
    210                 215                 220

Gly Leu Gly Leu Asp Asn Gly Ser Ser Lys Lys Ala Arg Val Val Trp
225                 230                 235                 240

Ser Val Glu Met His Gln Gln Phe Val Asn Ala Val Asn Gln Leu Gly
                245                 250                 255

Ile Asp Lys Ala Val Pro Lys Lys Ile Leu Glu Ile Met Asn Val Asp
            260                 265                 270

Gly Leu Thr Arg Glu Asn Val Ala Ser His Leu Gln Lys Tyr Arg Leu
        275                 280                 285

Tyr Leu Lys Arg Val Ser Gly Ala Gln Gln Pro Gly Gln Asn Arg Val
    290                 295                 300

Ser Arg Pro Ser Pro Pro Gln Pro Gln Ser Pro Gln Val Pro Ser Gln
305                 310                 315                 320

Gln Gln Gln Ser Leu Pro Gly Gly Gly Gly Ala Ala Ala Ala Gly Ala
                325                 330                 335

Gly Gln Leu Gln Gly Gly Gly Gly Ala Ala Ala Ala Ala Ala Ser Leu
            340                 345                 350

Ala Ser Ile Leu Ala Gly Gly Gly Pro Ala Gly Gly Gly Ala Gly Ala
        355                 360                 365

Gly Pro Pro Pro Gly Gly Gly Gln Leu Gly Ala Asp Gly Gly Gly Pro
    370                 375                 380

Gly Pro Gly Leu Ser Ser Ala Val Ala Asn Ala Met Ser Ala Ala Ala
385                 390                 395                 400

Ala Ala Gly Gly Phe Pro Thr Pro Pro Pro Pro Pro Pro Pro His Pro
                405                 410                 415

Ala Ala Leu Leu Ala Ala Asn Pro Met Met Ala Ala Ala Ala Gly Leu
            420                 425                 430

Asn Pro Leu Leu Gly Ala Met Gly Gly Leu Gly Val Gly Pro Leu Gly
        435                 440                 445

Pro Leu Asn Pro Leu Asn Gly Met Pro Met Pro Gly Met Gln Pro Pro
    450                 455                 460

Leu Gly Leu Leu Pro Gly Leu Pro Gly Pro Gly Gly Gln Leu Gly Leu
465                 470                 475                 480

Gly Pro Leu Gly Pro Ile Gly Leu Pro Gly Pro Gly Pro Leu Pro Ser
                485                 490                 495

Leu Pro Ala Gly Leu Pro Leu Asn Pro Met Ala Asn Gly Leu Gln Gln
            500                 505                 510

Met Ala Ala Ala Asn Leu Met Gln Gly Met Ala Gly Met Gly Gln Leu
        515                 520                 525

Pro Ala Leu Ser Met Asn Gly Met Asn Gly Ile Met Gly Pro Leu Pro
    530                 535                 540

Gly Val Gly Leu Pro Gly Pro Gln Gln His Leu Phe Pro Gln Gln Gln
545                 550                 555                 560

Gln Pro His Leu Gln Gln Gln Gln Gln Gln Gln Gln Gln Lys Asp Leu
                565                 570                 575

Gln Met Ala Gln Lys Gln His Gln Ala Ala Ala Ala Ala Ala Ala Val
            580                 585                 590

Ala Ala Ala Val Ala Ala Ala Gln His Gln Gln Gln Gln Pro Gln Ala
        595                 600                 605

Gln Gln Gln Pro Gln Pro Gln Gln Gln Gln Gln Pro Gly Lys Leu
    610                 615                 620

Pro Gln Ala Thr Val Gly Thr Pro Ala Leu Ala Ser Pro Ala Gly Ala
625                 630                 635                 640
```

```
Leu Pro Arg Gln Pro Ser Gly Gln His Pro His Thr Leu Ser Ser Ser
                645                 650                 655

Ser Leu His Thr Gln Gln Pro His Gln Gln Gln Leu Leu His Ser Gln
            660                 665                 670

Pro Ser Ser Thr His Leu Ala Thr Asn Asn Thr Leu Ala Met Ala Pro
        675                 680                 685

Ala Leu Asn Gly Thr Leu Asp Val Gly Gly Lys Gly His Leu His Ala
    690                 695                 700

Ala Gly Gly Gln Gly Ala Gly Ala Gly Ala Gly Ala Val Leu Asp Ile
705                 710                 715                 720

Pro Pro Asp Leu Ile Gly Gly Leu Ile Glu Asp Gly Phe Gly Ala Pro
                725                 730                 735

Pro Gly Pro Thr Ile Gln Leu Ala His Gly Thr Ala Ala Val Leu Asp
            740                 745                 750

Pro Thr Met Leu Leu Asp Glu Gly Asp Asn Ser Asp Phe Ala Ala Val
        755                 760                 765

Phe Gln Glu Met Ser Ser Tyr Gly Gly Gly Gly Val Ile Gly Gly Gly
    770                 775                 780

Gly Ser Gly Ala Gly Ala Met Gly Val Leu Gly His Gly Leu Leu Ala
785                 790                 795                 800

Ala Gly Gly Pro Val Met Val Asp Val Ala Ala Gly Leu Ala Gly Val
                805                 810                 815

Thr Glu Thr Ala Thr Arg Val Asp Asp Asp Phe Leu Asn Phe Leu Leu
            820                 825                 830

Lys Ser


<210> SEQ ID NO 14
<211> LENGTH: 446
<212> TYPE: PRT
<213> ORGANISM: Tetraselmis sp.

<400> SEQUENCE: 14

Met Ser Cys Thr Val Ala Ser Phe Pro Pro Ala Ala Gly Gly Gln Gly
1               5                   10                  15

Ser Pro Ala Thr Pro Val Pro Tyr Gln Asp Leu Leu Val Lys Arg Gln
            20                  25                  30

Asp Gln Trp Ser Asn Phe Pro Ala Gly Leu Arg Val Leu Val Ala Asp
        35                  40                  45

Asn Asp Pro Ala Ser Leu Gln Gln Val Glu Lys Met Leu Lys Lys Cys
    50                  55                  60

Ser Tyr Gln Val Thr Leu Cys Ser Ser Gly Lys Asn Ser Leu Glu Ile
65                  70                  75                  80

Leu Arg Lys Arg Arg Glu Glu Phe Asp Leu Val Leu Ala Asp Ala Asn
                85                  90                  95

Leu Pro Asp Ile Asp Gly Phe Lys Leu Leu His Val Cys His Thr Glu
            100                 105                 110

Leu Ser Leu Pro Val Val Leu Met Ser Gly Thr Ser Asp Thr Gln Leu
        115                 120                 125

Val Met Arg Gly Val Met Asp Gly Ala Arg Asp Phe Leu Ile Lys Pro
    130                 135                 140

Leu Arg Val Glu Glu Leu Lys Val Leu Trp Gln His Leu Val Arg Phe
145                 150                 155                 160

Thr Ser Glu Ile Thr Lys Thr Asp Ala Gln Leu Asn Val Val Lys Val
                165                 170                 175
```

```
Glu Leu Asp Gly Gly Arg Pro Ala Gly Glu Val Ser Thr Ser Gln Asn
            180                 185                 190

Gly Ser Gln Cys Thr Glu Arg Glu Gly Glu Gly Asn Ser Ser Lys Lys
        195                 200                 205

Gln Arg Met Asn Trp Ser Asp Glu Met His Gln Gln Phe Val Asn Ala
    210                 215                 220

Val Asn Gln Leu Gly Ile Asp Lys Ala Val Pro Lys Arg Ile Leu Asp
225                 230                 235                 240

Leu Met Ser Val Glu Gly Leu Thr Arg Glu Asn Val Ala Ser His Leu
                245                 250                 255

Gln Lys Tyr Arg Ile Tyr Leu Lys Arg Met Ala Asn His Gln Glu Asn
            260                 265                 270

Gly Lys Gln Ala Val Met Ser Thr Asp Thr Ile Ala Arg Ala Glu Ala
        275                 280                 285

Ala Tyr Gln Gly Gly Met Pro Gln Gly Gln Gln Met Met Gln Gln Glu
    290                 295                 300

His Ser Gly Gln Ala Val Gln Tyr Ser Gln Pro His Ala Pro Gly Gly
305                 310                 315                 320

Leu His Gln Gln Ala Met Pro Ala Gln Met His Met Gly Met Met Pro
                325                 330                 335

Ala Gly Pro Gln Pro Gly Ser Met Gln Met Ala Pro His His Val Met
            340                 345                 350

Gln Met Pro Asn Gly Gln Val Met Val Met Gln Gln Met Gly Pro Arg
        355                 360                 365

Pro Gly Met Pro Pro Gly Met Pro Gln Gln Met Met Ala Ser Ser Gln
    370                 375                 380

Gln Met Gly Met Leu Gln Pro Gly Met Pro Ala Gly Gln Met Leu His
385                 390                 395                 400

Phe Gln His Pro Gln Gln Val His Gln His Pro Pro Ser Ser Gly Pro
                405                 410                 415

Met His Ala Val Gln His Met Glu Tyr Ala Tyr Ser Gln Pro Met Gln
            420                 425                 430

Met Ala Gly Trp Pro Val Gln Gly Gln Pro Gly Asn Gln Ala
        435                 440                 445


<210> SEQ ID NO 15
<211> LENGTH: 490
<212> TYPE: PRT
<213> ORGANISM: Tetraselmis sp.

<400> SEQUENCE: 15

Met Thr Pro Thr Pro Pro Met Ser Cys Thr Val Ala Ser Phe Pro Pro
1               5                   10                  15

Ala Ala Gly Gly Gln Gly Ser Pro Ala Thr Pro Val Pro Tyr Gln Asp
            20                  25                  30

Leu Leu Val Lys Arg Gln Asp Gln Trp Ser Asn Phe Pro Ala Gly Leu
        35                  40                  45

Arg Val Leu Val Ala Asp Asn Asp Pro Ala Ser Leu Gln Gln Val Glu
    50                  55                  60

Lys Met Leu Lys Lys Cys Ser Tyr Gln Val Thr Leu Cys Ser Ser Gly
65                  70                  75                  80

Lys Asn Ser Leu Glu Ile Leu Arg Lys Arg Arg Glu Glu Phe Asp Leu
                85                  90                  95

Val Leu Ala Asp Ala Asn Leu Pro Asp Ile Asp Gly Phe Lys Leu Leu
```

```
            100                 105                 110

His Val Cys His Thr Glu Leu Ser Leu Pro Val Val Leu Met Ser Gly
        115                 120                 125

Thr Ser Asp Thr Gln Leu Val Met Arg Gly Val Met Asp Gly Ala Arg
    130                 135                 140

Asp Phe Leu Ile Lys Pro Leu Arg Val Glu Glu Leu Lys Val Leu Trp
145                 150                 155                 160

Gln His Leu Val Arg Phe Thr Ser Glu Ile Thr Lys Thr Asp Ala Gln
                165                 170                 175

Leu Asn Val Val Lys Val Glu Leu Asp Gly Gly Arg Pro Ala Gly Glu
            180                 185                 190

Val Ser Thr Ser Gln Asn Gly Ser Gln Cys Thr Glu Arg Glu Gly Glu
        195                 200                 205

Gly Asn Ser Ser Lys Lys Gln Arg Met Asn Trp Ser Asp Glu Met His
    210                 215                 220

Gln Gln Phe Val Asn Ala Val Asn Gln Leu Gly Ile Asp Lys Ala Val
225                 230                 235                 240

Pro Lys Arg Ile Leu Asp Leu Met Ser Val Glu Gly Leu Thr Arg Glu
                245                 250                 255

Asn Val Ala Ser His Leu Gln Lys Tyr Arg Ile Tyr Leu Lys Arg Met
            260                 265                 270

Ala Asn His Gln Glu Asn Gly Lys Gln Ala Val Met Ser Thr Asp Thr
        275                 280                 285

Ile Ala Arg Ala Glu Ala Ala Tyr Gln Gly Gly Met Pro Gln Gly Gln
    290                 295                 300

Gln Met Met Gln Gln Glu His Ser Gly Gln Ala Val Gln Tyr Ser Gln
305                 310                 315                 320

Pro His Ala Pro Gly Gly Leu His Gln Gln Ala Met Pro Ala Gln Met
                325                 330                 335

His Met Gly Met Met Pro Ala Gly Pro Gln Pro Gly Ser Met Gln Met
            340                 345                 350

Ala Pro His His Val Met Gln Met Pro Asn Gly Gln Val Met Val Met
        355                 360                 365

Gln Gln Met Gly Pro Arg Pro Gly Met Pro Pro Gly Met Pro Gln Gln
    370                 375                 380

Met Met Ala Ser Ser Gln Gln Met Gly Met Leu Gln Pro Gly Met Pro
385                 390                 395                 400

Ala Gly Gln Met Leu His Phe Gln His Pro Gln Gln Val His Gln His
                405                 410                 415

Pro Pro Ser Ser Gly Pro Met His Ala Gly Gly Glu Met Ile Asp Pro
            420                 425                 430

Gly Ser Met Gln Arg Leu His Gln Gln Pro His Tyr Ile Gly Pro Asn
        435                 440                 445

Gly Gln His Met Pro Ala Pro Ala Met Gly Met Pro Ser Gly Thr Val
    450                 455                 460

Gln His Met Glu Tyr Ala Tyr Ser Gln Pro Met Gln Met Ala Gly Trp
465                 470                 475                 480

Pro Val Gln Gly Gln Pro Gly Asn Gln Ala
                485                 490
```

<210> SEQ ID NO 16
<211> LENGTH: 574
<212> TYPE: PRT
<213> ORGANISM: Tetraselmis sp.

-continued

<400> SEQUENCE: 16

```
Met Thr Met Pro Leu Gly Gly Gly Leu Cys Met Lys Asp Arg Ile His
1               5                   10                  15

Gly Asp Glu Arg Tyr Arg Ser Lys Ala Lys Arg Gln Val Asn Thr Ile
            20                  25                  30

Phe Ala Phe Thr Gln Arg Asn Thr Trp Arg Gly Arg Phe Arg Leu Cys
        35                  40                  45

Ser Tyr Arg Thr Thr Glu Leu Leu Gly Gly Ser Lys Thr Thr Glu Pro
    50                  55                  60

Gly Arg Gly Thr Phe Val Leu Gln Ile Phe Met Cys Val Lys Asn Ala
65                  70                  75                  80

Ser Ile Asp Asp Gly Ser Arg His Ile Ser Thr Ser Arg Gly Leu Glu
                85                  90                  95

Ser Val Leu Lys Arg Arg Gly Gly Gln Gly Ala Pro Ala Ala Pro Val
            100                 105                 110

Pro Tyr His Asp Leu Leu Val Lys Arg Gln Asp Gln Trp Ser Asn Phe
        115                 120                 125

Pro Ala Gly Leu Arg Val Leu Val Ala Asp Asn Asp Pro Ala Ser Leu
    130                 135                 140

Gln Gln Val Glu Lys Met Leu Lys Lys Cys Ser Tyr Gln Val Thr Leu
145                 150                 155                 160

Cys Ser Ser Gly Lys Asn Ser Leu Glu Ile Leu Arg Lys Arg Arg Glu
                165                 170                 175

Glu Phe Asp Leu Val Leu Ala Asp Ala Asn Leu Pro Asp Ile Asp Gly
            180                 185                 190

Phe Lys Leu Leu His Val Cys His Thr Glu Leu Ser Leu Pro Val Val
        195                 200                 205

Leu Met Ser Gly Thr Ser Asp Thr Gln Leu Val Met Arg Gly Val Met
    210                 215                 220

Asp Gly Ala Arg Asp Phe Leu Ile Lys Pro Leu Arg Val Glu Glu Leu
225                 230                 235                 240

Lys Val Leu Trp Gln His Leu Val Arg Phe Thr Ser Glu Ile Thr Lys
                245                 250                 255

Thr Asp Ala Gln Leu Asn Val Val Lys Val Glu Leu Asp Ser Gly Arg
            260                 265                 270

Pro Ala Gly Glu Val Ser Thr Ser Gln Asn Gly Ser Gln Cys Ala Glu
        275                 280                 285

Arg Glu Gly Glu Gly Asn Ser Ser Lys Lys Gln Arg Met Asn Trp Ser
    290                 295                 300

Asp Glu Met His Gln Gln Phe Val Asn Ala Val Asn Gln Leu Gly Ile
305                 310                 315                 320

Asp Lys Ala Val Pro Lys Arg Ile Leu Asp Leu Met Ser Val Glu Gly
                325                 330                 335

Leu Thr Arg Glu Asn Val Ala Ser His Leu Gln Lys Tyr Arg Ile Tyr
            340                 345                 350

Leu Lys Arg Met Ala Asn His Gln Glu Asn Gly Lys Gln Ala Val Met
        355                 360                 365

Ser Thr Asp Thr Ile Ala Arg Ala Glu Ala Ala Tyr Gln Gly Gly Met
    370                 375                 380

Pro Gln Gly Gln Gln Met Met Gln Gln Glu His Ser Gly Gln Ala Val
385                 390                 395                 400

Gln Tyr Ser Gln Pro His Ala Pro Ser Gly Leu His Gln Gln Ala Met
```

```
                405                 410                 415

Pro Ala Gln Met His Met Gly Met Met Pro Ala Gly Pro Gln Pro Gly
            420                 425                 430

Ser Met Gln Met Ala Pro His His Val Met Gln Met Pro Asn Gly Gln
        435                 440                 445

Val Met Val Met Gln Gln Met Gly Pro Arg Pro Gly Met Pro Pro Gly
    450                 455                 460

Met Pro Gln Gln Met Met Ala Ser Ser Gln Gln Met Gly Met Leu Gln
465                 470                 475                 480

Pro Gly Met Pro Ala Gly Gln Met Leu His Phe Gln His Pro Gln Gln
                485                 490                 495

Val His Gln His Pro Pro Ser Ser Gly Pro Met His Ala Gly Gly Glu
            500                 505                 510

Met Ile Asp Pro Gly Ser Met Gln Arg Leu His Gln Gln Pro His Tyr
        515                 520                 525

Ile Val Pro Asn Ala Gln His Met Pro Ala Pro Ala Met Gly Met Pro
    530                 535                 540

Pro Gly Ala Val Gln His Met Glu Tyr Ala Tyr Ser Gln Pro Met Gln
545                 550                 555                 560

Met Ala Gly Trp Pro Val Gln Gly Gln Pro Gly Ser Gln Ala
                565                 570


<210> SEQ ID NO 17
<211> LENGTH: 674
<212> TYPE: PRT
<213> ORGANISM: Oocystis sp.

<400> SEQUENCE: 17

Met Leu Ala Phe Thr His Gln Arg Met Thr Thr Ala Pro Ala Leu Ala
1               5                   10                  15

Val Ala Thr Ser His Phe Phe Ala His Val Arg Val Thr Thr Gly Ser
            20                  25                  30

Ser Ala Ile Ala Thr Val Phe Ala Ala Arg Ser Arg Gly Ser Gly Leu
        35                  40                  45

Leu Ala Gly Phe Asn Thr Met Glu Asn Val Lys Val Glu Val Pro Glu
    50                  55                  60

Val Val Pro Glu Asn Val Asn Phe Pro Ala Gly Leu Lys Val Leu Val
65                  70                  75                  80

Val Asp Asp Asp Pro Leu Cys Leu Lys Val Ile Asp Gln Met Leu Arg
                85                  90                  95

Arg Cys Asn Tyr Ala Ala Thr Thr Cys Gln Ser Ser Leu Glu Ala Leu
            100                 105                 110

Glu Leu Leu Arg Ser Ser Lys Glu Asn His Phe Asp Leu Val Leu Ser
        115                 120                 125

Asp Val Tyr Met Pro Asp Met Asp Gly Phe Lys Leu Leu Glu Ile Ile
    130                 135                 140

Gly Leu Glu Met Gly Leu Pro Val Ile Met Met Ser Ser Asn Gly Glu
145                 150                 155                 160

Thr Gly Val Val Phe Arg Gly Val Thr His Gly Ala Val Asp Phe Leu
                165                 170                 175

Ile Lys Pro Val Arg Ile Glu Glu Leu Arg Asn Leu Trp Gln His Val
            180                 185                 190

Val Arg Lys Thr Met Val Val Pro Ser Asn Asp Lys Ala Thr Ser Glu
        195                 200                 205
```

```
Glu Asp Gly Glu Glu Ser Lys His Arg Val Asp Arg Lys Arg Lys Glu
    210                 215                 220

Ser Phe His Ser Arg Ala Arg Glu Gln Val Glu Ile Ala Cys Ser Val
225                 230                 235                 240

Val Pro Ala Leu Leu Trp Pro Thr Val Pro Pro Ser Ser Val His Pro
                245                 250                 255

Thr Ser Ser Ser Phe Leu Arg Ser His Val Leu Leu Leu Gln Arg Ser
            260                 265                 270

Ser Gly Gly Lys Asp Val Leu Asp Glu Gly Gly Ser Asn Ala Lys Lys
        275                 280                 285

Pro Arg Val Val Trp Ser Val Glu Met His Gln Gln Phe Val Asn Ala
    290                 295                 300

Val Asn Gln Leu Gly Ile Asp Lys Ala Val Pro Lys Arg Ile Leu Asp
305                 310                 315                 320

Leu Met Asn Val Asp Gly Leu Thr Arg Glu Asn Val Ala Ser His Leu
                325                 330                 335

Gln Lys Tyr Arg Leu Tyr Leu Lys Arg Val Ala Gly Ile Asn Thr Ala
            340                 345                 350

Thr Gly Ser Arg Asn Gly Lys Gly Arg Ser Asp Val Ser Gly Leu Ser
        355                 360                 365

Gly Met Pro Asn Gly Ser Leu Pro Met Pro Gly Met Met Pro Pro His
    370                 375                 380

Met Ala Ala Gly Met Leu Leu Ala Gly Met Ala Ala Asp Val Gly Pro
385                 390                 395                 400

Arg Pro His Pro Phe Pro Ile Met Pro Met Pro Ala Met Ala Leu Gln
                405                 410                 415

Gly Met His Gly Gly Met Ala Gln Met Met Gln Leu Pro Pro Gly Met
            420                 425                 430

Pro Pro Pro Met Met Met Pro Met Ala Pro Leu Leu Pro Ser Gln Leu
        435                 440                 445

Ala Ala Leu Gly Gln Gln Gln Gln Gln Gln Gln Gln Gln Gln Val Ala
    450                 455                 460

Arg Ser Glu Ser Met Pro Ser Glu Asn Gly Val Ala Gly Pro Ser Gly
465                 470                 475                 480

Ser Phe Thr Ala Met Leu Asn Gly Pro Ala Pro Met Glu Ser Ser Pro
                485                 490                 495

Phe Ala Ala Leu Gln Val Phe Gly Pro Pro Gln Gly Met Glu Gln Leu
            500                 505                 510

Thr Gln Gln Gln Gln Gln Gln Gln Gln Ala Gly Ala Ala Ala Phe Val
        515                 520                 525

Ala Ala Phe Ala Ala Ala Asn Gly Gly Asp Met Gln Gly Gly Gly Gly
    530                 535                 540

Gly Pro Gly Pro Met Leu Gly Gly Ala Gly Gly Ala Gly Pro Leu Leu
545                 550                 555                 560

Gly Gly Val Gly Gly Gly Asp Pro Leu His Gly Gly Gly Gly Ser Ser
                565                 570                 575

Ala Leu Gly Gly Arg Pro Met Met Ser Ala Glu Gln Pro Met Gly Gly
            580                 585                 590

Ser Gly Gly Leu Ala Ser Asn Ser Leu Thr Val Gln Gln Asn Asp Leu
        595                 600                 605

Ala Gln Met Cys Ser Gln Leu Asp Val Asn Gly Leu Gln Ala Val Ala
    610                 615                 620

Ala Ala Ala Ala Ala Gly Ala Met Gly Ala Pro Gly Gly Ala Gly Gly
```

```
625                 630                 635                 640

Ala Met Pro Pro Ser Ser Val Gly Gly Val Gly Pro Asp Met Lys Leu
                645                 650                 655

Thr Glu Gln Asp Asp Phe Phe Ser Phe Leu Leu Lys Asp Ser Asn Leu
            660                 665                 670

Ile Asp


<210> SEQ ID NO 18
<211> LENGTH: 488
<212> TYPE: PRT
<213> ORGANISM: Micromonas sp.

<400> SEQUENCE: 18

Met Ser Thr Pro Ala Val Ser Lys Gly Phe Pro Ile Gly Leu Arg Val
1               5                   10                  15

Leu Val Val Asp Asp Asp Pro Leu Cys Leu Lys Ile Val Glu Lys Met
            20                  25                  30

Leu Lys Arg Cys Gln Tyr Glu Val Thr Thr Phe Ser Arg Gly Ala Glu
        35                  40                  45

Ala Leu Lys Thr Leu Arg Glu Arg Lys Asp Asp Phe Asp Ile Val Leu
    50                  55                  60

Ser Asp Val His Met Pro Asp Met Asp Gly Phe Lys Leu Leu Glu His
65                  70                  75                  80

Ile Ala Leu Glu Leu Asp Ile Pro Val Met Met Met Ser Ala Asn Cys
                85                  90                  95

Ala Thr Asp Val Val Leu Arg Gly Ile Ile His Gly Ala Val Asp Tyr
            100                 105                 110

Leu Leu Lys Pro Val Arg Ile Glu Glu Leu Arg Asn Ile Trp Gln His
        115                 120                 125

Val Val Arg Arg Lys Arg Glu Ser Ser Gln Gly Asn Leu Arg Ser Gly
    130                 135                 140

Glu Gly Gly Ser Asn Gly Arg Thr Val Ser Gly Gly Ser Thr Gly Glu
145                 150                 155                 160

Gly Gly Gly Lys Asp Ser Lys Gly Ser Ser Glu Gln His Gly Asp Ala
                165                 170                 175

Lys Asp Lys Thr Gly Ser Ala Gly Gly Ser Gly Gly Ser Ser Lys Arg
            180                 185                 190

Lys Lys Gly Ser Gly Lys Lys Gly Asp Glu Gly Thr Asp Glu Val Lys
        195                 200                 205

Asp Gly Ser Gly Gly Asp Glu Asn Glu Asp Ser Ser Ala Leu Lys Lys
    210                 215                 220

Pro Arg Val Val Trp Ser Ala Glu Leu His Gln Gln Phe Val Thr Ala
225                 230                 235                 240

Val Asn Gln Leu Gly Ile Asp Lys Ala Val Pro Lys Arg Ile Leu Asp
                245                 250                 255

Leu Met Gly Val Gln Gly Leu Thr Arg Glu Asn Val Ala Ser His Leu
            260                 265                 270

Gln Lys Tyr Arg Leu Tyr Leu Lys Arg Leu Gln Gly Val Asn Ser Gly
        275                 280                 285

Gly Ala Pro Gly Gly Gly Pro Gly Phe Met Ser Pro Ile Ala Leu Asp
    290                 295                 300

Gly Ser Met Val Gln Gly Gly Pro Gly Gly Arg Val Gly Ser Pro Ala
305                 310                 315                 320

Ile Gly Gly Pro Asn Gly Pro Ile Met Val Gly His Gly His Ile Asp
```

-continued

```
                325                 330                 335

Pro Ala Met Leu Ala Gly Gly Ala Pro Gln Thr Ile Gln Met Gly Met
            340                 345                 350

Val Tyr Gly Gly Pro Gly Met Gly Pro Pro Gln Met Met Ala Pro Asn
        355                 360                 365

Gly Lys Gly Gly Gly Gly Met Pro Gly Gly Tyr Val Met Gln Pro Gly
    370                 375                 380

Gln Met Met Ala Pro Asn Gly Gln Met Met Pro Val Gly Gln Met Gly
385                 390                 395                 400

Pro Gly Gly Met Met Val Gln Gly Pro Gly Gly Gly Met Met Gln Met
                405                 410                 415

His Asp Gly Gly Met Met Asn Gly Asn Gly Ser Tyr Gly Ser Leu Gln
            420                 425                 430

Asn Met Lys Gln Gly Asn Gly Val Val Met Met Pro Asn Gly Gly Met
        435                 440                 445

Gly Gly Val Asp Gly Ala Ile Pro Asn Met Ala Thr Gly Leu Ile Asn
    450                 455                 460

Gly Gln Gly Leu Pro Asp Asp Asp Val Leu Asp Met Phe Leu Lys Asp
465                 470                 475                 480

Gly Leu Pro Glu Gly Glu Gly Phe
                485
```

<210> SEQ ID NO 19
<211> LENGTH: 544
<212> TYPE: PRT
<213> ORGANISM: Micromonas pusilla

<400> SEQUENCE: 19

```
Met Thr Ala Glu Lys Lys Glu Leu Lys Val Phe Pro Ala Gly Leu Arg
1               5                   10                  15

Val Leu Val Val Asp Asp Asp Pro Leu Cys Leu Arg Ile Val Glu Lys
            20                  25                  30

Met Leu Lys Arg Cys Gln Tyr Glu Val Thr Thr Phe Ser Arg Gly Ala
        35                  40                  45

Glu Ala Leu Glu Thr Leu Arg Ala Arg Arg Asp Asp Phe Asp Ile Val
    50                  55                  60

Leu Ser Asp Val His Met Pro Asp Met Asp Gly Phe Lys Leu Leu Glu
65                  70                  75                  80

His Ile Ala Leu Glu Leu Asp Val Pro Val Met Met Met Ser Ala Asn
                85                  90                  95

Cys Ala Thr Asp Val Val Leu Arg Gly Ile Ile His Gly Ala Val Asp
            100                 105                 110

Tyr Leu Leu Lys Pro Val Arg Leu Glu Glu Leu Arg Asn Ile Trp Gln
        115                 120                 125

His Val Val Arg Arg Gln Arg Glu Pro Ser Lys Asp Gly Ala Ala Gly
    130                 135                 140

Lys Gly Gly Gly Ala Ser Gly Ala Pro Glu Val Ser Gly Asp Thr His
145                 150                 155                 160

Ala Asn Thr Asp Asp Lys Gln Asp Gly Asn Ala Thr Asp Ser Lys Gly
                165                 170                 175

Ser Gly Ser Gln Lys Arg Lys Ser Gly Lys Ser Gly Asp Asp Gly Gly
            180                 185                 190

Lys Asp Gly Gly Gly Ser Gly Gly Lys Asp Gly Asp Ala Ser Asn Lys
        195                 200                 205
```

-continued

Gly Asn Asn Asn Lys Arg Lys Lys Gly Lys Ser Asn Asp Ala Thr Glu
    210                 215                 220

Thr Ala Gly Gly Ala Gly Val Glu Asp Asn Asp Asp Thr Ser Gly Leu
225                 230                 235                 240

Lys Lys Pro Arg Val Val Trp Ser Pro Glu Leu His Gln Gln Phe Val
                245                 250                 255

Thr Ala Val Asn Gln Leu Gly Ile Asp Lys Ala Val Pro Lys Arg Ile
            260                 265                 270

Leu Asp Leu Met Gly Val Gln Gly Leu Thr Arg Glu Asn Val Ala Ser
        275                 280                 285

His Leu Gln Lys Tyr Arg Leu Tyr Leu Lys Arg Leu Gln Gly Val Asn
    290                 295                 300

Asn Asn Gly Thr Val Pro Ser Gly Ala Ala Gly Phe Met Thr Gly Leu
305                 310                 315                 320

Ala Ile Asp Gly Val Gly Gly Val Met Gly Pro Pro Thr Thr Gly Ser
                325                 330                 335

Pro Ala Met Asn Gly Pro Gly Gly Pro Gly Gly Gly Leu Val Met Gly
            340                 345                 350

Pro Gly His Met Gly Gly Pro His Met Asp Gly Ser Gly Met Met His
        355                 360                 365

Met Gly Pro Gly Gly Pro Met Ala Gly Met Thr Val Val Tyr Gly Gly
    370                 375                 380

Gly Met Pro Gly Gly Met Pro Gly Gly Ala Asp Ser Lys Asn Gly Ala
385                 390                 395                 400

Ser Gly Gln Pro Pro Pro Gly Gly Tyr Val Val Met Gly Gly Pro His
                405                 410                 415

Gly Gly Gly Pro Gly Gly Ala Pro Met Met Met Gln His Gly Gly Met
            420                 425                 430

Val Pro Gly Pro Gly Pro Gly Leu Val Pro Gly Pro Gly Gly Ser Leu
        435                 440                 445

Met Met Pro Ala Gly Met Met Pro Asp Gly Gly Gly Gly Met Val Gly
    450                 455                 460

Val His Val Gly Pro Gly Val Val Met Gly Gln His Gln Leu Gly Gly
465                 470                 475                 480

Lys His Ser Ser Gly Gly Ala Gly Met Ala Gly Gly Ser Ala Ala Gly
                485                 490                 495

Lys Gly Ala Gln Arg Gly Gly Val Gly Gly Ala Phe Asp Val Pro Pro
            500                 505                 510

Thr Asn Gly Ser Leu Asp Ala Asp Glu Ile Gly Asp Asp Val Leu Thr
        515                 520                 525

Met Phe Leu Lys Asp Gly Leu Pro Glu Met Asn Asp Gly Asp Ala Leu
    530                 535                 540

<210> SEQ ID NO 20
<211> LENGTH: 776
<212> TYPE: PRT
<213> ORGANISM: Sphagnum fallax

<400> SEQUENCE: 20

Met Ser Gly Gly Asp Leu Ser Arg Val Arg Glu Gly Thr Ala Asp Leu
1               5                   10                  15

Asp Pro Val Met Ala Ser His Gln His Pro Pro Pro Arg Gln Gln Ser
            20                  25                  30

His Gln Gln Pro Lys Asn His Gln Gln Glu Ala His Gln Gln His Cys
        35                  40                  45

-continued

Ser Ser Ala Glu Thr Thr Ser Pro Asn Asn Thr Ala Arg Gly Ala Gly
50 55 60

Ala Thr Tyr Gly Lys Met Glu Pro Ala Asp Asp Phe Pro Ala Gly Leu
65 70 75 80

Arg Ile Leu Val Val Asp Asp Asp Pro Thr Cys Leu Ala Ile Leu Lys
85 90 95

Lys Met Leu Gln Gln Cys Ser Tyr Gln Val Thr Thr Cys Gly Arg Ala
100 105 110

Thr Arg Ala Leu Glu Leu Leu Arg Glu Asp Lys Asp Lys Phe Asp Leu
115 120 125

Val Ile Ser Asp Val Tyr Met Pro Asp Met Asp Gly Phe Lys Leu Leu
130 135 140

Glu Leu Val Gly Leu Glu Met Asp Leu Pro Val Ile Met Met Ser Gly
145 150 155 160

Asn Gly Glu Thr Ser Val Val Met Lys Gly Ile Thr His Gly Ala Cys
165 170 175

Asp Tyr Leu Leu Lys Pro Val Arg Ile Glu Glu Leu Ser Asn Ile Trp
180 185 190

Gln His Val Val Arg Lys Leu Arg Ser Glu Pro Lys Glu His Ser Ala
195 200 205

Ser Leu Glu Asp Gly Asp Arg Gln Arg Arg Gly Gly Ala Glu Asp Ala
210 215 220

Asp Asn Thr Ser Ser Ala Ala Asp Thr Ala Asp Gly Ile Trp Arg Asn
225 230 235 240

Lys Lys Lys Lys Glu Ala Lys Glu Asp Glu Glu Asp Phe Glu Gln Asp
245 250 255

Asn Asp Asp Pro Ser Thr Leu Lys Lys Pro Arg Val Val Trp Ser Val
260 265 270

Glu Leu His Gln Gln Phe Val Ser Ala Val Asn Gln Leu Gly Ile Asp
275 280 285

Lys Ala Val Pro Lys Arg Ile Leu Glu Leu Met Ser Val Gln Gly Leu
290 295 300

Thr Arg Glu Asn Val Ala Ser His Leu Gln Lys Tyr Arg Leu Tyr Leu
305 310 315 320

Lys Arg Leu Ser Gly Val Thr Ser Gln Ser Asn Ser Leu Asn Val Ser
325 330 335

Phe Gly Gly Pro Asp Ala Gly Tyr Gly Gly Leu Phe Gly Leu Asp Glu
340 345 350

Met Ser Asp Tyr Arg Asn Leu Val Thr Asn Gly His Leu Pro Ala Gln
355 360 365

Thr Ile Ala Ala Leu His His Ala Asn Met Ala Gly Arg Leu Gly Ala
370 375 380

Ser Ser Gly Met Val Gly Pro Ser Ser Pro Leu Asp Pro Ser Val Leu
385 390 395 400

Ala Gln Ile Ala Ala Leu Gln Ser Gly Ser Leu Pro Arg Pro Gly Met
405 410 415

Asp Gly Ser Leu Gln Gly Asn Gln Ala Gly Leu Leu Gln Ser Leu Ser
420 425 430

Gly Ala Leu Asp Tyr Asn Ser Leu His Gln Ser His Leu Leu Pro Ala
435 440 445

Ile Gly Gln Leu Gly Gln Leu Asp Glu Leu Pro Ser Leu Lys Ser Met
450 455 460

```
Gln His Gln Leu Gly Met Gly Ser Leu Gly Gly Ser Thr Arg Asn Leu
465                 470                 475                 480

Ala Gly Ser Pro Asn Glu Glu Leu Thr Met Gln Leu Leu Gln Gln Arg
                485                 490                 495

Ala Gln Gln Gln Ser Gly Gly Ser Pro Ile Asn Leu Pro Gln Ala Thr
            500                 505                 510

Gly Ile Leu Arg Pro Leu Ser Ser Asn Ile Asn Gln Gly Gly Ser Val
        515                 520                 525

Pro Asn Leu Val Gly Val Ile Pro Gly Thr Ala Ile Gly Leu Ser Asn
    530                 535                 540

Met Cys Ser Gly Gly Arg Glu Phe Gly Ser Ser Ser Gly Leu Leu Ser
545                 550                 555                 560

Ala Ser Gly Ser Leu Met Gln Ser Ser Thr Val Glu Ala Gln Asn Leu
                565                 570                 575

Asn Phe Gly Gly Ser Ser Gly Ser Ser Gly Cys Ser Phe Gln Ala Ser
            580                 585                 590

Val Leu Ser Ser Lys Thr Gly Gly Leu Glu Asp Leu Asn Pro Ala Lys
        595                 600                 605

Arg Val Arg Thr Thr Tyr Ser Ala Leu Ser His Ser Ser Pro Asp Leu
    610                 615                 620

Gly Gln Ser Ser Arg Pro Ala Trp Leu Gly Ser Gln Glu Gly Leu Val
625                 630                 635                 640

His Gly Asp Pro Val Tyr Ser Pro His Gln Leu Ser Leu Pro Arg Gln
                645                 650                 655

Asp Ile Val Gly Gly Ile Gly Ser Ser Gly Arg Pro Ala Tyr Met Gly
            660                 665                 670

Ser Gln Ser Met Gly Ser Leu Gly Met Asn Phe Pro Leu Ser Leu Ala
        675                 680                 685

Val Asp Ala Gly Ala Val Arg Pro Ser Leu Thr Arg Gly Gln Ser Leu
    690                 695                 700

Thr Glu Gln Val Ala Ala Asn Arg Glu Leu Lys Phe Pro Lys Glu Glu
705                 710                 715                 720

Arg Gly Arg Asp Asn Leu Met Cys Ala Arg Leu Gly Gly Gly Met Ile
                725                 730                 735

Thr Asn Glu Ser Ser Ser Glu Glu Leu Leu Asn Tyr Leu Lys Gln Ser
            740                 745                 750

His Glu Gly Leu Gly Phe Met Glu Gly Asp Leu Val Ser Asp Gly Tyr
        755                 760                 765

Pro Val Asp Asn Leu Tyr Val Lys
    770                 775
```

<210> SEQ ID NO 21
<211> LENGTH: 715
<212> TYPE: PRT
<213> ORGANISM: Physcomitrella patens

<400> SEQUENCE: 21

```
Met Gly Gly Gly Tyr Leu Ser Ser Thr Val Asn Met Gly Glu Ser Arg
1               5                   10                  15

Asp Gly Gly Ser Pro Ala Met Ala Thr Leu Gln Gln Gln Gln Lys His
            20                  25                  30

Gln Pro Leu Asn Pro Asn His Gln Asn Pro Arg Asn Arg Ser Asn Ser
        35                  40                  45

Ser Pro Thr Asn Cys Tyr Ser Asn Thr Ala Trp Gly Ala Lys Pro Ala
    50                  55                  60
```

-continued

```
Lys Leu Asp Thr Pro Asp Glu Phe Pro Val Gly Met Arg Val Leu Val
65                  70                  75                  80

Val Asp Asp Asn Pro Thr Cys Leu Met Ile Leu Glu Gln Met Leu Val
                85                  90                  95

Arg Cys Ala Tyr Arg Val Thr Thr Cys Gly Lys Ala Thr Glu Ala Leu
            100                 105                 110

Ser Met Leu Arg Glu Asp Ile Gly Lys Phe Asp Val Val Ile Ser Asp
        115                 120                 125

Val Asp Met Pro Asp Met Asp Gly Phe Lys Leu Leu Glu Leu Val Gly
    130                 135                 140

Leu Glu Met Asp Leu Pro Val Ile Met Val Ser Gly Asn Gly Glu Thr
145                 150                 155                 160

Ser Ala Val Met Lys Gly Ile Thr His Gly Ala Cys Asp Tyr Leu Leu
                165                 170                 175

Lys Pro Val Arg Ile Glu Glu Leu Arg Asn Ile Trp Gln His Val Val
            180                 185                 190

Arg Lys Lys Arg Arg Glu Val Lys Ala Val Ala Thr Lys Ser Val Glu
        195                 200                 205

Glu Ala Gly Gly Cys Glu Arg Pro Lys Arg Gly Gly Gly Ala Asp Asp
    210                 215                 220

Ala Asp Tyr Thr Ser Ser Ala Thr Asp Thr Thr Asp Ser Asn Trp Lys
225                 230                 235                 240

Leu Thr Lys Arg Arg Lys Gly Glu Phe Lys Asp Glu Asn Glu Glu Asp
                245                 250                 255

Asn Glu Gln Glu Asn Asp Asp Pro Ser Thr Leu Lys Arg Pro Arg Val
            260                 265                 270

Val Trp Ser Val Glu Leu His Gln Gln Phe Val Ser Ala Val Asn Gln
        275                 280                 285

Leu Gly Ile Asp Lys Ala Val Pro Lys Arg Ile Leu Glu Leu Met Gly
    290                 295                 300

Val Gln Gly Leu Thr Arg Glu Asn Val Ala Ser His Leu Gln Lys Tyr
305                 310                 315                 320

Arg Leu Tyr Leu Lys Arg Leu Ser Gly Val Thr Ser Gln Gln Gly Asn
                325                 330                 335

Met Ser Ala His Phe Gly Gly Ser Asp Pro Phe Cys Met Met Pro Pro
            340                 345                 350

Asp Met Ser Leu Ala Asn Gly Gln Leu Thr Pro Gln Ala Leu Ala Lys
        355                 360                 365

Phe His Met Leu Gly Arg Met Asn Ala Thr Asn Gly Ile Gly Phe Ser
    370                 375                 380

Gly Gly Gly Leu Asp Pro Gly Met Asn Gln Met Phe Leu Gln Asp Leu
385                 390                 395                 400

Pro Arg Pro Pro Gln Leu Asn Ser Met Leu Arg Asn Asn Thr Gly Leu
                405                 410                 415

Leu Ala Ser Val Pro Asn Gly Leu Gln His Leu Glu Gln Leu Ser Glu
            420                 425                 430

Pro His His Val His Val Val Asn Glu Leu Glu His Tyr Pro Ser Asn
        435                 440                 445

Thr Lys Val Tyr Pro Gln Leu Asn Gly Asn Leu Asp Val Ser Val Gly
    450                 455                 460

Pro Leu Gly Ala Ala Asn Gly Asn Leu Ala Ser Asn Pro Asn Ser Asp
465                 470                 475                 480
```

```
Thr Leu Leu Met His Ile Leu His Ser Arg Ala Ser Gln Gln Gly Val
                485                 490                 495

Gly Ser Pro Ser Thr Leu Pro Gln Pro Arg Cys Gly Leu Asn Pro Thr
            500                 505                 510

His Leu Leu Ser Asn Asp Ile Asn Phe Ala Pro Val Gly Ser Leu Pro
        515                 520                 525

Asn Leu Ala Gly Ser Leu Gly Pro Ala Val Gly Leu Ser Ala Ile Pro
    530                 535                 540

Gly Ser Ala Gly Gly Arg Asp Leu Ser Pro Ser Val Gly Gly Ser Gly
545                 550                 555                 560

Ala Ser Leu Ser Ser Pro Leu Gly Ser Leu Val Arg Arg Pro Leu Met
                565                 570                 575

Ala Glu Glu Gln Ser Asn Pro Val Asn Ser Thr Asn Gly Thr Tyr Ser
            580                 585                 590

Met Ala His Ser Gly Gln Ser Pro Lys Pro Ser Gly Asp Thr Leu Pro
        595                 600                 605

Thr Pro Leu Asn Glu Gly Leu Glu Gln Gln Gln Pro Leu Trp Ala Leu
    610                 615                 620

Tyr Gln Asn Pro Met Asn Gln Leu Ser His Gly Pro Ser Gln Gly Phe
625                 630                 635                 640

Pro His Asp Ser Leu Gln Trp Ser Val Leu Thr Glu Asn Leu Ser Phe
                645                 650                 655

Gly Asp Met Gly Gln Ser Leu Ser Ala Gly Leu Ile Ser Gln Phe Ser
            660                 665                 670

Ser Gln Gly Gln Asp Asn Gly Ile Gly Phe Ala Pro Pro Ser Gln Arg
        675                 680                 685

Gly Ser Tyr Thr Arg Gln Ser Val Ser Phe Pro Ala Ser Ser Ala Leu
    690                 695                 700

Asp Gly Arg Met Val Arg Ser Ser Tyr Glu Pro
705                 710                 715


<210> SEQ ID NO 22
<211> LENGTH: 664
<212> TYPE: PRT
<213> ORGANISM: Arabidopsis thaliana

<400> SEQUENCE: 22

Met Val Asn Pro Gly His Gly Arg Gly Pro Asp Ser Gly Thr Ala Ala
1               5                   10                  15

Gly Gly Ser Asn Ser Asp Pro Phe Pro Ala Asn Leu Arg Val Leu Val
            20                  25                  30

Val Asp Asp Asp Pro Thr Cys Leu Met Ile Leu Glu Arg Met Leu Met
        35                  40                  45

Thr Cys Leu Tyr Arg Val Thr Lys Cys Asn Arg Ala Glu Ser Ala Leu
    50                  55                  60

Ser Leu Leu Arg Lys Asn Lys Asn Gly Phe Asp Ile Val Ile Ser Asp
65                  70                  75                  80

Val His Met Pro Asp Met Asp Gly Phe Lys Leu Leu Glu His Val Gly
                85                  90                  95

Leu Glu Met Asp Leu Pro Val Ile Met Met Ser Ala Asp Asp Ser Lys
            100                 105                 110

Ser Val Val Leu Lys Gly Val Thr His Gly Ala Val Asp Tyr Leu Ile
        115                 120                 125

Lys Pro Val Arg Ile Glu Ala Leu Lys Asn Ile Trp Gln His Val Val
    130                 135                 140
```

-continued

```
Arg Lys Lys Arg Asn Glu Trp Asn Val Ser Glu His Ser Gly Gly Ser
145                 150                 155                 160

Ile Glu Asp Thr Gly Gly Asp Arg Asp Arg Gln Gln Gln His Arg Glu
                165                 170                 175

Asp Ala Asp Asn Asn Ser Ser Ser Val Asn Glu Gly Asn Gly Arg Ser
            180                 185                 190

Ser Arg Lys Arg Lys Glu Glu Glu Val Asp Asp Gln Gly Asp Asp Lys
        195                 200                 205

Glu Asp Ser Ser Ser Leu Lys Lys Pro Arg Val Val Trp Ser Val Glu
    210                 215                 220

Leu His Gln Gln Phe Val Ala Ala Val Asn Gln Leu Gly Val Asp Lys
225                 230                 235                 240

Ala Val Pro Lys Lys Ile Leu Glu Met Met Asn Val Pro Gly Leu Thr
                245                 250                 255

Arg Glu Asn Val Ala Ser His Leu Gln Lys Tyr Arg Ile Tyr Leu Arg
            260                 265                 270

Arg Leu Gly Gly Val Ser Gln His Gln Gly Asn Met Asn His Ser Phe
        275                 280                 285

Met Thr Gly Gln Asp Gln Ser Phe Gly Pro Leu Ser Ser Leu Asn Gly
    290                 295                 300

Phe Asp Leu Gln Ser Leu Ala Val Thr Gly Gln Leu Pro Pro Gln Ser
305                 310                 315                 320

Leu Ala Gln Leu Gln Ala Ala Gly Leu Gly Arg Pro Thr Leu Ala Lys
                325                 330                 335

Pro Gly Met Ser Val Ser Pro Leu Val Asp Gln Arg Ser Ile Phe Asn
            340                 345                 350

Phe Glu Asn Pro Lys Ile Arg Phe Gly Asp Gly His Gly Gln Thr Met
        355                 360                 365

Asn Asn Gly Asn Leu Leu His Gly Val Pro Thr Gly Ser His Met Arg
    370                 375                 380

Leu Arg Pro Gly Gln Asn Val Gln Ser Ser Gly Met Met Leu Pro Val
385                 390                 395                 400

Ala Asp Gln Leu Pro Arg Gly Gly Pro Ser Met Leu Pro Ser Leu Gly
                405                 410                 415

Gln Gln Pro Ile Leu Ser Ser Ser Val Ser Arg Arg Ser Asp Leu Thr
            420                 425                 430

Gly Ala Leu Ala Val Arg Asn Ser Ile Pro Glu Thr Asn Ser Arg Val
        435                 440                 445

Leu Pro Thr Thr His Ser Val Phe Asn Asn Phe Pro Ala Asp Leu Pro
    450                 455                 460

Arg Ser Ser Phe Pro Leu Ala Ser Ala Pro Gly Ile Ser Val Pro Val
465                 470                 475                 480

Ser Val Ser Tyr Gln Glu Glu Val Asn Ser Ser Asp Ala Lys Gly Gly
                485                 490                 495

Ser Ser Ala Ala Thr Ala Gly Phe Gly Asn Pro Ser Tyr Asp Ile Phe
            500                 505                 510

Asn Asp Phe Pro Gln His Gln Gln His Asn Lys Asn Ile Ser Asn Lys
        515                 520                 525

Leu Asn Asp Trp Asp Leu Arg Asn Met Gly Leu Val Phe Ser Ser Asn
    530                 535                 540

Gln Asp Ala Ala Thr Ala Thr Ala Thr Ala Ala Phe Ser Thr Ser Glu
545                 550                 555                 560
```

```
Ala Tyr Ser Ser Ser Ser Thr Gln Arg Lys Arg Arg Glu Thr Asp Ala
                565                 570                 575

Thr Val Val Gly Glu His Gly Gln Asn Leu Gln Ser Pro Ser Arg Asn
            580                 585                 590

Leu Tyr His Leu Asn His Val Phe Met Asp Gly Gly Ser Val Arg Val
        595                 600                 605

Lys Ser Glu Arg Val Ala Glu Thr Val Thr Cys Pro Pro Ala Asn Thr
    610                 615                 620

Leu Phe His Glu Gln Tyr Asn Gln Glu Asp Leu Met Ser Ala Phe Leu
625                 630                 635                 640

Lys Gln Glu Gly Ile Pro Ser Val Asp Asn Glu Phe Glu Phe Asp Gly
                645                 650                 655

Tyr Ser Ile Asp Asn Ile Gln Val
            660


<210> SEQ ID NO 23
<211> LENGTH: 1036
<212> TYPE: PRT
<213> ORGANISM: Arabidopsis halleri

<400> SEQUENCE: 23

Leu Ser Lys Lys Gln Asn Glu Asp Ala Ser Gly Arg Lys Glu Glu Asp
1               5                   10                  15

Gly Lys Gly Asn Glu His Asn Gly Met Glu Ser Cys Thr Arg Met Lys
            20                  25                  30

Arg Thr Val Trp Thr Val Glu Leu His Gln Lys Phe Val Asn Ala Phe
        35                  40                  45

Gln Gln Leu Gly Leu Asp Lys Ala Ser Pro Glu Gln Ile His Ala Leu
    50                  55                  60

Met Asn Val Glu Gly Leu Pro Val Ile Asn Val Ala Ser His Leu Gln
65                  70                  75                  80

Lys Tyr Arg Leu Phe Leu Lys Lys Ile Tyr Glu Gly Gln Gln Leu Asp
                85                  90                  95

Met Ala Thr Ile Gln Leu Leu Leu Ser Ala Gly Ser His Phe Pro Gln
            100                 105                 110

Thr Pro Trp Thr Asn His Cys Ser Ser Phe Ile Gln Gln Gly His His
        115                 120                 125

Gln Asn Ser Ser Asn Ser Ser Glu Thr Tyr His Thr Thr Leu Ser Pro
    130                 135                 140

Arg Val Gln Lys Val Asn Thr Phe Gln Pro Ser Ser Ser Pro Leu Lys
145                 150                 155                 160

Pro Leu Leu Phe Pro Lys Ser Asn Ile Ser Ala Phe Lys Glu Asp Phe
                165                 170                 175

Lys Ser Ile Lys Glu Pro Ala Ile Val Gly Asp Ser Ser Leu Asp Ser
            180                 185                 190

Ser Lys Pro Arg Asn Ser Phe Gln Thr Ala Ser Lys Phe Pro Lys Thr
        195                 200                 205

Asp Pro Cys Thr Gly Ser Tyr Ile Ile Glu Ile Met Thr Glu Pro Tyr
    210                 215                 220

Tyr Gly Lys Ser Ser Arg Arg His Ser Asn Phe Ser Ala Tyr Met Gly
225                 230                 235                 240

Asp Phe Lys Ser Ile Lys Asp Pro Glu Ile Val Gln Glu Ser Arg Thr
                245                 250                 255

Arg Lys Asn His Gly Arg Val Val Trp Ser His Glu Leu His Gln Lys
            260                 265                 270
```

-continued

```
Phe Leu Asn Ala Ile Asp Gln Leu Gly Gly Asn Glu Lys Ala Ile Pro
        275                 280                 285

Lys Lys Ile Leu Ala Val Met Asn Val Glu Gly Leu Thr Arg Leu Asn
    290                 295                 300

Val Ala Thr His Leu Gln Lys Tyr Arg Gln Cys Cys Ser Ala Glu Ala
305                 310                 315                 320

Gln Gln Leu Asn Met Ala Thr Arg Lys Leu Pro Ser Ser Glu His Leu
                325                 330                 335

Pro Gln Ser Pro Ser Thr Asn His His Ser Ser Leu Ser Pro Arg Val
            340                 345                 350

Gln Asp Val Asn Ile Arg Leu Trp Ser Ser Ser Pro Lys Arg Gln Asp
        355                 360                 365

Gln Ile Leu Val Tyr Val Leu Phe Ser Phe Glu Asn Asp Asn Gly Arg
    370                 375                 380

Glu Glu Thr Thr Cys Arg Arg Ile Ala Ser Thr Met Glu Leu Gly Ser
385                 390                 395                 400

Thr Glu Asp Gly Arg His Asp Lys Phe Pro Val Gly Met Arg Val Leu
                405                 410                 415

Ala Val Asp Asp Asn Pro Thr Cys Leu Arg Lys Leu Glu Glu Leu Leu
            420                 425                 430

Leu Arg Cys Lys Tyr His Val Thr Lys Thr Met Glu Ser Arg Lys Ala
        435                 440                 445

Leu Glu Leu Leu Arg Glu Asn Ser Asn Met Phe Asp Leu Val Ile Ser
    450                 455                 460

Asp Val Glu Met Pro Asp Thr Asp Gly Phe Lys Leu Leu Glu Ile Gly
465                 470                 475                 480

Leu Glu Met Asp Leu Pro Val Ile Met Leu Ser Ala His Ser Asp Tyr
                485                 490                 495

Asp Ser Val Met Lys Gly Ile Ile His Gly Ala Cys Asp Tyr Leu Val
            500                 505                 510

Lys Pro Val Gly Leu Lys Glu Leu Gln Asn Ile Trp His His Val Val
        515                 520                 525

Lys Lys Asn Ile Lys Ser Tyr Ala Lys Asn Ile Gly Pro Ser Arg Gln
    530                 535                 540

Leu Leu Pro Pro Ser Glu Ser Asn Leu Val Pro Ser Ala Ser Lys Lys
545                 550                 555                 560

Arg Lys Glu Lys Ala Ser Asp Ser Gly Asp Glu Asp Asp Ser Asp Arg
                565                 570                 575

Glu Glu Asp Asp Gly Glu Gly Ser Glu Gln Asp Gly Glu Glu Ser Gly
            580                 585                 590

Thr Arg Lys Lys Pro Arg Val Val Trp Ser Gln Glu Leu His Gln Lys
        595                 600                 605

Phe Val Ser Ala Val Gln Gln Leu Gly Leu Asp Lys Ala Val Pro Lys
    610                 615                 620

Lys Ile Leu Asp Leu Met Ser Ile Glu Gly Leu Thr Arg Glu Asn Val
625                 630                 635                 640

Ala Ser His Leu Gln Lys Tyr Arg Leu Tyr Leu Lys Lys Ile Asp Glu
                645                 650                 655

Gly Gln Gln Gln Asn Met Thr Pro Asp Ala Phe Gly Thr Arg Asp Ser
            660                 665                 670

Ser Tyr Phe Gln Met Ala Gln Leu Asp Gly Leu Arg Asp Phe Thr Ala
        675                 680                 685
```

```
Thr Arg Gln Ile Pro Ser Ser Gly Leu Leu Ser Arg Ser His Leu Thr
    690                 695                 700

Lys Leu Gln Pro Pro Met Tyr Ser Ser Ile Asn Leu Gln Gly Met Asn
705                 710                 715                 720

Ser Ser Ser Phe Ile Gln Gln Gly His His His Asn Ser Ser Asn Ser
                725                 730                 735

Ala Asn Pro Phe Gly Thr Tyr His Thr Thr Leu Ser Pro Arg Ile Gln
            740                 745                 750

Asn Val Asn Leu Leu Gln Arg Thr Ser Ser Pro Leu Glu Thr Leu Gln
        755                 760                 765

Phe Pro Arg Ser Lys Ser Tyr Ile Gly Asp Phe Lys Gly Ile Gly Asp
    770                 775                 780

Arg Ala Val Gly Gly Ser Phe Leu Asp Ser Cys Met Pro Phe Gly Ser
785                 790                 795                 800

Ser Ser Thr Ser Leu Pro Ser Ala Ser Thr Asn Thr Leu Met Leu Gln
                805                 810                 815

Ala Asn Tyr Thr Gln Pro Leu His Ile Ala Ser Asp Gly Asn Gln Pro
            820                 825                 830

Cys Ile Glu Gly Thr Pro Ser Asn Ser Ala Ser Pro Asn Ile Ser Phe
        835                 840                 845

Gln Gly Leu Ser Arg Phe Pro Ser His Ser Trp Gln Gly Asn Leu Asn
    850                 855                 860

Thr Thr Arg Phe Pro Pro Ser Ser Leu Pro Leu Asn Gln Ala Phe Leu
865                 870                 875                 880

Pro Asp Gln Val Thr Cys Ala Gly Asn Asn Leu Gly Asp Cys Thr Ser
                885                 890                 895

Leu Val Ser Ala Gly Asn Pro Gly Gly Glu Met Gln Cys Glu Pro Gln
            900                 905                 910

Leu Leu Gly Gly Phe Met Gln Asn Met Asn Pro Leu Asp Gly Gln Lys
        915                 920                 925

Trp Glu Gln Gln Asn Ser Met Leu Asn Asn Pro Phe Gly Asn Ile Glu
    930                 935                 940

Tyr Pro Leu Ser Ala Asp Asn Met Val Phe Arg Asp Asn Asn Ala Thr
945                 950                 955                 960

Arg Asn Lys Gly Leu Asp Glu Ser Leu Met Asn Pro Ile Asp Asn Ser
                965                 970                 975

Gln Glu Tyr Val Gly Lys Ala Thr Thr Met Leu Asp Pro Glu Met Lys
            980                 985                 990

Ser Gly Lys Pro Glu Asn Asp Asn  Gln His Asp Val Phe  Asp Asp Ile
        995                 1000                1005

Met Asn  Glu Met Met Lys Gln  Glu Glu Asn Asn Gly  Met Val Ser
    1010                1015                1020

Val Ala  Thr Arg Phe Gly Phe  Asp Ser Phe Pro Pro  Pro
1025                1030                1035
```

<210> SEQ ID NO 24
<211> LENGTH: 774
<212> TYPE: PRT
<213> ORGANISM: Arabidopsis lyrata

<400> SEQUENCE: 24

```
Met Gly Asp Phe Lys Ser Ile Lys Glu Pro Glu Ile Val Gln Glu Ser
1               5                   10                  15

Arg Thr Arg Lys Asn His Gly Arg Val Val Trp Ser His Glu Leu His
            20                  25                  30
```

-continued

```
Gln Lys Phe Leu His Ala Ile Asp Gln Leu Gly Gly Asn Asp Lys Ala
        35                  40                  45

Ile Pro Lys Lys Ile Leu Ala Val Met Asn Val Glu Gly Leu Thr Arg
    50                  55                  60

Leu Asn Val Ala Thr His Leu Gln Lys Tyr Arg Gln Cys Cys Ser Thr
65                  70                  75                  80

Glu Ala Gln Gln Leu Asn Met Ala Thr Arg Lys Leu Pro Ser Ser Glu
                85                  90                  95

His Leu Pro Gln Ser Pro Ser Thr Asn His His Ser Ser Leu Ser Pro
            100                 105                 110

Arg Val Gln Asp Asn Asp Asn Gly Arg Glu Glu Thr Thr Cys Arg Arg
        115                 120                 125

Ile Ala Ser Thr Met Glu Leu Gly Ser Thr Glu Asp Gly Arg His Asp
    130                 135                 140

Lys Phe Pro Val Gly Met Arg Val Leu Ala Val Asp Asp Asn Pro Thr
145                 150                 155                 160

Cys Leu Arg Lys Leu Glu Glu Leu Leu Leu Arg Cys Lys Tyr His Val
                165                 170                 175

Thr Lys Thr Met Glu Ser Arg Lys Ala Leu Glu Leu Leu Arg Glu Asn
            180                 185                 190

Ser Asn Met Phe Asp Leu Val Ile Ser Asp Val Glu Met Pro Asp Thr
        195                 200                 205

Asp Gly Phe Lys Leu Leu Glu Ile Gly Leu Glu Met Asp Leu Pro Val
    210                 215                 220

Ile Met Leu Ser Ala His Ser Asp Tyr Asp Ser Val Met Lys Gly Ile
225                 230                 235                 240

Ile His Gly Ala Cys Asp Tyr Leu Val Lys Pro Val Gly Leu Lys Glu
                245                 250                 255

Leu Gln Asn Ile Trp His His Val Val Lys Lys Asn Ile Lys Ser Tyr
            260                 265                 270

Ala Lys Asn Ile Gly Pro Ser Arg Gln Leu Leu Pro Pro Ser Glu Ser
        275                 280                 285

Asn Leu Val Pro Ser Ala Ser Lys Lys Arg Lys Glu Lys Ala Asn Asp
    290                 295                 300

Ser Gly Asp Glu Asp Asp Ser Asp Arg Glu Glu Asp Asp Gly Glu Gly
305                 310                 315                 320

Ser Glu Gln Asp Gly Asp Glu Ala Gly Thr Arg Lys Lys Pro Arg Val
                325                 330                 335

Val Trp Ser Gln Glu Leu His Gln Lys Phe Val Ser Ala Val Gln Gln
            340                 345                 350

Leu Gly Leu Asp Lys Ala Val Pro Lys Lys Ile Leu Asp Leu Met Ser
        355                 360                 365

Ile Glu Gly Leu Thr Arg Glu Asn Val Ala Ser His Leu Gln Lys Tyr
    370                 375                 380

Arg Leu Tyr Leu Lys Lys Ile Asp Glu Gly Gln Gln Gln Asn Met Thr
385                 390                 395                 400

Pro Asp Ala Phe Gly Thr Arg Asp Ser Ser Tyr Phe Gln Met Ala Gln
                405                 410                 415

Leu Asp Gly Leu Arg Asp Phe Thr Ala Thr Arg Gln Ile Pro Ser Ser
            420                 425                 430

Gly Leu Leu Ser Arg Ser His Leu Thr Lys Leu Gln Pro Pro Met Tyr
        435                 440                 445
```

-continued

```
Ser Ser Ile Asn Leu Gln Gly Met Asn Ser Ser Ser Phe Ile Gln Gln
    450                 455                 460

Gly His His His Asn Ser Ser Asn Ser Ala Asn Pro Phe Gly Thr Tyr
465                 470                 475                 480

His Thr Thr Leu Ser Pro Arg Ile Gln Asn Val Asn Leu Phe Gln Arg
                485                 490                 495

Thr Ser Ser Pro Leu Glu Thr Leu Gln Phe Pro Arg Ser Lys Ser Tyr
            500                 505                 510

Ile Gly Asp Phe Lys Gly Ile Gly Asp Arg Ala Val Gly Gly Ser Phe
        515                 520                 525

Leu Asp Ser Cys Met Pro Phe Gly Ser Ser Ser Thr Ser Leu Pro Ser
    530                 535                 540

Ala Ser Thr Asn Thr Leu Met Leu Gln Ala Asn Tyr Thr Gln Pro Leu
545                 550                 555                 560

His Ile Ser Ser Asp Gly Asn Gln Pro Cys Ile Glu Gly Thr Pro Ser
                565                 570                 575

Asn Ser Ala Ser Pro Asn Ile Ser Phe Gln Gly Leu Ser Arg Phe Pro
            580                 585                 590

Ser His Ser Trp Gln Gly Asn Leu Asn Thr Thr Arg Phe Pro Pro Ser
        595                 600                 605

Ser Leu Pro Leu Asn Pro Ala Phe Leu Pro Asp Gln Val Thr Cys Ala
    610                 615                 620

Gly Asn Asn Leu Gly Asp Cys Thr Ser Leu Val Ser Ala Gly Asn Pro
625                 630                 635                 640

Gly Gly Glu Ile Gln Cys Glu Pro Gln Leu Leu Gly Gly Phe Met Gln
                645                 650                 655

Asn Met Asn Pro Leu Asp Gly Gln Lys Trp Glu Gln Gln Asn Cys Thr
            660                 665                 670

Met Leu Asn Asn Pro Phe Gly Asn Ile Glu Tyr Pro Leu Pro Ala Asp
        675                 680                 685

Asn Met Val Phe Arg Asp Asn Asn Ala Thr Arg Ser Lys Gly Leu Asp
    690                 695                 700

Glu Ser Leu Met Asn Pro Ile Asp Asn Ser Gln Glu Tyr Val Gly Lys
705                 710                 715                 720

Ala Thr Thr Met Leu Asp Pro Glu Met Lys Ser Gly Lys Pro Glu Asn
                725                 730                 735

Asp Asn Gln His Asp Val Phe Asp Asp Leu Met Asn Glu Met Met Lys
            740                 745                 750

Gln Glu Glu Asn Asn Gly Met Val Ser Val Ala Thr Arg Phe Gly Phe
        755                 760                 765

Asp Ser Phe Pro Pro Pro
    770
```

<210> SEQ ID NO 25
<211> LENGTH: 578
<212> TYPE: PRT
<213> ORGANISM: Helianthus annuus

<400> SEQUENCE: 25

```
Met Thr Thr Gly Ser Ser Phe Gly Ser Gly Ser Leu Gly Cys Lys Gln
1               5                   10                  15

Glu Thr Gly Val Pro Asp Gln Phe Pro Ala Gly Leu Arg Val Leu Val
            20                  25                  30

Val Asp Asp Asp Val Ile Cys Leu Lys Ile Leu Glu Gln Met Leu Arg
        35                  40                  45
```

```
Arg Cys Ser Tyr His Val Thr Thr Cys Ser Gln Ala Thr Ala Ala Leu
    50                  55                  60

Asn Leu Leu Arg Glu Arg Lys Gly Cys Phe Asp Val Val Leu Ser Asp
65                  70                  75                  80

Val His Met Pro Asp Met Asp Gly Phe Lys Leu Leu Glu Leu Val Gly
                85                  90                  95

Leu Glu Met Asp Leu Pro Val Ile Met Met Ser Ala Asp Gly Arg Thr
            100                 105                 110

Asn Leu Val Leu Arg Gly Ile Arg His Gly Ala Cys Asp Tyr Leu Ile
        115                 120                 125

Lys Pro Ile Arg Glu Glu Gln Leu Lys Asn Ile Trp Gln His Val Ile
    130                 135                 140

Arg Lys Lys Trp Asn Glu Asn Lys Glu His Glu His Ser Gly Ser Val
145                 150                 155                 160

Asp Asp Lys Asp Arg His Lys Arg Gly Gly Asp Asp Asn Asp Tyr Ala
                165                 170                 175

Ser Ser Val Asn Glu Gly Gly Asp Gly Ile Leu Thr Ser His Lys Lys
            180                 185                 190

Lys Arg His Asn Asn Lys Glu Glu Asp Asp Gly Glu Leu Glu Thr Asp
        195                 200                 205

Glu Pro Gly Gly Ser Lys Lys Ala Arg Val Val Trp Ser Val Glu Leu
    210                 215                 220

His Gln Gln Phe Val Thr Ala Val Asn Gln Leu Gly Ile Asp Lys Ala
225                 230                 235                 240

Val Pro Lys Arg Ile Leu Glu Leu Met Asn Val Pro Gly Leu Thr Arg
                245                 250                 255

Glu Asn Val Ala Ser His Leu Gln Lys Phe Arg Leu Tyr Leu Lys Arg
            260                 265                 270

Leu Ser Gly Val Ala Gln Gln Gly Gly Gly Pro Asn Ser Phe Cys Gly
        275                 280                 285

Ser Ile Asp Gln Asn Pro Lys Leu Ala Ser Tyr Ala Arg Phe Glu Ile
    290                 295                 300

Gln Ala Leu Ala Ala Ser Gly Gln Ile Pro Pro Gln Thr Leu Val Ala
305                 310                 315                 320

Leu His Ala Glu Leu Leu Gly Gln Pro Thr Ala Asn Val Gly Met Pro
                325                 330                 335

Val Leu Asp His Gln Pro Leu Met Gln Pro Ser Lys Cys Gly Pro Val
            340                 345                 350

Asp His Val Met Ser Tyr Gly Gln Thr Leu Pro Ser Asn Val Thr Lys
        355                 360                 365

Gln Val Pro Gln Pro Ala Ile Glu Asp Val His Ser Gly Leu Gly Ala
    370                 375                 380

Trp His Ser Asn Asn Met Val Gly Gly Tyr Gly Gln Leu Gly Gly Gln
385                 390                 395                 400

Asn Trp His Asn Met Leu Leu Gly Met Leu Gln Ser Gln Ser His Gln
                405                 410                 415

Leu Gln Lys Gln Ser Ile Thr Val Gln Pro Ser Arg Leu Val Val Pro
            420                 425                 430

Ser Gln Ser Ser Asn Phe Gln Ala Val Asn Asn Gly Val Pro Val Asn
        435                 440                 445

Gln Thr Thr Gly Phe Asn Asn Ser Thr Val Ile Asn Tyr Ala Val Gly
    450                 455                 460
```

```
Gln Arg Thr Glu Arg Asp Val Glu Asn Gln Ile Gly Gly Gln Ser Ser
465                 470                 475                 480

Val Ser Asn Ile Ser Val Lys Glu Met Gly Glu Lys Gln Ile Ser Phe
                485                 490                 495

Gly Glu Ser Val His Val Leu Asp Gln Gly Ser Leu Arg Asn Leu Gly
            500                 505                 510

Phe Val Gly Lys Lys Ser Ser Ile Pro Ser Arg Phe Ala Val Tyr Glu
        515                 520                 525

Ala Ala Glu Ser Leu Thr His Asn Leu Asn Tyr Gly Asp Asn Asn Gly
    530                 535                 540

Glu Arg Arg Val Lys Gln Glu Pro Asn Ile Glu Phe Leu Glu Asn Ser
545                 550                 555                 560

Lys Ala Gly Ala His Arg Val Ser Gln Asn Asp Leu Met Ser Lys Gln
                565                 570                 575

Val Arg


<210> SEQ ID NO 26
<211> LENGTH: 428
<212> TYPE: PRT
<213> ORGANISM: Vitis vinifera

<400> SEQUENCE: 26

Met Ala Ala Leu Leu Lys Val Pro Pro Gln Ser Ser Gly Gly Thr Asn
1               5                   10                  15

Gly Ser Cys Lys Ala Asp Val Val Val Ser Asp Gln Phe Pro Ala Gly
            20                  25                  30

Leu Arg Val Leu Val Val Asp Asp Asp Val Thr Cys Leu Lys Ile Leu
        35                  40                  45

Glu Gln Met Leu Arg Arg Cys Leu Tyr His Val Thr Thr Cys Ser Gln
    50                  55                  60

Ala Thr Ile Ala Leu Asn Ile Leu Arg Glu Lys Lys Gly Cys Phe Asp
65                  70                  75                  80

Ile Val Leu Ser Asp Val His Met Pro Asp Met Asp Gly Tyr Lys Leu
                85                  90                  95

Leu Glu His Val Gly Leu Glu Met Asp Leu Pro Val Ile Met Met Ser
            100                 105                 110

Ala Asp Gly Arg Thr Ser Ala Val Met Arg Gly Ile Arg His Gly Ala
        115                 120                 125

Cys Asp Tyr Leu Ile Lys Pro Ile Arg Glu Glu Glu Leu Lys Asn Ile
    130                 135                 140

Trp Gln His Val Val Arg Lys Lys Trp Asn Glu Asn Lys Glu His Glu
145                 150                 155                 160

His Ser Gly Ser Leu Glu Asp Asn Asp Arg His Lys Arg Gly Gly Glu
                165                 170                 175

Asp Ala Glu Tyr Ala Ser Ser Val Asn Glu Gly Ala Glu Gly Ile Leu
            180                 185                 190

Lys Gly Gln Lys Lys Arg Arg Asp Ser Lys Asp Glu Asp Asp Gly Glu
        195                 200                 205

Leu Glu Asn Glu Asp Pro Ser Thr Ser Lys Lys Pro Arg Val Val Trp
    210                 215                 220

Ser Val Glu Leu His Gln Gln Phe Val Ser Ala Val Asn Gln Leu Gly
225                 230                 235                 240

Ile Asp Lys Ala Val Pro Lys Arg Ile Leu Glu Leu Met Asn Val Pro
                245                 250                 255
```

```
Gly Leu Thr Arg Glu Asn Val Ala Ser His Leu Gln Lys Phe Arg Leu
            260                 265                 270

Tyr Leu Lys Arg Leu Ser Gly Val Ala Gln Gln Gln Gly Gly Ile Pro
        275                 280                 285

Asn Ser Phe Cys Gly Pro Val Glu Pro Asn Val Lys Leu Gly Ser Leu
    290                 295                 300

Gly Arg Phe Asp Ile Gln Ala Leu Ala Ala Ser Gly Gln Ile Pro Pro
305                 310                 315                 320

Gln Thr Leu Ala Ala Leu Gln Ala Glu Leu Leu Gly Arg Pro Thr Ser
                325                 330                 335

Asn Leu Val Leu Pro Ala Met Asp Gln Pro Ala Leu Leu Gln Ala Ser
            340                 345                 350

Leu Gln Gly Pro Lys Cys Ile Pro Val Glu His Gly Val Ala Phe Gly
        355                 360                 365

Gln Pro Leu Val Lys Cys Gln Thr Asn Ile Ser Lys His Phe Pro Pro
    370                 375                 380

Thr Val Val Ser Thr Glu Asp Val Pro Ser Gly Phe Gly Ala Trp Pro
385                 390                 395                 400

Ser Asn Ser Leu Gly Thr Val Gly Thr Ser Gly Ser Leu Gly Gly Leu
                405                 410                 415

Ser Ala Gln Asn Asn Asn Ile Leu Met Asp Met Lys
            420                 425
```

<210> SEQ ID NO 27
<211> LENGTH: 659
<212> TYPE: PRT
<213> ORGANISM: Amborella trichopoda

<400> SEQUENCE: 27

```
Met Ala Asn Val Gln Lys Leu Pro His Ser Ser Ile Ser Thr Ala Ser
1               5                   10                  15

Ser Tyr Gly Ser Cys Arg Gly Glu Gly Val Pro Asp Gln Phe Pro Ala
            20                  25                  30

Gly Leu Arg Val Leu Val Val Asp Asp Asp Thr Thr Cys Leu Arg Ile
        35                  40                  45

Leu Glu Gln Met Leu Arg Lys Cys Met Tyr Lys Val Thr Thr Cys Cys
    50                  55                  60

Arg Ala Thr Asp Ala Leu Asp Thr Leu Arg Gly Ser Lys Gly Cys Phe
65                  70                  75                  80

Asp Val Val Ile Ser Asp Val Tyr Met Pro Asp Met Asp Gly Phe Lys
                85                  90                  95

Leu Leu Glu His Val Gly Leu Glu Met Asp Leu Pro Val Ile Met Met
            100                 105                 110

Ser Ala Asp Ala Arg Phe Ser Ala Val Met Lys Gly Ile Lys His Gly
        115                 120                 125

Ala Cys Asp Tyr Leu Ile Lys Pro Val Arg Ile Glu Glu Leu Lys Asn
    130                 135                 140

Ile Trp Gln His Val Val Arg Lys Lys Trp Asn Glu Thr Lys Glu His
145                 150                 155                 160

Asp Gln Ser Gly Ser Ile Glu Asp Asn Glu Arg His Lys Arg Gly Ser
                165                 170                 175

Asp Asp Ala Glu Tyr Ala Ser Ser Val Asn Glu Gly Thr Asp Gly Asn
            180                 185                 190

Trp Lys Val Gln Lys Lys Arg Lys Asp Ser Lys Glu Glu Glu Asp Asp
        195                 200                 205
```

-continued

```
Gly Glu Gln Glu Asn Glu Asp Pro Ser Ala Ala Lys Lys Pro Arg Val
    210                 215                 220

Val Trp Ser Val Glu Leu His Gln Gln Phe Val Asn Ala Val Asn Gln
225                 230                 235                 240

Leu Gly Ile Asp Lys Ala Val Pro Lys Arg Ile Leu Glu Leu Met Asn
                245                 250                 255

Val Gln Gly Leu Thr Arg Glu Asn Val Ala Ser His Leu Gln Lys Phe
            260                 265                 270

Arg Leu Tyr Leu Lys Arg Leu Ser Gly His Gln Ala Gly Val Ser Ser
        275                 280                 285

Ser Phe Cys Gly Ser Val Asp Pro Asn Ser Lys Leu Gly Pro Leu Ser
    290                 295                 300

Gln Leu Asp Ile Arg Ala Leu Thr Ala Ser Gly Gln Ile Pro Ser Gln
305                 310                 315                 320

Thr Leu Ala Ala Leu Gln Ala Glu Leu Leu Gly Arg Pro Ser Asn Asn
                325                 330                 335

Val Ala Met Pro Val Tyr Gly Gln Thr Leu Val Lys Cys Gln Pro Asn
            340                 345                 350

Leu Pro Lys Gln Phe Pro Gln Pro Asn Leu Pro Val Asp Asp Val Gln
        355                 360                 365

Ser Ser Leu Ser Ile Trp Gln His His Leu Ser Ser Gly Met Pro Leu
    370                 375                 380

Gly Gly Leu Asn Pro Gln Asn Asn Gly Leu Leu Met Gln Gln Gln Gln
385                 390                 395                 400

Gln Leu Thr Ile Glu Ser Asn Arg Pro Cys Asn Val Gln Pro Ser Cys
                405                 410                 415

His Val Ala Pro Ser Asn Gly Gly Phe Thr Met Arg Asn Asn Pro Thr
            420                 425                 430

Ser Ser Asn Ala Ser Ser Val Glu Tyr Asn Ser Leu Leu Ser Ser Gln
        435                 440                 445

Gly Asp Val Gly Gln Ile Ser Gln Ala Ser Gly Ser Asp Leu Ala Thr
    450                 455                 460

Thr Val Gln Ser Asn Gly Gly Phe Lys Ser Leu Asp Tyr Arg Asn Met
465                 470                 475                 480

Gly Gln Val Ser Leu Glu Ser Thr Ser Asp Leu Val Ser Thr Gln Asn
                485                 490                 495

Asn Gly Phe Lys Gly Met Glu Leu Arg Asn Val Gly Ser Leu Gly Gly
            500                 505                 510

Tyr Pro Leu Ser Ser Ser Val Ser Ala Gly Ser Thr Lys Thr Glu Asn
        515                 520                 525

Gly Gln Ser Phe Ser Gln Val Arg Thr Gly Pro Arg Met Ser Met Gly
    530                 535                 540

Pro Thr Gly Gln Phe Val Gly Pro Pro Thr Ile Arg Arg Leu Pro Met
545                 550                 555                 560

Val Asp Gly Gly Thr His Arg Asn Ser Leu Gly Phe Val Gly Lys Gly
                565                 570                 575

Val Ser Ile Pro Ser Arg Phe Met Pro Asp Ser Gly Ser Pro Thr Gly
            580                 585                 590

Val Gly Glu Glu Cys Thr Leu Pro Lys Gln Glu Val Asp Pro Asp Phe
        595                 600                 605

Phe Asp Ser Leu Lys Val Gly Pro Val Gly Val Gln His Tyr Ala Ser
    610                 615                 620
```

```
Gly Asp Leu Met Ser Val Leu Ser Lys Gln Gln Gln Ala Ser Thr Gly
625                 630                 635                 640

Asn Leu Asp Cys Glu Phe Gly Ile Asp Gly Tyr Gln Leu Gly Asn Ile
                645                 650                 655

His Val Lys


<210> SEQ ID NO 28
<211> LENGTH: 669
<212> TYPE: PRT
<213> ORGANISM: Ricinus communis

<400> SEQUENCE: 28

Met Ala Ala Leu Gln Arg Val Ala Ser Ser Val Ser Ala Thr Ala Ser
1               5                   10                  15

Asn Tyr Ser Ser Cys Lys Gly Asn Gly Val Val Thr Ala Thr Ala Asp
            20                  25                  30

Val Ala Val Ser Asp Gln Phe Pro Ala Gly Leu Arg Val Leu Val Val
        35                  40                  45

Asp Asp Asp Thr Thr Cys Leu Arg Ile Leu Glu Gln Met Leu Arg Arg
    50                  55                  60

Cys Leu Tyr His Val Thr Thr Cys Ser Gln Ala Lys Val Ala Leu Asn
65                  70                  75                  80

Leu Leu Arg Glu Arg Lys Gly Cys Phe Asp Val Val Leu Ser Asp Val
                85                  90                  95

His Met Pro Asp Met Asp Gly Phe Lys Leu Leu Glu His Val Gly Leu
            100                 105                 110

Glu Met Asp Leu Pro Val Ile Met Met Ser Ala Asp Gly Arg Thr Ser
        115                 120                 125

Ala Val Met Arg Gly Ile Arg His Gly Ala Cys Asp Tyr Leu Ile Lys
    130                 135                 140

Pro Ile Arg Glu Glu Glu Leu Lys Asn Ile Trp Gln His Val Val Arg
145                 150                 155                 160

Lys Lys Trp His Glu Asn Lys Glu Ile Glu His Ser Gly Ser Leu Glu
                165                 170                 175

Asp Asn Asp Arg His Lys Arg Gly Asn Glu Asp Ala Glu Tyr Thr Ser
            180                 185                 190

Ser Val Asn Glu Gly Thr Glu Gly Val Leu Lys Gly Gln Lys Arg Arg
        195                 200                 205

Ser Asn Ser Lys Asp Glu Asp Asp Gly Glu Pro Asp Ser Asp Asp Pro
    210                 215                 220

Ser Thr Ser Lys Lys Pro Arg Val Val Trp Ser Val Glu Leu His Gln
225                 230                 235                 240

Gln Phe Val Ser Ala Val Asn Gln Leu Gly Ile Asp Lys Ala Val Pro
                245                 250                 255

Lys Arg Ile Leu Glu Leu Met Asn Val Pro Gly Leu Thr Arg Glu Asn
            260                 265                 270

Val Ala Ser His Leu Gln Lys Phe Arg Leu Tyr Leu Lys Arg Leu Ser
        275                 280                 285

Gly Val Ala Gln Gln Gly Gly Ile Ser Ser Thr Phe Cys Gly Pro Met
    290                 295                 300

Asp Ser Asn Val Lys Leu Asn Ser Leu Gly Arg Phe Asp Ile Gln Ala
305                 310                 315                 320

Leu Ala Ala Ser Gly Gln Ile Pro Pro Gln Thr Leu Ala Ala Leu His
                325                 330                 335
```

```
Ala Glu Leu Phe Gly Arg Pro Thr Gly Ser Leu Val Thr Thr Met Asp
            340                 345                 350

Gln Pro Thr Leu Leu Gln Ala Ser Arg Gln Ser Pro Lys Cys Ile Pro
        355                 360                 365

Val Glu His Gly Val Thr Phe Gly Gln Pro Ile Val Lys Cys Ser Ser
    370                 375                 380

Gly Ile Ser Lys His Phe Pro Gln Asn Met Val Ser Val Glu Glu Val
385                 390                 395                 400

Ser Ser Gly Tyr Gly Ala Trp Pro Ser Asn Ser Leu Gly Thr Val Gly
                405                 410                 415

Pro Ser Thr Asn Leu Gly Gly Met Thr Thr Gln Asn Gly Asn Met Leu
            420                 425                 430

Met Asp Ile Phe His Gln Gln Gln Lys Gln Gln Gln Pro Gln Gln Gln
        435                 440                 445

Gln Ser Leu Ala Asp Pro Ser Arg Ser Ile Asn Val Gln Pro Ser Cys
    450                 455                 460

Leu Val Val Pro Ser Gln Ser Ser Ala Cys Phe Gln Ala Gly Asn Ser
465                 470                 475                 480

Pro Ala Ser Val Asn Gln Ser Asn Phe Asn Arg Asn Val Val Ile Asp
                485                 490                 495

Tyr Ser Leu Leu Ser Ser Gln Ser Asn Asn Ser Ala Leu Asn Ile Gly
            500                 505                 510

His Ile Pro Glu Gly Asp Leu Lys Thr Thr Gly Ala Val Asn Gly Tyr
        515                 520                 525

Ser Ala Pro Gly Ser Leu Ser Pro Pro Ala Ser Ser Cys Ser Val Asn
    530                 535                 540

Ala Asp Ser Gly Val Pro Arg Gln Val Gln Asn Pro Thr Leu Ala Phe
545                 550                 555                 560

Gly Ala Val Arg Gln Leu Pro Ala Leu Ser Pro Asn Ile Phe Asn Ile
                565                 570                 575

Gln Gly Ser Tyr Gly Val Arg Ser Asp Asp Ile Leu Asp Gln Gly Pro
            580                 585                 590

Phe Phe Lys Asn Leu Gly Phe Val Gly Lys Gly Thr Cys Ile Pro Ser
        595                 600                 605

Arg Phe Ala Val Asp Glu Phe Glu Thr Pro Ser Ser Asn Leu Ser His
    610                 615                 620

Gly Lys Leu Tyr Val Glu Asn Asn Asp Asn Lys Val Lys Gln Glu Pro
625                 630                 635                 640

Asn Ile Asp Phe Thr Asp Thr Ser Arg Val Gly Ile Pro Val Leu Gln
                645                 650                 655

Gln Tyr Pro Pro Asn Asp Leu Met Ser Val Phe Thr Glu
            660                 665
```

<210> SEQ ID NO 29
<211> LENGTH: 654
<212> TYPE: PRT
<213> ORGANISM: Solanum lycopersicum

<400> SEQUENCE: 29

```
Met Val Ser Met Ser Gly Glu Val Ala Thr Cys Lys Ser Glu Ala Thr
1               5                   10                  15

Val Val Thr Asp His Phe Pro Val Gly Leu Arg Val Leu Val Val Asp
            20                  25                  30

Asp Asp Val Val Cys Leu Arg Ile Ile Glu Gln Met Leu Arg Arg Cys
        35                  40                  45
```

```
Lys Tyr Ser Val Thr Thr Cys Thr Gln Ala Met Val Ala Leu Asn Leu
    50                  55                  60

Leu Arg Glu Lys Arg Gly Thr Phe Asp Ile Val Leu Ser Asp Val His
65                  70                  75                  80

Met Pro Asp Met Asp Gly Phe Lys Leu Leu Glu Leu Val Gly Leu Glu
                85                  90                  95

Met Asp Leu Pro Val Ile Met Met Ser Gly Asp Gly Arg Thr Asn Leu
            100                 105                 110

Val Met Arg Gly Val Gln His Gly Ala Cys Asp Tyr Leu Ile Lys Pro
        115                 120                 125

Ile Arg Asp Glu Glu Leu Lys Asn Ile Trp Gln His Val Val Arg Lys
    130                 135                 140

Arg Tyr Asn Ser Ser Lys Glu Pro Glu Cys Ser Gly Ser Leu Asp Asp
145                 150                 155                 160

Asn Asp Arg Tyr Arg Arg Arg Ser Asp Asp Ala Glu Cys Ala Ser Ser
                165                 170                 175

Val Ile Glu Gly Ala Asp Gly Val Leu Lys Pro Gln Lys Lys Lys Arg
            180                 185                 190

Glu Ala Lys Glu Asp Asp Thr Glu Met Glu Asn Asp Asp Pro Ser Thr
        195                 200                 205

Thr Lys Lys Pro Arg Val Val Trp Ser Val Glu Leu His Gln Gln Phe
    210                 215                 220

Val Ser Ala Val Asn Gln Leu Gly Ile Asp Lys Ala Val Pro Lys Arg
225                 230                 235                 240

Ile Leu Glu Leu Met Asn Val Pro Gly Leu Thr Arg Glu Asn Val Ala
                245                 250                 255

Ser His Leu Gln Lys Phe Arg Leu Tyr Leu Lys Arg Leu Ser Gly Val
            260                 265                 270

Val Gln Gln Gln Gly Gly Leu Pro Ser Thr Phe Cys Gly Pro Ile Glu
        275                 280                 285

Gln Asn Ser Glu Leu Gly Ser Leu Gly Arg Phe Asp Ile Gln Ala Leu
    290                 295                 300

Ala Ala Ser Gly Gln Ile Pro Pro Glu Thr Leu Thr Ala Leu His Ala
305                 310                 315                 320

Glu Leu Leu Gly Arg Ser Thr Ser Asn Leu Val Leu Pro Ala Val Glu
                325                 330                 335

Gln Gln Asn Leu Val Gln Val Ser Leu Gln Gln Ala Lys Cys Ile Pro
            340                 345                 350

Val Asp Gln Val Met Ala Tyr Gly Gln Pro Leu Leu Lys Cys Pro Ala
        355                 360                 365

Ser Ile Ser Asn Ser Lys His Leu Ser Gln Ala Ile Leu Ser Ala Glu
    370                 375                 380

Asp Val His Ser Gly Phe Gly Ser Gln Arg Ala Lys Asn Ile Cys Met
385                 390                 395                 400

Val Pro Ser Ser Asn Pro Ile Ala Pro Asn Ser Asn Met Leu Thr Ala
                405                 410                 415

Met Met Gln Gln Gln Gln Trp Gln Lys Gln Gln Gln Ile Glu Leu Gln
            420                 425                 430

His Arg Gln Ser Gly Pro Pro Glu Val Asn Arg Ser Ile Asn Val Gln
        435                 440                 445

Pro Ser Cys Leu Val Leu Pro Ser Gln Leu Pro Gly His Phe Gln Val
    450                 455                 460
```

```
Gly Asp Ser Pro Ala Ser Ile Ser Arg Ala Gly Ser Leu Ser Lys Ser
465                 470                 475                 480

Ser Val Ile Asp Tyr Gly Val Leu Ser Pro Gln Ser Asn Asn Ser Ser
                485                 490                 495

Gly Val Val Gln Val Leu Asp Arg Glu Leu Lys Pro Glu Cys Gly Leu
            500                 505                 510

Asn Arg Leu Pro Ser Gly Gly Ser Leu Ser Arg Ser Cys Ser Ile Asn
        515                 520                 525

Ala Asp Asn Ser Val Asp Leu Gln Leu His Asn Ser Ser Ser Ala Phe
    530                 535                 540

Gly Ser Ser Lys Gln Leu Pro Gly Leu Ile Pro Ser His Leu Gly Ser
545                 550                 555                 560

Pro Val Pro Tyr Cys Ile Asn Ser Ser Leu Val Leu Asp Gln Gly Arg
                565                 570                 575

Met Lys Gly Ala Ser Ile Pro Ser Arg Phe Ala Val Asp Glu Ser Asp
            580                 585                 590

Ser Pro Met Cys Asn Phe Asn Thr Ala Lys Ile Tyr Leu Glu Glu Thr
        595                 600                 605

Lys Val Lys Gln Glu Pro Asn Met Asn Val Met Glu Asn Ala Lys Val
    610                 615                 620

Gly Pro Ala Ile Phe Gln Lys Phe Gln Pro Gly Asp Leu Met Ser Val
625                 630                 635                 640

Phe Arg Leu Ser Phe Ala Arg Val Lys Val Ser Ser Ser Pro
                645                 650
```

<210> SEQ ID NO 30
<211> LENGTH: 653
<212> TYPE: PRT
<213> ORGANISM: Solanum tuberosum

<400> SEQUENCE: 30

```
Met Ser Gly Asp Val Ala Thr Cys Lys Ser Glu Ala Thr Val Val Thr
1               5                   10                  15

Asp His Phe Pro Leu Gly Leu Arg Val Leu Val Val Asp Asp Asp Val
            20                  25                  30

Val Cys Leu Arg Ile Ile Glu Gln Met Leu Arg Arg Cys Lys Tyr Ser
        35                  40                  45

Val Thr Thr Cys Thr Gln Ala Met Val Ala Leu Asn Leu Leu Arg Glu
    50                  55                  60

Lys Arg Gly Thr Phe Asp Ile Val Leu Ser Asp Val His Met Pro Asp
65                  70                  75                  80

Met Asp Gly Phe Lys Leu Leu Glu Leu Val Gly Leu Glu Met Asp Leu
                85                  90                  95

Pro Val Ile Met Met Ser Gly Asp Gly Arg Thr Asn Leu Val Met Arg
            100                 105                 110

Gly Val Gln His Gly Ala Cys Asp Tyr Leu Ile Lys Pro Ile Arg Asp
        115                 120                 125

Glu Glu Leu Lys Asn Ile Trp Gln His Val Val Arg Lys Arg Tyr Asn
    130                 135                 140

Ser Ser Lys Glu Leu Glu Cys Ser Gly Ser Leu Asp Asp Asn Asp Arg
145                 150                 155                 160

Tyr Lys Arg Gly Ser Asp Asp Ala Glu Cys Ala Ser Ser Val Ile Glu
                165                 170                 175

Gly Ala Asp Gly Val Leu Lys Pro Gln Lys Lys Lys Arg Glu Ala Lys
            180                 185                 190
```

-continued

```
Glu Glu Asp Asp Thr Glu Met Glu Asn Asp Asp Pro Ser Thr Ser Lys
        195                 200                 205

Lys Pro Arg Val Val Trp Ser Val Glu Leu His Gln Gln Phe Val Ser
    210                 215                 220

Ala Val Asn Gln Leu Gly Ile Asp Lys Ala Val Pro Lys Arg Ile Leu
225                 230                 235                 240

Glu Leu Met Asn Val Pro Gly Leu Thr Arg Glu Asn Val Ala Ser His
                245                 250                 255

Leu Gln Glu Asn Gln Lys Phe Arg Leu Tyr Leu Lys Arg Leu Ser Gly
            260                 265                 270

Val Val Gln Gln Gln Gly Gly Leu Pro Ser Thr Phe Cys Gly Pro Ile
        275                 280                 285

Glu Gln Asn Ser Glu Leu Gly Ser Leu Gly Arg Phe Asp Ile Gln Ala
    290                 295                 300

Leu Ala Ala Ser Gly Gln Ile Pro Pro Glu Thr Leu Thr Ala Leu His
305                 310                 315                 320

Ala Glu Leu Leu Gly Arg Ser Thr Ser Asn Leu Val Leu Pro Ala Val
                325                 330                 335

Glu Ile Gln Asn Leu Leu Gln Ala Ser Leu Gln Gln Ala Lys Cys Ile
            340                 345                 350

Pro Ala Asp Gln Val Met Ala Tyr Gly Gln Pro Leu Leu Lys Cys His
        355                 360                 365

Pro Ser Ile Ser Asn Ser Lys His Leu Ser Gln Ser Ile Leu Ser Ala
    370                 375                 380

Glu Asp Val His Ser Gly Phe Gly Ser Gln Arg Ala Lys Asn Ile Cys
385                 390                 395                 400

Leu Val Pro Ser Ser Asn Pro Ile Gly Leu Ala Ala Pro Asn Ser Asn
                405                 410                 415

Met Leu Met Ala Met Met Gln Gln Gln Gln Trp Gln Lys Gln Gln Gln
            420                 425                 430

Met Glu Leu Gln His Arg Arg Ser Gly Pro Pro Glu Val Asn His Ser
        435                 440                 445

Ile Asn Val Gln Pro Ser Cys Leu Val Leu Pro Ser Gln Leu Pro Gly
    450                 455                 460

Asn Phe Gln Val Gly Asp Ser Pro Ala Ser Ile Ser Arg Ala Gly Ser
465                 470                 475                 480

Leu Ser Lys Ser Ser Val Ile Asp Tyr Gly Val Leu Ser Pro Gln Ser
                485                 490                 495

Asn Asn Ser Ser Gly Val Val Gln Val Leu Asp Arg Glu Leu Lys Pro
            500                 505                 510

Glu Cys Gly Leu Asn Arg Leu Pro Ser Gly Gly Ser Leu Ser Arg Ser
        515                 520                 525

Cys Ser Ile Asn Ala Asp Asn Ser Val Gly Leu Gln Leu His Asn Ser
    530                 535                 540

Ser Ser Ala Phe Gly Ser Ser Lys Gln Leu Pro Ala Leu Ile Pro Asn
545                 550                 555                 560

His Leu Gly Ser Pro Val Pro Tyr Tyr Ile Asn Ser Ser Gln Val Leu
                565                 570                 575

Asp Gln Gly His Thr Arg Asn Pro Gly Val Gly Lys Cys Ala Ser Ile
            580                 585                 590

Pro Ser Arg Phe Ala Val Asp Glu Ser Asp Ser Pro Met Cys Asn Phe
        595                 600                 605
```

```
Asn Thr Ala Lys Asn Tyr Leu Glu Glu Thr Lys Val Lys Gln Glu Pro
    610                 615                 620

Asn Met Asn Val Met Glu Asn Ala Lys Val Gly Pro Ala Ile Phe Gln
625                 630                 635                 640

Lys Phe Gln Pro Gly Asp Leu Met Ser Val Phe Ser Asp
                645                 650


<210> SEQ ID NO 31
<211> LENGTH: 669
<212> TYPE: PRT
<213> ORGANISM: Gossypium hirsutum

<400> SEQUENCE: 31

Met Ala Thr Met His Arg Val Val Gln Ser Ser Val Ser Thr Ser Asp
1               5                   10                  15

Ala Thr Thr Thr Ser Tyr Asp Gly Leu Thr Ser Cys Lys Ala Ala Asp
            20                  25                  30

Ile Val Ile Ser Asp Gln Phe Pro Ala Gly Leu Arg Val Leu Val Val
        35                  40                  45

Asp Asp Asp Ile Thr Cys Leu Lys Ile Leu Glu Lys Met Leu His Arg
    50                  55                  60

Cys Arg Tyr His Val Thr Thr Cys Pro Gln Ala Lys Val Ala Leu Asn
65                  70                  75                  80

Leu Leu Arg Glu Arg Lys Gly Cys Phe Asp Val Ile Leu Ser Asp Val
                85                  90                  95

Tyr Met Pro Asp Met Asp Gly Tyr Lys Leu Leu Glu His Val Gly Leu
            100                 105                 110

Glu Met Asp Leu Pro Val Ile Met Met Ser Ala Asp Gly Ser Thr Arg
        115                 120                 125

Ala Val Met Lys Gly Ile Arg His Gly Ala Cys Asp Tyr Leu Ile Lys
    130                 135                 140

Pro Ile Arg Glu Glu Glu Leu Lys Asn Ile Trp Gln His Val Val Arg
145                 150                 155                 160

Lys Lys Trp Asn Glu Asn Lys Glu Leu Glu His Ser Gly Ser Leu Asp
                165                 170                 175

Asp Thr Asp Gln His Lys Gln Arg His Asp Asp Ala Glu Tyr Ala Ser
            180                 185                 190

Ser Val Asn Asp Ala Thr Glu Thr Ser Leu Lys Pro Leu Lys Lys Arg
        195                 200                 205

Ser Asn Ser Lys Glu Glu Asp Asp Gly Glu Ile Asp Asn Asp Asp Pro
    210                 215                 220

Ser Thr Ser Lys Lys Pro Arg Val Val Trp Ser Val Glu Leu His Gln
225                 230                 235                 240

Gln Phe Val Ser Ala Val Asn Gln Leu Gly Ile Asp Lys Ala Val Pro
                245                 250                 255

Lys Arg Ile Leu Glu Leu Met Asn Val Pro Gly Leu Thr Arg Glu Asn
            260                 265                 270

Val Ala Ser His Leu Gln Lys Phe Arg Leu Tyr Leu Lys Arg Ile Ser
        275                 280                 285

Gly Val Ala Gln Gln Gly Gly Ile Ala Asn Pro Leu Cys Gly Pro Val
    290                 295                 300

Glu Ala Asn Val Lys Ile Gly Ser Leu Gly Ser Phe Asn Ile Gln Ala
305                 310                 315                 320

Leu Ala Ala Ser Gly Gln Ile Pro Pro Gln Thr Leu Ala Ala Val His
                325                 330                 335
```

```
Ala Glu Leu Leu Gly Arg Ser Ala Gly Asn Leu Val Val Ala Thr Asp
            340                 345                 350

Gln Pro Ala Leu Leu Gln Ala Thr Pro Gln Gly Ala Lys Cys Ile Gln
        355                 360                 365

Val Asp Gln Gly Val Ala Phe Val Gln His Ser Val Lys Ser Glu Ser
    370                 375                 380

Ser Ser Ser Lys His Phe Ser Gln Ser Phe Ala Pro Val Glu Asp Val
385                 390                 395                 400

Ala Ser Gly Phe Arg Ser Trp Pro Ser Asn Asn Ile Gly Thr Ala Gly
                405                 410                 415

Pro Ser Asn Ser Gly Gly Leu Ser Ser Gln Asn Gly Asn Met Leu Ile
            420                 425                 430

Asp Leu Leu Gln Gln Gln Gln Gln Leu Gln Lys Pro Gln Gln Arg Ser
        435                 440                 445

Thr Val Ser Glu Leu Arg Arg Ser Ile Asn Val Gln Pro Ser Cys His
    450                 455                 460

Val Val Pro Ser Gln Ser Ser Ala Ser Phe Arg Ala Gly Asn Ser Pro
465                 470                 475                 480

Val Ser Val Thr Gln Asn Gly Ser Tyr Ser Arg Thr Ala Val Ile Asp
                485                 490                 495

Tyr Ser Leu Leu Ser Ser Gln Ser Asn Cys Pro Ser Leu Asn Ile Gly
            500                 505                 510

Gln Val Ser Asp Val Asn Leu Gln Thr Thr Gly Val Leu Ser Gly Tyr
        515                 520                 525

Ile Pro Pro Ala Ser Val Ser Pro Ser Val Ser Ser Cys Ser Val Asn
    530                 535                 540

Ala Asp Asn Cys Ala Ser Gln Gln Val Gln Thr Ser Ser Met Thr Phe
545                 550                 555                 560

Lys Ala Ser Arg His Leu Pro Gly Phe Val His Ser Thr Ser Asn Ile
                565                 570                 575

Pro Asp Pro Tyr Gly Ser Thr Lys Ser Gly Asp Leu Leu Asn Gln Glu
            580                 585                 590

Pro Phe Asn Asn Leu Gly Tyr Ile Asn Lys Gly Thr Cys Leu Pro Ala
        595                 600                 605

Lys Phe Ala Val Asp Glu Phe Gln Ser His Leu Ser Ser Ser Ser His
    610                 615                 620

Gly Lys Val Phe Ser Glu Asn Ile Gly Thr Arg Val Lys Gln Glu Pro
625                 630                 635                 640

Ser Met Glu Phe Gly Asp Asn Ala Lys Val Gly Ile Pro Met Leu Gln
                645                 650                 655

Gln Phe Arg Pro Asn Asp Leu Met Ser Val Phe Thr Glu
            660                 665


<210> SEQ ID NO 32
<211> LENGTH: 681
<212> TYPE: PRT
<213> ORGANISM: Theobroma cacao

<400> SEQUENCE: 32

Met Asn Ser Ser Ser Gly Lys Gly Ser Met Ser Ala Ala Ser Ser Ser
1               5                   10                  15

Ala Ala Trp Lys Ala Gly Asp Val Val Pro Asp Gln Phe Pro Ala Gly
            20                  25                  30

Leu Arg Val Leu Val Val Asp Asp Asp Pro Thr Cys Leu Met Ile Leu
```

-continued

```
        35                  40                  45

Glu Lys Met Leu Arg Thr Cys Leu Tyr Glu Val Thr Lys Cys Asn Arg
    50                  55                  60

Ala Glu Thr Ala Leu Ser Leu Leu Arg Glu Asn Lys Asn Gly Phe Asp
65                  70                  75                  80

Ile Val Ile Ser Asp Val His Met Pro Asp Met Asp Gly Phe Lys Leu
                85                  90                  95

Leu Glu His Ile Gly Leu Glu Met Asp Leu Pro Val Ile Met Met Ser
            100                 105                 110

Ala Asp Asp Gly Lys His Val Val Met Lys Gly Val Thr His Gly Ala
        115                 120                 125

Cys Asp Tyr Leu Ile Lys Pro Val Arg Ile Glu Ala Leu Lys Asn Ile
    130                 135                 140

Trp Gln His Val Val Arg Lys Arg Lys Asn Glu Trp Lys Asp Phe Glu
145                 150                 155                 160

Gln Ser Gly Ser Val Glu Glu Gly Asp Arg Gln Pro Lys Gln Ser Glu
                165                 170                 175

Glu Ala Asp Tyr Ser Ser Ser Ala Asn Glu Gly Asn Trp Lys Ser Ser
            180                 185                 190

Lys Lys Arg Lys Asp Asp Asp Asp Glu Ala Glu Glu Arg Asp Asp Thr
        195                 200                 205

Ser Thr Leu Lys Lys Pro Arg Val Val Trp Ser Val Glu Leu His Gln
    210                 215                 220

Gln Phe Val Ala Ala Val Asn Gln Leu Gly Ile Asp Lys Ala Val Pro
225                 230                 235                 240

Lys Lys Ile Leu Glu Leu Met Asn Val Pro Gly Leu Thr Arg Glu Asn
                245                 250                 255

Val Ala Ser His Leu Gln Lys Tyr Arg Leu Tyr Leu Arg Arg Leu Ser
            260                 265                 270

Gly Val Ser Gln His Gln Ser Asn Leu Asn Asn Ser Phe Met Ser Pro
        275                 280                 285

Gln Glu Ala Thr Phe Gly Pro Leu Ser Pro Leu Asn Gly Leu Asp Leu
    290                 295                 300

Gln Thr Leu Ala Ala Thr Gly Gln Leu Pro Ala Gln Ser Leu Ala Thr
305                 310                 315                 320

Phe Gln Ala Ala Gly Leu Gly Arg Ser Thr Ala Lys Ser Gly Ile Ala
                325                 330                 335

Met Pro Leu Val Asp Gln Arg Asn Ile Phe Ser Phe Glu Asn Pro Lys
            340                 345                 350

Leu Arg Phe Gly Glu Gly Gln Gln Gln His Met Asn Asn Asn Lys Gln
        355                 360                 365

Leu Asn Leu Leu His Gly Ile Pro Thr Thr Met Glu Pro Lys Gln Leu
    370                 375                 380

Ala Ser Leu His His Ser Ala Gln Ser Ile Gly Asn Ile Asn Met Gln
385                 390                 395                 400

Val Thr Ser His Gly Val Gln Gly Ser Gln Asn Asn Ser Leu Leu Ile
                405                 410                 415

Gln Met Ala Gln Pro Gln Pro Arg Gly Gln Ile Leu Asn Asp Ser Thr
            420                 425                 430

Gly Ser His Ala Pro Arg Leu Pro Ser Thr Leu Gly Gln Pro Ile Leu
        435                 440                 445

Ser Asn Gly Ile Ala Ala Asn Val Ser Thr Arg Asn Gly Ile Pro Glu
    450                 455                 460
```

```
Asn Ile Arg Gly Pro Gly Tyr Asn Pro Val Ser Gln Thr Ser Ser Leu
465                 470                 475                 480

Leu Asn Phe Pro Met Asn His Thr Ser Glu Leu Pro Gly Asn Ser Phe
                485                 490                 495

Pro Leu Gly Thr Thr Pro Gly Ile Ser Ser Leu Thr Ser Lys Gly Ala
            500                 505                 510

Phe Gln Glu Asp Ile Asn Ser Asp Val Lys Gly Ser Gly Gly Phe Met
        515                 520                 525

Pro Ser Tyr Asp Ile Phe Asn Asp Leu Asn Gln His Lys Pro Gln Asn
    530                 535                 540

Trp Glu Leu Gln Asn Val Gly Met Thr Phe Asp Ala Ser Gln His Ser
545                 550                 555                 560

Asn Ser Leu Gln Gly Asn Leu Asp Leu Ala Gln Ser Ile Leu Val Gln
                565                 570                 575

Gln Gly Phe Ser Ser Gly Gln Met Asn Gly Gln Asn Arg Ser Ala Ala
            580                 585                 590

Val Val Ser Lys Ala Met Phe Ser Ala Gly Asp Cys Thr Glu Gln Gly
        595                 600                 605

Asn Ala Gln Asn Val Asn His His Leu Asn Asn Leu Leu Val Asp Asn
    610                 615                 620

Thr Ile Arg Ile Lys Ser Glu Arg Val Ala Asp Ala Gly Pro Ala Asn
625                 630                 635                 640

Leu Phe Pro Asp His Phe Gly Gln Glu Asp Leu Met Ser Ala Leu Leu
                645                 650                 655

Lys Gln Gln Asp Gly Ile Ala Pro Ala Glu Asn Glu Phe Asp Phe Asp
            660                 665                 670

Gly Tyr Ser Met Asp Asn Ile Pro Val
        675                 680
```

<210> SEQ ID NO 33
<211> LENGTH: 579
<212> TYPE: PRT
<213> ORGANISM: Phaseolus vulgaris

<400> SEQUENCE: 33

```
Met Asn Leu Ser Asn Gly Lys Gly Ser Met Ser Thr Val Thr Thr Thr
1               5                   10                  15

Ala Val Met Lys Ser Gly Asp Ala Val Ser Asp Gln Phe Pro Ala Gly
            20                  25                  30

Leu Arg Val Leu Val Val Asp Asp Asp Pro Thr Cys Leu Met Ile Leu
        35                  40                  45

Glu Lys Met Leu Arg Thr Cys Leu Tyr Glu Val Thr Lys Cys Asn Arg
    50                  55                  60

Ala Glu Thr Ala Leu Ser Leu Leu Arg Glu Asn Lys Asn Gly Phe Asp
65                  70                  75                  80

Ile Val Ser Ala Asn Glu Gly Ser Trp Arg Asn Ser Lys Lys Arg Arg
                85                  90                  95

Asp Glu Glu Glu Glu Ala Glu Asp Arg Asp Asp Thr Ser Thr Leu Lys
            100                 105                 110

Lys Pro Arg Val Val Trp Ser Val Glu Leu His Gln Gln Phe Val Ala
        115                 120                 125

Ala Val Asp Gln Leu Gly Ile Asp Lys Ala Val Pro Lys Lys Ile Leu
    130                 135                 140

Glu Leu Met Asn Val Pro Gly Leu Thr Arg Glu Asn Val Ala Ser His
```

```
145                 150                 155                 160

Leu Gln Lys Tyr Arg Leu Tyr Leu Arg Arg Leu Ser Gly Val Ser Gln
                165                 170                 175

His Gln Asn Asn Leu Asn Asn Ser Phe Leu Gly Ser Gln Glu Ala Thr
            180                 185                 190

Phe Gly Thr Ile Ser Ser Ile Asn Gly Ile Asp Leu Gln Thr Leu Ala
        195                 200                 205

Val Thr Gly Gln Leu Pro Ala Gln Ser Leu Ala Thr Leu Gln Ala Ala
    210                 215                 220

Gly Leu Gly Arg Ser Thr Ala Lys Thr Gly Val Pro Met Pro Leu Met
225                 230                 235                 240

Asp Gln Arg Asn Leu Phe Ser Phe Glu Asn Pro Arg Val Arg Phe Gly
                245                 250                 255

Glu Gly Gln Gln Gln His Leu Ser Ser Ser Lys Pro Met Asn Leu Leu
            260                 265                 270

Leu Gly Ile Pro Thr Asn Met Glu Pro Lys Gln Leu Ala Asn Leu His
        275                 280                 285

Gln Ser Thr Gln Ser Ile Ala Ser Leu Asn Met Arg Val Asn Ala Ser
    290                 295                 300

Ala Thr Gln Gly Asn Pro Leu Met Met Gln Met Pro Gln Ser Gln Pro
305                 310                 315                 320

Arg Gly Gln Met Leu Ser Glu Asn Thr Gly Pro Arg Val Pro Arg Leu
                325                 330                 335

Pro Ser Ser Leu Gly Gln Pro Thr Val Ser Asn Gly Ile Ser Asn Gly
            340                 345                 350

Phe Leu Gly Arg Asn Gly Ile Ala Gly Asn Asn Arg Gly Pro Ala Tyr
        355                 360                 365

Asn Pro Val Pro Pro Asn Ser Ser Leu Leu Ser Phe Pro Met Asn Gln
    370                 375                 380

Ser Ser Glu Val Ser Val Asn Asn Ser Leu Pro Leu Gly Ser Ser Pro
385                 390                 395                 400

Gly Ile Ser Ser Ile Thr Thr Lys Gly Ser Phe Gln Glu Glu Val Thr
                405                 410                 415

Ser Gly Ile Lys Ala Thr Gly Gly Phe Pro Ser Tyr Asp Ile Phe Asn
            420                 425                 430

Glu Leu His His Gln Lys Ser His Asp Trp Glu Ile Thr Asn Pro Ser
        435                 440                 445

Leu Thr Tyr Ser Ala Ser His His Ala Asn Pro Leu Gln Gly Asn Ile
    450                 455                 460

Asp Val Ser Pro Ser Val Leu Val His Gln Gly Phe Ser Ser Thr Gln
465                 470                 475                 480

Gln Asn Gly Gln Ser Arg Asp Ala Thr Leu Ile Gly Lys Ala Met Phe
                485                 490                 495

Ser Leu Gly Glu Gly Ser Glu Gln Asp Asn Leu Gln Asn Ala Val Gln
            500                 505                 510

His Leu His Pro Leu Leu Val Asp Asn Ser Ile Arg Val Lys Ala Glu
        515                 520                 525

Arg Ile Pro Asp Ala Ser Ser Gln Thr Asn Leu Phe Pro Asp His Tyr
    530                 535                 540

Val Gln Glu Asp Leu Met Ser Ala Leu Leu Lys Gln Gln Glu Gly Met
545                 550                 555                 560

Gly Pro Ala Glu Ser Glu Phe Glu Phe Asp Ala Tyr Ser Leu Asp Asn
                565                 570                 575
```

Ile Pro Val

<210> SEQ ID NO 34
<211> LENGTH: 679
<212> TYPE: PRT
<213> ORGANISM: Glycine max

<400> SEQUENCE: 34

```
Met Asn Leu Ser Asn Gly Lys Gly Ser Met Ser Thr Leu Thr Ala Ser
1               5                   10                  15

Val Val Met Lys Ser Gly Asp Ala Val Ser Asp Gln Phe Pro Ala Gly
            20                  25                  30

Leu Arg Val Leu Val Val Asp Asp Asp Pro Thr Cys Leu Met Ile Leu
        35                  40                  45

Glu Lys Met Leu Arg Thr Cys Leu Tyr Glu Val Thr Lys Cys Asn Arg
    50                  55                  60

Ala Glu Thr Ala Leu Ser Leu Leu Arg Glu Asn Lys Asn Gly Phe Asp
65                  70                  75                  80

Ile Val Ile Ser Asp Val His Met Pro Asp Met Asp Gly Phe Lys Leu
                85                  90                  95

Leu Glu His Ile Gly Leu Glu Met Asp Leu Pro Val Ile Met Met Ser
            100                 105                 110

Ala Asp Asp Gly Lys Ser Val Val Met Lys Gly Val Thr His Gly Ala
        115                 120                 125

Cys Asp Tyr Leu Ile Lys Pro Val Arg Ile Glu Ala Leu Lys Asn Ile
    130                 135                 140

Trp Gln His Val Val Arg Lys Arg Lys Asn Glu Trp Lys Asp Ala Glu
145                 150                 155                 160

Gln Ser Gly Ser Ala Glu Glu Gly Asp Arg Gln Pro Lys Ala Ser Asp
                165                 170                 175

Glu Ala Asp Tyr Ser Ser Ser Ala Asn Glu Gly Ser Trp Arg Asn Ser
            180                 185                 190

Lys Lys Arg Arg Asp Glu Glu Glu Glu Ala Glu Asp Arg Asp Asp Thr
        195                 200                 205

Ser Thr Leu Lys Lys Pro Arg Val Val Trp Ser Val Glu Leu His Gln
    210                 215                 220

Gln Phe Val Ala Ala Val Asp Gln Leu Gly Ile Asp Lys Ala Val Pro
225                 230                 235                 240

Lys Lys Ile Leu Glu Leu Met Asn Val Pro Gly Leu Thr Arg Glu Asn
                245                 250                 255

Val Ala Ser His Leu Gln Lys Tyr Arg Leu Tyr Leu Arg Arg Leu Ser
            260                 265                 270

Gly Val Ser Gln His Gln Asn Asn Met Asn Asn Ser Phe Leu Ser Pro
        275                 280                 285

Gln Glu Ala Thr Phe Gly Thr Ile Ser Ser Ile Asn Gly Ile Asp Leu
    290                 295                 300

Gln Thr Leu Ala Val Ala Gly Gln Leu Pro Ala Gln Ser Leu Ala Thr
305                 310                 315                 320

Leu Gln Ala Ala Gly Leu Gly Arg Pro Thr Gly Lys Ala Gly Val Pro
                325                 330                 335

Met Pro Leu Met Asp Gln Arg Asn Leu Phe Ser Phe Glu Asn Pro Arg
            340                 345                 350

Leu Arg Phe Gly Glu Gly Gln Gln Gln His Leu Ser Thr Ser Lys Pro
        355                 360                 365
```

```
Met Asn Leu Leu His Gly Ile Pro Thr Asn Met Glu Pro Lys Gln Leu
    370                 375                 380

Ala Asn Leu His Gln Ser Thr Gln Ser Ile Gly Ser Leu Asn Met Arg
385                 390                 395                 400

Val Asn Ala Ser Ala Thr Gln Gly Ser Pro Leu Leu Met Gln Met Ala
                405                 410                 415

Gln Ser Gln Pro Arg Gly Gln Met Leu Ser Glu Asn Ile Gly Pro Arg
            420                 425                 430

Val Pro Arg Leu Pro Ser Ser Leu Gly Gln Pro Thr Val Ser Asn Gly
        435                 440                 445

Ile Ser Asn Gly Leu Leu Gly Arg Asn Gly Ile Ala Gly Asn Asn Arg
    450                 455                 460

Gly Pro Ala Tyr Asn Pro Val Pro Pro Ser Ser Ser Leu Leu Ser Phe
465                 470                 475                 480

Pro Met Asn Gln Thr Ser Glu Met Ser Val Asn Asn Ser Phe Pro Leu
                485                 490                 495

Gly Ser Thr Pro Gly Ile Ser Ser Ile Thr Thr Lys Gly Ser Phe Gln
            500                 505                 510

Glu Glu Val Thr Ser Gly Ile Lys Gly Ser Gly Gly Phe Pro Ser Tyr
        515                 520                 525

Asp Ile Phe Asn Glu Leu His His Gln Lys Pro His Asp Trp Glu Ile
    530                 535                 540

Thr Asn Pro Asn Leu Thr Tyr Asn Ala Ser Gln His Ala Asn Pro Leu
545                 550                 555                 560

Gln Gly Asn Ile Asp Val Thr Pro Ser Val Leu Val His Gln Gly Phe
                565                 570                 575

Ser Ser Thr Gln Gln Thr Gly Gln Ser Arg Asp Ala Ala Leu Ile Gly
            580                 585                 590

Lys Ala Met Phe Ser Met Gly Glu Gly Leu Glu Gln Asn Asn Phe Gln
        595                 600                 605

Asn Ala Ser Gln Asn Leu Asn Ser Leu Leu Leu Asp Asn Ser Ile Arg
    610                 615                 620

Val Lys Ala Glu Arg Ile Pro Asp Ala Ser Ser Gln Thr Asn Leu Phe
625                 630                 635                 640

Pro Glu His Tyr Gly Gln Glu Asp Leu Met Ser Ala Leu Leu Lys Gln
                645                 650                 655

Gln Glu Gly Met Gly Pro Ser Glu Asn Glu Phe Asp Phe Asp Gly Tyr
            660                 665                 670

Ser Leu Asp Asn Ile Pro Val
        675
```

<210> SEQ ID NO 35
<211> LENGTH: 668
<212> TYPE: PRT
<213> ORGANISM: Chenopodium quinoa

<400> SEQUENCE: 35

```
Met Asn Leu Gly Gly Gly Leu Met Gly Ser Met Ala Met Pro Ser Ser
1               5                   10                  15

Thr Val Ser Arg Lys Ser Ser Glu Val Val Thr Ala Asp Gln Phe Pro
            20                  25                  30

Val Gly Leu Arg Val Leu Val Val Asp Asp Asp Pro Thr Cys Leu Thr
        35                  40                  45

Ile Leu Glu Lys Met Leu Arg Thr Cys Arg Tyr Glu Val Thr Lys Thr
```

```
    50                  55                  60

Asn Arg Ala Glu His Ala Leu Asn Met Leu Arg Glu Asn Lys Asn Gly
65                  70                  75                  80

Phe Asp Val Val Ile Ser Asp Val His Met Pro Asp Met Asp Gly Phe
                85                  90                  95

Lys Leu Leu Glu Gln Val Gly Leu Glu Met Asp Leu Pro Val Ile Met
            100                 105                 110

Met Ser Ala Asp Asp Ser Lys Gln Val Val Met Lys Gly Val Thr His
        115                 120                 125

Gly Ala Cys Asp Tyr Leu Ile Lys Pro Val Arg Ile Glu Ala Leu Lys
    130                 135                 140

Asn Ile Trp Gln His Val Val Arg Lys Lys Lys Tyr Glu Tyr Asn Lys
145                 150                 155                 160

Asp Val Glu Gln Ser Gly Ser Trp Asp Glu Gly Asp Arg Gln Leu Lys
                165                 170                 175

His Asp Asp Ala Val Ser Ser Pro Ala Asn Asp Gly Ser Trp Lys Asn
            180                 185                 190

Ser Lys Arg Lys Ser Gly Glu Asp Asp Glu Ala Asp Asp Lys Asp Asp
        195                 200                 205

Thr Thr Thr Leu Lys Lys Pro Arg Val Val Trp Ser Val Glu Leu His
    210                 215                 220

Gln Gln Phe Val Ala Ala Val Asn Gln Leu Gly Ile Asp Lys Ala Val
225                 230                 235                 240

Pro Lys Lys Ile Leu Glu Leu Met Asn Val Pro Gly Leu Thr Arg Glu
                245                 250                 255

Asn Val Ala Ser His Leu Gln Lys Tyr Arg Leu Tyr Leu Arg Arg Leu
            260                 265                 270

Ser Gly Val Ser Gln His Gln Gly Gly Leu Asn Ser Ser Phe Met Pro
        275                 280                 285

Gln Asp Pro Ser Phe Ser Thr Met Ser Ser Leu Gly Gly Ile Asp Leu
    290                 295                 300

Gln Thr Leu Ala Ala Thr Gly Gln Leu Ser Ala Gln Thr Leu Ala Ala
305                 310                 315                 320

Tyr Thr Arg Leu Pro Pro Thr Ile Lys Pro Gly Ile Ser Met Pro Phe
                325                 330                 335

Val Asp Gln Arg Asn Leu Phe Ser Phe Glu Asn Ser Lys Leu Arg Tyr
            340                 345                 350

Gly Asp Gly Gln Gln Ser Gln Ile Ser Asn Val Ser Lys Gln Met Asn
        355                 360                 365

Leu Leu His Gly Phe Pro Thr Thr Met Glu Pro Lys Gln Leu Ala Val
    370                 375                 380

Leu Asn Gln Ser Ala Gln Thr Leu Gly Ser Met Asn Met Gln Ala Asn
385                 390                 395                 400

Ala Ser Ser Ser His Gln Ser Ser Ser Leu Leu Met Gln Gln Met Val
                405                 410                 415

Pro Gln Gln Arg Gly His Ile Ser Asn Glu Ser Ile Ser Ser Gln Val
            420                 425                 430

Pro Arg Ile Gln Pro Ser Val Gly Gln Pro Leu Gln Ser Asn Gly Asn
        435                 440                 445

Ala Asn Ala Val Leu Ser Arg Asn Gly Ile Pro Tyr Asp Pro Val Asn
    450                 455                 460

Gln Ser Ala Ser Val Val Asp Phe Ser Val Asn His Ile Pro Glu Leu
465                 470                 475                 480
```

```
Pro Gly Asn Ser Phe Pro Leu Gly Ser Thr Pro Gly Ile Thr Ser Ile
                485                 490                 495

Thr Ser Lys Gly Phe Asn Gln Glu Glu Ile Gly Ser Asp Ile Lys Val
            500                 505                 510

Ser Arg Gly Phe Val Gly Ser Tyr Asp Met Phe Ser Glu Leu Gln His
        515                 520                 525

Lys Pro Gln Glu Trp Gln Met Gln Asn Pro Asn Met Gly Phe Ala Gly
    530                 535                 540

Ser Ser Gln His Val Pro Ser Val Gln Ser Gly Val Asn Val Ala Pro
545                 550                 555                 560

Ser Ile Met Val Asn Gln Ser Tyr Val Ser Gly Gln Lys Asn Glu Gln
                565                 570                 575

Asn Gly His Ser Met Ala Gly Lys Pro Met Tyr Ser Ala Gly Leu Glu
            580                 585                 590

Asn Gln His Met Gly Met Gln Asn Val Asn Gln Asn Tyr Asn Ser Ile
        595                 600                 605

His Val Asn Asn Ser Ser Arg Val Lys Ala Glu Ser Val Ser Asp Val
    610                 615                 620

Val Asn Leu Gly Ala Asn Leu Phe Asp Tyr Ser Pro Glu Asp Met Leu
625                 630                 635                 640

Ser Thr Ile Met Leu Lys Gln Gln Glu Gly Ile Gly Ser Gly Asp Phe
                645                 650                 655

Asp Phe Asp Gly Tyr Thr Leu Asp Asn Ile Pro Val
            660                 665
```

<210> SEQ ID NO 36
<211> LENGTH: 670
<212> TYPE: PRT
<213> ORGANISM: Malus domestica
<220> FEATURE:
<221> NAME/KEY: MOD_RES
<222> LOCATION: (195)..(195)
<223> OTHER INFORMATION: Any amino acid
<220> FEATURE:
<221> NAME/KEY: MOD_RES
<222> LOCATION: (215)..(215)
<223> OTHER INFORMATION: Any amino acid
<220> FEATURE:
<221> NAME/KEY: MOD_RES
<222> LOCATION: (530)..(530)
<223> OTHER INFORMATION: Any amino acid
<220> FEATURE:
<221> NAME/KEY: MOD_RES
<222> LOCATION: (540)..(540)
<223> OTHER INFORMATION: Any amino acid
<220> FEATURE:
<221> NAME/KEY: MOD_RES
<222> LOCATION: (579)..(579)
<223> OTHER INFORMATION: Any amino acid

<400> SEQUENCE: 36

```
Met Ala Ala Leu Gln Arg Val Ala Gln Ser Ser Val Ser Thr Thr Ala
1               5                   10                  15

Ser Ser Tyr Gly Ser Cys Lys Val Gly Gly Gly Val Leu Ser Pro Ser
            20                  25                  30

Ala Gly Ile Glu Met Ala Val Pro Asn Gln Phe Pro Ala Gly Leu Arg
        35                  40                  45

Val Leu Val Val Asp Asp Asp Thr Thr Cys Leu Arg Ile Leu Glu Leu
    50                  55                  60

Met Leu Leu Arg Cys Leu Tyr Gln Val Thr Thr Cys Ser Glu Ala Thr
65                  70                  75                  80
```

```
Val Ala Leu Asn Leu Leu Arg Glu Arg Lys Asp Cys Phe Asp Val Val
                85                  90                  95

Leu Ser Asp Val His Met Pro Asp Met Asp Gly Phe Lys Leu Leu Glu
            100                 105                 110

His Val Gly Leu Glu Met Asp Leu Pro Val Ile Met Met Ser Ala Asp
        115                 120                 125

Gly Arg Thr Ser Val Val Met Arg Gly Ile Arg His Gly Ala Cys Asp
    130                 135                 140

Phe Leu Ile Lys Pro Ile Ser Glu Ala Glu Leu Lys Asn Ile Trp Gln
145                 150                 155                 160

His Val Val Arg Lys Lys Trp Asn Gly Ser Lys Glu Leu Glu His Ser
                165                 170                 175

Gly Ser Leu Glu Asp Asn Asp Pro His Lys Arg Gly Asn Asn Asp Phe
            180                 185                 190

Glu Tyr Xaa Ser Ser Val Asn Glu Gly Thr Glu Val Ser Leu Lys Gly
        195                 200                 205

His Lys Lys Arg Ile Asn Xaa Lys Glu Asp Asp Asp Gly Asp Thr Glu
    210                 215                 220

Asn Asp Asp Leu Ser Thr Ser Lys Lys Pro Arg Val Val Trp Ser Val
225                 230                 235                 240

Glu Leu His Gln Gln Phe Val Thr Ala Val Asn Gln Leu Gly Leu Asp
                245                 250                 255

Lys Ala Val Pro Lys Arg Ile Leu Glu Leu Met Asn Val Pro Gly Leu
            260                 265                 270

Thr Arg Glu Asn Val Ala Ser His Leu Gln Lys Phe Arg Leu Tyr Leu
        275                 280                 285

Lys Arg Leu Ser Gly Val Ala Gln Gln Gln Ser Gly Ile Ala Asn Pro
    290                 295                 300

Leu Cys Gly Pro Val Asp Ser Asn Gly Lys Leu Gly Ser Leu Ser Arg
305                 310                 315                 320

Phe Asp Phe Gln Ala Leu Ala Ala Ser Gly Gln Ile Pro Pro Gln Thr
                325                 330                 335

Leu Ala Ala Leu Gln Ala Glu Leu Leu Gly Gln Pro Ala Gly Asn Leu
            340                 345                 350

Val Pro Ala Met Asp Gln Pro Ala Leu Leu His Ala Ser Leu Gln Ala
        355                 360                 365

Pro Lys Arg Pro Pro Val Glu His Gly Val Pro Phe Met Gln Pro Phe
    370                 375                 380

Val Lys Ser Gln Ser Asn Val Ser Lys His Phe Pro Gln Ser Val Ile
385                 390                 395                 400

Ser Ala Glu Asp Ala Ser Leu Gly Phe Gly Gln Trp Arg Ser Asn Ser
                405                 410                 415

Arg Ser Thr Val Ala Pro Ser Asn Asp His Gly Gly Leu Ser Thr Gln
            420                 425                 430

Asn Ser Asn Leu Leu Met Gly Ile Val Pro Gln Glu Gln Arg Gln His
        435                 440                 445

Lys Arg Thr Gln Gln Gln Ser Val Leu Thr Glu Pro Ser Arg Ser Phe
    450                 455                 460

Asn Val Gln Pro Ser Cys Leu Val Val Pro Ser Gln Ser Ser Thr Gly
465                 470                 475                 480

Phe Gln Ala Gly Asn Ser Pro Ala Ser Val Asn Gln Ser Ser Ser Phe
                485                 490                 495
```

```
Asn Arg Ser Thr Val Val Asp Tyr Ser Leu Pro Ser Asp Gln Ser Asn
            500                 505                 510

Asn Ser Leu Asn Val Gly His Ile Pro Thr Gly Asn Pro Lys Thr Ser
        515                 520                 525

Gly Xaa Leu Gly Gly Tyr Ser Gly Pro Gly Ser Xaa Cys Ala Thr Ser
    530                 535                 540

Cys Leu Val Asn Ala Asp Asn Ser Thr Ser Tyr Gln Asn Ser Thr Ala
545                 550                 555                 560

Thr Phe Ser Asp Ser Arg Glu Leu Pro Gly Phe Leu His Asn Thr Ala
                565                 570                 575

Asn Ser Xaa Gly Phe Tyr Val Asp Lys Ser Gly Glu Met Leu Asp Gln
            580                 585                 590

Gly Pro Leu Arg Asn Leu Gly Phe Val Gly Lys Glu Thr Cys Ile Pro
        595                 600                 605

Ser Arg Phe Ala Val Asp Asp Phe Glu Ser Gln Met Ser Asn Leu Asn
    610                 615                 620

Pro Gly Arg Ile His Val Glu Ser Ser Gly Thr Leu Val Lys Gln Glu
625                 630                 635                 640

Pro Ser Glu Asp Tyr Val Asp Asn Ala Lys Leu Gly Ile Pro Ile Leu
                645                 650                 655

His Gln Tyr Ser Ser Ser Asp Phe Met Ser Pro Phe Ala Asp
            660                 665                 670


<210> SEQ ID NO 37
<211> LENGTH: 802
<212> TYPE: PRT
<213> ORGANISM: Zea mays

<400> SEQUENCE: 37

Pro Tyr Pro Thr His Thr Leu Leu Pro Gln Pro His Leu Ser Leu Ser
1               5                   10                  15

Ala Cys Val Leu Leu Val Leu Leu Ser Leu Ser Ser Pro Ala Leu Thr
            20                  25                  30

Ser Pro Pro Phe Pro Ala Val Ser Trp Ile Ser Arg Ile Gln Thr Thr
        35                  40                  45

Ala Leu Val Ser Leu Pro Ser Cys Leu Leu Pro Ala Tyr Val Gln Glu
    50                  55                  60

Gly Pro Cys Leu Gly Asp Pro Gly Ala Trp Phe Leu Gly Ser Ala Ala
65                  70                  75                  80

Ser Ala Ala Val Gly Phe Ala Glu Pro Glu Pro Pro Glu Met Thr Val
                85                  90                  95

Asp Glu Leu Lys Leu Gln Ala Arg Ala Ser Gly Gly His Gly Ala Lys
            100                 105                 110

Asp Gln Phe Pro Val Gly Met Arg Val Leu Ala Val Asp Asp Asp Pro
        115                 120                 125

Thr Cys Leu Lys Ile Leu Glu Asn Leu Leu Leu Arg Cys Gln Tyr His
    130                 135                 140

Val Thr Thr Thr Gly Gln Ala Ala Thr Ala Leu Lys Leu Leu Arg Glu
145                 150                 155                 160

Lys Lys Asp Gln Phe Asp Leu Val Ile Ser Asp Val His Met Pro Asp
                165                 170                 175

Met Asp Gly Phe Lys Leu Leu Glu Leu Val Gly Leu Glu Met Asp Leu
            180                 185                 190

Pro Val Ile Met Leu Ser Ala Asn Gly Glu Thr Gln Thr Val Met Lys
        195                 200                 205
```

-continued

```
Gly Ile Thr His Gly Ala Cys Asp Tyr Leu Leu Lys Pro Val Arg Ile
    210                 215                 220

Glu Gln Leu Arg Thr Ile Trp Gln His Val Val Arg Arg Arg Ser Cys
225                 230                 235                 240

Asp Ala Lys Asn Ser Gly Asn Asp Asn Asp Asp Ser Gly Lys Lys Leu
                245                 250                 255

Gln Val Val Ser Ala Glu Gly Asp Asn Gly Gly Val Asn Arg Asn Lys
            260                 265                 270

Arg Ile Ser Arg Lys Gly Arg Asp Asp Asn Gly Asp Asp Gly Asp Asp
        275                 280                 285

Ser Asp Asp Asn Ser Asn Glu Asn Gly Asp Ser Ser Ser Gln Lys Lys
    290                 295                 300

Pro Arg Val Val Trp Ser Val Glu Leu His Arg Lys Phe Val Ala Ala
305                 310                 315                 320

Val Asn Gln Leu Gly Ile Asp Lys Ala Val Pro Lys Lys Ile Leu Asp
                325                 330                 335

Leu Met Asn Val Glu Asn Ile Thr Arg Glu Asn Val Ala Ser His Leu
            340                 345                 350

Gln Lys Tyr Arg Leu Tyr Leu Lys Arg Leu Ser Ala Asp Ala Ser Arg
        355                 360                 365

Gln Ala Asn Leu Thr Ala Ala Phe Gly Gly Arg Asn Pro Ala Tyr Val
    370                 375                 380

Asn Met Gly Leu Asp Ala Phe Arg Gln Tyr Asn Ala Tyr Gly Arg Tyr
385                 390                 395                 400

Arg Pro Val Pro Thr Thr Asn His Ser Gln Pro Asn Asn Leu Leu Ala
                405                 410                 415

Arg Met Asn Ser Pro Ala Phe Gly Met His Gly Leu Leu Pro Ser Gln
            420                 425                 430

Pro Leu Gln Ile Gly His Asn Gln Asn Asn Leu Ser Thr Ser Leu Gly
        435                 440                 445

Asn Val Gly Gly Met Asn Asn Gly Asn Leu Ile Arg Gly Ala His Met
    450                 455                 460

Pro Leu Gln Asp Thr Ser Lys Cys Phe Pro Thr Gly Pro Ser Gly Asn
465                 470                 475                 480

Ser Phe Ala Asn Ile Ser Asn Ser Thr Gln Leu Val Thr Thr Asn Asn
                485                 490                 495

Leu Pro Leu Gln Ser Leu Glu Pro Ser Asn Gln Gln His Leu Gly Arg
            500                 505                 510

Leu His Ser Ser Ala Asp Pro Phe Asn Ser Phe Val Gly Glu Pro Pro
        515                 520                 525

Gln Phe Ala Asp Leu Gly Arg Cys Asn Thr Thr Trp Pro Thr Ala Val
    530                 535                 540

Ser Ser Ser Asn Val Gln Glu Ile Gly Gln Lys Asp Arg Ile Val Asn
545                 550                 555                 560

Arg Pro Lys Leu Glu Pro Leu Ser Ser Phe Thr Glu Ala Ser Ser Gln
                565                 570                 575

Ile Pro Leu Leu Gly Asn Glu Met Gln Ser His Gln Val Ala Ser Leu
            580                 585                 590

Ala Ser Asn Gly Leu Pro Met Pro Phe Thr Gln Glu Ala Val Pro Phe
        595                 600                 605

Ala Tyr Gly Ser Ser Thr Asn Ser Arg Glu Met Leu Asn Asn Asn Leu
    610                 615                 620
```

Ala Leu Ser Asn Ser Gly Val Asn Ser Thr Leu Pro Asn Leu Arg Ile
625 630 635 640

Asp Gly Ser Val Val Pro Gly Gln Thr Leu Gly Gly Ser Asn Ser Gly
645 650 655

Gly Cys Val Val Pro Pro Leu Gln Asp Gly Arg Ile Asp His Gln Ala
660 665 670

Val Ser Ser His Leu Asn Tyr Asn Asn Glu Leu Met Gly Thr Gly Arg
675 680 685

Leu Gln Arg Gly Leu Ser Gly Gly Leu Asp Asp Ile Val Val Asp Met
690 695 700

Phe Arg Pro Asp Arg Ala Asp Asp Gly Val Ser Phe Ile Asp Gly Asp
705 710 715 720

Trp Glu Leu Arg Pro Gly Ser Ser Val Thr Ser Glu Tyr Gln Leu Cys
725 730 735

Gly Ile Cys Tyr Leu Asn Ser Tyr Asp Tyr Val Phe Lys Ser Gly Val
740 745 750

Asn Cys Gly Tyr Arg Asp Ile Gln His Val Tyr Glu Pro Arg Asn Asp
755 760 765

Val Leu Phe Pro Leu Gly Asn Arg Phe Ala Val Pro Phe Val Asp Cys
770 775 780

His Cys Ile Val Ala Ser Leu Ala Glu Thr Glu Val Lys Gly Lys Asp
785 790 795 800

Gln Ala

<210> SEQ ID NO 38
<211> LENGTH: 591
<212> TYPE: PRT
<213> ORGANISM: Brassica rapa

<400> SEQUENCE: 38

Met Leu Asn Pro Gly Val Val Gly Gly Ser Ser Asn Ser Asp Pro Phe
1 5 10 15

Pro Ser Gly Leu Arg Val Leu Val Val Asp Asp Asp Pro Thr Cys Leu
20 25 30

Met Ile Leu Glu Arg Met Leu Lys Thr Cys Leu Tyr Arg Val Thr Lys
35 40 45

Cys Asn Arg Ala Glu Ile Ala Leu Ser Leu Leu Arg Lys Asn Lys Asn
50 55 60

Gly Phe Asp Ile Val Ile Ser Asp Val His Met Pro Asp Met Asn Gly
65 70 75 80

Phe Lys Leu Leu Glu His Val Gly Leu Glu Met Asp Leu Pro Val Ile
85 90 95

Met Met Ser Ala Asp Asp Ser Lys Ser Val Val Leu Lys Gly Val Thr
100 105 110

His Gly Ala Val Asp Tyr Leu Ile Lys Pro Val Arg Ile Glu Ala Leu
115 120 125

Lys Asn Ile Trp Gln His Val Val Arg Lys Lys Gln Asn Val Ser Glu
130 135 140

His Ser Gly Ser Val Glu Glu Thr Gly Gly Asp Arg Gln Gln Gln Gln
145 150 155 160

Arg Gly Asp Asp Asp Asp Asp Gly Asn Asn Ser Ser Ser Gly Asn Asn
165 170 175

Glu Gly Asn Leu Arg Lys Arg Lys Glu Glu Glu Gln Gly Asp Asp Lys
180 185 190

-continued

```
Glu Asp Thr Ser Ser Leu Lys Lys Pro Arg Val Val Trp Ser Val Glu
        195                 200                 205

Leu His Gln Gln Phe Val Ala Ala Val Asn His Leu Gly Val Asp Lys
    210                 215                 220

Ala Val Pro Lys Lys Ile Leu Glu Met Met Asn Val Gln Gly Leu Thr
225                 230                 235                 240

Arg Glu Asn Val Ala Ser His Leu Gln Lys Tyr Arg Ile Tyr Leu Lys
                245                 250                 255

Arg Leu Gly Gly Val Ser Gln Gly Asn Met Asn His Ser Phe Leu Thr
            260                 265                 270

Gly Gln Asp Pro Ser Tyr Gly Pro Leu Asn Gly Phe Asp Leu Gln Gly
        275                 280                 285

Leu Ala Thr Ala Gly Gln Leu Gln Ala Gln Ser Leu Ala Gln Leu Gln
    290                 295                 300

Ala Val Gly Leu Gly Gln Ser Ser Ser Pro Leu Ile Lys Pro Gly Ile
305                 310                 315                 320

Thr Ser Val Asp Gln Arg Ser Phe Phe Thr Phe Gln Asn Ser Lys Ser
                325                 330                 335

Arg Phe Gly Asp Gly His Gly Pro Met Met Met Asn Gly Gly Gly Gly
            340                 345                 350

Asn Lys Gln Thr Ser Leu Leu His Gly Val Pro Thr Gly His Met Arg
        355                 360                 365

Leu Gln Gln Gln Gln Met Ala Gly Met Arg Val Ala Gly Pro Ser Met
    370                 375                 380

Gln Gln Gln Gln Gln Gln Ser Met Leu Ser Arg Arg Ser Val Pro Glu
385                 390                 395                 400

Thr Arg Ser Ser Arg Val Leu Pro Ala Ala Thr His Ser Ala Leu Asn
                405                 410                 415

Asn Ser Phe Pro Leu Ala Ser Ala Pro Gly Met Met Ser Val Ser Asp
            420                 425                 430

Thr Lys Gly Val Asn Glu Phe Cys Asn Pro Ser Tyr Asp Ile Leu Asn
        435                 440                 445

Asn Phe Pro Gln Gln Gln His His Asn Asn Asn Asn Asn Arg Val Asn
    450                 455                 460

Glu Trp Asp Leu Arg Asn Val Gly Met Val Phe Asn Ser His Gln Asp
465                 470                 475                 480

Asn Thr Thr Ser Ala Ala Phe Ser Thr Ser Glu Ala Tyr Ser Ser Ser
                485                 490                 495

Ser Thr His Lys Arg Lys Arg Glu Ala Glu Leu Val Val Glu His Gly
            500                 505                 510

Gln Asn Gln Gln Gln Pro Gln Ser Arg Ser Val Lys Pro Met Asn Gln
        515                 520                 525

Thr Tyr Met Asp Gly Gly Gly Ser Val Arg Met Lys Thr Glu Thr Val
    530                 535                 540

Thr Cys Pro Pro Gln Ala Thr Thr Met Phe His Glu Gln Tyr Ser Asn
545                 550                 555                 560

Gln Asp Asp Leu Leu Ser Asp Leu Leu Lys Gln Glu Gly Leu Leu Asp
                565                 570                 575

Thr Glu Phe Asp Phe Glu Gly Tyr Ser Phe Asp Ser Ile Leu Val
            580                 585                 590
```

<210> SEQ ID NO 39
<211> LENGTH: 691
<212> TYPE: PRT

<213> ORGANISM: Oryza sativa

<400> SEQUENCE: 39

Met Ala Pro Val Glu Asp Gly Gly Gly Val Glu Phe Pro Val Gly Met
1               5                   10                  15

Lys Val Leu Val Val Asp Asp Asp Pro Thr Cys Leu Ala Val Leu Lys
            20                  25                  30

Arg Met Leu Leu Glu Cys Arg Tyr Asp Ala Thr Thr Cys Ser Gln Ala
        35                  40                  45

Thr Arg Ala Leu Thr Met Leu Arg Glu Asn Arg Arg Gly Phe Asp Val
    50                  55                  60

Ile Ile Ser Asp Val His Met Pro Asp Met Asp Gly Phe Arg Leu Leu
65                  70                  75                  80

Glu Leu Val Gly Leu Glu Met Asp Leu Pro Val Ile Met Met Ser Ala
                85                  90                  95

Asp Ser Arg Thr Asp Ile Val Met Lys Gly Ile Lys His Gly Ala Cys
            100                 105                 110

Asp Tyr Leu Ile Lys Pro Val Arg Met Glu Glu Leu Lys Asn Ile Trp
        115                 120                 125

Gln His Val Ile Arg Lys Lys Phe Asn Glu Asn Lys Glu His Glu His
    130                 135                 140

Ser Gly Ser Leu Asp Asp Thr Asp Arg Thr Arg Pro Thr Asn Asn Asp
145                 150                 155                 160

Asn Glu Tyr Ala Ser Ser Ala Asn Asp Gly Ala Glu Gly Ser Trp Lys
                165                 170                 175

Ser Gln Lys Lys Lys Arg Asp Lys Asp Asp Asp Asp Gly Glu Leu Glu
            180                 185                 190

Ser Gly Asp Pro Ser Ser Thr Ser Lys Lys Pro Arg Val Val Trp Ser
        195                 200                 205

Val Glu Leu His Gln Gln Phe Val Asn Ala Val Asn His Leu Gly Ile
    210                 215                 220

Asp Lys Ala Val Pro Lys Lys Ile Leu Glu Leu Met Asn Val Pro Gly
225                 230                 235                 240

Leu Thr Arg Glu Asn Val Ala Ser His Leu Gln Lys Phe Arg Leu Tyr
                245                 250                 255

Leu Lys Arg Ile Ala Gln His His Ala Gly Ile Ala Asn Pro Phe Cys
            260                 265                 270

Pro Pro Ala Ser Ser Gly Lys Val Gly Ser Leu Gly Gly Leu Asp Phe
        275                 280                 285

Gln Ala Leu Ala Ala Ser Gly Gln Ile Pro Pro Gln Ala Leu Ala Ala
    290                 295                 300

Leu Gln Asp Glu Leu Leu Gly Arg Pro Thr Asn Ser Leu Val Leu Pro
305                 310                 315                 320

Gly Arg Asp Gln Ser Ser Leu Arg Leu Ala Ala Val Lys Gly Asn Lys
                325                 330                 335

Pro His Gly Glu Arg Glu Ile Ala Phe Gly Gln Pro Ile Tyr Lys Cys
            340                 345                 350

Gln Asn Asn Ala Tyr Gly Ala Phe Pro Gln Ser Ser Pro Ala Val Gly
        355                 360                 365

Gly Met Pro Ser Phe Ser Ala Trp Pro Asn Asn Lys Leu Gly Met Ala
    370                 375                 380

Asp Ser Thr Gly Thr Leu Gly Gly Met Ser Asn Ser Gln Asn Ser Asn
385                 390                 395                 400

```
Ile Val Leu His Glu Leu Gln Gln Gln Pro Asp Ala Met Leu Ser Gly
                405                 410                 415

Thr Leu His Ser Leu Asp Val Lys Pro Ser Gly Ile Val Met Pro Ser
            420                 425                 430

Gln Ser Leu Asn Thr Phe Ser Ala Ser Glu Gly Leu Ser Pro Asn Gln
        435                 440                 445

Asn Thr Leu Met Ile Pro Ala Gln Ser Ser Gly Phe Leu Ala Ala Met
    450                 455                 460

Pro Pro Ser Met Lys His Glu Pro Val Leu Ala Thr Ser Gln Pro Ser
465                 470                 475                 480

Ser Ser Leu Leu Gly Gly Ile Asp Leu Val Asn Gln Ala Ser Thr Ser
                485                 490                 495

Gln Pro Leu Ile Ser Ala His Gly Gly Gly Asn Leu Ser Gly Leu Val
            500                 505                 510

Asn Arg Asn Pro Asn Val Val Pro Ser Gln Gly Ile Ser Thr Phe His
        515                 520                 525

Thr Pro Asn Asn Pro Tyr Leu Val Ser Pro Asn Ser Met Gly Met Gly
    530                 535                 540

Ser Lys Gln Pro Pro Gly Val Leu Lys Thr Glu Asn Ser Asp Ala Leu
545                 550                 555                 560

Asn His Ser Tyr Gly Tyr Leu Gly Gly Ser Asn Pro Pro Met Asp Ser
                565                 570                 575

Gly Leu Leu Ser Ser Gln Ser Lys Asn Thr Gln Phe Gly Leu Leu Gly
            580                 585                 590

Gln Asp Asp Ile Thr Gly Ser Trp Ser Pro Leu Pro Asn Val Asp Ser
        595                 600                 605

Tyr Gly Asn Thr Val Gly Leu Ser His Pro Gly Ser Ser Ser Ser Ser
    610                 615                 620

Phe Gln Ser Ser Asn Val Ala Leu Gly Lys Leu Pro Asp Gln Gly Arg
625                 630                 635                 640

Gly Lys Asn His Gly Phe Val Gly Lys Gly Thr Cys Ile Pro Ser Arg
                645                 650                 655

Phe Ala Val Asp Glu Ile Glu Ser Pro Thr Asn Asn Leu Ser His Ser
            660                 665                 670

Ile Gly Ser Ser Gly Asp Ile Met Ser Pro Asp Ile Phe Gly Phe Ser
        675                 680                 685

Gly Gln Met
    690
```

<210> SEQ ID NO 40
<211> LENGTH: 428
<212> TYPE: PRT
<213> ORGANISM: Oocystis sp.

<400> SEQUENCE: 40

```
Met Ala Leu Lys Arg Val Pro Ser Phe Ser Gly Arg Pro Asn Phe Pro
1               5                   10                  15

Ala Gly Leu Gln Ile Leu Val Val Asp Ser Asp Ser Ser Ser Arg Glu
            20                  25                  30

Ala Val Glu Met Gln Leu Lys Ser His Ser Tyr Leu Ala Thr Cys Cys
        35                  40                  45

Cys Thr Cys Gly Glu Ala Val Glu Gln Leu Gly Thr Ser Lys Tyr Asp
    50                  55                  60

Ile Val Leu Ala Glu Ser Lys Leu Val Ala Ala Glu Cys Val Asp Ser
65                  70                  75                  80
```

Thr Arg Leu Cys Glu Ala Ala Arg Ala Leu Pro Leu Val Leu Met Cys
85 90 95

Glu Asp Ser Thr Ala Asp Asp Val Leu Lys Gly Ile Arg Leu Gly Ala
100 105 110

Cys Asp Phe Leu Glu Lys Pro Leu Ser Pro Leu Lys Leu Lys Asn Ile
115 120 125

Trp Gln His Val Val Arg Lys Met Met Glu Gln Met His Val Arg Arg
130 135 140

Thr Asp Asp Ala Asp Thr Cys Thr Thr Lys Ser Ser Arg Asp Gln Ser
145 150 155 160

Cys Ala Ile Lys Gly Lys Ser Val Ala Ser Thr Pro Ser Cys Pro Lys
165 170 175

Thr Pro Ser Pro Ala Ala Ser Gly Ala Asp Ile Gly Cys Ser Ile Ala
180 185 190

Thr Ser Val Ser Lys Ala Gly Asp Val Val Gly Glu Ser Ser Ser Ser
195 200 205

Glu Thr Arg Lys Glu His Cys Ser Glu Thr Thr Glu Cys Ser Asp Leu
210 215 220

Lys Ser Cys Ala Ala Lys Ser Ala Val Ser Ala Gln Thr Pro Val Ser
225 230 235 240

Thr Ala Thr Val Ala Ala Thr Trp Gly Ala Ser Lys Lys Lys Ser Thr
245 250 255

Ala Ser Ala Thr Thr Ser Ser Val Ser Asn Arg Pro Pro Leu Ala Ile
260 265 270

Lys Met Pro Ala Pro Ala Val Ala Tyr Thr Ser Gly Leu Ala Pro Phe
275 280 285

Pro Pro Pro Met Phe Val Pro Gly Gly Trp Gly Gln Ser Ser Asn Pro
290 295 300

Cys Val Val Gly Thr Pro Met Met Pro Pro Pro Pro Gly Met Gly Met
305 310 315 320

Pro Pro His His His Ala Pro Tyr Gly Gln Val Pro Pro Pro Gly Tyr
325 330 335

Pro Val Ala Cys Met Pro Ser Ala Phe Val Pro Thr Pro Met Gly Pro
340 345 350

Gly Gly Val Ala Phe Ala Pro Pro Pro Gly Ala Ser Cys Thr Ser Ala
355 360 365

Ala Tyr Tyr Pro His Pro Ala Val Asp Ala Ser Ala Ser Ala Thr Ala
370 375 380

Thr Phe Thr Gly His Val Gln Ile Asp Leu Thr Asn Val Ser Ala Glu
385 390 395 400

Glu Pro Ala Pro Ile Gly Leu Ala Leu Arg Lys Thr Ala Ser Leu Leu
405 410 415

Asp Leu Val Ser Asp Arg Leu Gly Gln Arg Ala Cys
420 425

<210> SEQ ID NO 41
<211> LENGTH: 341
<212> TYPE: PRT
<213> ORGANISM: Tetraselmis sp.

<400> SEQUENCE: 41

Met Leu Cys Pro Ala Val Gln Val Ala Thr Met Ala Thr Val Leu Ala
1 5 10 15

Ser Thr His Phe Ser Glu Arg Pro Ser Phe Pro Ala Asp Leu Glu Val 20 25 30

Leu Leu Leu Asp Ser Ala Thr Gln Gly Ala Glu Thr Ala Ser Lys Leu
35 40 45

Leu Leu Ser Cys Ser Tyr Arg Val Thr Val Cys Arg Ser Val Ser Glu
50 55 60

Ala Leu Ser His Met Ala Cys Lys Ala Phe Asp Val Val Leu Val Glu
65 70 75 80

Gln Lys Leu Phe Ser Gly Arg Asp Ala Ala Ala Ala Gln Leu Lys Ala
85 90 95

Leu Ala Gly Val Ile Pro Thr Val Val Leu Ser Asp Ser Gly Ser Ala
100 105 110

Lys Asp Thr Trp Ala Ala Ile Val Gly Gln Ala Ala Asp Val Leu Ile
115 120 125

Arg Pro Leu Thr Lys Gln Lys Leu Gln Thr Leu Trp Gln His Thr Val
130 135 140

Arg Met Gln Arg Ala Ala Ser Ser Ala Ser Ala Ala Thr Ser Met Val
145 150 155 160

Ala Lys Pro Val Ala Val Leu Ser Ser Ala Leu Lys Pro Ala Ala Ser
165 170 175

Ser Ala Ser Leu Asp Lys Gly Gln Lys Arg Lys Leu Lys Asp His Met
180 185 190

Met Gly Pro Ile Met Ala His Pro Gln Val Ser Asn Pro Gly Phe Ile
195 200 205

Trp Gly Ala Pro Val Met Gly Val Pro Ala Gly Gln Gln Ala Pro Gln
210 215 220

Lys Ser Glu Ala Pro Val Thr Pro Gln Lys Pro Gly Ser Glu Met His
225 230 235 240

Pro Glu Leu Asp Ala Thr Ser His Ile Ala Met Gly Ser Ser Asp Asn
245 250 255

Phe Asn Val Pro Val Tyr Glu Ser Gly Thr Asp Ser Gln Glu Ser Gln
260 265 270

Pro Thr Cys Asp Pro Thr Ser Leu Asp Asp Ile Asn Glu Asp Asp Tyr
275 280 285

Ala Phe Ile Asp Phe Ala Leu Ser Asp Ser Phe Pro Thr Val Glu Glu
290 295 300

Asp Glu Ile Leu Pro Pro Ile Gly Leu Ser Leu Lys Lys Ser Ser Ser
305 310 315 320

Leu Leu Asn Met Leu Asn Gly Val Leu Leu Ser Ala His Ser Val Pro
325 330 335

Leu Gln Leu Pro Gln
340

<210> SEQ ID NO 42
<211> LENGTH: 558
<212> TYPE: PRT
<213> ORGANISM: Arabidopsis thaliana

<400> SEQUENCE: 42

Met Ser Ser Ser Glu Glu Val Val Glu Val Thr Val Val Lys Ala Pro
1 5 10 15

Glu Ala Gly Gly Gly Lys Leu Ser Arg Arg Lys Ile Arg Lys Lys Asp
20 25 30

Ala Gly Val Asp Gly Leu Val Lys Trp Glu Arg Phe Leu Pro Lys Ile
35 40 45

```
Ala Leu Arg Val Leu Leu Val Glu Ala Asp Asp Ser Thr Arg Gln Ile
    50                  55                  60

Ile Ala Ala Leu Leu Arg Lys Cys Ser Tyr Arg Val Ala Ala Val Pro
65                  70                  75                  80

Asp Gly Leu Lys Ala Trp Glu Met Leu Lys Gly Lys Pro Glu Ser Val
                85                  90                  95

Asp Leu Ile Leu Thr Glu Val Asp Leu Pro Ser Ile Ser Gly Tyr Ala
            100                 105                 110

Leu Leu Thr Leu Ile Met Glu His Asp Ile Cys Lys Asn Ile Pro Val
        115                 120                 125

Ile Met Met Ser Thr Gln Asp Ser Val Asn Thr Val Tyr Lys Cys Met
    130                 135                 140

Leu Lys Gly Ala Ala Asp Tyr Leu Val Lys Pro Leu Arg Arg Asn Glu
145                 150                 155                 160

Leu Arg Asn Leu Trp Gln His Val Trp Arg Arg Gln Thr Ser Leu Ala
                165                 170                 175

Pro Asp Ser Phe Pro Trp Asn Glu Ser Val Gly Gln Gln Lys Ala Glu
            180                 185                 190

Gly Ala Ser Ala Asn Asn Ser Asn Gly Lys Arg Asp Asp His Val Val
        195                 200                 205

Ile Gly Asn Gly Gly Asp Ala Gln Ser Ser Cys Thr Arg Pro Glu Met
    210                 215                 220

Glu Gly Glu Ser Ala Asp Val Glu Val Ser Ala Arg Asp Ala Val Gln
225                 230                 235                 240

Met Glu Cys Ala Lys Ser Gln Phe Asn Glu Thr Gln Leu Leu Ala Asn
                245                 250                 255

Glu Leu Gln Ser Lys Gln Ala Glu Ala Ile Asp Phe Met Gly Ala Ser
            260                 265                 270

Phe Arg Arg Thr Gly Arg Arg Asn Arg Glu Glu Ser Val Ala Gln Tyr
        275                 280                 285

Glu Ser Arg Ile Glu Leu Asp Leu Ser Leu Arg Arg Pro Asn Ala Ser
    290                 295                 300

Glu Asn Gln Ser Ser Gly Asp Arg Pro Ser Leu His Pro Ser Ser Ala
305                 310                 315                 320

Ser Ala Phe Thr Arg Tyr Val His Arg Pro Leu Gln Thr Gln Cys Ser
                325                 330                 335

Ala Ser Pro Val Val Pro Asp Gln Arg Lys Asn Val Ala Ala Ser Gln
            340                 345                 350

Asp Asp Asn Ile Val Leu Met Asn Gln Tyr Asn Thr Ser Glu Pro Pro
        355                 360                 365

Pro Asn Ala Pro Arg Arg Asn Asp Thr Ser Phe Tyr Thr Gly Thr Asp
    370                 375                 380

Ser Pro Gly Pro Pro Phe Ser Asn Gln Met Asn Ser Trp Pro Gly Gln
385                 390                 395                 400

Gly Ser Tyr Pro Thr Pro Thr Pro Ile Asn Asn Ile Gln Phe Arg Gly
                405                 410                 415

Pro Asn Thr Ala Tyr Thr Ser Ala Met Ala Pro Ala Ser Leu Ser Pro
            420                 425                 430

Ser Pro Ser Ser Val Ser Pro His Glu Tyr Ser Ser Met Phe His Pro
        435                 440                 445

Phe Asn Ser Lys Pro Glu Gly Leu Gln Asp Arg Asp Cys Ser Met Asp
    450                 455                 460

Val Asp Asp Arg Arg Tyr Val Ser Ser Ala Thr Glu His Ser Ala Ile
```

```
465                 470                 475                 480

Gly Asn His Ile Asp Gln Leu Ile Glu Lys Lys Asn Glu Asp Gly Tyr
                485                 490                 495

Ser Ser Ser Val Gly Lys Ile Gln Gln Ser Leu Gln Arg Glu Ala Ala
            500                 505                 510

Leu Thr Lys Phe Arg Met Lys Arg Lys Asp Arg Cys Phe Glu Lys Lys
        515                 520                 525

Val Arg Tyr Glu Ser Arg Lys Lys Leu Ala Glu Gln Arg Pro Arg Ile
    530                 535                 540

Lys Gly Gln Phe Val Arg Gln Val Gln Ser Thr Gln Ala Pro
545                 550                 555


<210> SEQ ID NO 43
<211> LENGTH: 186
<212> TYPE: PRT
<213> ORGANISM: Arabidopsis thaliana

<400> SEQUENCE: 43

Met Ala Glu Val Met Leu Pro Arg Lys Met Glu Ile Leu Asn His Ser
1               5                   10                  15

Ser Lys Phe Gly Ser Pro Asp Pro Leu His Val Leu Ala Val Asp Asp
            20                  25                  30

Ser His Val Asp Arg Lys Phe Ile Glu Arg Leu Leu Arg Val Ser Ser
        35                  40                  45

Cys Lys Val Thr Val Val Asp Ser Ala Thr Arg Ala Leu Gln Tyr Leu
    50                  55                  60

Gly Leu Asp Val Glu Glu Lys Ser Val Gly Phe Glu Asp Leu Lys Val
65                  70                  75                  80

Asn Leu Ile Met Thr Asp Tyr Ser Met Pro Gly Met Thr Gly Tyr Glu
                85                  90                  95

Leu Leu Lys Lys Ile Lys Glu Ser Ser Ala Phe Arg Glu Val Pro Val
            100                 105                 110

Val Ile Met Ser Ser Glu Asn Ile Leu Pro Arg Ile Asp Arg Cys Leu
        115                 120                 125

Glu Glu Gly Ala Glu Asp Phe Leu Leu Lys Pro Val Lys Leu Ser Asp
    130                 135                 140

Val Lys Arg Leu Arg Asp Ser Leu Met Lys Val Glu Asp Leu Ser Phe
145                 150                 155                 160

Thr Lys Ser Ile Gln Lys Arg Glu Leu Glu Thr Glu Asn Val Tyr Pro
                165                 170                 175

Val His Ser Gln Leu Lys Arg Ala Lys Ile
            180                 185


<210> SEQ ID NO 44
<211> LENGTH: 727
<212> TYPE: PRT
<213> ORGANISM: Arabidopsis thaliana

<400> SEQUENCE: 44

Met Asn Ala Asn Glu Glu Gly Glu Gly Ser Arg Tyr Pro Ile Thr Asp
1               5                   10                  15

Arg Lys Thr Gly Glu Thr Lys Phe Asp Arg Val Glu Ser Arg Thr Glu
            20                  25                  30

Lys His Ser Glu Glu Glu Lys Thr Asn Gly Ile Thr Met Asp Val Arg
        35                  40                  45

Asn Gly Ser Ser Gly Gly Leu Gln Ile Pro Leu Ser Gln Gln Thr Ala
```

-continued

```
    50                  55                  60

Ala Thr Val Cys Trp Glu Arg Phe Leu His Val Arg Thr Ile Arg Val
65                  70                  75                  80

Leu Leu Val Glu Asn Asp Asp Cys Thr Arg Tyr Ile Val Thr Ala Leu
                85                  90                  95

Leu Arg Asn Cys Ser Tyr Glu Val Val Glu Ala Ser Asn Gly Ile Gln
            100                 105                 110

Ala Trp Lys Val Leu Glu Asp Leu Asn Asn His Ile Asp Ile Val Leu
        115                 120                 125

Thr Glu Val Ile Met Pro Tyr Leu Ser Gly Ile Gly Leu Leu Cys Lys
    130                 135                 140

Ile Leu Asn His Lys Ser Arg Arg Asn Ile Pro Val Ile Met Met Ser
145                 150                 155                 160

Ser His Asp Ser Met Gly Leu Val Phe Lys Cys Leu Ser Lys Gly Ala
                165                 170                 175

Val Asp Phe Leu Val Lys Pro Ile Arg Lys Asn Glu Leu Lys Ile Leu
            180                 185                 190

Trp Gln His Val Trp Arg Arg Cys Gln Ser Ser Ser Gly Ser Gly Ser
        195                 200                 205

Glu Ser Gly Thr His Gln Thr Gln Lys Ser Val Lys Ser Lys Ser Ile
    210                 215                 220

Lys Lys Ser Asp Gln Asp Ser Gly Ser Ser Asp Glu Asn Glu Asn Gly
225                 230                 235                 240

Ser Ile Gly Leu Asn Ala Ser Asp Gly Ser Ser Asp Gly Ser Gly Ala
                245                 250                 255

Gln Ser Ser Trp Thr Lys Lys Ala Val Asp Val Asp Asp Ser Pro Arg
            260                 265                 270

Ala Val Ser Leu Trp Asp Arg Val Asp Ser Thr Cys Ala Gln Val Val
        275                 280                 285

His Ser Asn Pro Glu Phe Pro Ser Asn Gln Leu Val Ala Pro Pro Ala
    290                 295                 300

Glu Lys Glu Thr Gln Glu His Asp Asp Lys Phe Glu Asp Val Thr Met
305                 310                 315                 320

Gly Arg Asp Leu Glu Ile Ser Ile Arg Arg Asn Cys Asp Leu Ala Leu
                325                 330                 335

Glu Pro Lys Asp Glu Pro Leu Ser Lys Thr Thr Gly Ile Met Arg Gln
            340                 345                 350

Asp Asn Ser Phe Glu Lys Ser Ser Ser Lys Trp Lys Met Lys Val Gly
        355                 360                 365

Lys Gly Pro Leu Asp Leu Ser Ser Glu Ser Pro Ser Ser Lys Gln Met
    370                 375                 380

His Glu Asp Gly Gly Ser Ser Phe Lys Ala Met Ser Ser His Leu Gln
385                 390                 395                 400

Asp Asn Arg Glu Pro Glu Ala Pro Asn Thr His Leu Lys Thr Leu Asp
                405                 410                 415

Thr Asn Glu Ala Ser Val Lys Ile Ser Glu Glu Leu Met His Val Glu
            420                 425                 430

His Ser Ser Lys Arg His Arg Gly Thr Lys Asp Asp Gly Thr Leu Val
        435                 440                 445

Arg Asp Asp Arg Asn Val Leu Arg Arg Ser Glu Gly Ser Ala Phe Ser
    450                 455                 460

Arg Tyr Asn Pro Ala Ser Asn Ala Asn Lys Ile Ser Gly Gly Asn Leu
465                 470                 475                 480
```

```
Gly Ser Thr Ser Leu Gln Asp Asn Asn Ser Gln Asp Leu Ile Lys Lys
                485                 490                 495

Thr Glu Ala Ala Tyr Asp Cys His Ser Asn Met Asn Glu Ser Leu Pro
            500                 505                 510

His Asn His Arg Ser His Val Gly Ser Asn Asn Phe Asp Met Ser Ser
        515                 520                 525

Thr Thr Glu Asn Asn Ala Phe Thr Lys Pro Gly Ala Pro Lys Val Ser
    530                 535                 540

Ser Ala Gly Ser Ser Ser Val Lys His Ser Ser Phe Gln Pro Leu Pro
545                 550                 555                 560

Cys Asp His His Asn Asn His Ala Ser Tyr Asn Leu Val His Val Ala
                565                 570                 575

Glu Arg Lys Lys Leu Pro Pro Gln Cys Gly Ser Ser Asn Val Tyr Asn
            580                 585                 590

Glu Thr Ile Glu Gly Asn Asn Asn Thr Val Asn Tyr Ser Val Asn Gly
        595                 600                 605

Ser Val Ser Gly Ser Gly His Gly Ser Asn Gly Pro Tyr Gly Ser Ser
    610                 615                 620

Asn Gly Met Asn Ala Gly Gly Met Asn Met Gly Ser Asp Asn Gly Ala
625                 630                 635                 640

Gly Lys Asn Gly Asn Gly Asp Gly Ser Gly Ser Gly Ser Gly Ser Gly
                645                 650                 655

Ser Gly Asn Leu Ala Asp Glu Asn Lys Ile Ser Gln Arg Glu Ala Ala
            660                 665                 670

Leu Thr Lys Phe Arg Gln Lys Arg Lys Glu Arg Cys Phe Arg Lys Lys
        675                 680                 685

Val Arg Tyr Gln Ser Arg Lys Lys Leu Ala Glu Gln Arg Pro Arg Val
    690                 695                 700

Arg Gly Gln Phe Val Arg Lys Thr Ala Ala Ala Thr Asp Asp Asn Asp
705                 710                 715                 720

Ile Lys Asn Ile Glu Asp Ser
                725
```

<210> SEQ ID NO 45
<211> LENGTH: 444
<212> TYPE: PRT
<213> ORGANISM: Arabidopsis thaliana

<400> SEQUENCE: 45

```
Met Gly Glu Ile Val Val Leu Ser Ser Asp Asp Gly Met Glu Thr Ile
1               5                   10                  15

Lys Asn Arg Val Lys Ser Ser Glu Val Val Gln Trp Glu Lys Tyr Leu
            20                  25                  30

Pro Lys Thr Val Leu Arg Val Leu Leu Val Glu Ser Asp Tyr Ser Thr
        35                  40                  45

Arg Gln Ile Ile Thr Ala Leu Leu Arg Lys Cys Cys Tyr Lys Val Val
    50                  55                  60

Ala Val Ser Asp Gly Leu Ala Ala Trp Glu Val Leu Lys Glu Lys Ser
65                  70                  75                  80

His Asn Ile Asp Leu Ile Leu Thr Glu Leu Asp Leu Pro Ser Ile Ser
                85                  90                  95

Gly Phe Ala Leu Leu Ala Leu Val Met Glu His Glu Ala Cys Lys Asn
            100                 105                 110

Ile Pro Val Ile Met Met Ser Ser Gln Asp Ser Ile Lys Met Val Leu
```

-continued

```
        115                 120                 125

Lys Cys Met Leu Arg Gly Ala Ala Asp Tyr Leu Ile Lys Pro Met Arg
    130                 135                 140

Lys Asn Glu Leu Lys Asn Leu Trp Gln His Val Trp Arg Arg Leu Thr
145                 150                 155                 160

Leu Arg Asp Asp Pro Thr Ala His Ala Gln Ser Leu Pro Ala Ser Gln
                165                 170                 175

His Asn Leu Glu Asp Thr Asp Glu Thr Cys Glu Asp Ser Arg Tyr His
            180                 185                 190

Ser Asp Gln Gly Ser Gly Ala Gln Ala Ile Asn Tyr Asn Gly His Asn
        195                 200                 205

Lys Leu Met Glu Asn Gly Lys Ser Val Asp Glu Arg Asp Glu Phe Lys
    210                 215                 220

Glu Thr Phe Asp Val Thr Met Asp Leu Ile Gly Gly Ile Asp Lys Arg
225                 230                 235                 240

Pro Asp Ser Ile Tyr Lys Asp Lys Ser Arg Asp Glu Cys Val Gly Pro
                245                 250                 255

Glu Leu Gly Leu Ser Leu Lys Arg Ser Cys Ser Val Ser Phe Glu Asn
            260                 265                 270

Gln Asp Glu Ser Lys His Gln Lys Leu Ser Leu Ser Asp Ala Ser Ala
        275                 280                 285

Phe Ser Arg Phe Glu Glu Ser Lys Ser Ala Glu Lys Ala Val Val Ala
    290                 295                 300

Leu Glu Glu Ser Thr Ser Gly Glu Pro Lys Thr Pro Thr Glu Ser His
305                 310                 315                 320

Glu Lys Leu Arg Lys Val Thr Ser Asp Gln Gly Ser Ala Thr Thr Ser
                325                 330                 335

Ser Asn Gln Glu Asn Ile Gly Ser Ser Ser Val Ser Phe Arg Asn Gln
            340                 345                 350

Val Leu Gln Ser Thr Val Thr Asn Gln Lys Gln Asp Ser Pro Ile Pro
        355                 360                 365

Val Glu Ser Asn Arg Glu Lys Ala Ala Ser Lys Glu Val Glu Ala Gly
    370                 375                 380

Ser Gln Ser Thr Asn Glu Gly Ile Ala Gly Gln Ser Ser Ser Thr Glu
385                 390                 395                 400

Lys Pro Lys Glu Glu Glu Ser Ala Lys Gln Arg Trp Ser Arg Ser Gln
                405                 410                 415

Arg Glu Ala Ala Leu Met Lys Phe Arg Leu Lys Arg Lys Asp Arg Cys
            420                 425                 430

Phe Asp Lys Lys Val Arg Asp Thr Gln Ala Ser Ser
        435                 440


<210> SEQ ID NO 46
<211> LENGTH: 204
<212> TYPE: PRT
<213> ORGANISM: Arabidopsis thaliana

<400> SEQUENCE: 46

Met Ala Leu Arg Asp Leu Ser Ser Ser Ser Ser Ser Pro Glu Leu His
1               5                   10                  15

Val Leu Ala Val Asp Asp Ser Phe Val Asp Arg Lys Val Leu Glu Arg
            20                  25                  30

Leu Leu Lys Ile Ser Ala Cys Lys Val Thr Thr Val Glu Ser Gly Thr
        35                  40                  45
```

```
Arg Ala Leu Gln Tyr Leu Gly Leu Asp Gly Asp Asn Gly Ser Ser Gly
    50                  55                  60

Leu Lys Asp Leu Lys Val Asn Leu Ile Val Thr Asp Tyr Ser Met Pro
65                  70                  75                  80

Gly Leu Thr Gly Tyr Glu Leu Leu Lys Lys Ile Lys Glu Ser Ser Ala
                85                  90                  95

Leu Arg Glu Ile Pro Val Val Ile Met Ser Ser Glu Asn Ile Gln Pro
            100                 105                 110

Arg Ile Glu Gln Cys Met Ile Glu Gly Ala Glu Glu Phe Leu Leu Lys
        115                 120                 125

Pro Val Lys Leu Ala Asp Val Lys Arg Leu Lys Glu Leu Ile Met Arg
    130                 135                 140

Gly Gly Glu Ala Glu Glu Gly Lys Thr Lys Lys Leu Ser Pro Lys Arg
145                 150                 155                 160

Ile Leu Gln Asn Asp Ile Asp Ser Ser Pro Ser Ser Ser Ser Ser Thr
                165                 170                 175

Ser Ser Ser Ser Ser Ser His Asp Val Ser Ser Leu Asp Asp Asp Thr
            180                 185                 190

Pro Ser Ser Lys Arg Ile Lys Leu Glu Ser Arg Gly
        195                 200


<210> SEQ ID NO 47
<211> LENGTH: 691
<212> TYPE: PRT
<213> ORGANISM: Glycine max

<400> SEQUENCE: 47

Met Gly Glu Val Val Ile Met Ser Gly Glu Lys Lys Ser Val Arg Val
1               5                   10                  15

Glu Gly Val Glu Lys Glu Asp Ser Gly Gly Ser Gly Ser Lys Ala Gly
            20                  25                  30

Glu Phe Lys Gly Leu Met Arg Trp Glu Lys Phe Leu Pro Lys Met Val
        35                  40                  45

Leu Arg Val Leu Leu Val Glu Ala Asp Asp Ser Thr Arg Gln Ile Ile
    50                  55                  60

Ala Ala Leu Leu Arg Lys Cys Ser Tyr Lys Val Val Ala Val Pro Asp
65                  70                  75                  80

Gly Leu Lys Ala Trp Glu Leu Leu Lys Gly Arg Pro His Asn Val Asp
                85                  90                  95

Leu Ile Leu Thr Glu Val Asp Leu Pro Ser Ile Ser Gly Tyr Ala Leu
            100                 105                 110

Leu Thr Leu Ile Met Glu His Glu Ile Cys Lys Asn Ile Pro Val Ile
        115                 120                 125

Met Met Ser Ser Gln Asp Ser Ile Ser Thr Val Tyr Lys Cys Met Leu
    130                 135                 140

Arg Gly Ala Ala Asp Tyr Leu Val Lys Pro Ile Arg Lys Asn Glu Leu
145                 150                 155                 160

Arg Asn Leu Trp Gln His Val Trp Arg Arg Gln Ser Ser Thr Thr Gly
                165                 170                 175

Ile Asn Gly Leu Gln Asp Glu Ser Val Ala Gln Gln Lys Val Glu Ala
            180                 185                 190

Thr Ala Glu Asn Asn Ala Ala Ser Asn Arg Ser Ser Gly Asp Ala Ala
        195                 200                 205

Cys Ile Gln Arg Asn Ile Glu Leu Ile Glu Lys Gly Ser Asp Ala Gln
    210                 215                 220
```

```
Ser Ser Cys Thr Lys Pro Asp Cys Glu Ala Glu Ser Asp Pro Val Gly
225                 230                 235                 240

Asn Met Gln Glu Phe Ser Leu Leu Lys Cys Gly Glu Ala Tyr Pro Ser
                245                 250                 255

Gly Thr Glu Thr Gln Gln Val Glu Thr Ser Phe Arg Leu Gly Gln Thr
            260                 265                 270

Leu Met Met His Asp Cys His Ala Gly Gly Leu Asn Val Ser Ile Arg
        275                 280                 285

Lys Asn Gly Glu Ala Ser Thr Thr Asn Asp Lys Asp Thr Asp Thr Glu
    290                 295                 300

His Phe Gly Asn Ala Ser Ile Ser Gly Glu Ala His Asp Asn Pro Tyr
305                 310                 315                 320

Val Gln Ile Asn Ser Ser Lys Glu Ala Met Asp Leu Ile Gly Ala Phe
                325                 330                 335

His Thr His Pro Asn Cys Ser Leu Lys Asn Ser Thr Val Asn Cys Thr
            340                 345                 350

Gly Asn Phe Asp His Ser Pro Gln Leu Asp Leu Ser Leu Arg Arg Ser
        355                 360                 365

Cys Pro Gly Ser Phe Glu Asn Lys Leu Thr Glu Glu Arg His Thr Leu
    370                 375                 380

Met His Ser Asn Ala Ser Ala Phe Lys Arg Tyr Thr Thr Arg Gln Leu
385                 390                 395                 400

Gln Ile Ser Met Pro Ala Val Leu Ile Asn Phe Ser Asp Gln Gln Arg
                405                 410                 415

Glu Gln Ile Thr Asn Cys Glu Lys Asn Ile Ser His Ile Ala Thr Gly
            420                 425                 430

Ser Asn Ser Asp Ser Ser Thr Pro Met Gln Arg Cys Ile Val Ser Pro
        435                 440                 445

Thr Thr Val Gln Ser Lys Glu Ser Glu Leu Ala Thr Ser His Pro Pro
    450                 455                 460

Gln Gly His Ser Leu Pro Ile Pro Val Lys Gly Val Arg Phe Asn Asp
465                 470                 475                 480

Leu Cys Thr Ala Tyr Gly Ser Val Leu Pro Ser Val Phe His Thr Gln
                485                 490                 495

Ser Gly Pro Pro Ala Met Pro Ser Pro Asn Ser Val Val Leu Leu Glu
            500                 505                 510

Pro Asn Phe Gln Val Asn Ala Phe Tyr Gln Ser Asn Met Lys Glu Ser
        515                 520                 525

Ser Ser Glu Gln Leu Tyr Glu Ser Arg Gly Pro Asn Gly Asn Thr Thr
    530                 535                 540

Gln Asn His Ile Val Tyr Thr Gln Glu His Lys Ser Glu His Ala Glu
545                 550                 555                 560

Asp Arg Gly His Ile Ser Pro Thr Thr Asp Gln Ser Val Ser Ser Ser
                565                 570                 575

Phe Cys Asn Gly Asn Ala Ser His Leu Asn Ser Ile Gly Tyr Gly Ser
            580                 585                 590

Asn Cys Gly Ser Ser Ser Asn Val Asp Gln Val Asn Thr Val Trp Ala
        595                 600                 605

Ala Ser Glu Gly Lys His Glu Asp Leu Thr Asn Asn Ala Asn Ser His
    610                 615                 620

Arg Ser Ile Gln Arg Glu Ala Ala Leu Asn Lys Phe Arg Leu Lys Arg
625                 630                 635                 640
```

-continued

```
Lys Glu Arg Cys Tyr Glu Lys Lys Val Arg Tyr Glu Ser Arg Lys Lys
                645                 650                 655

Leu Ala Glu Gln Arg Pro Arg Val Lys Gly Gln Phe Val Arg Gln Val
            660                 665                 670

His Pro Asp Pro Leu Val Ala Glu Lys Asp Gly Lys Glu Tyr Asp His
        675                 680                 685

Ser Asp Phe
    690


<210> SEQ ID NO 48
<211> LENGTH: 747
<212> TYPE: PRT
<213> ORGANISM: Vitis vinifera

<400> SEQUENCE: 48

Met Gly Glu Val Val Val Ser Ser Glu Ala Gly Gly Gly Gly Met Glu
1               5                   10                  15

Gly Glu Val Glu Lys Lys Glu Val Gly Ser Gly Val Val Arg Trp Glu
            20                  25                  30

Arg Phe Leu Pro Arg Met Val Leu Arg Val Leu Leu Val Glu Ala Asp
        35                  40                  45

Asp Ser Thr Arg Gln Ile Ile Ala Ala Leu Leu Arg Lys Cys Ser Tyr
    50                  55                  60

Lys Val Ala Ala Val Pro Asp Gly Leu Lys Ala Trp Glu Val Leu Lys
65                  70                  75                  80

Ala Arg Pro His Asn Ile Asp Leu Ile Leu Thr Glu Val Glu Leu Pro
                85                  90                  95

Ser Ile Ser Gly Phe Ala Leu Leu Thr Leu Val Met Glu His Glu Ile
            100                 105                 110

Cys Lys Asn Ile Pro Val Ile Met Met Ser Ser His Gly Ser Ile Asn
        115                 120                 125

Thr Val Tyr Lys Cys Met Leu Arg Gly Ala Ala Asp Phe Leu Val Lys
    130                 135                 140

Pro Val Arg Arg Asn Glu Leu Lys Asn Leu Trp Gln His Val Trp Arg
145                 150                 155                 160

Arg Gln Ser Ser Thr Val Ser Gly Asn Gly Pro Gln Asp Glu Ser Val
                165                 170                 175

Ala Gln Gln Lys Val Glu Ala Thr Ser Glu Asn Asn Pro Thr Ser Asn
            180                 185                 190

His Ser Ser Asp His Val Ala Cys Ile Gln Lys Asn Lys Glu Ala Leu
        195                 200                 205

Asn Lys Val Ser Asp Ala Gln Ser Ser Cys Ser Lys Pro Asp Leu Glu
    210                 215                 220

Ala Glu Ser Ala Tyr Met Glu Thr Met Gln Asp Phe Ser Asn Pro Thr
225                 230                 235                 240

Trp Ser Arg Ser Leu Val Ser Asp Thr Lys Met Gln Lys Asn Glu Glu
                245                 250                 255

Cys Ala Lys Leu Gly Pro Lys Phe Leu Met His Asn Lys Glu Ala Gly
            260                 265                 270

Gly Thr Leu Glu Ala Ala Cys Arg Asp Val Asn Thr Met Thr Gln Pro
        275                 280                 285

Glu Ala Val Glu Pro Glu Asn Asp Gly Gln Gly Ala Asn Ala Pro Ser
    290                 295                 300

Glu Ala Cys Gly Asn Asn Ala Ile Leu Gly Ser Ser Ser Arg Glu Ala
305                 310                 315                 320
```

```
Ile Asp Leu Ile Gly Val Phe Asp Asn Ser Lys Lys Cys Thr Tyr Gly
                325                 330                 335

Asn Ser Ser Ser Asn Asn Gly Thr Lys Lys Ser Asp Ser Ile Pro Gln
            340                 345                 350

Leu Asp Leu Ser Leu Arg Arg Ser His Pro Ser Ser Pro Glu Asn Gln
        355                 360                 365

Val Ala Asp Glu Arg His Thr Leu Asn His Ser Asn Gly Ser Ala Phe
    370                 375                 380

Ser Arg Tyr Ile Asn Arg Ser Leu Gln Pro Pro His Leu Pro Ser Thr
385                 390                 395                 400

Gly Val Phe Asn Gln Gln Lys Asn Phe Gly Ala Asp Ser Asp Lys Arg
                405                 410                 415

Leu Ser Gln Leu Val Thr Gly Tyr Asn Ser Asp Ile Thr Ser Pro Thr
            420                 425                 430

Leu Ser Thr Gln Arg Ser Val Ile Ser Leu Ala Thr Ser Pro Ser Gly
        435                 440                 445

Arg Val Glu Ile Ala Leu Cys Gly Pro Gln Gln Arg Ala Phe Pro Ala
    450                 455                 460

Pro Val Pro Gln Asn Ala Asn Asn Ser Thr Ser Gln Thr Asn His Lys
465                 470                 475                 480

Pro Glu His Lys Leu Asp Ser Leu Glu Gly Gln Gly His Phe Ser Pro
                485                 490                 495

Ala Thr Asp Gln Asn Ser Ser Ser Ser Phe Gly Asn Gly Gly Ala Ser
            500                 505                 510

Asn Leu Asn Ser Phe Gly Cys Gly Ser Ile Cys Gly Ser Asn Gly Asn
        515                 520                 525

Ala Asn Thr Val Ala Val Val Gln Ala Ala Ala Glu Gly Lys Asn Glu
    530                 535                 540

Glu Gly Ile Phe Ser His Glu Gly His Ser Gln Arg Ser Ile Gln Arg
545                 550                 555                 560

Glu Ala Ala Leu Thr Lys Phe Arg Leu Lys Arg Lys Asp Arg Cys Phe
                565                 570                 575

Glu Lys Lys Val Arg Tyr Glu Ser Arg Lys Lys Leu Ala Glu Gln Arg
            580                 585                 590

Pro Arg Val Lys Gly Gln Phe Val Arg Gln Val His Thr Ile Pro Pro
        595                 600                 605

Pro Ala Glu Pro Asp Thr Tyr Tyr Gly Ser Ser Phe Asp Val Gln Pro
    610                 615                 620

Gln Arg Ser Arg Tyr Leu Ser Ala Gln Pro Leu Arg Ala Ser Ser Ser
625                 630                 635                 640

Gln Leu Leu Tyr Pro Thr His Thr Pro Leu Gln Glu Ser Lys Tyr Glu
                645                 650                 655

Gly His Glu Glu Ser Asn Leu Leu Thr Ala Ser Leu Val Gly Thr Ala
            660                 665                 670

Leu Pro Val Ala Pro Ser Phe Gly Tyr Glu Val Gly Arg Asp Gln Thr
        675                 680                 685

Ala Gly Lys Leu Val Leu Ser Leu Lys Leu Asp Gly Arg Val Arg Trp
    690                 695                 700

Lys Val Gly Thr Trp Val Ser Gly Arg Tyr Arg Leu Asn Val Asn Cys
705                 710                 715                 720

Val Ala Val Met Ala Phe Gly Pro Ser Ile Pro Ser Gly Pro Leu Ser
                725                 730                 735
```

Ser Lys Glu Gly Thr Gln Cys Ser Thr Thr Val
740 745

<210> SEQ ID NO 49
<211> LENGTH: 799
<212> TYPE: PRT
<213> ORGANISM: Theobroma cacao

<400> SEQUENCE: 49

Met Gly Ile Val Gln Met Asn Asn Asn Gly Pro Val Ala Asn Gly Leu
1 5 10 15

Val Glu Leu Asn Thr His Ile His Asp Glu His Lys Lys Ile Arg Gly
20 25 30

Gly Val Ile Gly Glu Gly Gln Gly Leu Ser Val Glu Glu Glu Ser Trp
35 40 45

Ile Asn Glu Asp Val Glu Asp Arg Asn Asp Gly Lys Thr Glu Leu Val
50 55 60

Gln Val Gln Gly His Ala His Gly Glu Gln Glu Arg Ser Gln Gln Gln
65 70 75 80

Pro Gln Gly Pro Leu Val His Trp Glu Arg Phe Leu Pro Leu Arg Ser
85 90 95

Leu Lys Val Leu Leu Val Glu Asn Asp Asp Ser Thr Arg His Val Val
100 105 110

Cys Ala Leu Leu Arg Asn Cys Gly Phe Glu Val Thr Ala Val Ser Asn
115 120 125

Gly Leu Gln Ala Trp Lys Ile Leu Glu Asp Leu Thr Asn His Ile Asp
130 135 140

Leu Val Leu Thr Glu Val Val Met Pro Cys Leu Ser Gly Ile Gly Leu
145 150 155 160

Leu Cys Lys Ile Met Ser His Lys Thr Arg Met Asn Ile Pro Val Ile
165 170 175

Met Met Ser Ser His Asp Ser Met Ser Thr Val Phe Arg Cys Leu Ser
180 185 190

Lys Gly Ala Val Asp Phe Leu Val Lys Pro Ile Arg Lys Asn Glu Leu
195 200 205

Lys Asn Leu Trp Gln His Val Trp Arg Lys Cys His Ser Ser Ser Ser
210 215 220

Ser Gly Gly Gln Ser Gly Thr Gln Thr Gln Lys Ser Ser Lys Ser Lys
225 230 235 240

Gly Thr Asp Ser Asp Asn Asn Thr Gly Ser Asn Asp Glu Asp Asp Asn
245 250 255

Gly Ser Val Gly Leu Asn Val Gln Asp Gly Ser Asp Asn Gly Ser Gly
260 265 270

Thr Gln Ser Ser Trp Thr Lys Arg Ala Val Glu Val Asp Ser Ser Gln
275 280 285

Pro Ile Ser Pro Trp Asp Gln Leu Ala Asp Pro Pro His Ser Thr Cys
290 295 300

Ala Gln Val Ile His Ser Arg His Glu Val Leu Gly Asp Ser Trp Val
305 310 315 320

Pro Val Thr Ala Thr Arg Glu Tyr Asp Glu Leu Asp Asn Glu Leu Glu
325 330 335

Asn Val Val Met Gly Lys Asp Leu Glu Ile Gly Val Pro Lys Ile Thr
340 345 350

Ala Ser Gln Leu Glu Asp Pro Ser Glu Lys Val Met Thr Asn Ile Ala
355 360 365

-continued

```
Gly Val Asn Lys Asp Lys Leu Ser Ala Ile Asn Pro Lys Lys Asp Asp
    370                 375                 380

Glu Lys Leu Glu Lys Ala Gln Leu Glu Leu Asn Ser Glu Lys Ser Gly
385                 390                 395                 400

Gly Asp Leu Arg Asn Gln Ala Ala Asp Leu Ile Gly Val Ile Thr Asn
                405                 410                 415

Asn Thr Glu Pro His Ile Glu Ser Ala Val Phe Asp Ile Pro Asn Gly
            420                 425                 430

Leu Pro Lys Val Ser Asp Ala Lys Glu Lys Val Asn Tyr Asp Thr Lys
        435                 440                 445

Glu Met Pro Phe Leu Glu Leu Ser Leu Lys Arg Leu Arg Asp Val Gly
    450                 455                 460

Asp Thr Gly Thr Ser Ala His Glu Arg Asn Val Leu Arg His Ser Asp
465                 470                 475                 480

Leu Ser Ala Phe Ser Arg Tyr Asn Ser Gly Ser Thr Ala Asn Gln Ala
                485                 490                 495

Pro Thr Gly Asn Val Gly Ser Cys Ser Pro Leu Asp Asn Ser Ser Glu
            500                 505                 510

Ala Val Lys Thr Asp Ser Met Lys Asn Phe Gln Ser Thr Ser Asn Ser
        515                 520                 525

Ile Pro Pro Lys Gln Gln Ser Asn Gly Ser Ser Asn Asn Asn Asp Met
    530                 535                 540

Gly Ser Thr Thr Asn Asn Ala Phe Ser Lys Pro Ala Val Leu Ser Asp
545                 550                 555                 560

Lys Pro Ala Pro Lys Thr Ser Ala Lys Ser Phe His Pro Ser Ser Ala
                565                 570                 575

Phe Gln Pro Val Gln Ser Gly His Gly Ser Ala Leu Gln Pro Val Ala
            580                 585                 590

Gln Gly Lys Ala Asp Ala Ala Leu Gly Asn Met Ile Leu Val Lys Ala
        595                 600                 605

Arg Gly Thr Asp Gln Gln Gly Lys Val Gln His His His His His Tyr
    610                 615                 620

His His His His His His His Val His Asn Met Leu Pro Asn Gln Lys
625                 630                 635                 640

Leu Gly Asn His Asp Asp Leu Ser Leu Glu Asn Met Ala Ala Ala Ala
                645                 650                 655

Pro Gln Cys Gly Ser Ser Asn Leu Ser Ser Leu Pro His Val Glu Gly
            660                 665                 670

Asn Ala Ala Asn His Ser Leu Thr Arg Ser Ala Ser Gly Ser Asn His
        675                 680                 685

Gly Ser Asn Gly Gln Asn Gly Ser Ser Thr Val Leu Asn Thr Arg Gly
    690                 695                 700

Met Asn Leu Glu Ser Glu Asn Gly Val Pro Gly Lys Gly Gly Ala Gly
705                 710                 715                 720

Gly Gly Ile Gly Ser Gly Gly Arg Asn Val Val Asp Gln Asn Arg Phe
                725                 730                 735

Ala Gln Arg Glu Ala Ala Leu Asn Lys Phe Arg Gln Lys Arg Lys Glu
            740                 745                 750

Arg Cys Phe Glu Lys Lys Val Arg Tyr Gln Ser Arg Lys Lys Leu Ala
        755                 760                 765

Glu Gln Arg Pro Arg Ile Arg Gly Gln Phe Val Arg Gln Ile Ser Thr
    770                 775                 780
```

```
Thr Gly Lys Glu Ala Phe Arg Phe Arg Gly Ala Gly Leu Cys Thr
785                 790                 795


<210> SEQ ID NO 50
<211> LENGTH: 742
<212> TYPE: PRT
<213> ORGANISM: Oryza sativa

<400> SEQUENCE: 50

Met Met Gly Thr Ala His His Asn Gln Thr Ala Gly Ser Ala Leu Gly
1               5                   10                  15

Val Gly Val Gly Asp Ala Asn Asp Ala Val Pro Gly Ala Gly Gly Gly
            20                  25                  30

Gly Tyr Ser Asp Pro Asp Gly Gly Pro Ile Ser Gly Val Gln Arg Pro
        35                  40                  45

Pro Gln Val Cys Trp Glu Arg Phe Ile Gln Lys Lys Thr Ile Lys Val
    50                  55                  60

Leu Leu Val Asp Ser Asp Asp Ser Thr Arg Gln Val Val Ser Ala Leu
65                  70                  75                  80

Leu Arg His Cys Met Tyr Glu Val Ile Pro Ala Glu Asn Gly Gln Gln
                85                  90                  95

Ala Trp Thr Tyr Leu Glu Asp Met Gln Asn Ser Ile Asp Leu Val Leu
            100                 105                 110

Thr Glu Val Val Met Pro Gly Val Ser Gly Ile Ser Leu Leu Ser Arg
        115                 120                 125

Ile Met Asn His Asn Ile Cys Lys Asn Ile Pro Val Ile Met Met Ser
    130                 135                 140

Ser Asn Asp Ala Met Gly Thr Val Phe Lys Cys Leu Ser Lys Gly Ala
145                 150                 155                 160

Val Asp Phe Leu Val Lys Pro Ile Arg Lys Asn Glu Leu Lys Asn Leu
                165                 170                 175

Trp Gln His Val Trp Arg Arg Cys His Ser Ser Ser Gly Ser Gly Ser
            180                 185                 190

Glu Ser Gly Ile Gln Thr Gln Lys Cys Ala Lys Ser Lys Ser Gly Asp
        195                 200                 205

Glu Ser Asn Asn Asn Asn Gly Ser Asn Asp Asp Asp Asp Asp Asp Gly
    210                 215                 220

Val Ile Met Gly Leu Asn Ala Arg Asp Gly Ser Asp Asn Gly Ser Gly
225                 230                 235                 240

Thr Gln Ala Gln Ser Ser Trp Thr Lys Arg Ala Val Glu Ile Asp Ser
                245                 250                 255

Pro Gln Ala Met Ser Pro Asp Gln Leu Ala Asp Pro Pro Asp Ser Thr
            260                 265                 270

Cys Ala Gln Val Ile His Leu Lys Ser Asp Ile Cys Ser Asn Arg Trp
        275                 280                 285

Leu Pro Cys Thr Ser Asn Lys Asn Ser Lys Lys Gln Lys Glu Thr Asn
    290                 295                 300

Asp Asp Phe Lys Gly Lys Asp Leu Glu Ile Gly Ser Pro Arg Asn Leu
305                 310                 315                 320

Asn Thr Ala Tyr Gln Ser Ser Pro Asn Glu Arg Ser Ile Lys Pro Thr
                325                 330                 335

Asp Arg Arg Asn Glu Tyr Pro Leu Gln Asn Asn Ser Lys Glu Ala Ala
            340                 345                 350

Met Glu Asn Leu Glu Glu Ser Ser Val Arg Ala Ala Asp Leu Ile Gly
        355                 360                 365
```

```
Ser Met Ala Lys Asn Met Asp Ala Gln Gln Ala Ala Arg Ala Ala Asn
    370                 375                 380

Ala Pro Asn Cys Ser Ser Lys Val Pro Glu Gly Lys Asp Lys Asn Arg
385                 390                 395                 400

Asp Asn Ile Met Pro Ser Leu Glu Leu Ser Leu Lys Arg Ser Arg Ser
                405                 410                 415

Thr Gly Asp Gly Ala Asn Ala Ile Gln Glu Glu Gln Arg Asn Val Leu
            420                 425                 430

Arg Arg Ser Asp Leu Ser Ala Phe Thr Arg Tyr His Thr Pro Val Ala
        435                 440                 445

Ser Asn Gln Gly Gly Thr Gly Phe Met Gly Ser Cys Ser Leu His Asp
    450                 455                 460

Asn Ser Ser Glu Ala Met Lys Thr Asp Ser Ala Tyr Asn Met Lys Ser
465                 470                 475                 480

Asn Ser Asp Ala Ala Pro Ile Lys Gln Gly Ser Asn Gly Ser Ser Asn
                485                 490                 495

Asn Asn Asp Met Gly Ser Thr Thr Lys Asn Val Val Thr Lys Pro Ser
            500                 505                 510

Thr Asn Lys Glu Arg Val Met Ser Pro Ser Ala Val Lys Ala Asn Gly
        515                 520                 525

His Thr Ser Ala Phe His Pro Ala Gln His Trp Thr Ser Pro Ala Asn
    530                 535                 540

Thr Thr Gly Lys Glu Lys Thr Asp Glu Val Ala Asn Asn Ala Ala Lys
545                 550                 555                 560

Arg Ala Gln Pro Gly Glu Val Gln Ser Asn Leu Val Gln His Pro Arg
                565                 570                 575

Pro Ile Leu His Tyr Val His Phe Asp Val Ser Arg Glu Asn Gly Gly
            580                 585                 590

Ser Gly Ala Pro Gln Cys Gly Ser Ser Asn Val Phe Asp Pro Pro Val
        595                 600                 605

Glu Gly His Ala Ala Asn Tyr Gly Val Asn Gly Ser Asn Ser Gly Ser
    610                 615                 620

Asn Asn Gly Ser Asn Gly Gln Asn Gly Ser Thr Thr Ala Val Asn Ala
625                 630                 635                 640

Glu Arg Pro Asn Met Glu Ile Ala Asn Gly Thr Ile Asn Lys Ser Gly
                645                 650                 655

Pro Gly Gly Gly Asn Gly Ser Gly Ser Gly Ser Gly Asn Asp Met Tyr
            660                 665                 670

Leu Lys Arg Phe Thr Gln Arg Glu His Arg Val Ala Ala Val Ile Lys
        675                 680                 685

Phe Arg Gln Lys Arg Lys Glu Arg Asn Phe Gly Lys Lys Val Arg Tyr
    690                 695                 700

Gln Ser Arg Lys Arg Leu Ala Glu Gln Arg Pro Arg Val Arg Gly Gln
705                 710                 715                 720

Phe Val Arg Gln Ala Val Gln Asp Gln Gln Gln Gln Gly Gly Gly Arg
                725                 730                 735

Glu Ala Ala Ala Asp Arg
            740
```

<210> SEQ ID NO 51
<211> LENGTH: 766
<212> TYPE: PRT
<213> ORGANISM: Zea mays

<400> SEQUENCE: 51

```
Met Gly Ser Ala Cys Gln Ala Gly Thr Asp Gly Pro Ser Arg Lys Asp
1               5                   10                  15

Val Leu Gly Ile Gly Asn Ala Ala Leu Glu Asn Gly His His Gln Ala
            20                  25                  30

Glu Ala Asp Ala Asp Glu Trp Arg Glu Lys Glu Glu Asp Leu Ala Asn
        35                  40                  45

Asn Gly His Ser Ala Pro Pro Pro Gly Met Gln Gln Val Asp Glu His
    50                  55                  60

Lys Glu Glu Gln Arg Gln Ser Ile His Trp Glu Arg Phe Leu Pro Val
65                  70                  75                  80

Lys Thr Leu Arg Val Leu Leu Val Glu Asn Asp Asp Ser Thr Arg Gln
                85                  90                  95

Val Val Ser Ala Leu Leu Arg Lys Cys Cys Tyr Glu Val Ile Pro Ala
            100                 105                 110

Glu Asn Gly Leu His Ala Trp Arg Tyr Leu Glu Asp Leu Gln Asn Asn
        115                 120                 125

Ile Asp Leu Val Leu Thr Glu Val Phe Met Pro Cys Leu Ser Gly Ile
    130                 135                 140

Gly Leu Leu Ser Lys Ile Thr Ser His Lys Ile Cys Lys Asp Ile Pro
145                 150                 155                 160

Val Ile Met Met Ser Thr Asn Asp Ser Met Ser Met Val Phe Lys Cys
                165                 170                 175

Leu Ser Lys Gly Ala Val Asp Phe Leu Val Lys Pro Leu Arg Lys Asn
            180                 185                 190

Glu Leu Lys Asn Leu Trp Gln His Val Trp Arg Arg Cys His Ser Ser
        195                 200                 205

Ser Gly Ser Glu Ser Gly Ile Gln Thr Gln Lys Cys Ala Lys Leu Asn
    210                 215                 220

Thr Gly Asp Glu Tyr Glu Asn Gly Ser Asp Ser Asn His Asp Asp Glu
225                 230                 235                 240

Glu Asn Asp Asp Gly Asp Asp Asp Asp Phe Ser Val Gly Leu Asn Ala
                245                 250                 255

Arg Asp Gly Ser Asp Asn Gly Ser Gly Thr Gln Ser Ser Trp Thr Lys
            260                 265                 270

Arg Ala Val Glu Ile Asp Ser Pro Gln Pro Ile Ser Pro Asp Gln Leu
        275                 280                 285

Val Asp Pro Pro Asp Ser Thr Cys Ala Gln Val Ile His Pro Arg Ser
    290                 295                 300

Glu Ile Cys Ser Asn Lys Trp Leu Pro Thr Ala Asn Lys Arg Asn Val
305                 310                 315                 320

Lys Lys Gln Lys Glu Asn Lys Asp Glu Ser Met Gly Arg Tyr Leu Gly
                325                 330                 335

Ile Gly Ala Pro Arg Asn Ser Ser Ala Glu Tyr Gln Ser Ser Leu Asn
            340                 345                 350

Asp Val Ser Val Asn Pro Ile Glu Lys Gly His Glu Asn His Met Ser
        355                 360                 365

Lys Cys Lys Ser Lys Lys Glu Thr Met Ala Glu Asp Asp Cys Thr Asn
    370                 375                 380

Met Pro Ser Ala Thr Asn Ala Glu Thr Ala Asp Leu Ile Ser Ser Ile
385                 390                 395                 400

Ala Arg Asn Thr Glu Gly Gln Gln Ala Val Gln Ala Val Asp Ala Pro
                405                 410                 415
```

Asp Gly Pro Ser Lys Met Ala Asn Gly Asn Asp Lys Asn His Asp Ser
420 425 430

His Ile Glu Val Thr Pro His Glu Leu Gly Leu Lys Arg Ser Arg Thr
435 440 445

Asn Gly Ala Thr Ala Glu Ile His Asp Glu Arg Asn Ile Leu Lys Arg
450 455 460

Ser Asp Gln Ser Ala Phe Thr Arg Tyr His Thr Ser Val Ala Ser Asn
465 470 475 480

Gln Gly Gly Ala Arg Tyr Gly Glu Ser Ser Ser Pro Gln Asp Asn Ser
485 490 495

Ser Glu Ala Met Lys Thr Asp Ser Thr Cys Lys Met Lys Ser Asn Ser
500 505 510

Asp Ala Ala Pro Ile Lys Gln Gly Ser Asn Gly Ser Ser Asn Asn Asp
515 520 525

Val Gly Ser Ser Thr Lys Asn Val Ala Ala Arg Pro Ser Gly Asp Arg
530 535 540

Glu Arg Val Ala Ser Pro Leu Ala Ile Lys Ser Thr Gln His Ala Ser
545 550 555 560

Ala Phe His Thr Ile Gln Asn Gln Thr Ser Pro Ala Asn Leu Ile Gly
565 570 575

Glu Asp Lys Ala Asp Glu Gly Ile Ser Asn Thr Val Lys Met Ser His
580 585 590

Pro Thr Glu Val Pro Gln Gly Cys Val Gln His His His His Val His
595 600 605

Tyr Tyr Leu His Val Met Thr Gln Lys Gln Pro Ser Thr Asp Arg Gly
610 615 620

Ser Ser Asp Val His Cys Gly Ser Ser Asn Val Phe Asp Pro Pro Val
625 630 635 640

Glu Gly His Ala Ala Asn Tyr Ser Val Asn Gly Gly Val Ser Val Gly
645 650 655

His Asn Gly Cys Asn Gly Gln Asn Gly Ser Ser Ala Val Pro Asn Ile
660 665 670

Ala Arg Pro Asn Ile Glu Ser Ile Asn Gly Thr Met Ser Gln Asn Ile
675 680 685

Ala Gly Gly Gly Ile Val Ser Gly Ser Gly Ser Gly Asn Asp Met Tyr
690 695 700

Gln Asn Arg Phe Leu Gln Arg Glu Ala Ala Leu Asn Lys Phe Arg Leu
705 710 715 720

Lys Arg Lys Asp Arg Asn Phe Gly Lys Lys Val Arg Tyr Gln Ser Arg
725 730 735

Lys Arg Leu Ala Glu Gln Arg Pro Arg Val Arg Gly Gln Phe Val Arg
740 745 750

Gln Ser Glu Gln Glu Asp Gln Thr Ala Gln Gly Ser Glu Arg
755 760 765

<210> SEQ ID NO 52
<211> LENGTH: 917
<212> TYPE: PRT
<213> ORGANISM: Physcomitrella patens

<400> SEQUENCE: 52

Met Thr Ala Asp Leu Cys Glu Phe Glu Ser Glu Ser Asp Pro Leu Gln
1 5 10 15

Pro Leu Ser Ala Val Gly Arg Ala Trp Val Glu Pro Ile Val Gly Thr

```
            20                  25                  30

Pro Val Gly Ala Glu Trp Arg Ile Lys Gly Gly Phe Lys Ala His Lys
        35                  40                  45

Glu Val Asp Arg Ser Arg Glu Gln Val Gly Ser Lys Arg Val Asp Asp
    50                  55                  60

Arg Glu Lys Asn Ser Gly Arg Leu Glu Asn Gly Cys Arg Phe Ala Asp
65                  70                  75                  80

Arg Thr Gly Gly Ala Val Leu Lys Ala Arg Glu Asp Pro Lys Asp Ile
                85                  90                  95

Ala Glu Gln Ile Arg Arg Glu Leu Asp His Gln Phe Pro Val Asn Asp
            100                 105                 110

Val Leu Arg Thr Ser Glu Ser Asp Glu Asp Gly Arg Arg Glu Asp Ser
        115                 120                 125

Ala Glu Asp His Tyr Glu Glu Gly Asp Ala Val Ala Ala Val Val Phe
    130                 135                 140

Glu Lys Gln Arg Pro Arg Glu Ile Ala Gln Thr Arg Glu Gln Gln Gln
145                 150                 155                 160

Gly Gly Asn Ala Ala Ala Ala Ala Ala Gly Thr Gln Gly Gly Gly Gly
                165                 170                 175

Trp Glu Ser Phe Leu Leu Lys Arg Asn Leu Lys Val Leu Leu Val Glu
            180                 185                 190

Asp Asp Asp Ala Thr Arg His Val Val Gly Ala Leu Leu Arg Asn Cys
        195                 200                 205

Asn Tyr Glu Val Thr Pro Val Ala Asn Gly Ser Leu Ala Trp Gly Leu
    210                 215                 220

Leu Glu Glu Ala Asn Ser Asn Phe Asp Leu Val Leu Thr Asp Val Val
225                 230                 235                 240

Met Pro Tyr Leu Ser Gly Val Gly Leu Leu Ser Lys Met Met Lys Arg
                245                 250                 255

Glu Ala Cys Lys Arg Val Pro Ile Val Ile Met Ser Ser Tyr Asp Ser
            260                 265                 270

Leu Gly Ile Val Phe Arg Cys Leu Ser Lys Gly Ala Cys Asp Tyr Leu
        275                 280                 285

Val Lys Pro Val Arg Lys Asn Glu Leu Lys Asn Leu Trp Gln His Val
    290                 295                 300

Trp Arg Lys Cys His Ser Ser Ser Gly Ser Arg Ser Gly Ser Gly Ser
305                 310                 315                 320

Gln Thr Gly Glu Val Ala Lys Pro Arg Ser Arg Gly Val Ala Ala Ala
                325                 330                 335

Asp Asn Pro Ser Gly Ser Asn Asp Gly Asn Gly Ser Ser Asp Gly Ser
            340                 345                 350

Asp Asn Gly Ser Ser Arg Val Asn Ala Gln Gly Gly Ser Asp Asn Gly
        355                 360                 365

Ser Gly Asn Gln Ala Cys Met Gln Pro Val Gln Val Leu Arg Asn Ser
    370                 375                 380

Ala Ile Pro Glu Ala Val Asp Gly Asp Glu Glu Gly Gln Ala Thr Ser
385                 390                 395                 400

Gln Asp Lys Gly Ala Asp Leu Asp Gly Glu Met Gly His Asp Leu Glu
                405                 410                 415

Met Ala Thr Arg Arg Ser Ala Cys Val Thr Thr Gly Lys Asp Gln Gln
            420                 425                 430

Pro Glu Asp Ala Gln Lys Gln Asp Glu Asp Ala Val Cys Ile Leu Gln
        435                 440                 445
```

-continued

```
Asp Ala Gly Pro Ser Pro Asp Gly Ala Asn Ala Glu Ser Pro Ser Ser
    450                 455                 460

Ser Gly Arg Asn Asp Ala Ala Glu Glu Ser Ser Pro Lys Ile Ile Asp
465                 470                 475                 480

Leu Ile Asn Val Ile Ala Cys Gln Pro Gln Thr Gln Asp Ala Glu Pro
                485                 490                 495

Gln Glu Ser Glu Asn Asp Asp Glu Glu Leu Asp Pro Arg Gly Arg Ser
            500                 505                 510

Ser Pro Lys Asn Asn Ser Ala Ser Asp Ser Gly Thr Ser Leu Glu Leu
        515                 520                 525

Ser Leu Lys Arg Pro Arg Ser Ala Val Gly Asn Gly Gly Glu Leu Glu
    530                 535                 540

Glu Arg Gln Pro Leu Arg His Ser Gly Gly Ser Ala Phe Ser Arg Tyr
545                 550                 555                 560

Gly Ser Gly Gly Thr Ile Ile Gln Gln Tyr His Gln Thr Gly Gly Ser
                565                 570                 575

Leu Pro Leu Ser Gly Tyr Pro Val Ser Gly Gly Tyr Gly Val Tyr Gly
            580                 585                 590

Met Ser Gly Gly Ser Pro Gly Gly Ser Leu Arg Leu Gly Met Gly Met
        595                 600                 605

Asp Arg Ser Gly Ser Ser Lys Gly Ser Val Glu Gly Thr Thr Pro Pro
    610                 615                 620

Pro Ser His Pro Gln Ser Met Glu Lys Val Gly Gly Gln Asp Gly Tyr
625                 630                 635                 640

Gly Asn Ala Arg Gln Thr Thr Glu Asp Ala Met Ile Val Pro Gly Met
                645                 650                 655

Pro Met Ala Ile Pro Leu Pro Pro Pro Gly Met Leu Ala Tyr Asp Gly
            660                 665                 670

Val Ile Gly Thr Tyr Gly Pro Ala Met His Pro Met Tyr Tyr Ala His
        675                 680                 685

Pro Ser Ala Trp Met Ala Ala Pro Ser Arg His Met Gly Glu Arg Gly
    690                 695                 700

Asp Val Tyr Asn Gln Ser Pro Ala Phe Gln Glu Gln Asp Ser Gly Ser
705                 710                 715                 720

Gly Asn His Ser Gln Ala Gly Gln Thr His Gln His Met His His His
                725                 730                 735

Gln Gly Asn Gln His His His His His His His His His His Gly Ser
            740                 745                 750

Gly Ala Gln Pro Ser Gly Asn Ala Gly Val Gln Asp Glu Gln Gln Gln
        755                 760                 765

Ser Val Val Pro Pro Gly Ser Ser Ala Pro Arg Cys Gly Ser Thr Gly
    770                 775                 780

Val Asp Gly Arg Ser Gly Ser Ser Asn Gly Tyr Gly Ser Thr Gly Asn
785                 790                 795                 800

Gly Asn Gly Ser Met Asn Gly Ser Ala Ser Gly Ser Asn Thr Gly Val
                805                 810                 815

Asn Asn Gly Gln Ser Gly Phe Gly Ala Thr Pro Met Leu Thr Asp Asn
            820                 825                 830

Ser Gly Ser Asn Gly Val Gly Gly Thr Asp Ala Ala Met Asp Gly Val
        835                 840                 845

Ser Gly Gly Asn Gly Leu Cys Thr Glu Gln Met Arg Phe Ala Arg Arg
    850                 855                 860
```

Glu Ala Ala Leu Asn Lys Phe Arg Gln Lys Arg Lys Glu Arg Cys Phe
865 870 875 880

Glu Lys Lys Val Arg Tyr Gln Ser Arg Lys Arg Leu Ala Glu Gln Arg
885 890 895

Pro Arg Val Arg Gly Gln Phe Val Arg Gln Ala Val His Asp Pro Ser
900 905 910

Ala Gly Asp Ala Glu
915

<210> SEQ ID NO 53
<211> LENGTH: 1359
<212> TYPE: PRT
<213> ORGANISM: Volvox carteri

<400> SEQUENCE: 53

Met Glu Phe His Val Leu Leu Val Glu Asp Asp Arg Val Thr Leu Lys
1 5 10 15

Thr Val Glu Gln Leu Leu Arg Lys Cys Asn Tyr Lys Val Thr Cys Ala
20 25 30

Ala Asn Gly Arg Glu Ala Ile Lys Val Leu Thr Ala Cys Arg His Ser
35 40 45

Gly Val Lys Val Asp Leu Ile Leu Thr Asp Ile Leu Met Pro Glu Val
50 55 60

Thr Gly Phe Asp Leu Ile Asn Glu Val Val His Gly Asp Thr Phe Cys
65 70 75 80

Asp Val Pro Val Val Val Met Ser Ser Gln Asp Ser Gln Glu Asn Val
85 90 95

Leu Gln Ala Phe Gln Ala Gly Ala Ala Asp Tyr Leu Ile Lys Pro Ile
100 105 110

Arg Lys Asn Glu Leu Ala Thr Leu Trp Gln His Val Trp Arg Ala Asn
115 120 125

Lys Ala Lys Gly Ser Gly Ser Gly Thr Thr Thr Asn Val Thr Gly Gln
130 135 140

Pro Leu Ser Gly Arg Glu Asp Leu Glu Ala Gly Glu Ala Val Ala Val
145 150 155 160

Ala Ala Ala Ala Ala Ala Ala Ser Gly Lys Ala Cys Ala Ala Thr His
165 170 175

Gly His Leu Lys Asp Ser Ser Gly Gly Ser Ser Gly Ala Ala Ala Ser
180 185 190

Val Leu Gln Ser Thr Gly Gly Thr Leu Leu Pro Asp Arg Ala Ala Thr
195 200 205

Val Arg Tyr Pro Ala Ala Ala Ala Ala Pro Pro Pro Pro Gly Ala Ser
210 215 220

Glu Leu Ser Gly Asn Val Thr Ala Gly Glu Ala Gln Gly Ser Arg Thr
225 230 235 240

Gln His Leu Arg His Leu Ser Gly Leu Ala Gly Met Glu Ser Thr Ala
245 250 255

Ala Thr Ser Ala Ala Ala Gln Gly Ser Ser Ala Ala Gly Pro Leu Arg
260 265 270

Gly Cys Gly Gly Ala Gly Thr Ala Ile Ala Gly Gly Pro Arg Ala Pro
275 280 285

Leu Gly Pro Leu Ser Phe Ala Pro Phe Gly Thr Ser Val Ala Val His
290 295 300

Phe Asp Leu Asn Pro Ala Ser Gly Ala Ala Arg Arg Leu Val Asn Ser
305 310 315 320

-continued

```
Ser Gly Ala Ile Asp Ala Ser Thr Gly Ser Gly Thr Ala Gly Val Ala
                325                 330                 335

Ala Ser Ser Arg Cys Ala Ala Gly Thr Ser Ala Thr Val Ile Ser Trp
            340                 345                 350

Ser His Val Asp Pro Thr Glu Thr Asp Pro Ala Glu Ala Glu Pro Met
        355                 360                 365

Tyr Asp Thr Asn Ala Asp Ala Thr Ala Ala Lys Ala Ala Ala Asp Gly
    370                 375                 380

Val Ala Glu Ala Asp Asp Asp Asp Val Gly Asp Asp Gly Gly Ala Gly
385                 390                 395                 400

Pro Asn His Asn Asp Asp Asp Asp Glu Gly Gly Gly Asp Asp Asp Val
                405                 410                 415

Ser Gly Asp Gly Asp Glu Asp Gly Asn Arg Pro Arg Lys Arg Pro Arg
            420                 425                 430

Leu Leu Gln Gly Ser Ser His His His Ser His Gln His Arg Leu His
        435                 440                 445

Ser Leu Gly Gly Thr Thr Thr Asn Thr Thr Thr Thr Thr Thr Ala Ala
    450                 455                 460

Lys Pro Lys Ser Thr Ala Gly Glu Arg Gly Gly Ala Ala Ala Leu Leu
465                 470                 475                 480

Ala Cys Arg Thr Ala Ala Ala Ala Pro Leu Arg Gly Ser Gly Cys Ala
                485                 490                 495

Thr Ala Gly Ala Thr Gly Ala Cys Arg Leu Ala Ala Ala Ala Ala Ala
            500                 505                 510

Ala Glu Gly Ser Gln Gly Ser Arg Ala Ala Ser Ala Ser Ala Gly Pro
        515                 520                 525

Asp Gly Gly Ala Arg Glu Ser Thr Ala Thr Pro Ser Gly Asp Thr Phe
    530                 535                 540

Ala Glu Ser Pro Ser Ala Tyr Thr Ala Thr Ala Thr Thr Thr Ser Thr
545                 550                 555                 560

Ala Thr Thr Ser Thr Thr Thr Gly Ser Gly Ile Glu Met Gln Asp Asp
                565                 570                 575

Glu Gln Gln Gln Arg Gln Gln Pro Lys Gln Arg Pro Pro Ala Ser Gln
            580                 585                 590

Pro Glu Leu Glu Gly His His His Gln Gln Gln Tyr His His Tyr Tyr
        595                 600                 605

Arg Arg Thr Ser Leu Glu Gly Gly Cys Ala Asn Ala Pro Pro Leu Pro
    610                 615                 620

Val Pro Ser Ser Ala Arg Gly Ala Ser Pro Ala Gly Thr Gly Pro Thr
625                 630                 635                 640

Glu Ser Gly Ser Gly Arg Asp Ser Gly Cys Ala Arg Ile Thr Asn Gly
                645                 650                 655

Thr Ala Ala Gly Ala Thr Ala Ala Met Pro Pro Ser His Val Ser Ser
            660                 665                 670

Ala Ser Pro Pro Arg Cys Thr Ala Thr Ser Ala Ala Ala Thr Arg Gly
        675                 680                 685

Ser Ser Gly Ala Ala Thr Ala Ala Ala Gly Ala Met Thr Thr Ala Leu
    690                 695                 700

Ala Thr Ala Gly Ser Tyr Pro Arg Gly Val Asp Ala Ser Pro Pro Pro
705                 710                 715                 720

Asn Arg Ser Met Gly Ser Ser Gly Gly Asp Gly Gly Gly Thr Ala Ala
                725                 730                 735
```

```
Ala Ala Ala Gly Thr Ala Arg Gly Ser Ser Pro Ala Ala Ala Thr Pro
            740                 745                 750

Pro Leu Pro Pro Ser Thr Gln Gln His Gly Leu Pro His Pro Ala Ala
        755                 760                 765

Ala Pro Pro Pro Gly Ala Ala Ser Pro Gly Gly Ala Val Thr Leu Pro
    770                 775                 780

Pro Ala Leu Gln Glu Leu Ala Ala Leu Gly Ala Ala Arg His Ala Gly
785                 790                 795                 800

Leu Trp Thr Gln Arg Ala Leu Leu His Gln Gln Gln Leu Leu Leu Gln
                805                 810                 815

Gln Gln Lys Gln Gln Lys Gln Gln Gln His Gln Gln Asp Gln Val Val
            820                 825                 830

Gly Ala Glu Lys Ile His Gly Gly Ser Thr Ser Ala Val Ala Asn Ala
        835                 840                 845

Ala Glu Gln Gln Gln Gln Gln Pro Leu Gly Ala Ala Ala Ala Arg Arg
    850                 855                 860

Pro Ser Lys Ala Gly Val Asp Gly Thr Glu Ala Gly Ser Gly Ala Val
865                 870                 875                 880

Gly Gly Cys Ala Ser Ala Thr Ala Ala Val Met Ala Met Glu Ala Ser
                885                 890                 895

Glu Pro His Gly Ala Val Gly Ser Ser Phe Thr Ala Ala Asp Arg Gln
            900                 905                 910

Glu Thr Pro Leu Gln Pro Leu His Ala Glu Ser Ala Ala Ala Gly Gly
        915                 920                 925

Asp Met Asp Gly Asn Arg Ser Thr Pro Ala Thr Met Pro Ser Gly Pro
    930                 935                 940

Thr Ala Ala Ala Ser Gly Pro Ser Gln Thr Ser Asn Ser Leu Thr Val
945                 950                 955                 960

Leu Arg His Ser Asp Arg Ser Ala Phe Thr Ala Phe Thr Val Phe Leu
                965                 970                 975

Pro Ser Arg Val Ala Gly Ala Ala Ala Ala Ala Ala Ala Ala Ala Ala
            980                 985                 990

Ala Arg Pro Pro Pro Pro Pro Ala  Pro Val Gln Pro Pro  Ala Pro Ile
        995                 1000                1005

Phe Thr  His Pro Ala Ala Ala  Ala Ala Ala Ala Ala  Ala Ala Ala
    1010                 1015                 1020

Ala Gly  Ser Gly Gly Ala Ala  Ser Val Trp Tyr Pro  His Leu His
    1025                 1030                 1035

His His  His His Tyr Leu Gln  Gln Gln Gln Thr His  Met Gly Pro
    1040                 1045                 1050

Leu Pro  Pro Leu Pro Gly Ala  Val His Val Leu Pro  Ser Ile Met
    1055                 1060                 1065

Gln Leu  His Met Gly Val Leu  Ala Pro Gly Pro Pro  Pro Gln Gln
    1070                 1075                 1080

Gln Gln  Gln Gln His Leu Gln  Ala Lys Ala Pro Gln  Lys Pro His
    1085                 1090                 1095

Asp Ser  Ala Ala Ala Ala Gly  Gly Ala Asn Gly Ser  Leu Gly Pro
    1100                 1105                 1110

Ala Thr  Ser Ala Ala Ala Ala  Thr His Met Ser Tyr  Thr Gly Met
    1115                 1120                 1125

Gln Gln  Arg Pro Gly Ala Ser  Ser Ala Thr Thr Thr  Ser Ala Gly
    1130                 1135                 1140

Ala Val  Ala Phe Gly Gln Ser  Pro Pro His Gly Leu  Ala Ala Ala
```

```
    1145                1150                1155

Ala Ala  Ala Ala Ser Thr Pro  Pro Pro Pro Pro Pro  Pro Pro Val
    1160                1165                1170

Cys Ile  Pro Glu Ser Val Leu  Gln Leu Ile Ala His  Leu Ser Gly
    1175                1180                1185

Arg Ala  Ala Ala Glu Leu Pro  Val Pro Glu Thr Val  Thr Thr Ala
    1190                1195                1200

Pro Leu  Val Val Gln Lys Ala  Pro Ser Ala Ala Arg  Leu Ala Ala
    1205                1210                1215

Val Ala  Lys Tyr Leu Glu Lys  Arg Lys His Arg Asn  Phe Gln Lys
    1220                1225                1230

Lys Val  Arg Tyr Glu Ser Arg  Lys Arg Leu Ala Glu  Ala Arg Pro
    1235                1240                1245

Arg Val  Arg Gly Gln Phe Val  Lys Ala Ser Thr Ser  Ala Val Ala
    1250                1255                1260

Ala Thr  Thr Pro Ala Ala Thr  Gly Ala Thr Val Thr  Ser Thr Ser
    1265                1270                1275

Leu Arg  Gln Pro Val Tyr Thr  Ala Ala Gly Pro Ala  Gly Leu Ala
    1280                1285                1290

Leu Pro  Pro Ala Ala Ala Ala  Ala Ala Ala Ser Ala  Ala Ala Ala
    1295                1300                1305

Arg Gly  Val Pro Pro Pro Ser  Ser Arg Ile Gly Ala  Val Glu Leu
    1310                1315                1320

Ala Glu  Leu Val Pro Asp His  Asp Ala Asp Ile Glu  Asp Glu Gly
    1325                1330                1335

Cys Asp  Glu Pro Ala Ala Ala  Glu Asp Ser Asp Gly  Ser Val Ala
    1340                1345                1350

Val Glu  Leu Ala Glu Val
    1355


<210> SEQ ID NO 54
<211> LENGTH: 1102
<212> TYPE: PRT
<213> ORGANISM: Chlamydomonas reinhardtii

<400> SEQUENCE: 54

Met Glu Ala Asn Gly Phe His Val Val Leu Val Glu Asp Asp Asn Ile
1               5                   10                  15

Cys Leu Lys Val Val Glu Gln Leu Leu Arg Lys Leu Ser Tyr Arg Val
            20                  25                  30

Ser Thr Ala Ser Asp Gly Ala Ala Ala Leu Lys Val Leu Ala Asp Cys
        35                  40                  45

Lys Gln Arg Gly Asp Lys Val Asp Leu Ile Leu Thr Asp Ile Leu Met
    50                  55                  60

Pro Glu Val Thr Gly Phe Asp Leu Ile Asn Glu Val Val His Gly Glu
65                  70                  75                  80

Thr Phe Ala Asp Ile Pro Val Val Val Met Ser Ser Gln Asp Ser Gln
                85                  90                  95

Glu Ser Val Leu Gln Ala Phe Gln Ala Gly Ala Ala Asp Tyr Leu Ile
            100                 105                 110

Lys Pro Ile Arg Lys Asn Glu Leu Ala Thr Leu Trp Gln His Val Trp
        115                 120                 125

Arg Ala Asn Arg Ala Lys Gly Gly Gln Thr Ser Ser Gly Ala Ala His
    130                 135                 140
```

```
Val Gly Ala Gly Gly Arg Gly Gly Thr Ser Ser Arg Asp Gly Gly Gly
145                 150                 155                 160

Val Ala Gly Thr Arg Cys Gly Pro Gly Asp Arg Gly Gly Ser Gly Gly
                165                 170                 175

Asp Ala Glu Gly Ser Gly Leu Gly Gly Gly Ala Gly Ala Val Lys Asp
            180                 185                 190

Ser Ser Gly Gly Ser Thr Gly Ala Ala Thr Ser Val Leu His Ser Thr
        195                 200                 205

Gly Gly Thr Thr Leu Pro Ser Arg Ala Ala Thr Gly Arg His Ala Ser
    210                 215                 220

Thr Ser Ala Gly His Gly Val Thr Ser Ala Asp Pro Ser Asn Asn Gln
225                 230                 235                 240

Thr Ser His Ala His Ala His Ala His Ala His Ala His Gly Asn Ala
                245                 250                 255

His Ala His Ala His Leu His Met His Gly Ala Thr Asp Arg Ala Ala
            260                 265                 270

Gln Gly Ser Ser Ala Asn Gly Pro Ala Asn His Gly Ala Ala Gly Thr
        275                 280                 285

Gly Leu Gln Ser Ala Gly Met Ala Gly Ser Thr Ala Ala Gly Ala Ala
    290                 295                 300

Ala Pro Ala Gly Glu Ser Leu Ala Lys Pro Pro Phe Ala Ser Leu Ala
305                 310                 315                 320

Val His Phe Asp Leu His Ser Val Leu Ala Gly Ala Gly Ala Ala Ala
                325                 330                 335

Ala Asn Gly Gly Ala Asn Ala Ala Ala His Thr Ala Gly Ala Thr Gly
            340                 345                 350

Arg Glu Ser Gly Gln Ala Ala Gly Ala Ala Thr Gly Gly Ile Ala Ala
        355                 360                 365

Ala Gly Thr Val Ile Gly Trp Ser His Ala Asp Met Asp Val Asp Gly
    370                 375                 380

Gly Glu Ala Gly Ala Gln Asp Glu Asp Asp Glu Asp Glu Asp Asp Gly
385                 390                 395                 400

Val Glu Ala Pro Ala Gly Thr Gln Asn Arg Lys Arg Ala Ala Asp Asp
                405                 410                 415

Ser Gly Cys Asp Gly Ala Ala Ala Asn Asn Asn Gly Asn Thr Ala Ala
            420                 425                 430

Lys Ala Gly Ala Ala Ala Ile Ala Ala Gly Gly Pro Gly Ser Ser Gly
        435                 440                 445

Arg Ala Lys Ala Thr Asp Gly Ala Arg Ala Glu Ile Arg His Asn Gly
    450                 455                 460

Gly Pro Met Ala Ala Arg Met Ala Ala Ala Glu Gly Ser Gln Gly Ser
465                 470                 475                 480

Arg Ala Ala Ser Gly Ser Ala Ala Thr Gly Pro Gly Gly Ala Arg Glu
                485                 490                 495

Gly Thr Ala Thr Pro Ser Gly Asp Thr Phe Ala Glu Ser Pro Ser Thr
            500                 505                 510

Phe Thr Ser Ile Ile Asn Thr Thr Gly Ser Gly Ser Glu Ala Asp Glu
        515                 520                 525

Gln Pro Val Pro Leu Lys His Gln Glu Gln Gln Gln Gln Gln Gln Gln
    530                 535                 540

Gln Arg Val Gly Glu Gly Asp Arg Ala Lys Pro Glu Pro His Pro Gln
545                 550                 555                 560

Asn Pro Ala Gln Ala Ala His Leu Pro His Pro Ser Ala Ala Pro Cys
```

-continued

```
                565                 570                 575

Ser Gly Gly Gly Gly Ile Ala Gln Ala Ala Leu Pro Leu Gly Leu Gln
            580                 585                 590

Glu Leu Ala Ala Leu Gly Ala Ala Arg His Lys Glu Leu Trp Thr Gln
        595                 600                 605

Arg His Leu Met His Gln Arg Gln Ala Ala Ala Ala Ala Thr Ala Ala
    610                 615                 620

Ala Ala Ser Ala Ala Ala Ala Ala Ala Met Pro Thr Ala Gly Ala Ser
625                 630                 635                 640

Ala Ala Ala Pro Ala Gly Pro Pro Ser Ala Arg Pro Ser Ala Ser Leu
                645                 650                 655

Ala Asp Thr Gly Gly Asp Gly Pro Ala Ala Ala Thr Ala Pro Glu Thr
            660                 665                 670

Arg Ala Asp Gly Pro Ser Gly Pro Ala Thr Thr Gln Gly Pro Lys Arg
        675                 680                 685

Asp Ala Val Ala Gly Ala Ala Ala Val Gly Ser Ser Ala Arg Ser Asp
    690                 695                 700

Ser Pro Leu Pro Ala Ala Ala Ala Ala Thr Ala Gly Ala Asn Gly Ala
705                 710                 715                 720

Ser Gly Ala Ala Ser Asp Val Leu Ala Gly Ala Gly Ser Leu Ala Leu
                725                 730                 735

Leu Arg His Ser Asp Arg Ser Ala Phe Thr Ala Phe Thr Val Phe Leu
            740                 745                 750

Pro Gly Arg Val Ala Ala Ala Ala Ala Ala Ala Ala Ala Ala Ala Ala
        755                 760                 765

Ala Ala Thr Ser Ala Gly Ala Ser Thr Gly Thr Ala Asn Gly Ala Pro
    770                 775                 780

Pro Ala Pro Gly Thr Ala Leu Ala Ala Ala Ala Ala Ala Ala Ala Ala
785                 790                 795                 800

Ala Ala Ser Ala Val Pro Leu Pro His Pro His Thr Ala Pro Pro Ala
                805                 810                 815

Leu Phe Gly Val Pro Pro Pro Ser Ser Val Pro Pro Ser Ser Leu Ser
            820                 825                 830

Val Leu Pro Pro Val Met Pro Leu His Pro Ala Ala Ala Ala Ala Ala
        835                 840                 845

Ala Thr Ala Gly Gly Gly Lys Pro Ser Asp Ala Ala Thr Tyr Ala Ala
    850                 855                 860

Ala Ala Ala Ala Gly Leu Val Pro Tyr Pro Gly Phe Ala Pro Ala Arg
865                 870                 875                 880

Pro Gly Pro Phe Pro Pro Pro Pro Gly Ser Gly Gly Pro Gly Ala Pro
                885                 890                 895

Pro Val Tyr Ile Pro Glu Ser Val Leu Gln Leu Ile Ala His Leu Ser
            900                 905                 910

Gly Arg Ala Ala Ala Glu Ile Pro Ala Val Pro Ala Glu Ser Val Thr
        915                 920                 925

Ala Ala Pro Val Val Val Gln Lys Ser Gly Gly Pro Ala Ser Ala Ala
    930                 935                 940

Arg Leu Ala Ala Val Ala Lys Tyr Leu Glu Lys Arg Lys His Arg Asn
945                 950                 955                 960

Phe Gln Lys Lys Val Arg Tyr Glu Ser Arg Lys Arg Leu Ala Glu Ala
                965                 970                 975

Arg Pro Arg Val Arg Gly Gln Phe Val Lys Ala Gly Thr Ala Gly Ala
            980                 985                 990
```

```
Ala Ala Ala Ala Ala Ala Ala Ala  Ala Ala Ala Ala Ala  Gly Thr Ala
        995                 1000                1005

Ala Thr  Ala Ala Gly Thr Gly  Thr Ala Arg Gly Ala  Ala Thr Ala
    1010                 1015                1020

Ser Gly  Ala Ala Gly Lys Pro  Glu Leu Gln Gly Pro  Asp Thr Ala
    1025                 1030                1035

Glu Glu  Ala Ala Ala Ala Thr  Leu Leu Ser Ala Ala  Ala Ala Met
    1040                 1045                1050

Ala Ala  Ala Ala Ala Gly Thr  Ser Gly Pro Ser Gly  Ser Gly Ser
    1055                 1060                1065

Gly Ala  Met Asp Val Asp Gly  Ala Asp Pro Glu Ala  Asp Ala Asp
    1070                 1075                1080

Val Met  Asp Glu Asp Asp Gly  Glu Asp Asp Gly Ser  Asp Glu Ser
    1085                 1090                1095

Ala Gly  Glu Pro
    1100


<210> SEQ ID NO 55
<211> LENGTH: 936
<212> TYPE: PRT
<213> ORGANISM: Chromochloris zofingiensis

<400> SEQUENCE: 55

Met Ser Ala Asp Ala Gly Gly Gln Lys Pro Gly Val Ala Glu Pro Gly
1               5                   10                  15

Ala Arg Thr Gly Pro Gly Phe Ser Val Asn Ser Ser Phe His Val Leu
            20                  25                  30

Leu Val Asp Asp Asp Ala Val Thr Leu Lys Tyr Val Glu Gln Leu Leu
        35                  40                  45

Arg Lys Cys Ser Tyr Glu Val Thr Thr Ala Thr Asn Gly Arg Glu Ala
    50                  55                  60

Ile Glu Val Leu Glu Gly Arg Arg Gly Gln Val His Ile Asp Leu Ile
65                  70                  75                  80

Leu Thr Asp Ile Ser Met Pro Glu Val Asn Gly Val Gln Leu Ile Glu
                85                  90                  95

Glu Val Val Asn Gly Gly Lys Trp Lys Asn Leu Pro Val Ile Val Met
            100                 105                 110

Ser Ser His Glu Ala Gln Ala Asn Val Leu Glu Ala Phe Gln Ala Gly
        115                 120                 125

Ala Ser Asp Tyr Leu Ile Lys Pro Leu Arg Arg Asn Glu Leu Ser Thr
    130                 135                 140

Leu Trp Gln His Val Trp Lys Ala Ser Lys Leu His Gln Pro His Leu
145                 150                 155                 160

His Gly Glu Asp Asp Glu Asp Glu Asp Asp Thr Ala Leu Asp Asn Gly
                165                 170                 175

Lys Phe Asp Ser Ser Ala Gly Asn Asn Lys Gly Ser Ser Gly Ala Ser
            180                 185                 190

Thr Ser Ala Ala Gly Asp Ala Thr Ala Leu Ser Met Ala Asp Ala Ser
        195                 200                 205

Arg Ala Leu Tyr Glu His His Pro Ser His His His Asn His Ile Gly
    210                 215                 220

Glu Pro Ser Ile Asp Thr Gln Ala Ser Gly Gln Val Gly Ser Asn Asp
225                 230                 235                 240

Pro Ser Leu Val Ile His Pro Leu Asp Ile Ser Pro Leu Pro Ala Ala
```

```
                245                 250                 255

Ala Pro Pro Leu Ala Val Ala Gly Asp Pro Ala Leu Ala Ala Ala Pro
            260                 265                 270

Leu Gly Thr Gly Gly Gln Asp Thr Pro Gly Ser Gly Asp Glu Gln Ala
        275                 280                 285

Thr Ala Gly Thr Ser Val Gln Gln His Gln His Ser Gln Ala His His
    290                 295                 300

His Ser Arg His Ile Pro Ala Ser Gly Ser Gly Thr Thr Glu His Ala
305                 310                 315                 320

Pro Gln Ser Leu Ser Gln His Pro His His His Asn His Gln His His
                325                 330                 335

His Asn Ser His His His His His Gln His Asp Leu Ala Gln Gln Arg
            340                 345                 350

Gln Gln His His His His His Ser Asn Gly Val Asn Gln Asp His Ser
        355                 360                 365

Gln Pro Asn Pro Asp Leu Thr Gln Met Pro Ser Ala Asp Gln Gln Ser
    370                 375                 380

Leu Leu Thr Leu Pro His Ser Pro Asn Gly Ala Met Pro Leu Phe Lys
385                 390                 395                 400

Pro Ser Thr Ser Ser Ala Ala Met Asp Cys Ser Thr Gln Gln Pro Leu
                405                 410                 415

Gln Gln Gln Gln Gln His Glu His Gly Ser Ser Ser Pro Ala Leu Ser
            420                 425                 430

Arg Pro His Ala Glu Lys Ser Pro Phe Gly Val Arg Tyr Gly Gly Gly
        435                 440                 445

Asn Gly Gly Tyr Ser Ser Ser Met Ser Gly Ala Ser Leu Pro Pro Gly
    450                 455                 460

Leu Gln Glu Leu Ala Val Leu Gly Gln Gln Arg Gln Ala Ala Arg Glu
465                 470                 475                 480

Lys Asp Leu Gln Gln Arg Gln Gln Gln Gln Gln Lys Gln Gln Gln Gln
                485                 490                 495

Gln Gln Gln Thr Ser Ala Leu Arg His Ser Asp Ser Ser Ala Phe Thr
            500                 505                 510

Ala Phe Thr Val Phe Leu Pro Lys Gly Ser Asn Gly Leu Asn Arg Ser
        515                 520                 525

Ser Gly Val Gly Val His Gly Ser Asn Ser Gln Thr Ser Gly Gly Gly
    530                 535                 540

Ala Ala Asp Leu Gly Arg Ser Ala Ser Ser Met Glu Ile Leu Ser Thr
545                 550                 555                 560

Ala Glu Thr Leu Val Gly Gln Thr Ala Gly Gly Ala Gly Val Asn Gly
                565                 570                 575

Val Gly Ser Ala Lys Pro Gly Gly Asp Cys Leu Lys Glu Glu Ser Pro
            580                 585                 590

Asn Asp Ser Thr Pro Ser Ala Glu Glu Gly Asp Glu Gln Asp Val Lys
        595                 600                 605

Pro Pro Gln Ser Thr Ser Gly Ala Ala Ala Ala Glu Pro Ala Val Ala
    610                 615                 620

Thr Ala Ser Gly Arg Ala Ala Thr Ala Ala Ile Ala Val Val Ala Asp
625                 630                 635                 640

Ala Thr Val Ala Lys Pro Asp Ala Pro Val Ala Thr Ser Asp Gln Lys
                645                 650                 655

Gln Val Leu Pro Phe Pro Gly Val Asn Gly Ala Ala His Leu Thr Gly
            660                 665                 670
```

Met Asn Asn Gly Val Ser His Ser Gly Thr Ala Gly Ser Tyr Ser Glu
675 680 685

Leu Thr Gln Met Leu Tyr Ala Gln Leu Pro His Gln Gly Gln Pro Leu
690 695 700

Pro Asp His Val Met His Phe Leu His Asn Phe Tyr Arg Thr Met Met
705 710 715 720

Glu His Gln His Gln Gln Gln Ser Gln Gln Met Asp Gln Leu His His
725 730 735

His Val Gln Gln Gln Gln Gln Gln Gln Val Gln Gln Gln Gln Arg His
740 745 750

Leu Gln Gln Phe Ala Thr Ala Pro Asn Gly Gln Ala Pro Pro Asn His
755 760 765

Ser Asn Thr Asn Gln His Leu Gln Gln Gln Gln Gln Ala Cys Gly Asn
770 775 780

Gln Pro Leu Gln His Thr Ser Gln Pro His Cys Asn Gly Ala Ala His
785 790 795 800

Leu Gln His Leu Gln Gln Ser His Ser Ala Pro Ser Leu His Thr Pro
805 810 815

Gly Phe Thr Cys Thr Thr Thr Ala Thr Gln Ser Asn Thr Glu Pro Ser
820 825 830

Cys Met Leu Thr Gln Ser Glu Gly Ala Pro Cys Ala Ser Ser Tyr Arg
835 840 845

Ala Ala Ala Val Ala Lys Tyr Arg Glu Lys Arg Lys Asn Arg Asn Tyr
850 855 860

Asp Lys Lys Val Arg Tyr Glu Ser Arg Lys Arg Leu Ala Glu Ser Arg
865 870 875 880

Pro Arg Val Lys Gly Gln Phe Val Lys Gln Glu Val Leu Ala Ala Ala
885 890 895

Gly Leu Thr Ala Leu Ala Glu Leu Ala Thr Ala Asn Lys Arg Ala Arg
900 905 910

Leu Asp Val Asp Tyr Val Thr Ala Thr Gly Met Thr Asp Ala Asp His
915 920 925

Met Asp Thr Ala Glu Glu Ser Ser
930 935

<210> SEQ ID NO 56
<211> LENGTH: 444
<212> TYPE: PRT
<213> ORGANISM: Coccomyxa subellipsoidea

<400> SEQUENCE: 56

Met Ala Ala Gly Leu Lys Arg Ile Pro Ser Phe Ser Gly Arg Pro Gly
1 5 10 15

Phe Pro Asn Gly Leu Gln Val Leu Val Val Asp Gly Asp Thr Ser Ser
20 25 30

Ser Gln Cys Leu Arg Gln Lys Leu Glu Glu Leu Ala Tyr Glu Val Ser
35 40 45

Cys Cys Ser Ser Gly Ser Asp Ala Ser Ala Leu Leu Arg Lys Glu Asp
50 55 60

Ser Ser Tyr Asp Ile Leu Leu Val Glu Ala Lys Ala Leu Ala Lys Asp
65 70 75 80

Ala Thr Asp Gly Gly Ser Leu Arg Asp Ser Ala Ala His Leu Pro Leu
85 90 95

Val Leu Met Ser Glu Lys Ser Ser Ser Thr Asp Ala Val Trp Arg Gly

```
            100                 105                 110

Ile Glu Leu Gly Ala Ala Asp Val Leu Glu Lys Pro Leu Ser Ser Leu
        115                 120                 125

Lys Leu Arg Asn Ile Trp Gln His Val Val Arg Lys Met Met Ser Ser
    130                 135                 140

Ser Gln Asp Ser Ser Arg Glu Ala Val Pro Cys Lys Met Glu Pro Lys
145                 150                 155                 160

Ser Lys Gly Lys Gly Val Ser Ala Pro Ser Ser Pro Arg Thr Pro Ser
                165                 170                 175

Pro Ala Ala Ser Leu Leu Thr Ile Ser Ser Gly Thr Met Thr Glu Lys
            180                 185                 190

Ser Cys Lys Gly Gly Gly Asp Glu Ala Ser Phe Ser Gly Val Gly Asp
        195                 200                 205

Val Lys Met Ser Cys Ser Ala Glu Ala Pro Glu Pro Cys Asp Ser Arg
    210                 215                 220

Ala Thr Ala Glu Ser Pro Ala Ser Thr Gln Thr Lys Val Thr Phe Pro
225                 230                 235                 240

Gly Cys Leu Asn Ser Gly Gly Thr Ala Leu Ala Ala Ser Lys Asn Cys
                245                 250                 255

Ser Arg Lys Arg Lys Ala Lys Ala Pro Asp Thr Pro Ala Ser Val Ala
            260                 265                 270

Ser Arg Pro Pro Leu Ala Ile Arg Pro Pro Ala Trp Ala Ser Pro Phe
        275                 280                 285

Gly Pro Pro His Gln Gly Asn Thr His Val Val Gly Met Ala Pro Pro
    290                 295                 300

Gln Cys Tyr Met Gln Gly Val Asp Pro Thr Asn Gly Cys Val Trp Gly
305                 310                 315                 320

Thr Pro Ala Gly Gly Val Ser Gln Ala Pro Ala Tyr Met Pro Gly Trp
                325                 330                 335

Gly Phe Ser Pro Gln Pro Met Leu Ser Gly Ser Phe Leu Gln His Pro
            340                 345                 350

Ser Thr Ser Asp Leu His Lys Cys Pro Ser Val Gly Ala Ser Ser Leu
        355                 360                 365

Ala Ser Ser Leu Asp Ser Ser Leu Thr Leu Cys Gly Phe Gly Ala Asp
    370                 375                 380

Leu Pro Asp Asp Asp Leu Leu Leu Glu Asp Val Leu Leu Pro Asp Glu
385                 390                 395                 400

Asp Leu Leu Asp Leu Ala Pro Asp Glu Pro Ala Thr Met Lys Ala Pro
                405                 410                 415

Glu Gln Pro Pro Ile Gly Leu Lys Leu Lys Lys Ser Ala Ser Leu Ile
            420                 425                 430

Asp Leu Ile Asn Ala Gln Leu Ser Ala Ala Thr Ala
        435                 440


<210> SEQ ID NO 57
<211> LENGTH: 1284
<212> TYPE: DNA
<213> ORGANISM: Oocystis sp.

<400> SEQUENCE: 57

atggcgctga agcgcgttcc tagcttttcc ggtcggccga actttcccgc cggtctgcag      60

atcctggtgg tggacagcga ttcttcctca agggaggctg tagagatgca actcaaatcg     120

cactcctatc tagcaacctg ttgttgcacc tgcggcgagg ctgtggagca gctcggcacg     180
```

```
tcaaagtatg acatcgtgct ggcagagtcc aagctggttg ctgcggagtg cgttgactcg    240
acacggttgt gcgaggccgc aagggctctg cctctggttt tgatgtgcga ggactcgacg    300
gcggacgacg tgttgaaggg aatcaggctc ggcgcttgcg actttctgga gaagccgctg    360
tccccactga agctcaagaa catatggcag cacgttgttc gcaagatgat ggagcagatg    420
cacgtccgcc gcacggacga cgcggatacg tgcactacta agagcagccg cgaccaaagc    480
tgcgcgatca agggcaagtc ggtggcttcc acgccctcgt gtcccaagac accttctccc    540
gcggcttctg gcgcagacat cggctgcagc atagccacgt cggtcagcaa ggccggggac    600
gtggtcggcg agtccagcag ttccgagacg cgcaaggagc attgcagcga gaccacggag    660
tgctccgacc tcaagagctg cgccgcaaag tcagctgtgt cggcgcaaac gccggtatcc    720
accgcgaccg ttgcagctac ctggggtgcg tcgaagaaga agtcgacagc atcagccact    780
accagcagtg tcagcaaccg gccgccgctg gcgatcaaga tgccggcgcc agctgtggca    840
tacacgtcag ggcttgcgcc ctttccgccg ccgatgtttg tacctggcgg ctggggccag    900
tcaagcaacc catgcgtggt gggcacgcca atgatgccac cgccgcccgg catgggcatg    960
ccgccccacc accacgcgcc ctatggccag gtgccgccgc cgggctatcc agtcgcatgc   1020
atgcccagcg cctttgtgcc gacgccgatg ggccctggcg gcgtggcgtt tgcgccgcca   1080
cctggcgcca gctgcacatc tgctgcgtac tacccccatc ctgctgtgga tgcaagcgcg   1140
tctgcaactg ccaccttcac gggccatgtg cagatcgacc tgactaacgt gtctgctgaa   1200
gagccggcgc ccattggttt ggcgctgcgc aagaccgcgt cgctgctcga cctggtcagc   1260
gatcgcctgg gccagcgtgc gtgc                                          1284
```

<210> SEQ ID NO 58
<211> LENGTH: 1026
<212> TYPE: DNA
<213> ORGANISM: Tetraselmis sp.

<400> SEQUENCE: 58

```
atgctgtgcc ctgctgtcca ggttgccacc atggccactg tcctggcttc cacgcatttt     60
tcggagcgcc ccagcttccc ggctgatctg gaggtgctgc ttctggattc agcaacgcag    120
ggcgcagaaa ctgcctcgaa gctgttgctg tcgtgttcct atcgtgtcac cgtgtgccga    180
tccgtgtctg aggctctgag ccacatggca tgcaaggctt tcgacgtggt cctggtggag    240
cagaaacttt tcagcggcag ggatgcggcc gctgcgcagc tcaaggccct ggcaggcgtc    300
atccccaccg tggtcctgag tgacagcggc agtgcgaagg atacctgggc tgccatcgtt    360
gggcaggcag ccgatgtcct catccgcccg ctgaccaagc agaagctgca gacgctgtgg    420
cagcacactg tccgtatgca gcgcgcagca tcttcggctt cggcggctac tagcatggtt    480
gccaagcctg ttgccgtgct ctcctcggct ctgaagcccg ctgcttccag tgcttcactg    540
gacaaggggc agaagcgcaa gttgaaggat catatgatgg ggcccatcat ggcacacccg    600
caagtgtcca accctggctt tatctggggc gcaccagtga tgggcgttcc ggctggacag    660
caggctcccc agaagtcaga ggccccggtc accccccaga agccaggctc agagatgcac    720
cccgagctgg atgccacaag ccacatcgcc atgggctcca gcgacaactt caacgtacct    780
gtgtatgaaa gcggcactga cagccaggag tcgcagccaa cctgcgaccc cacctctctt    840
gatgacatca atgaggatga ctacgcgttt atcgatttcg cgctcagcga ttcttttccc    900
actgtggagg aggatgagat ccttccaccc attggccttt cgctgaagaa gtccagctcc    960
ctcctgaaca tgctgaacgg tgtgcttctc tcggctcact ctgtaccgct gcagctgccc   1020
```

cagtag 1026

<210> SEQ ID NO 59
<211> LENGTH: 2076
<212> TYPE: DNA
<213> ORGANISM: Glycine max

<400> SEQUENCE: 59
atgggagagg tggtcatcat gagtggagag aagaagtcag ttagagtgga gggggtggag 60
aaggaagata gtggtggaag tgggagcaag gctggtgaat ttaaggggtt gatgaggtgg 120
gagaagttct tgcccaagat ggttttgagg gtgctgttgg ttgaagcaga tgattccaca 180
agacaaatta ttgccgcgct tctcagaaaa tgcagctaca aagtggttgc tgttcctgat 240
ggcttgaagg catgggaatt actcaaggga agaccgcaca atgttgatct aattctgaca 300
gaagtggatt tgccatccat atctggctat gcacttctca cattaattat ggagcacgag 360
atttgcaaaa acatccctgt tataatgatg tcttcccaag attcaattag cacagtatac 420
aaatgcatgt tgagaggtgc tgctgattat cttgttaagc ctattagaaa aaatgaactg 480
aggaacttgt ggcaacatgt ttggagaaga caatcatcaa ccactggtat taatggcctc 540
caagatgaga gtgttgcaca acagaaggtt gaagccactg cagaaaataa tgctgctagt 600
aatcgttcaa gtggtgatgc tgcttgcatt cagagaaata tagaactaat tgagaaggga 660
agtgatgcac agagctcttg taccaagcct gactgtgaag ctgagagtga ccctgtcggt 720
aacatgcagg aattttctct gctgaaatgt ggggaagcat atccaagtgg aacagagaca 780
caacaggttg aaacaagctt tcgcttaggc cagacattaa tgatgcatga ctgtcatgct 840
ggaggattaa atgtgagtat ccgcaaaaat ggtgaggcaa gcacgactaa tgacaaggat 900
actgatacag agcattttgg gaatgctagc atcagtggtg aggctcatga caatccctat 960
gttcaaatta actcttccaa ggaagctatg gacttgattg gagcatttca tactcatcca 1020
aactgttccc tgaaaaattc cacagttaat tgcacaggca actttgacca ttctcctcaa 1080
ttggatcttt ctttgagaag atcttgtccc ggaagctttg agaataaact cactgaagaa 1140
aggcacaccc tgatgcattc taatgcttca gctttcaagc ggtatactac caggcaattg 1200
caaatatcaa tgcctgcagt gttaattaac ttctctgatc aacaaagaga acagataaca 1260
aattgtgaga aaaacatctc acacatcgct actggcagca actcagatag ttcaacacct 1320
atgcaaagat gtattgtgtc tccaactaca gtccaatcaa aagaatctga acttgcaacc 1380
tcacaccccc cgcaaggaca ttctctccca attccagtaa agggtgtaag gttcaatgat 1440
ctatgcacag cctatggttc tgtacttcct tcagtgtttc atacacagtc aggtccacca 1500
gcaatgccaa gtccaaattc agttgtgctc cttgaaccaa actttcaagt aaatgcattt 1560
tatcagtcaa atatgaaaga gagtagttca gagcagcttt atgaatctcg tggtccaaat 1620
ggaaacacca cccaaaacca cattgtgtac acacaggagc acaaatcaga acatgcagaa 1680
gatcgaggac atatctctcc tacaactgat caaagtgtgt caagtagttt ctgcaatgga 1740
aatgcaagcc atcttaacag cattggttat ggaagcaact gtggaagtag cagcaatgtt 1800
gatcaagtta acactgtttg ggcagcttca gagggaaagc atgaagacct cacaaataat 1860
gcaaactctc atcgatctat ccaaagagaa gcagctctaa acaaatttcg cttgaaaagg 1920
aaagagagat gctatgagaa gaaggttcga tacgagagca gaaaaaaact agcagagcag 1980
cgtcccagag ttaaaggaca atttgttcgt caagtgcatc ctgatcctct tgttgcagaa 2040
aaagatggca aagaatatga tcattcagat ttctga 2076

<210> SEQ ID NO 60
<211> LENGTH: 2244
<212> TYPE: DNA
<213> ORGANISM: Vitis vinifera

<400> SEQUENCE: 60
atgggtgagg ttgtggtgag cagtgaggca ggaggaggag gcatggaggg tgaggtggag 60
aagaaggagg tgggcagtgg ggttgtgagg tgggagaggt ttcttcccag aatggttctc 120
agggttttgt tggttgaagc ggacgattcc accaggcaaa ttatcgctgc gcttctcagg 180
aaatgcagtt acaaagttgc tgctgttcct gatggcttaa aggcatggga ggtactgaag 240
gctagacccc acaacattga cctcatattg acagaagtgg agttgccatc aatatctggc 300
tttgctctcc tcaccttggt tatggaacat gagatctgca aaaacattcc tgttataatg 360
atgtcctcac atggttcgat aaacacggtt tataaatgca tgttgagagg tgcagctgac 420
tttcttgtta agcctgttag aagaaatgag ctgaagaatt tgtggcaaca tgtctggaga 480
agacaatcgt caactgttag cggaaatggc ccccaagatg agagtgttgc acaacagaag 540
gtcgaagcca cttctgaaaa caaccccaca agtaatcact caagtgatca tgttgcttgt 600
attcagaaaa ataaggaagc actcaataaa gtgagtgatg ctcagagctc ttgttcaaag 660
ccagacttgg aagctgagag tgcctacatg gaaactatgc aggatttctc aaatccgaca 720
tggagcagat ctcttgtgag tgacacaaaa atgcagaaga atgaagaatg tgccaaattg 780
ggcccgaaat ttcttatgca caataaagaa gctgggggaa cactggaggc tgcctgcagg 840
gatgtgaaca caatgactca gcctgaagca gtggaaccag aaaatgatgg gcaaggtgct 900
aacgctccta gtgaggcttg tggtaacaat gccatattgg gcagctcatc tagagaagcc 960
atcgacttga ttggagtatt tgataattct aaaaaatgca cttatggaaa ttcttcttca 1020
aataatggca ccaaaaagag tgattctatt ccacagttgg acctttcctt gagaagatct 1080
catcctagta gccctgagaa tcaagttgct gatgaaaggc atacactgaa ccattctaat 1140
ggctcggcct tttcacgcta cataaacagg tcattgcagc caccacatct accatcaaca 1200
ggtgttttca atcagcagaa aaactttgga gctgattctg ataaacgttt atctcagctg 1260
gttactggtt ataactctga tattactagt cccacactga gtactcaaag aagtgtgatc 1320
tctctagcta ctagtccatc tggacgagtt gaaattgcac tttgtggccc tcaacagaga 1380
gcttttcctg ctccagttcc acaaaatgcc aacaattcca ccagccagac taatcacaag 1440
ccagagcaca aattggactc actggagggt caagggcact tctctcctgc cactgatcag 1500
aattcaagta gtagttttgg taatggtggt gcaagtaatc tgaatagctt tgggtgtgga 1560
agcatttgtg gaagtaatgg gaatgccaat acagttgctg ttgttcaggc cgctgcagag 1620
ggcaagaatg aagaaggtat cttcagtcat gaaggacact ctcaacgatc tatccaaaga 1680
gaagctgctc taaccaagtt tcgcttgaag cggaaagaca gatgctttga gaagaaggtt 1740
cgttatgaaa gcagaaagaa gcttgcagag cagcgacccc gagtaaaagg acagtttgtt 1800
cgacaagtgc ataccatccc cccacctgca gagcctgata catactatgg cagttcgttt 1860
gatgttcagc ctcaaagaag ccgatatcta tcagctcaac ctctcagggc ctcatcttct 1920
caactcctct atccaactca cactcctctc caagaatcca aatacgaagg tcatgaagaa 1980
agcaatctct tgacggcgtc cttggttgga actgccctac cggtggctcc atcttttggt 2040
tatgaagttg gacgtgatca gacggcagga aaacttgttc tgagtttaaa gctcgatggc 2100

```
cgggttcgat ggaaggtggg gacttgggtt tctggccgat accgacttaa cgttaattgt   2160

gttgctgtga tggcatttgg accctccatc ccatctggtc cactgagttc aaaagaagga   2220

actcagtgct ctactactgt ttga                                          2244
```

<210> SEQ ID NO 61
<211> LENGTH: 2400
<212> TYPE: DNA
<213> ORGANISM: Theobroma cacao

<400> SEQUENCE: 61

```
atggggatag ttcaaatgaa taataatggt cctgtggcca atgggttggt tgaattgaat     60

acacatattc atgatgagca caagaaaata aggggtgggg tcataggtga ggggcagggc    120

ctctcagtgg aagaagagtc atggattaat gaggatgtgg aagacaggaa tgatgggaag    180

acagagttgg ttcaggttca gggccatgcg catggtgagc aagagaggtc acagcaacag    240

cctcaaggtc ctttggttca ctgggagagg tttttacctc taaggtcttt gaaggttcta    300

ctggtggaaa atgatgactc aactcgccat gttgtctgtg cattgctgcg aaattgtgga    360

tttgaagtta ctgctgtgtc aaatggactg caagcttgga agatcttgga agatctaacc    420

aatcatattg atcttgtttt aactgaggta gtgatgcctt gtttgtcagg cattggcctt    480

ttatgcaaga taatgagcca caaaactcgc atgaatattc cagtgattat gatgtcatct    540

catgattcta tgagtacagt ctttaggtgt ttgtccaagg gtgcagttga ctttttagtg    600

aagcctatac gaaagaatga gcttaaaaat ctttggcagc atgtttggag gaaatgccac    660

agctctagca gtagtggagg ccaaagtggt acacagaccc aaaaatcctc aaaatcaaaa    720

ggtactgatt cagacaacaa tactggaagt aatgatgagg atgacaacgg cagtgttggt    780

ttgaatgttc aggatggaag tgacaatgga agtggcactc agagctcatg gacaaagaga    840

gcagtagaag tcgacagctc ccagccaata tcaccatggg accagttagc tgatcctcct    900

catagcactt gtgcccaggt tatccattct agacatgaag tgttaggtga cagctgggtt    960

ccagtaacag cgacgaggga gtatgatgag ctggataatg aactagaaaa tgttgttatg   1020

ggcaaagact tggagatagg ggtacctaaa attacagctt cgcagcttga agacccaagt   1080

gaaaaagtaa tgaccaacat agctggtgtt aataaagaca aattatctgc aataaaccct   1140

aagaaagatg atgagaaact agagaaagcg caattggaac ttaacagtga gaaatcaggt   1200

ggtgatttga gaaatcaagc tgctgacctg ataggtgtca tcaccaataa tactgaacct   1260

catatagaaa gcgcagtctt tgacatccca aatggcctcc ctaaggtctc tgatgcaaaa   1320

gagaaggtga actacgacac gaaggaaatg ccttttcttg agctcagttt aaagagactg   1380

agagatgtag gagacactgg aacaagtgcc catgaacgaa atgtattgag acattcagac   1440

ctttcagcct tctcaagata caattctggt tcaactgcca atcaggctcc aacaggaaat   1500

gttggtagtt gttctccact tgataatagc tcggaggcag ttaaaacaga ttctatgaag   1560

aattttcagt ctacctcaaa tagcatacct ccaaagcaac agtccaatgg aagtagtaac   1620

aataatgaca tgggttccac cactaataat gccttcagca aaccagcggt actcagtgac   1680

aagccagcac ctaaaacttc agctaaatct ttccatccct cttctgcctt ccaaccagtg   1740

cagagtggcc atggttctgc cctgcaacct gtagcacaag gtaaggctga tgctgcacta   1800

ggtaacatga ttttagttaa agcaaggggc acagaccaac aggggaaagt gcagcatcac   1860

catcatcatt atcaccacca ccaccaccac catgtccata acatgctccc aaatcaaaag   1920
```

-continued

```
ttaggtaacc atgatgattt atctttggaa aatatggcag cagcagctcc ccagtgtggg   1980

tcatccaatc tgtcaagttt accacatgtt gaaggcaatg ctgctaacca cagtttgact   2040

agaagtgcat caggaagtaa ccatggaagc aatggacaga acgggagcag cactgtgtta   2100

aataccagag gaatgaatct tgaaagtgaa aatggggtgc ctgggaaagg tggagctggc   2160

ggtggaattg gatctggagg caggaatgta gttgatcaaa accgttttgc tcaaagagaa   2220

gctgctttga acaaattccg ccagaaaagg aaagaaagat gctttgagaa gaaggttcga   2280

tatcagagca gaaagaaact ggctgagcag agaccacgca ttcgaggaca gtttgtgcga   2340

cagattagca ctactgggaa ggaagcattc agatttcgtg gtgcaggatt gtgcacttag   2400
```

<210> SEQ ID NO 62
<211> LENGTH: 2229
<212> TYPE: DNA
<213> ORGANISM: Oryza sativa

<400> SEQUENCE: 62

```
atgatgggaa ccgctcatca caaccaaacc gccggctctg ccctcggagt cggagtcgga     60

gatgccaacg acgccgtgcc tggggctggg ggtgggggct acagcgaccc ggatggcgga    120

ccaatctccg gtgtgcagcg gccaccgcag gtctgctggg agcgcttcat ccagaagaag    180

actatcaaag tcttgctagt tgatagcgat gactccacca ggcaggtggt cagtgccctg    240

cttcgtcact gcatgtatga agtcatccct gctgaaaatg gccagcaagc atggacatat    300

ctagaagata tgcaaaacag cattgatctt gttttgacag aggttgttat gcctggtgta    360

tctggaattt ctctattgag taggatcatg aaccacaata tttgcaagaa tattccagtg    420

attatgatgt cttcaaatga tgctatgggt acagttttta agtgtttgtc aaagggcgct    480

gttgacttct tagtcaagcc catacgtaag aatgaactta agaacctatg gcagcatgtg    540

tggagacggt gccacagctc cagtggcagt ggaagtgaaa gtggcattca gacacaaaag    600

tgtgccaaat caaaaagtgg ggatgaatcc aataataaca atggcagcaa tgacgatgat    660

gacgacgatg gtgtaatcat gggacttaat gcaagagatg gcagtgataa cggcagtggc    720

actcaagcgc agagctcatg gacaaagcgc gctgttgaga ttgacagtcc acaggctatg    780

tctccagatc aattagctga tccacctgat agcacttgtg cacaagtgat ccacctgaag    840

tcagatatat gcagcaatag atggttacca tgtacaagca acaaaaattc caagaaacaa    900

aaagaaacta atgatgactt caaggggaag gacttggaaa taggttctcc tagaaattta    960

aacacagctt atcaatcctc tccgaatgag agatccatca aaccaacaga tagacggaat   1020

gaatatccac tgcaaaacaa ttcaaaggag gcagcgatgg aaaatctgga ggagtcaagt   1080

gttcgagctg ctgacttaat tggttcgatg gccaaaaaca tggatgcaca acaggcagca   1140

agagccgcaa atgcccctaa ttgctcctcc aaagtgccag aagggaaaga taagaaccgt   1200

gataatatta tgccatcact tgaattaagt ttgaaaaggt caagatcgac tggggatggt   1260

gcaaacgcaa tccaagagga acaacggaat gttttgagac gatcagatct ctcggcattt   1320

acgaggtacc atacacctgt ggcttccaat caaggtggga caggattcat gggaagctgt   1380

tcgctgcatg ataatagctc agaggctatg aaaacggatt ctgcttacaa catgaagtca   1440

aactcagatg ctgcaccaat aaaacaaggt tctaatggta gtagcaataa caatgacatg   1500

ggttccacta caaagaacgt tgtgacaaag cctagtacaa ataaggagag agtaatgtca   1560

ccctcagctg ttaaggctaa tggacacaca tcagcatttc atcctgcaca gcactggacg   1620

tctccagcta atacaacagg aaaagaaaag actgatgaag tggctaacaa tgcagcaaag   1680
```

```
agggctcagc ctggtgaagt acagagcaac ctcgtacaac accctcgccc aatacttcat   1740

tatgttcatt tcgatgtgtc acgtgagaat ggtggatccg gggcccctca atgtggttca   1800

tccaatgtat ttgatcctcc tgtcgaaggt catgctgcca actatggtgt caatggaagc   1860

aactcaggca gtaacaatgg aagcaatggg cagaatggga gtacgactgc tgtaaatgct   1920

gaacggccaa atatggagat cgctaatggc accatcaaca aaagtggacc tggaggtggc   1980

aatggaagtg gaagcggcag tggcaatgac atgtatctga aacgcttcac tcaacgagag   2040

catagagtgg ctgcagtgat caagtttaga cagaaaagga aagagcgcaa cttcggaaaa   2100

aaggtgcggt accagagcag aaagaggctg gccgagcagc ggccaagggt ccgcggacag   2160

ttcgtgcggc aagctgtgca agaccaacaa cagcagggtg gtgggcgcga agcggcagcg   2220

gacagatga                                                           2229
```

<210> SEQ ID NO 63
<211> LENGTH: 2301
<212> TYPE: DNA
<213> ORGANISM: Zea mays

<400> SEQUENCE: 63

```
atgggcagtg cttgccaagc tggcacagac gggccttccc gcaaggatgt gttagggata     60

gggaatgccg ccttagagaa tggccaccat caggctgaag ctgacgcaga tgaatggagg    120

gaaaaggaag aggacttggc caacaacggg cacagtgcgc caccgccagg catgcagcag    180

gtggatgagc ataaggagga acaaagacaa agcattcact gggagaggtt cctacctgtg    240

aagacactga gagtcttgct ggtggagaat gatgactcta ctcgtcaggt ggtcagtgcc    300

ctgctccgta agtgctgcta tgaagttatt cctgctgaaa atggtttgca tgcatggcga    360

tatcttgaag atctgcagaa caacatcgac cttgtattga ctgaggtttt catgccttgt    420

ctatctggta tcggtctgct tagcaaaatc acaagtcaca aaatttgcaa agacattcct    480

gtgattatga tgtctacgaa tgattctatg agtatggtgt ttaagtgttt gtcgaaggga    540

gcagttgatt tcttggtaaa accactacgt aagaatgagc ttaagaacct ttggcagcat    600

gtttggaggc gatgccacag ttccagtgga agtgaaagtg gcatccagac acagaagtgt    660

gccaaactaa atactggcga cgagtatgag aacggcagtg acagcaatca tgatgatgaa    720

gaaaatgatg acggcgacga tgacgacttc agtgttggac tcaatgctag ggatggaagt    780

gacaatggca gtggtactca aagctcatgg acaaagcgtg ctgtggagat tgacagccca    840

caacctatat ctcccgatca actagttgat ccacctgata gtacatgtgc acaagtaatt    900

caccctagat cagagatatg cagtaacaag tggttaccga cagcaaacaa aaggaatgtc    960

aagaaacaga aggagaataa agatgaatct atgggaagat acttaggaat aggtgctcct   1020

aggaactcaa gtgcagaata tcaatcatct ctcaatgatg tatctgttaa tccaatagaa   1080

aaaggacatg agaatcacat gtccaaatgc aaatctaaaa aggaaacaat ggcagaagat   1140

gattgtacaa acatgcctag tgcaacaaat gctgaaactg ctgatttgat tagctcaata   1200

gccagaaaca cagaaggcca acaagcagta caagccgttg acgcaccaga tggcccttcc   1260

aaaatggcta atggaaatga taagaatcat gattctcata tcgaagtgac accccatgag   1320

ttgggtttga agagatcgag aacaaatgga gctacagcgg aaatccatga tgagcgaaat   1380

attctgaaaa gatcagatca gtcagccttc accaggtacc atacatctgt ggcttccaat   1440

caaggtggag caagatatgg ggaaagctct tcaccacaag ataacagttc tgaggccatg   1500
```

-continued

```
aaaacggact ctacatgcaa gatgaagtca aattcagatg ctgctccaat aaagcagggc   1560

tccaatggca gtagcaataa cgatgtggga tccagtacaa agaatgttgc tgcaaggcct   1620

tcgggtgaca gggagagagt agcgtcacca ttagccatca aatctaccca gcatgcctca   1680

gcatttcata ctatacagaa tcaaacgtca ccagctaatc tgattgggga agacaaagct   1740

gatgaaggaa tttccaatac agtgaaaatg agccacccaa cagaggttcc acaaggctgc   1800

gtccagcatc atcatcatgt gcattattac ctccatgtta tgacacagaa acagccatca   1860

acagaccgtg gatcatcaga tgttcactgt ggttcgtcaa atgtgtttga tcctcctgtt   1920

gaaggacatg ctgcaaacta cagtgtgaat gggggtgtct cagttggtca taatgggtgc   1980

aatgggcaga atggaagtag cgctgtcccc aatattgcaa gaccaaacat agagagtatt   2040

aatggtacca tgagccaaaa tattgccgga ggtggcattg taagtgggag tgggagtggc   2100

aatgacatgt atcagaatcg gttcctgcaa cgagaagctg cattgaacaa attcagactg   2160

aagcggaaag atcggaactt tggtaaaaag gttcgctacc aaagcaggaa gaggcttgct   2220

gagcagcggc cacgggtccg aggacagttt gtgcgacaat ctgagcaaga agatcaaaca   2280

gcgcaaggtt cagaaagatg a                                             2301
```

<210> SEQ ID NO 64
<211> LENGTH: 2034
<212> TYPE: DNA
<213> ORGANISM: Physcomitrella patens

<400> SEQUENCE: 64

```
atgccatatc tgtccggagt tgggcttctg tcgaagatga tgaagcggga agcatgcaag     60

agagtgccta ttgtcatcat gtcatcgtac gacagtcttg gcatcgtgtt ccgctgcctc    120

tcgaaaggag cttgcgacta tctcgtgaaa ccagttagga aaaacgagtt gaagaatctg    180

tggcagcacg tatggaggaa gtgccacagt tcgagtggga gcagaagtgg aagcggaagc    240

cagactgggg aagtagctaa gcctcggagt cgtggtgtag cagccgctga caatcctagt    300

ggaagcaatg atgggaatgg cagcagtgat gggagtgata atgggagcag ccgggtaaat    360

gcccagggtg gaagcgacaa tggtagtggc aatcaagctt gcatgcaacc tgtacaggtt    420

ctgaggaaca gcgcaattcc agaagcagta gacggggatg aggaggggca ggcgacatcg    480

caagataagg gtgctgactt ggatggagag atggggcatg atctggagat ggcaactcga    540

aggtctgctt gtgttaccac cggaaaagat cagcaaccag aggatgccca gaagcaagat    600

gaggatgctg tatgtatctt gcaagatgcg gggccatcac ctgatggggc taatgccgag    660

agcccatcat ctagcggtcg gaatgatgcc gcagaggagt cttctccaaa gatcattgac    720

ctgataaacg tcatagcgtg tcagccacag acccaggatg cagaacctca agaaagtgag    780

aacgatgacg aagaattgga tccgcgggga aggagcagcc ctaaaaacaa ctccgcttca    840

gattccggta cttcgctgga gttaagtttg aaacggccac gatcggcggt tggtaacggc    900

ggagaattag aagagcgtca accactgcga cattcaggag gctcggcctt ttctaggtat    960

ggcagcggag gaaccattat acagcaatac catcagactg gaggttcact ccctctcagt   1020

ggttatcctg tgtctggtgg atatggtgta tatggcatgt ccggcggtag ccctggagga   1080

tctcttcgtc tgggaatggg aatggatcga agtgggtcat cgaaaggaag tgtagagggg   1140

actacacccc caccctcgca tcctcagagc atggagaaag tgggtgggca agatgggtac   1200

ggcaatgcaa gacagactac ggaggatgca atgatcgtac ctggaatgcc catggctatt   1260

cctctcccac cacctgggat gcttgcatat gatggcgtta ttggaacgta tggtccggcg   1320
```

atgcacccga tgtattatgc tcaccctagc gcgtggatgg cagctccgtc tcgtcacatg 1380
ggagagcggg gagatgtcta caatcaatct cctgcatttc aagagcagga ttctgggtct 1440
gggaatcatt ctcaagcggg gcagactcac cagcacatgc accaccacca aggcaaccag 1500
caccaccatc atcatcacca tcaccaccat gggagtggcg cccagccttc tggaaatgca 1560
ggggtgcaag atgaacaaca gcaatcagtg gtaccgcctg ggtcgagtgc tcctcgctgc 1620
ggctcgaccg gtgtggatgg tcgaagtggt agcagcaacg gctacgggag caccgggaat 1680
gggaatgggt ccatgaacgg aagtgcttcg ggaagtaata ctggcgtgaa caacggtcag 1740
agtggatttg gtgcgacgcc gatgttaact gacaacagtg ggagtaacgg cgtcggtgga 1800
acggatgcag ccatggatgg ggtgagtggg ggcaatgggc tgtgcacaga gcaaatgcgt 1860
ttcgccagac gagaggctgc cttgaataag tttaggcaga agagaaagga gcgatgcttt 1920
gagaagaagg tgcgatacca aagcaggaaa cggcttgcag aacaaagacc acgagtccgc 1980
ggtcagtttg tgcggcaagc ggtacatgat ccgtctgctg gtgacgccga atag 2034

<210> SEQ ID NO 65
<211> LENGTH: 4080
<212> TYPE: DNA
<213> ORGANISM: Volvox carteri

<400> SEQUENCE: 65
atggagttcc acgtactgct ggtcgaagac gacagggtga cgctgaagac agttgagcag 60
ctactccgga aatgcaatta caaagttacc tgtgcagcaa atggacggga ggcaataaag 120
gtccttactg cctgccggca cagcggcgtc aaagtggacc ttattttgac cgatatactg 180
atgccggagg ttaccggctt tgacttaatc aatgaagtgg tacatgggga cacctttttgc 240 gatgtgccag tggtcgtcat gtcctctcaa gactcgcagg agaacgtgtt acaggcattc 300
caagcaggcg ctgccgacta ccttataaag cccattcgca aaaatgagct ggctacgctc 360
tggcagcatg tctggcgcgc caacaaggcc aaggggtccg gcagcggcac caccactaac 420
gtcaccgggc agcccctttc cggtcgggag gatctggagg caggcgaagc cgtcgctgtc 480
gccgccgccg ccgccgctgc cagcggcaag gcctgtgcag caacgcatgg gcatttgaag 540
gacagcagcg gcggcagcag cggcgccgcc gcttctgtat tgcagtccac gggcggaaca 600
ctactgccgg accgtgctgc cactgtacgg tatccagctg cggcggcagc gccaccgcca 660
cctggcgcat ccgagctatc agggaacgtg acggcgggcg aagctcaagg gagccgtacg 720
cagcatctgc gccatctgtc cggcttggcg gggatggaaa gcacagcggc gacgtcagcg 780
gcggcgcaag gcagtagcgc agcagggccg ctgcggggct gcggcggtgc tggtactgct 840
atagctggtg ggccgcgcgc gcccttgggc ccactttcat tcgcgccctt cggcacttcc 900
gttgccgtac actttgacct gaaccccgca tccggcgcag ctcgacggct ggtcaactcc 960
agcggcgcca tcgatgcgtc gacgggcagc ggcactgctg gcgtcgccgc ttcatcgcgt 1020
tgcgccgccg gcacctccgc caccgtcatc agttggtcgc acgtcgatcc gacggagacg 1080
gacccagcgg aggcggagcc catgtacgac acgaacgcgg acgccaccgc ggcgaaggca 1140
gcggctgacg gtgtggcgga agctgacgac gacgatgttg gcgacgacgg cggtgctggg 1200
cccaaccaca atgacgatga tgacgagggt ggcggcgacg acgacgtcag cggcgacggt 1260
gacgaggacg gaaaccggcc tcgcaagcgt ccgcggctgc ttcagggatc ctcgcatcac 1320
cacagccacc agcatcgcct tcacagccta ggcggtacga ctaccaacac caccaccact 1380

-continued acgacagccg cgaagcctaa gtcgacagcg ggagaacgcg gcggcgcggc ggcgctactc 1440
gcatgccgta ctgcggcggc cgcaccccta cgcggcagtg gctgcgccac cgctggcgcc 1500
accggagcat gtcgactggc ggcggcggca gcggcggcgg agggctccca gggttctcgc 1560
gccgcgtcgg cgtcggcagg ccctgacggc ggcgcgcgtg agagtacggc tacccccagt 1620
ggtgacacct ttgcagagag cccgtccgcg tacactgcaa ccgccacaac gaccagtacg 1680
gcaacaacca gtacgacaac gggatccggg attgagatgc aggacgacga gcaacagcag 1740
cgacagcagc ctaagcagcg tccgccggca tctcagccgg aactggaggg tcatcatcac 1800
caacaacaat atcaccatta ttatcgacgc accagcctgg agggcggttg cgccaacgca 1860
ccccctctcc ctgtcccttc atctgcacgg ggtgcttccc cggcaggcac gggtccgacg 1920
gaaagcggct ccgggaggga tagcggctgt gccaggatta caaatggtac ggcggcgggg 1980
gcgacggcgg caatgccgcc atctcacgtc agctcggcaa gccccccccg ctgtaccgcc 2040
acttccgcgg cggcgactcg cgggtcctct ggtgctgcta ctgcggcagc gggtgccatg 2100
acaacagcct tggcgacggc cggcagctat ccgcgaggag tggacgccag cccgccgccg 2160
aatagaagta tggggtccag cggcggtgat ggcggcggaa ccgccgctgc agctgccggt 2220
acggcacgag ggagctcgcc tgcggctgct acgccgccgc tgccaccttc tacgcagcag 2280
cacgggttgc cgcatcccgc ggcggcgccg ccgccgggcg ctgcatcgcc tggcggcgcc 2340
gtgacgctgc cgccagcgct tcaggagctg gcggcactgg gggcggcccg ccatgcgggg 2400
ctatggaccc agcgggcctt attgcatcag cagcaattgt tgctgcagca gcagaagcag 2460
cagaagcaac aacagcacca acaagaccag gtagtggggg cagagaagat tcatggtggg 2520
tcgacgtcgg ctgtagccaa cgccgccgag cagcagcagc agcagccgct gggggcggcg 2580
gcggcacgtc gtcccagcaa agcgggcgtg gacggaactg aggcgggaag tggcgcggtc 2640
ggcggatgcg catcggcgac agcggcggtc atggcgatgg aggcgtcgga gccgcatggc 2700
gcggttggca gctcctttac ggcggcagat cggcaggaga cgccgttgca gcctctgcat 2760
gctgaatctg cggcggcagg cggcgacatg gacggcaacc gcagtacacc cgcaactatg 2820
ccgtcggggc ctacggcagc cgcatcgggc ccttcgcaga cgtcgaacag cttgacggtg 2880
ctgcgacata gcgacagatc cgctttcacc gcattcaccg ttttcttgcc aagcagggtt 2940
gccggcgccg cggcggcggc ggcggcggca gcagctgctc ggccgccacc accgccggcg 3000
ccggtgcagc cgccggcgcc aatcttcacg caccctgctg ctgctgctgc agccgcggcg 3060
gcggctgccg ctggcagcgg cggtgcagcc tcagtgtggt atcctcacct ccatcatcac 3120
caccactact tgcagcagca gcagacgcac atgggtccct tgccgccact gccaggtgcc 3180
gtacatgttc tgccgtcgat catgcagctt cacatgggag tactggcgcc agggccgccg 3240
ccacagcagc agcagcagca gcaccttcag gccaaggcgc ctcagaagcc tcatgattcc 3300
gccgccgccg ccggcggagc taacggctcg ctaggtcccg cgacatcggc tgcagcggcc 3360
acgcacatgt cgtacactgg catgcaacag cgcccgggcg cctcatccgc caccaccacc 3420
agcgccggcg ctgtagcgtt cggtcaatct ccacctcacg ggctggcggc ggcggcggcc 3480
gccgctagca cgcctccgcc gcctccaccg ccgcctgttt gtattcccga atcggtacta 3540
cagctcattg cgcatctgtc tggtcgggcg gcggcggagc tgcccgtacc ggaaaccgtc 3600
acgacggcac cgttggtcgt acagaaggcg ccgtcggcag cgcgattggc tgctgtagcg 3660
aagtaccttg aaaagcggaa gcaccgaaac ttccaaaaga aggttcggta cgagagccgt 3720
aaacggctgg cggaggccag gcctcgcgta cgcggccaat tcgtcaaggc aagtacttcc 3780
gcggtggcgg caaccacccc tgccgccacg ggcgccaccg tcacctctac gtcgctccgt 3840
cagcccgttt atacggcggc cggcccggct ggcctggcgc tgccgccggc ggcggcagca 3900
gcggcggcca gcgccgccgc cgcgaggggg gttccgccgc cgtcatcccg catcggagcg 3960
gtggagctgg cggagttggt gcccgaccac gacgccgaca ttgaggacga ggggtgtgac 4020
gagcccgccg ccgccgagga ctccgacggg tccgtcgcgg tggagctggc ggaggtgtag 4080

<210> SEQ ID NO 66
<211> LENGTH: 3309
<212> TYPE: DNA
<213> ORGANISM: Chlamydomonas reinhardtii

<400> SEQUENCE: 66
atggaggcta acggcttcca cgtcgtatta gtcgaggatg ataacatttg cctgaaagtg 60
gtggagcagc tgctgcggaa gctttcgtac agagtcagca ccgcatccga tggtgccgca 120
gcgctcaaag tcctggctga ctgcaagcag aggggcgaca aagtagacct cattctcacg 180
gacatcctga tgccagaggt taccgggttt gacctcatca acgaggtcgt gcatggagag 240
acctttgccg atattccggt cgtggttatg tcgtctcaag actcgcagga aagtgtcttg 300
caggcatttc aggcgggcgc agcggactac ctcatcaagc ccattcggaa aaatgagctt 360
gcaacgctct ggcagcacgt ctggcgtgca aaccgcgcca agggtggaca gaccagcagc 420
ggcgccgcgc atgtgggcgc aggcggcagg gggggcacca gcagccgcga tggcggtggc 480
gttgccggga cgcggtgcgg cccaggcgac cgcggcggca gcggcggcga cgctgagggt 540
agtgggctag gcggcggcgc gggtgcagtc aaggacagca gcggcggcag taccggcgcc 600
gccacttcag tgctgcactc cactggtggc acgacgctgc cctcacgtgc ggccaccggt 660
cggcacgcta gcacctcagc tggacacggc gtcaccagcg ctgaccccag caacaaccaa 720
acctcgcacg cgcacgcgca tgcgcatgcg cacgctcacg ggaacgcgca cgcgcacgcg 780
caccttcata tgcacggcgc aacagatcgt gcggcgcagg gcagcagcgc taacggcccg 840
gccaaccacg gggccgctgg gacagggctg cagtccgctg ggatggcagg ttccacggct 900
gcaggcgcgg ctgcgcccgc cggtgagtcg ctggccaagc cgcccttcgc ctccctagcc 960
gtccacttcg acctgcactc agtcctggcg ggcgcgggag cggctgcagc caatggtggc 1020
gccaatgccg cagctcacac tgctggcgcc accgggcgag agagcggcca ggcggcgggc 1080
gcggccacag gcggcattgc cgccgccggc accgtcatcg gctggtcgca tgcggacatg 1140
gacgtggacg gaggggaggc cggcgcgcag gatgaagatg acgaggacga ggacgacggc 1200
gtggaggcgc cggcgggcac acagaaccgg aagcgcgccg cggatgactc gggttgcgac 1260
ggcgccgccg ccaacaacaa cggcaacact gccgcaaagg ctggcgcagc ggcaatcgcc 1320
gcgggcgggc ctgggagctc gggcagggcg aaggccacgg acggcgcccg cgctgagatt 1380
cgccacaacg gtgggccgat ggcggcgcgg atggcggctg cagagggctc tcaaggctcg 1440
cgcgctgcat cgggctcggc ggcaacggga ccgggaggag cgcgggaggg cactgcgacg 1500
cctagcggcg acacctttgc ggagagccct tccaccttca cttccatcat caacaccacc 1560
ggctcgggca gcgaggccga cgagcagcca gtgccgctga agcaccagga acagcaacag 1620
cagcaacagc agcagcgggt cggcgagggt gacagggcga agcccgaacc gcacccacag 1680
aaccctgccc aggcagcaca cctgccgcac ccgtccgcgg ccccatgctc gggcggtggc 1740
ggtattgcgc aagcggccct acccctaggg ctacaggagc tggcagcgct gggggcggct 1800

-continued

```
cggcacaaag agctgtggac gcagcggcac cttatgcatc agcggcaggc ggcggcagcg   1860

gcgacagcag cggcggcctc ggcagctgct gcagcggcaa tgcccacggc cggcgcgagc   1920

gccgcggctc ctgcaggccc accttcggcg cggccctccg cttccttggc agacacgggc   1980

ggcgacggcc ccgcggctgc gacggcgcct gagacgcgcg cagatgggcc ctctggccct   2040

gccacgacgc agggccccaa acgagatgcc gtcgcaggtg ccgcggctgt cggcagctct   2100

gcacggagcg acagtccgct gccggcagcc gccgccgcga cggcaggcgc caacggcgcg   2160

agcggcgccg cttctgacgt gttggcgggc gcaggcagcc ttgcgcttct ccggcacagc   2220

gatcggtctg ccttcaccgc gttcacggtc ttcctgcccg ggcgtgttgc cgccgccgcg   2280

gccgctgcag cggccgccgc cgcagctgct accagcgcgg gcgccagcac cggcactgcc   2340

aacggggctc cgccggcacc gggcaccgct ctggctgccg ctgccgcagc agctgccgcc   2400

gctgcgtcag cagtgccgct gccgcatcca cacacagcgc ccccagcgct gttcggcgtc   2460

cctccgccgt cctccgtgcc tcccagctcg ctttctgtgc tacctcctgt gatgccgctc   2520

catccggccg ctgccgctgc agcggcgacg gcgggtgggg gcaagcccag cgacgcagcc   2580

acgtatgccg cggctgctgc agctggattg gtgccgtatc cagggtttgc gccggcgcgg   2640

ccggggccat ttccgccgcc gccaggttct ggtggccccg gcgcgccgcc tgtgtacata   2700

cccgagtcag tcctgcagct gattgcgcac ctgtccggcc gcgcggctgc ggaaattccg   2760

gcggtgccgg cggagtcagt gacggcagca ccggtggttg tgcagaagag cggcggccct   2820

gcctcggcgg cgcgactggc ggcagtggcc aagtacctgg agaagcggaa gcaccgcaat   2880

ttccagaaga aggtgcgcta cgagagccgc aagcggctcg ccgaggcccg gccacgcgtc   2940

agggggcagt tcgtcaaggc gggcaccgcg ggtgcagcgg cagcggcagc ggcagcggca   3000

gccgcagccg cagccggcac tgccgctact gctgccggca ccggcacggc cagaggtgct   3060

gccaccgctt ctggggctgc tgggaagccg gagctacagg gccccgacac ggcagaagag   3120

gctgcggctg cgacgctgct tagcgcagca gctgctatgg cagcagcggc tgcgggcacc   3180

agtggcccca gcggctctgg gtccggcgcg atggatgtgg acggtgccga cccggaagca   3240

gatgcagacg tcatggatga ggacgatggc gaagacgacg ggtcggacga gtccgctggg   3300

gagccctag                                                          3309
```

```
<210> SEQ ID NO 67
<211> LENGTH: 1335
<212> TYPE: DNA
<213> ORGANISM: Coccomyxa subellipsoidea

<400> SEQUENCE: 67

atggctgcag gcctcaagcg gatacccagc ttctcggggc gaccaggatt ccccaacggt     60

ctgcaggtgt tggttgtgga cggggacacc agcagcagcc agtgcttgcg gcagaagctg    120

gaggagctgg catatgaagt cagctgctgc tcgtccggat ctgacgcttc ggcgctcctg    180

cgcaaggagg actccagcta cgacattctc ctagttgagg ccaaagctct ggcaaaggat    240

gctactgatg gaggcagtct cagagattct gcagcgcacc tgccgctggt cctcatgtca    300

gaaaagagca gcagcacaga cgctgtatgg cgaggcatag agctcggggc agcggacgtt    360

ctggagaagc cgctgtcctc cttgaagctg cgcaacatct ggcaacatgt cgttcgcaag    420

atgatgagct cgtcccagga cagcagcagg gaggcggtgc cctgcaagat ggagccgaag    480

agcaagggca agggcgtgtc agcgccctcc agccctcgca ctccctcccc tgcagcctcc    540

ctcctcacca tcagcagcgg cacgatgaca gagaagagct gcaagggcgg cggcgatgag    600
```

```
gcctccttct caggtgtggg agatgtgaag atgtcctgct cggcagaggc gccggagccc    660

tgcgattcgc gcgcgaccgc tgagtcaccc gccagcacgc agaccaaggt cacgttcccg    720

gggtgcttga atagcggcgg cacggcgctc gcggctagca agaattgcag ccgcaagaga    780

aaggcaaagg cgccggacac tcctgcatcg gtggcgagcc ggccgcctct ggccatcagg    840

ccccccgcat gggcctcccc atttggtccc ccccaccagg gcaacaccca cgtcgtcggc    900

atggccccgc cacagtgcta tatgcagggg gttgacccca cgaacgggtg cgtatggggc    960

acgccagcag ggggcgtcag ccaagcgcca gcctacatgc ccggctgggg cttctcgccg   1020

cagccaatgc tttccggcag cttcttgcag catccctcca ccagcgacct gcacaagtgc   1080

cccagcgtgg gtgccagcag cctggcaagc agcctggaca gcagcctgac gctgtgcggc   1140

tttggcgcgg acctgcctga cgacgatctc ctgttggagg acgtgcttct gccggacgag   1200

gatcttctgg acttggcccc agatgagccc gccaccatga aggcccccga gcagccgccc   1260

atcggcctca agctcaagaa gtccgcttca ctcatcgacc tcatcaatgc gcaactgtcc   1320

gccgccaccg cctga                                                    1335
```

<210> SEQ ID NO 68
<211> LENGTH: 568
<212> TYPE: PRT
<213> ORGANISM: Parachlorella sp.

<400> SEQUENCE: 68

```
Met Leu Arg Gln Gln Leu Leu His Ser Gly Arg Gln Pro Gly Ala Thr
1               5                   10                  15

Cys Ser Leu Leu Thr Cys Ser Thr Trp Arg Pro Ser Ala Leu Phe Gly
            20                  25                  30

Arg Pro Lys Pro Gln Lys Leu His Ser Gln Arg Leu Gln His Gln Gly
        35                  40                  45

Arg Pro Ser Arg Leu Val Val Arg Ser Ala Met Phe Asp Asn Leu Ser
    50                  55                  60

Arg Ser Leu Glu Arg Ala Trp Asp Met Val Arg Lys Asp Gly Arg Leu
65                  70                  75                  80

Thr Ala Asp Asn Ile Lys Glu Pro Met Arg Glu Ile Arg Arg Ala Leu
                85                  90                  95

Leu Glu Ala Asp Val Arg Leu Gly Ala Pro Leu Ile Arg Phe Leu Val
            100                 105                 110

Ser Thr Pro Pro Pro Ser Gln Val Ser Leu Pro Val Val Arg Lys Phe
        115                 120                 125

Val Lys Ala Val Glu Glu Lys Ala Leu Gly Ser Ala Val Thr Lys Gly
    130                 135                 140

Val Thr Pro Asp Gln Gln Leu Val Lys Val Val Tyr Asp Gln Leu Arg
145                 150                 155                 160

Glu Leu Met Gly Gly Gln Gln Glu Gly Leu Val Pro Thr Ser Pro Glu
                165                 170                 175

Glu Pro Gln Val Ile Leu Met Ala Gly Leu Gln Gly Thr Gly Lys Thr
            180                 185                 190

Thr Ala Ala Gly Lys Leu Ala Leu Phe Leu Gln Lys Lys Gly Gln Lys
        195                 200                 205

Val Leu Leu Val Ala Thr Asp Ile Tyr Arg Pro Ala Ala Ile Asp Gln
    210                 215                 220

Leu Val Lys Leu Gly Asp Arg Ile Gly Val Pro Val Phe Gln Leu Gly
225                 230                 235                 240
```

-continued

```
Thr Gln Val Gln Pro Pro Glu Ile Ala Arg Gln Gly Leu Glu Lys Ala
                245                 250                 255

Arg Ala Glu Gly Phe Asp Ala Val Ile Val Asp Thr Ala Gly Arg Leu
            260                 265                 270

Gln Ile Asp Gln Ser Met Met Glu Glu Leu Val Gln Ile Lys Ser Thr
        275                 280                 285

Val Lys Pro Ser Asp Thr Leu Leu Val Val Asp Ala Met Thr Gly Gln
    290                 295                 300

Glu Ala Ala Gly Leu Val Lys Ala Phe Asn Asp Ala Val Asp Ile Thr
305                 310                 315                 320

Gly Ala Val Leu Thr Lys Leu Asp Gly Asp Ser Arg Gly Gly Ala Ala
                325                 330                 335

Leu Ser Val Arg Gln Val Ser Gly Arg Pro Ile Lys Phe Val Gly Met
            340                 345                 350

Gly Glu Gly Met Glu Ala Leu Glu Pro Phe Tyr Pro Glu Arg Met Ala
        355                 360                 365

Ser Arg Ile Leu Gly Met Gly Asp Val Val Thr Leu Val Glu Lys Ala
    370                 375                 380

Glu Glu Ser Ile Lys Glu Glu Glu Ala Gln Glu Ile Ser Arg Lys Met
385                 390                 395                 400

Leu Ser Ala Lys Phe Asp Phe Asp Asp Phe Leu Lys Gln Tyr Lys Met
                405                 410                 415

Val Ala Gly Met Gly Asn Met Ala Gln Ile Met Lys Met Leu Pro Gly
            420                 425                 430

Met Asn Lys Phe Thr Glu Lys Gln Leu Ala Gly Val Glu Lys Gln Tyr
        435                 440                 445

Lys Val Tyr Glu Ser Met Ile Gln Ser Met Thr Val Lys Glu Arg Lys
    450                 455                 460

Gln Pro Glu Leu Leu Val Lys Ser Pro Ser Arg Arg Arg Arg Ile Ala
465                 470                 475                 480

Arg Gly Ser Gly Arg Ser Glu Arg Glu Val Thr Glu Leu Leu Gly Val
                485                 490                 495

Phe Thr Asn Leu Arg Thr Gln Met Gln Ser Phe Ser Lys Met Met Ala
            500                 505                 510

Met Gly Gly Met Gly Met Gly Ser Met Met Ser Asp Glu Glu Met Met
        515                 520                 525

Gln Ala Thr Leu Ala Gly Ala Gly Pro Arg Pro Val Pro Ala Gly Lys
    530                 535                 540

Val Arg Arg Lys Lys Leu Ala Ala Ala Gly Gly Ser Arg Gly Met Ala
545                 550                 555                 560

Glu Leu Ala Ser Leu Lys Ala Glu
                565
```

<210> SEQ ID NO 69
<211> LENGTH: 23
<212> TYPE: DNA
<213> ORGANISM: Parachlorella sp.

<400> SEQUENCE: 69
gggacatggt gcgcaaggac ggg 23

<210> SEQ ID NO 70
<211> LENGTH: 2667
<212> TYPE: DNA
<213> ORGANISM: Parachlorella sp.

<400> SEQUENCE: 70
atggccaaac tgacatccgc tgttcctgtg ttgacagcaa gagatgttgc aggtgcagtg 60
gagttttgtg agttctgaga agctgattgt tgtttaactt ctttgaaagc tttatcgaag 120
attctgcaag cgatgaacat tgcttgtcaa gaccgagagc tgcatgccca cttgacatcc 180
agctttgaac ggctcttcat gtttgatttg tttctgattg tagggacaga tagactgggg 240
tttagcaggg actttgtgga ggacgatttt gcaggagtgg tgagggatga tgtgacactg 300
tttatctcag cagtgcagga tcaagtgagt gcagcgtcag ctgtggcagt tgttggcttt 360
cgtctcagtc agtagtttgc tgggattgat tatggagggc acagttgcaa ttttgagttg 420
cacgttgcga caagcgtgtt gacaaagcgt ggtcaagccg gccagtcttg ccggtggcgg 480
gtggcttggt ctaacttccg ctctacagca atcgttttgt tcatggttac ggggctggcg 540
tgccagaaag tcctggtcag ccaccctcgc ttcaaagccg tagcccaaca actttgcgaa 600
tatgttcgat ttgcaggtgg tgcccgataa tacactggca tgggtttggg tgagaggtac 660
agctctgcgt gcaacaggtt gcaagatgca gcgcaggtct tccctggtca aacgatgtat 720
gcagagttga gaggcacttg agctgggtga atggcgtggg ctcgtaggta gtgtgcaggg 780
caggaagggc agccaatttt ggagttgtgg tccggtgtcg ttgcttcgag ccttattagg 840
actcttgctc atcaaagcgt tagttgtgaa taagttgatc tgaaaggatg ttatgtacag 900
caagcagcag cagttaagag tctggggagt agctgcacag ggcgaggtgt caagatggga 960
agggtcctgc ctccttatgt gtttttccct gtaggggagg aagcctctta tgggcaatgg 1020
ttgggcatat tttccagcca gcccttcttt ctataggggc cagggtgggc ccagctcgtc 1080
ttggcttcca ccaccaggag agtgagggca ttgaagggcc ataaatagtc ctcccatcta 1140
cgtgcaccag agggtgtcgt ctaggctgtg catgccacga ggggaaggag ccaagaatga 1200
gtgtatgggt tgttttcatg tttaggctgg gataaaactg ttttcaattg cgcctgccgg 1260
gtgaaaacca cagcagcatc agcaagcttg gagaaggcca gcccgcccag cacaggctca 1320
cgttcccact caggcggtca gtcgggcggg ggtgtgagtc aggcaggcga gggtgtctgt 1380
gcctgacatc agcacctctg cttagccact gcagcccctg gagcagggta gggcgtcatt 1440
tgcagcaatc acctgctgcc tcacacgtcg cagcttggaa tttcaacgac catcagcgct 1500
ggggttgttg agggatcata gcagattttg gtgcagcctg gttgtcatgc tctttgtgga 1560
atggcctcta tgttcgagca attcgttgga tgttgaggtg cttggggaca gagagtcgaa 1620
tgatgggcca gggtcaaaca tgcgagcgtt tggctgagtc agcggttttt gctggtcact 1680
ttttcttttg tttcttattt aggtttgatg gatgtgtttt gtgctgctgc cctgaagctg 1740
cagcagcgtg tctgccctgc gctactgcgg gcaccaaggc tatgtgctgg tgcactcggc 1800
tgcgctgcac ctgtgcacct cgcactccgt ccagcctcca tgcagcacac gtactcacgg 1860
tgtcctcctg acctgtcgta cgctattcca aacttgctct tttgctgccg ctgctctcgt 1920
acacaattgc tgttgattat cgatatctaa tcgagcgcct gctgactgaa ctccgcaggt 1980
ttggatgaac tgtatgcaga gtggtctgaa gtggtgagca ccaactttag gtgggtgggc 2040
tctgaaggag gaggagggag cgggtgatta aacagggcct gcatgaagag gagcaggggc 2100
tgcatggaca gcagggggaa ggtgcagaag ggagggtcaa gcggggttca ggtggctgtg 2160
ggtttctgca cgagcagtga aagaagctgt atccttccac ctgctttcac tggcgaaagg 2220
ttgaaaacag gatgtcgcag ctggaaagat gttgcgctgt caagtgcaag ccatggttga 2280

```
gggtatgcct gtgtgcatgt gcttcttaaa gttactcctg ttctatggtt ctgggtgctt   2340

gttgtttgtg gtgcagggat gcaagcggac ctgcaatgac agagattgga gaacaacctt   2400

ggggaaggga gtttgcattg agagatcctg caggtgaggg ggcatgtaag caatggcagg   2460

caattcaaga acgaatcatt gctgcaaatg ctgggatggt atgcagctga ggtatctatt   2520

gccttgtatt ttgtctcgca ttgcatcggt ggtgcgttct gtggcctgag gcacagttct   2580

tgctgtttga taagggttcg actgagttgt cgtgtgtgct gtgctgcagg caattgcgtg   2640

cactttgttg cagaagaaca ggactga                                       2667
```

<210> SEQ ID NO 71
<211> LENGTH: 530
<212> TYPE: DNA
<213> ORGANISM: Parachlorella sp.

<400> SEQUENCE: 71

```
ccaccatggg ggaggtttga agtgtgcgcc tgatataatc atacacctaa aagcaccact     60

tgctgattgt gaagggacta tgtcgtttat gacgggacgt tacgctggcc gatggtttga    120

atttggacgc tgtggtagaa tgttatatgg acgtaaaggt tggcatattg aaaatcgtct    180

tcgcaggcaa acttctagac gtgtgaccca ccggtaaaac gacaagcgtg gcgcgtcgat    240

tgcgctttga acgtcgtttg ttggactcca gatgaacctc aaaatcaaag cggtgattga    300

cgaaaatcaa atgacagccc gcaaaatttc atcagccttc ggatcggatt ctcagaatct    360

gattgtccct gctggctaca tttatgaaat ttcgtacatt ttggcagaaa tgtcccaata    420

ccatagcact gccgcctgag ctcacccgag caatgcatac tgggtacctc gcccatctcg    480

ccctctttcc aagcccagtg ctgttgtaat agccaaaggg ctcagtaaca               530
```

<210> SEQ ID NO 72
<211> LENGTH: 546
<212> TYPE: DNA
<213> ORGANISM: Parachlorella sp.

<400> SEQUENCE: 72

```
gcatagcatc agcctgtggc agggttgtgg tagggctgag tggcagggtt aaaggggttg     60

cctaccccac ccctactctc atgacaccag caacagcagc agctcatgca gtactcaaat    120

cactgatgtc aatggtgtga cacatttggt taaggctgct ttttaaagtg ctgctttggg    180

ggcagtgact gtgcagagct tggagcgtat ccccatgtaa tcagaaccga cgagagttcg    240

gggcaacctt tcatcttcac attttttgtg atcagctaca gagtctgaaa tcaaatagag    300

gctgccatct aaacgcagga gtcacaacga aggcgaaaac tccaattgct gtactcaatg    360

cactaagtga ttgttcaatg gataaataca ctatgctcaa ttcatgccag cagagctgct    420

ccttccagcc agctacaatg gctttttcca cgccttttga agtatgaatg ttcagcttgc    480

tgtgcttgat gcatcaccat aaacacaatt ctacaacatt tcatgccaac aacagtacgg    540

gctttc                                                               546
```

<210> SEQ ID NO 73
<211> LENGTH: 23
<212> TYPE: DNA
<213> ORGANISM: Parachlorella sp.

<400> SEQUENCE: 73

```
tgcggtgaag cttggagctg tgg                                             23
```

<210> SEQ ID NO 74
<211> LENGTH: 23
<212> TYPE: DNA
<213> ORGANISM: Parachlorella sp.

<400> SEQUENCE: 74
acaccacctt aaggcacatg agg 23

<210> SEQ ID NO 75
<211> LENGTH: 549
<212> TYPE: PRT
<213> ORGANISM: Chlamydomonas reinhardtii

<400> SEQUENCE: 75

```
Met Gln Thr Ala Leu Arg Ala Arg Ser Ala Ala Pro Arg Gly Ala Cys
1               5                   10                  15

Asn Arg Thr Ala Val Ala Pro Val Ala Ser Ala His Leu Arg Gly Gln
            20                  25                  30

Tyr Ala Pro Phe Ser Gly Ala Gln Ala Arg Pro Ala Leu Gly Arg Gln
        35                  40                  45

Arg Gln Gln Gln Gln Gln Gln Arg Arg Gly Ala Leu Val Ile Arg Ser
    50                  55                  60

Ala Met Phe Asp Ser Leu Ser Arg Ser Ile Glu Lys Ala Gln Arg Leu
65                  70                  75                  80

Ile Gly Lys Ser Gly Thr Leu Thr Ala Glu Asn Met Lys Glu Pro Leu
                85                  90                  95

Lys Glu Val Arg Arg Ala Leu Leu Glu Ala Asp Val Ser Leu Pro Val
            100                 105                 110

Val Arg Arg Phe Ile Lys Lys Val Glu Glu Arg Ala Leu Gly Thr Lys
        115                 120                 125

Val Arg Glu Gly Arg Ala Met Gly Thr Lys Trp Lys Ser Val Val Asn
    130                 135                 140

Cys Pro Leu Gln Asp Gly Leu Gly Asn Arg Gly Val Gly Arg Ala Arg
145                 150                 155                 160

Thr Glu Val Gly His Arg Ala Ala Cys Val His Gly Ala Arg Gly Val
                165                 170                 175

Gly Lys Thr Thr Ala Ala Gly Lys Leu Ala Leu Tyr Leu Lys Lys Ala
            180                 185                 190

Lys Lys Ser Cys Leu Leu Val Ala Thr Asp Val Tyr Arg Pro Ala Ala
        195                 200                 205

Ile Asp Gln Leu Val Lys Leu Gly Ala Ala Ile Asp Val Pro Val Phe
    210                 215                 220

Glu Met Gly Thr Asp Val Ser Pro Val Glu Ile Ala Lys Lys Gly Val
225                 230                 235                 240

Glu Glu Ala Arg Arg Leu Gly Val Asp Ala Val Ile Ile Asp Thr Ala
                245                 250                 255

Gly Arg Leu Gln Val Asp Glu Gly Met Met Ala Glu Leu Arg Asp Val
            260                 265                 270

Lys Ser Ala Val Arg Pro Ser Asp Thr Leu Leu Val Val Asp Ala Met
        275                 280                 285

Thr Gly Gln Glu Ala Ala Asn Leu Val Arg Ser Phe Asn Glu Ala Val
    290                 295                 300

Asp Ile Ser Gly Ala Ile Leu Thr Lys Met Asp Gly Asp Ser Arg Gly
305                 310                 315                 320

Gly Ala Ala Leu Ser Val Arg Glu Val Ser Gly Lys Pro Ile Lys Phe
                325                 330                 335
```

Val Gly Val Gly Glu Lys Met Glu Ala Leu Glu Pro Phe Tyr Pro Glu
340 345 350

Arg Met Ala Ser Arg Ile Leu Gly Met Gly Asp Val Leu Thr Leu Tyr
355 360 365

Glu Lys Ala Glu Ala Ala Ile Lys Glu Glu Asp Ala Gln Lys Thr Met
370 375 380

Glu Arg Leu Met Glu Glu Lys Phe Asp Phe Asn Asp Phe Leu Asn Gln
385 390 395 400

Trp Lys Ala Met Asn Asn Met Gly Gly Leu Gln Met Leu Lys Met Met
405 410 415

Pro Gly Phe Asn Lys Ile Ser Glu Lys Gln Leu Tyr Glu Ala Glu Lys
420 425 430

Gln Phe Gly Val Tyr Glu Ala Ile Ile Gly Ala Met Asp Glu Glu Glu
435 440 445

Arg Ser Asn Pro Glu Val Leu Ile Lys Asn Leu Ala Arg Arg Arg Arg
450 455 460

Val Ala Gln Asp Ser Gly Lys Ser Glu Ala Glu Val Thr Lys Leu Met
465 470 475 480

Ala Ala Tyr Thr Ser Met Lys Ala Gln Val Gly Gly Met Ser Lys Leu
485 490 495

Leu Lys Leu Gln Lys Ala Gly Ala Asp Pro Gln Lys Ala Asn Ser Leu
500 505 510

Leu Gln Glu Leu Val Ala Ser Ala Gly Lys Lys Val Ala Pro Gly Lys
515 520 525

Val Arg Arg Lys Lys Glu Lys Glu Pro Leu Ser Lys Ala Arg Gly Phe
530 535 540

Gly Ser Ser Ser Lys
545

<210> SEQ ID NO 76
<211> LENGTH: 559
<212> TYPE: PRT
<213> ORGANISM: Micromonas pusilla

<400> SEQUENCE: 76

Met Arg His Leu Leu Ser Ser Ala Ser Ile Arg Gln Tyr Asp Lys Trp
1 5 10 15

Ser Leu Val Ser Ser His Ala Lys Lys Pro Ala Leu Val Cys Ala Ser
20 25 30

Lys His Thr Lys Ser Ala Val Lys Leu Gln Cys Thr Ser Arg Gly Ser
35 40 45

Ser Asn Arg Thr Ile Gln Leu Leu Leu Phe Gln Gln Phe Arg Pro Ala
50 55 60

Lys Arg Gly Lys Leu Leu Ile Thr Arg Ala Asp Ser Phe Gly Thr Leu
65 70 75 80

Ser Glu Arg Leu Asn Ser Ala Trp Ser Ala Leu Lys Asp Glu Asp Asp
85 90 95

Leu Ser Val Glu Asn Ile Ser Leu Pro Leu Lys Asp Ile Arg Arg Ala
100 105 110

Leu Leu Glu Ala Asp Val Ser Leu Pro Val Val Arg Arg Phe Ile Lys
115 120 125

Ser Val Glu Glu Lys Ser Ile Gly Val Lys Val Thr Lys Gly Val Ser
130 135 140

Ala Ser Gln Gln Leu Thr Lys Val Val Ala Asp Glu Leu Cys Glu Leu

-continued

```
145                 150                 155                 160

Met Gly Gly Phe Gly Gly Asp Lys Leu Ile Phe Arg Lys Glu Gly Glu
                165                 170                 175

Gly Pro Thr Val Ile Leu Met Ala Gly Leu Gln Gly Val Gly Lys Thr
            180                 185                 190

Thr Ala Cys Gly Lys Leu Ala Leu Phe Leu Lys Ala Gln Gly Lys Gln
        195                 200                 205

Ser Leu Leu Val Ala Thr Asp Val Tyr Arg Pro Ala Ala Ile Asp Gln
    210                 215                 220

Leu Lys Lys Leu Gly Glu Gln Ile Asp Val Pro Val Phe Glu Leu Gly
225                 230                 235                 240

Thr Asp Phe Ser Pro Pro Asp Ile Ala Arg Ser Gly Val Glu Lys Ala
                245                 250                 255

Lys Leu Glu Asn Phe Asp Val Val Ile Val Asp Thr Ala Gly Arg Leu
            260                 265                 270

Gln Val Asp Glu Met Leu Met Ala Glu Leu Leu Ala Thr Lys Ala Ala
        275                 280                 285

Thr Arg Ala Asp Glu Thr Leu Leu Val Val Asp Ala Met Thr Gly Gln
    290                 295                 300

Glu Ala Ala Ser Leu Thr Ala Ala Phe Asn Asp Ala Val Gly Ile Thr
305                 310                 315                 320

Gly Ala Val Leu Thr Lys Met Asp Gly Asp Thr Arg Gly Gly Ala Ala
                325                 330                 335

Leu Ser Val Arg Glu Val Ser Gly Lys Pro Ile Lys Phe Ile Gly Ser
            340                 345                 350

Gly Glu Lys Leu Asp Ala Leu Glu Pro Phe Phe Pro Glu Arg Met Thr
        355                 360                 365

Thr Arg Ile Leu Gly Met Gly Asp Val Val Ser Leu Val Glu Arg Ala
    370                 375                 380

Gln Val Ala Val Lys Glu Glu Gln Ala Asn Leu Met Arg Asp Lys Ile
385                 390                 395                 400

Leu Ser Ala Thr Phe Asp Phe Asn Asp Phe Leu Ser Gln Leu Glu Met
                405                 410                 415

Met Gly Lys Met Gly Gly Met Gly Gly Leu Thr Lys Met Met Pro Gly
            420                 425                 430

Met Asn Thr Met Ser Asp Lys Glu Leu Gln Asp Ala Glu Lys Ser Leu
        435                 440                 445

Ser Val Ala Lys Ser Leu Ile Met Ser Met Thr Pro Arg Glu Arg Gln
    450                 455                 460

Phe Pro Asp Leu Leu Val Ala Gly Ser Ser Ala Ala Ser Arg Arg Gly
465                 470                 475                 480

Arg Val Val Glu Gly Ser Gly Arg Ser Asp Lys Asp Leu Ala Asn Leu
                485                 490                 495

Ile Val Met Phe Gly Ser Met Arg Val Lys Met Gln Ser Leu Ser Ala
            500                 505                 510

Gln Met Asn Gly Thr Ala Lys Glu Val Gly Leu Val Pro Gln Leu Ser
        515                 520                 525

Glu Val Asp Leu Asn Lys Leu Ala Phe Glu Gly Val Gly Lys Arg Val
    530                 535                 540

Ser Pro Gly Met Val Arg Arg Arg Lys Leu Asn Ala Ser Phe Gly
545                 550                 555
```

<210> SEQ ID NO 77

<211> LENGTH: 568
<212> TYPE: PRT
<213> ORGANISM: Micromonas sp.

<400> SEQUENCE: 77

Met Glu Ala Arg Thr Lys Gln Ala Arg Ala Pro Lys Gly Ser Ile Trp
1 5 10 15

Cys Ala Gln Arg Ala Arg Lys Asp Leu Arg Ala Arg Gly Cys Arg Gly
20 25 30

Leu Gly Ser Arg Ile Ser Lys Gly Gln Pro Phe Ser Pro Leu Thr Leu
35 40 45

Ser Thr Pro Ala Val Thr Glu Ile Gly Phe Gly Thr Leu Leu Tyr Gly
50 55 60

Ser Arg Leu Ser Ala Gly Gly Ser Arg Arg Gly Glu Thr Met Leu Arg
65 70 75 80

Arg Ala Ser Ala Phe Gly Ser Leu Thr Glu Arg Leu Asn Ser Val Trp
85 90 95

Ala Thr Leu Lys Asp Glu Asp Asp Leu Ser Leu Glu Asn Ile Lys Gly
100 105 110

Pro Leu Lys Asp Ile Arg Arg Ala Leu Leu Glu Ala Asp Val Ser Leu
115 120 125

Pro Val Val Arg Arg Phe Ile Lys Asn Ile Glu Gln Lys Ala Ile Gly
130 135 140

Thr Arg Val Thr Lys Gly Val Asn Ala Gly Gln Gln Leu Thr Lys Val
145 150 155 160

Val Ala Asp Glu Leu Cys Glu Leu Met Gly Gly Phe Gly Gly Asp Ser
165 170 175

Leu Ala Phe Lys Asp Pro Ser Met Gly Pro Thr Val Ile Leu Met Ala
180 185 190

Gly Leu Gln Gly Val Gly Lys Thr Thr Ala Cys Gly Lys Leu Ala Leu
195 200 205

Tyr Leu Lys Lys Gln Gly Lys Asp Ser Leu Leu Val Ala Thr Asp Val
210 215 220

Tyr Arg Pro Ala Ala Ile Glu Gln Leu Lys Arg Leu Gly Glu Gln Val
225 230 235 240

Lys Thr Pro Val Phe Asp Met Gly Val Arg Val Asp Pro Pro Glu Val
245 250 255

Ala Arg Leu Gly Leu Glu Lys Ala Arg Ala Glu Gly Ile Asp Val Val
260 265 270

Ile Ile Asp Thr Ala Gly Arg Leu Gln Val Asp Val His Leu Met Glu
275 280 285

Glu Leu Arg Ala Thr Lys Ile Ala Thr Ala Ala Asp Glu Ile Leu Leu
290 295 300

Val Val Asp Ala Met Thr Gly Gln Glu Ala Ala Ala Leu Thr Ala Ala
305 310 315 320

Phe Asp Glu Ala Val Gly Ile Thr Gly Ala Val Leu Thr Lys Met Asp
325 330 335

Gly Asp Thr Arg Gly Gly Ala Ala Leu Ser Val Arg Glu Val Ser Gly
340 345 350

Lys Pro Ile Lys Phe Thr Gly Val Gly Glu Lys Met Glu Ala Leu Glu
355 360 365

Pro Phe Tyr Pro Glu Arg Met Ala Ser Arg Ile Leu Gly Met Gly Asp
370 375 380

Val Val Thr Leu Val Glu Arg Ala Gln Gln Val Val Lys Asn Glu Glu 385 390 395 400

Ala Glu Gln Met Arg Asp Lys Ile Leu Ser Ala Thr Phe Asp Phe Asn
405 410 415

Asp Phe Ile Lys Gln Met Glu Met Met Gly Gln Met Gly Gly Met Asp
420 425 430

Gly Phe Met Lys Leu Leu Pro Gly Met Ser Gly Met Ser Glu Arg Glu
435 440 445

Met Gln Glu Ala Asp Lys Ser Leu Lys Val Ala Lys Ser Leu Ile Leu
450 455 460

Ser Met Thr Ser Lys Glu Arg Gln Phe Pro Asp Ile Leu Val Ala Gly
465 470 475 480

Ala Ser Ala Lys Ser Arg Arg Lys Arg Ile Ile Glu Gly Ala Gly Arg
485 490 495

Ser Glu Lys Asp Leu Ser Gln Leu Ile Val Leu Phe Gly Ser Met Arg
500 505 510

Val Lys Met Gln Lys Met Thr Ala Glu Ile Thr Gly Ala Ser Ala Glu
515 520 525

Val Gly Leu Thr Pro Gln Leu Ser Glu Glu Asp Met Asn Thr Leu Ala
530 535 540

Asn Glu Gly Leu Arg Lys Asn Val Ser Pro Gly Met Val Arg Arg Leu
545 550 555 560

Arg Ile Arg Arg Leu Thr Gly Ser
565

<210> SEQ ID NO 78
<211> LENGTH: 481
<212> TYPE: PRT
<213> ORGANISM: Paulinella chromatophora

<400> SEQUENCE: 78

Met Phe Asp Glu Leu Ser Ala Arg Phe Glu Glu Ala Val Lys Ser Leu
1 5 10 15

Lys Gly Leu Ser Ala Ile Thr Glu Asn Asn Val Glu Asn Ala Leu Lys
20 25 30

Gln Val Arg Arg Ala Leu Ile Glu Ala Asp Val Ser Leu Val Val Val
35 40 45

Lys Glu Phe Met Glu Glu Val Arg Ser Lys Ser Ile Gly Ile Glu Val
50 55 60

Val Arg Gly Ile Lys Pro Asp Gln Lys Phe Ile Gln Val Val Tyr Glu
65 70 75 80

Gln Leu Ile Glu Ile Met Gly Ala Asn Asn Thr Pro Leu His Lys Gln
85 90 95

Ser His Thr Val Thr Val Val Leu Met Ala Gly Leu Gln Gly Ala Gly
100 105 110

Lys Thr Thr Ala Ala Ala Lys Leu Ala Leu Tyr Leu Lys Asn Gln Gly
115 120 125

Glu Lys Val Leu Met Val Ala Ala Asp Val Tyr Arg Pro Ala Ala Ile
130 135 140

Asp Gln Leu Phe Val Leu Gly Lys Gln Ile Asp Val Glu Val Phe Thr
145 150 155 160

Leu Asn Pro Glu Ser Ile Pro Glu Asp Ile Ala Ala Ala Gly Leu Gln
165 170 175

Lys Ala Ile Arg Glu Gly Phe Asp Tyr Leu Ile Val Asp Thr Ala Gly
180 185 190

```
Arg Leu Gln Ile Asp Thr Ala Met Met Gln Glu Met Val Arg Ile Arg
        195                 200                 205

Ser Ala Val Asn Pro Asn Glu Ile Leu Leu Val Val Asp Ser Met Ile
    210                 215                 220

Gly Gln Glu Ala Ala Glu Leu Thr Arg Ala Phe His Glu Gln Ile Gly
225                 230                 235                 240

Ile Thr Gly Ala Val Leu Thr Lys Leu Asp Gly Asp Ala Arg Gly Gly
                245                 250                 255

Ala Ala Leu Ser Ile Arg Lys Val Ser Gly Ala Pro Ile Lys Phe Ile
            260                 265                 270

Gly Thr Gly Glu Lys Val Glu Ala Leu Gln Pro Phe His Pro Glu Arg
        275                 280                 285

Met Ala Ser Arg Ile Leu Gly Met Gly Asp Ile Val Thr Leu Val Glu
    290                 295                 300

Lys Ala Gln Glu Glu Val Glu Leu Ala Asp Val Glu Lys Met Gln Arg
305                 310                 315                 320

Lys Leu Gln Glu Ala Ser Phe Asp Phe Ser Asp Phe Leu Gln Gln Met
                325                 330                 335

Arg Leu Val Lys Arg Met Gly Ser Leu Gly Gly Leu Met Lys Met Ile
            340                 345                 350

Pro Gly Met Asn Lys Ile Asp Ser Thr Met Leu Arg Glu Gly Glu Ala
        355                 360                 365

Gln Leu Lys Arg Ile Glu Ser Met Ile Gly Ser Met Thr Pro Thr Glu
    370                 375                 380

Arg Glu Lys Pro Glu Leu Leu Ala Ser Gln Pro Ser Arg Arg Gly Arg
385                 390                 395                 400

Ile Ala Lys Gly Ser Gly His Lys Ile Ala Asp Val Asp Lys Met Leu
                405                 410                 415

Val Asp Phe Gln Lys Met Arg Gly Phe Met Gln Gln Met Thr Lys Gly
            420                 425                 430

Asn Asn Phe Ala Asn Pro Leu Ser Met Gly Ala Asn Met Phe Ser Gln
        435                 440                 445

Pro Asn Met Thr Val Pro Gln Thr Lys Ile Ser Asn Thr Asn Glu Ser
    450                 455                 460

Arg Met Arg Asn Ser Arg Ala Thr Lys Lys Lys Lys Gly Phe Gly Gln
465                 470                 475                 480

Leu
```

<210> SEQ ID NO 79
<211> LENGTH: 498
<212> TYPE: PRT
<213> ORGANISM: Ostreococcus lucimarinus

<400> SEQUENCE: 79

```
Met Thr Arg Ala Asp Ala Phe Ala Gly Met Ser Asp Lys Leu Asp Lys
1               5                   10                  15

Ala Trp Ala Arg Leu Gln Gly Glu Lys Asp Leu Asn Ala Asp Asn Val
            20                  25                  30

Lys Ala Pro Leu Lys Asp Val Arg Arg Ala Leu Leu Glu Ala Asp Val
        35                  40                  45

Ser Leu Pro Val Val Arg Arg Phe Ile Ala Arg Cys Glu Glu Lys Ala
    50                  55                  60

Val Gly Met Lys Val Thr Lys Gly Val Glu Pro Gly Gln Met Leu Val
65                  70                  75                  80
```

-continued

```
Lys Cys Val Ala Asp Glu Leu Cys Glu Leu Met Gly Gly Val Gly Ala
                85                  90                  95

Glu Gly Ile Lys Phe Arg Asp Asp Gly Glu Pro Thr Val Val Leu Met
            100                 105                 110

Ala Gly Leu Gln Gly Val Gly Lys Thr Thr Ala Cys Gly Lys Leu Ser
        115                 120                 125

Leu Ala Leu Arg Lys Gln Gly Lys Ser Val Leu Leu Val Ala Thr Asp
    130                 135                 140

Val Tyr Arg Pro Ala Ala Ile Asp Gln Leu Lys Thr Leu Gly Lys Gln
145                 150                 155                 160

Ile Gly Val Pro Val Phe Asp Met Gly Val Asp Gly Asn Pro Pro Glu
                165                 170                 175

Ile Ala Ala Arg Gly Val Arg Lys Ala Lys Asp Glu Asp Ile Asp Val
            180                 185                 190

Val Ile Val Asp Thr Ala Gly Arg Leu Asn Ile Asp Glu Lys Leu Met
        195                 200                 205

Gly Glu Leu Lys Ala Thr Lys Glu Ala Thr Ser Ala Asp Glu Thr Leu
    210                 215                 220

Leu Val Val Asp Ala Met Thr Gly Gln Glu Ala Ala Thr Leu Thr Ala
225                 230                 235                 240

Ser Phe Asn Glu Ala Val Glu Ile Thr Gly Ala Ile Leu Thr Lys Met
                245                 250                 255

Asp Gly Asp Thr Arg Gly Gly Ala Ala Leu Ser Val Arg Glu Val Ser
            260                 265                 270

Gly Lys Pro Ile Lys Phe Thr Gly Val Gly Glu Lys Met Asp Ala Leu
        275                 280                 285

Glu Pro Phe Tyr Pro Glu Arg Met Thr Ser Arg Ile Leu Gly Met Gly
    290                 295                 300

Asp Ile Val Ser Leu Val Glu Lys Val Gln Ala Gly Val Lys Glu Glu
305                 310                 315                 320

Glu Ala Glu Lys Ile Lys Gln Lys Ile Met Ser Ala Thr Phe Asp Phe
                325                 330                 335

Asn Asp Phe Val Gly Gln Leu Glu Met Met Asn Asn Met Gly Gly Met
            340                 345                 350

Lys Gln Ile Met Gln Met Met Pro Gly Thr Ala Lys Leu Ser Glu Ala
        355                 360                 365

Asp Met Glu Ala Ala Gly Lys Ser Met Thr Ile Ala Lys Ser Leu Ile
    370                 375                 380

Asn Ser Met Thr Lys Glu Glu Arg Gln Tyr Pro Asp Met Leu Val Ala
385                 390                 395                 400

Ser Thr Thr Ala Asp Ser Arg Arg Gln Arg Ile Val Lys Gly Ser Gly
                405                 410                 415

Arg Thr Glu Ala Asp Leu Ala Gln Leu Ile Met Met Phe Gly Gly Met
            420                 425                 430

Arg Thr Gln Met Gln Lys Met Ser Gly Gln Leu Gly Gly Gln Ala Gly
        435                 440                 445

Asp Val Gly Leu Gln Pro Gln Leu Ser Glu Ala Glu Leu Ser Lys Leu
    450                 455                 460

Ala Met Asn Lys Ile Arg Lys Thr Val Lys Pro Gly Met Val Arg Arg
465                 470                 475                 480

Gln Lys Ala Lys Lys Val Pro Lys Phe Leu Ala Glu Arg Glu Ser Phe
                485                 490                 495

Ser Gln
```

<210> SEQ ID NO 80
<211> LENGTH: 426
<212> TYPE: PRT
<213> ORGANISM: Ostreococcus tauri

<400> SEQUENCE: 80

```
Met Lys Val Thr Lys Gly Val Glu Pro Gly Gln Met Leu Val Lys Ala
1               5                   10                  15

Val Ala Asp Glu Leu Cys Glu Leu Met Gly Gly Val Gly Ala Glu Gly
            20                  25                  30

Ile Lys Phe Arg Asp Asp Gly Glu Pro Thr Val Ile Leu Met Ala Gly
        35                  40                  45

Leu Gln Gly Val Gly Lys Thr Thr Ala Cys Gly Lys Leu Ser Leu Ala
    50                  55                  60

Met Arg Lys Gln Gly Lys Thr Val Leu Leu Val Ala Thr Asp Val Tyr
65                  70                  75                  80

Arg Pro Ala Ala Ile Asp Gln Leu Lys Thr Leu Gly Thr Gln Ile Gly
                85                  90                  95

Val Pro Val Phe Asp Met Gly Val Asp Ala Ser Pro Pro Glu Val Ala
            100                 105                 110

Ala Arg Gly Val Arg Lys Ala Lys Glu Glu Asp Ile Asp Val Val Ile
        115                 120                 125

Val Asp Thr Ala Gly Arg Leu Asn Ile Asp Glu Lys Leu Met Ser Glu
    130                 135                 140

Leu Lys Asp Thr Lys Leu Ala Thr Lys Ala Asp Glu Thr Leu Leu Val
145                 150                 155                 160

Val Asp Ala Met Thr Gly Gln Glu Ala Ala Asn Leu Thr Ala Ser Phe
                165                 170                 175

Gln Arg Gly Asp Gly Arg Arg Thr Arg Arg Gly Gly Ala Ala Leu Ser
            180                 185                 190

Val Ala Arg Ser Phe Arg Lys Ala His Gln Phe Thr Ala Ser Val Lys
        195                 200                 205

Met Asp Ala Leu Glu Pro Phe Tyr Pro Glu Arg Met Thr Ser Arg Ile
    210                 215                 220

Leu Gly Met Gly Asp Ile Val Ser Leu Val Glu Lys Val Gln Ser Glu
225                 230                 235                 240

Val Lys Glu Ala Glu Ala Glu Lys Leu Lys Glu Lys Ile Leu Lys Ala
                245                 250                 255

Thr Phe Asp Phe Asn Asp Phe Val Thr Gln Leu Glu Met Met Asn Asn
            260                 265                 270

Met Gly Ser Met Lys Gln Ile Met Gln Met Leu Pro Gly Thr Thr Lys
        275                 280                 285

Leu Ser Glu Ser Glu Met Glu Ala Ala Glu Lys Ser Phe Lys Ile Ala
    290                 295                 300

Arg Ser Leu Ile Asn Ser Met Thr Lys Glu Glu Arg Gln Phe Pro Asp
305                 310                 315                 320

Met Leu Val Ala Ser Thr Thr Ala Glu Ser Arg Arg Ala Arg Ile Val
                325                 330                 335

Lys Gly Ser Gly Arg Thr Glu Ala Asp Leu Ala Gln Leu Ile Ile Met
            340                 345                 350

Phe Gly Ser Met Arg Gly Lys Met Gln Gln Leu Ser Gly Glu Leu Gly
        355                 360                 365

Gly Glu Ala Gly Asn Val Gly Leu Gln Pro Gln Leu Ser Ala Ala Glu
```

370 375 380

Leu Glu Lys Leu Thr Thr Asn Lys Leu Arg Lys Asn Ile Lys Pro Gly
385 390 395 400

Met Val Arg Arg Leu Lys Ser Lys Lys Ile Pro Ile Ala Lys Asn Gly
405 410 415

Asp Arg Met Gly Ile Ser Ala Ser Ala Asp
420 425

<210> SEQ ID NO 81
<211> LENGTH: 510
<212> TYPE: PRT
<213> ORGANISM: Volvox carteri

<400> SEQUENCE: 81

Met Ser Arg Pro Ala Ala Leu Arg Gly Ala Gly Asn Arg Lys Leu Thr
1 5 10 15

Ala Thr Val Thr Ala Ala His Leu Arg Gly Ile Ala Phe Thr Ser Ile
20 25 30

Arg Thr Cys Gln Gly Ala Lys Gly Gly Ser Leu Gly Leu Pro His Pro
35 40 45

Ser Pro Pro Leu Ala Leu Pro Arg Arg Gly Arg Gly Arg Gly Ala Ala
50 55 60

Val Val Val Arg Ala Ala Met Phe Asp Asn Leu Ser Lys Ser Leu Glu
65 70 75 80

Lys Ala Gln Arg Leu Ile Gly Gly Cys Glu Val Pro Gly Val Gly Val
85 90 95

Val Gly Lys Ser Gly Thr Leu Thr Ala Glu Asn Met Lys Glu Pro Leu
100 105 110

Lys Glu Val Arg Arg Ala Leu Leu Glu Ala Asp Val Ser Leu Pro Val
115 120 125

Val Arg Arg Phe Val Lys Lys Val Glu Glu Arg Ala Leu Gly Thr Lys
130 135 140

Val Ile Glu Gly Val Thr Pro Asp Val Gln Phe Ile Lys Val Val Ser
145 150 155 160

Asn Glu Leu Ile Glu Leu Met Gly Gly Gly Val Gly Ala Lys Asp Leu
165 170 175

Glu Pro Gly Phe Pro Gln Ile Ile Leu Met Ala Gly Leu Gln Gly Val
180 185 190

Gly Lys Thr Thr Ala Ala Gly Lys Leu Ala Leu Tyr Leu Lys Lys Ala
195 200 205

Lys Lys Ser Cys Leu Leu Val Ala Thr Asp Val Tyr Arg Pro Ala Ala
210 215 220

Ile Asp Gln Leu Val Lys Leu Gly Ala Ala Ile Asp Val Pro Val Phe
225 230 235 240

Glu Leu Gly Thr Gln Val Ser Gly Lys Pro Ile Lys Phe Val Gly Val
245 250 255

Gly Glu Lys Met Glu Ala Leu Glu Pro Phe Tyr Pro Glu Arg Met Ala
260 265 270

Ser Arg Ile Leu Gly Met Gly Asp Val Leu Thr Leu Tyr Glu Lys Ala
275 280 285

Glu Ala Ala Ile Lys Glu Glu Asp Ala Lys Ala Val Met Asp Arg Leu
290 295 300

Met Glu Glu Lys Phe Asp Phe Asn Asp Phe Leu Asn Gln Trp Lys Ser
305 310 315 320

Met Asn Asn Met Gly Gly Met Gln Ile Leu Lys Met Met Pro Gly Phe
325 330 335

Asn Lys Glu Arg Ser Asn Pro Glu Val Ile Ile Lys Ser Leu Ala Arg
340 345 350

Arg Arg Arg Val Ala Gln Asp Ser Gly His Ser Glu Ala Glu Val Ala
355 360 365

Lys Leu Met Thr Ala Tyr Thr Ala Met Arg Thr Gln Val Gly Gly Met
370 375 380

Ser Lys Leu Leu Lys Leu Gln Lys Ser Gly Gly Asp Pro Ser Gln Ala
385 390 395 400

Glu Lys Leu Leu Lys Glu Leu Val Ala Ser Ala Gly Lys Lys Val Ala
405 410 415

Pro Gly Lys Pro Pro Gly Asp Pro Ala Gly Ser Phe Ile Ser Thr Pro
420 425 430

Arg Thr Pro His Pro Pro Pro Gly Pro Leu Gly Pro Arg Ser Gln Val
435 440 445

Arg Arg Lys Lys Glu Lys Glu Pro Ile Ser Lys Ala Arg Gly Phe Gly
450 455 460

Ser Pro Ser Asn Phe Asn His Asp Leu Ser Pro Pro Gly Ser Ser Pro
465 470 475 480

Ala Ala Tyr Thr Tyr Thr Leu Ser Arg Leu Ser Cys Gln Arg Leu Cys
485 490 495

Asp Gly Gly Gly Leu Leu Asp Asp Trp Asn Leu Trp Arg Arg
500 505 510

<210> SEQ ID NO 82
<211> LENGTH: 448
<212> TYPE: PRT
<213> ORGANISM: Phaeodactylum tricornutum

<400> SEQUENCE: 82

Met Ser Glu Ala Ser Ile Gln Pro Ala Leu Arg Glu Val Arg Arg Ala
1 5 10 15

Leu Leu Asp Ala Asp Val Asn Val Asp Val Ala Asp Thr Leu Ile Glu
20 25 30

Gly Val Arg Ala Arg Ser Leu Gly Gln Glu Val Leu Glu Gly Val Thr
35 40 45

Ala Glu Gln Gln Phe Val Lys Ala Met Tyr Asp Glu Leu Leu Asp Met
50 55 60

Met Gly Gly Asp Ser Ser Val Pro Met Ser Asp Gly Pro Ser Asn Val
65 70 75 80

Pro Val Ala Thr Leu Ala Ser Gly Thr Ala Ala Asp Pro Ala Val Ile
85 90 95

Leu Leu Ala Gly Leu Gln Gly Ala Gly Lys Thr Thr Ala Ala Gly Lys
100 105 110

Leu Ala Leu Phe Leu Lys Glu Gln Arg Lys Val Leu Leu Val Ala Ala
115 120 125

Asp Ile Tyr Arg Pro Ala Ala Ile Lys Gln Leu Gln Val Leu Gly Glu
130 135 140

Ser Ile Gly Val Glu Val Phe Thr Lys Gly Thr Asp Val Asp Pro Val
145 150 155 160

Glu Ile Val Asn Ala Gly Ile Gln Lys Ala Arg Asp Glu Gly Tyr Asp
165 170 175

Thr Val Ile Val Asp Thr Ala Gly Arg Gln Val Ile Asp Thr Asp Leu
180 185 190

```
Met Asp Glu Leu Gln Arg Met Lys Arg Ala Ala Ser Pro Gln Glu Thr
        195                 200                 205

Leu Leu Ile Val Asp Ala Met Thr Gly Gln Glu Ala Ala Ser Leu Thr
    210                 215                 220

Ala Ala Phe Asp Ser Ala Ile Gly Leu Thr Gly Ala Ile Leu Thr Lys
225                 230                 235                 240

Met Asp Gly Asp Ser Arg Gly Gly Ala Ala Val Ser Val Arg Gly Val
                245                 250                 255

Ser Gly Lys Pro Ile Lys Phe Val Gly Thr Gly Glu Lys Thr Ala Asp
            260                 265                 270

Leu Glu Pro Phe Tyr Pro Asp Arg Met Ala Ser Arg Ile Leu Gly Met
        275                 280                 285

Gly Asp Val Val Ser Leu Val Glu Lys Ala Ala Ser Glu Val Ser Asp
    290                 295                 300

Ala Asp Ala Leu Lys Met Gln Gln Lys Met Leu Asp Ala Ser Phe Asp
305                 310                 315                 320

Phe Asp Asp Phe Val Lys Gln Ser Glu Leu Val Thr Lys Met Gly Ser
                325                 330                 335

Val Ala Gly Ile Ala Lys Leu Met Pro Gly Met Ala Asn Gln Leu Asn
            340                 345                 350

Met Asn Gln Ile Arg Glu Val Glu Ala Arg Leu Lys Lys Ser Lys Ser
        355                 360                 365

Met Ile Ser Ser Met Thr Lys Lys Glu Arg Ala Asn Pro Glu Leu Leu
    370                 375                 380

Ile Lys Asp Ser Ser Ala Arg Ser Arg Leu Ile Arg Ile Thr Lys Gly
385                 390                 395                 400

Ser Gly Cys Gly Leu Asp Glu Gly Gln Gln Phe Met Ser Glu Phe Gln
                405                 410                 415

Arg Met Lys Thr Met Met Ser Thr Arg Arg Phe Trp Arg Phe Trp Leu
            420                 425                 430

Met Ile Gln Ser Leu Ala Leu Ala Val Thr Arg Pro Glu Asn Thr Val
        435                 440                 445
```

<210> SEQ ID NO 83
<211> LENGTH: 486
<212> TYPE: PRT
<213> ORGANISM: Thalassiosira pseudonana

<400> SEQUENCE: 83

```
Met Phe Asp Gln Leu Ser Asn Ala Leu Thr Glu Val Ala Lys Asn Phe
1               5                   10                  15

Gly Gly Lys Gln Arg Met Thr Glu Asn Ser Ile Gln Pro Ala Leu Lys
            20                  25                  30

Ser Val Arg Arg Ala Leu Leu Asp Ala Asp Val Asn Leu Asp Val Ala
        35                  40                  45

Thr Ala Leu Ile Asp Gly Val Lys Arg Arg Ser Leu Gly Lys Glu Val
    50                  55                  60

Thr Lys Gly Val Thr Ala Glu Gln Gln Phe Ile Lys Ala Met Tyr Asp
65                  70                  75                  80

Glu Leu Leu Asp Met Met Gly Gly Glu Ala Asn Glu Ser Asn Thr Met
                85                  90                  95

Ala Thr Leu Ala His Ser Ser Val Ala Asn Glu Pro Ala Val Ile Leu
            100                 105                 110

Leu Ala Gly Leu Gln Gly Ala Gly Lys Thr Thr Ala Ala Gly Lys Leu
```

```
        115                 120                 125

Ala Phe Arg Leu Pro Lys Arg Asn Arg Lys Val Leu Leu Val Ala Ala
    130                 135                 140

Asp Val Tyr Arg Pro Ala Ala Ile Glu Gln Leu Gln Ile Leu Gly Lys
145                 150                 155                 160

Gln Ile Gly Val Glu Val Phe Ser Met Gly Val Asp Ala Asp Pro Ala
                165                 170                 175

Asp Ile Ala Lys Glu Ala Val Glu Lys Ala Lys Arg Glu Gly Phe Asp
            180                 185                 190

Thr Val Val Val Asp Thr Ala Gly Arg Gln Val Val Asp Glu Glu Leu
        195                 200                 205

Met Glu Glu Leu Arg Arg Val Lys Lys Thr Val Glu Pro Asp Glu Thr
    210                 215                 220

Leu Leu Val Val Asp Ala Met Thr Gly Gln Ala Ala Ala Ser Leu Thr
225                 230                 235                 240

Ala Ser Phe Asp Ala Ala Val Gly Ile Ser Gly Ala Ile Leu Thr Lys
                245                 250                 255

Leu Asp Gly Asp Ser Arg Gly Gly Ala Ala Val Ser Ile Arg Gly Val
            260                 265                 270

Ser Gly Lys Pro Ile Lys Phe Val Gly Val Gly Glu Lys Thr Asn Asp
        275                 280                 285

Leu Glu Pro Phe Tyr Pro Asp Arg Met Ala Ser Arg Ile Leu Gly Met
    290                 295                 300

Gly Asp Val Ile Ser Leu Val Glu Lys Ala Ser Met Glu Val Ser Asp
305                 310                 315                 320

Ala Asp Ala Ala Lys Met Gln Glu Lys Met Ala Lys Ala Glu Phe Asp
                325                 330                 335

Phe Asp Asp Phe Met Thr Gln Ser Arg Met Val Ser Lys Met Gly Ser
            340                 345                 350

Met Ala Gly Val Ala Lys Met Leu Pro Gly Met Gly Asn Met Ile Asp
        355                 360                 365

Ser Ser Gln Met Arg Gln Val Glu Glu Arg Ile Lys Arg Ser Glu Ala
    370                 375                 380

Met Ile Cys Ser Met Asn Lys Lys Glu Arg Ala Asn Pro Gly Leu Leu
385                 390                 395                 400

Leu Thr Asp Lys Ser Ala Arg Ser Arg Leu Met Arg Ile Thr Lys Gly
                405                 410                 415

Ser Gly Leu Ala Phe Glu Asp Gly Leu Ala Phe Met Ser Glu Phe Gln
            420                 425                 430

Lys Met Arg Thr Met Ile Ser Arg Met Ala Lys Gln Thr Gly Met Gly
        435                 440                 445

Gln Pro Asp Gly Glu Gly Glu Met Glu Pro Ala Met Ala Gly Asn Arg
    450                 455                 460

Asn Ala Arg Arg Ala Ala Lys Lys Lys Gly Lys Lys Gly Gly Arg Gly
465                 470                 475                 480

Gly Gly Met Gly Phe Ala
                485
```

<210> SEQ ID NO 84
<211> LENGTH: 530
<212> TYPE: PRT
<213> ORGANISM: Aureococcus anophagefferens

<400> SEQUENCE: 84

-continued

```
Met Thr Met Ala Arg Arg Ala Ala Thr Ala Ala Leu Val Leu Ala Ala
1               5                   10                  15

Ala Trp Ala Phe Ala Pro Pro Gln Thr Lys Arg Ala Thr Thr Gln Leu
            20                  25                  30

Tyr Phe Phe Asp Lys Leu Ala Glu Ser Ile Thr Ala Ala Thr Asp Val
        35                  40                  45

Leu Ser Gly Lys Ser Arg Met Thr Glu Ala Asn Thr Lys Ser Ala Leu
    50                  55                  60

Arg Asp Val Arg Arg Ser Leu Leu Asp Ala Asp Val Ala Lys Val Val
65                  70                  75                  80

Val Asp Gly Phe Val Glu Asn Val Gln Ala Ser Ala Leu Asp Gly Glu
                85                  90                  95

Val Ala Glu Gly Val Asp Pro Gly Gln Gln Phe Val Lys Ile Val Tyr
            100                 105                 110

Asp Glu Leu Lys Arg Val Met Gly Gly Asp Asp Asp Glu Leu Leu Phe
        115                 120                 125

Ser Asp Asp Pro Glu Ala Ala Ala Lys Ala Arg Ala Gly Leu Ala Tyr
    130                 135                 140

Arg Asp Asp Gly Ala Pro Thr Val Val Leu Leu Cys Gly Leu Gln Gly
145                 150                 155                 160

Ala Gly Lys Thr Thr Ala Ala Ala Lys Leu Ala Leu Arg Leu Lys Glu
                165                 170                 175

Glu Glu Gly Lys Thr Pro Met Leu Val Ala Ala Asp Val Tyr Arg Pro
            180                 185                 190

Ala Ala Val Glu Gln Leu Gln Ile Leu Gly Glu Gln Val Gly Val Pro
        195                 200                 205

Val Tyr Ala Glu Ala Phe Glu Ala Gly Ala Gly Asp Ala Val Ala Ile
    210                 215                 220

Ala Thr Ala Gly Val Arg Ala Ala Lys Glu Arg Gly Ala Asp Val Val
225                 230                 235                 240

Ile Val Asp Thr Ala Gly Arg Gln Val Ile Glu Glu Ser Leu Met Ala
                245                 250                 255

Glu Leu Arg Ser Val Arg Ala Ala Thr Lys Pro Asp Glu Thr Leu Leu
            260                 265                 270

Val Leu Asp Ala Met Thr Gly Gln Asp Ala Ala Ser Leu Ala Lys Arg
        275                 280                 285

Phe Asp Asp Ala Cys Pro Leu Thr Gly Ser Val Leu Thr Lys Leu Asp
    290                 295                 300

Gly Asp Ala Arg Gly Gly Ala Ala Leu Ser Val Arg Ala Val Ser Gly
305                 310                 315                 320

Lys Pro Ile Lys Phe Val Gly Val Gly Glu Lys Val Gly Asp Leu Glu
                325                 330                 335

Pro Phe Phe Pro Ala Arg Met Ala Ser Arg Ile Leu Gly Met Gly Asp
            340                 345                 350

Val Val Ser Leu Val Glu Lys Ala Ser Lys Gln Gln Ser Ala Ala Glu
        355                 360                 365

Ala Lys Ala Val Met Glu Arg Thr Lys Gln Ala Lys Phe Asn Phe Asp
    370                 375                 380

Asp Tyr Leu Asp Gln Ala Arg Met Val Ser Asn Met Gly Ser Phe Gly
385                 390                 395                 400

Ala Val Ala Lys Met Met Pro Gly Met Gly Gly Ile Asp Asn Asp Gln
                405                 410                 415

Ile Ala Ala Ala Glu Ala Lys Ile Lys Ile Gln Ala Ser Leu Ile Asn
```

```
            420                 425                 430

Ser Met Thr Pro Lys Glu Arg Gly Glu Pro Asp Leu Ile Ile Arg Asp
        435                 440                 445

Lys Ser Ala Leu Ala Arg Gln Lys Arg Ile Ala Ala Gly Ser Gly Arg
    450                 455                 460

Ser Val Asp Gln Ala Lys Gln Phe Leu Ser Glu Phe Gln Gln Met Arg
465                 470                 475                 480

Thr Met Met Ala Lys Met Ala Gly Gln Ala Pro Pro Asp Gly Ala Asp
                485                 490                 495

Ala Ala Ala Ala Pro Asp Pro Asp Ala Leu Leu Asn Arg Ala Ala Arg
            500                 505                 510

Arg Ala Lys Lys Lys Lys Gly Gly Lys Arg Lys Leu Lys Thr Ala Gly
        515                 520                 525

Phe Gly
    530


<210> SEQ ID NO 85
<211> LENGTH: 556
<212> TYPE: PRT
<213> ORGANISM: Ectocarpus siliculosus

<400> SEQUENCE: 85

Met Ile Met Ala Ser Leu Lys His Arg Ser Pro Pro Arg Gly Gly Ala
1               5                   10                  15

Ala Ala Thr Leu Ser Phe Phe Cys Cys Val Cys Ala Leu Phe Ala Gln
            20                  25                  30

Ser Ser Val Ala Phe Val Pro Ala Gly Gly Leu Ser Arg Cys Gly Val
        35                  40                  45

Asn Asp Arg Ser Ser Ser Ser Cys Arg Ala Ala Ala Ile Gly Ala Ala
    50                  55                  60

Gly Arg Ser Ser Leu Pro Val Ser Arg Ser Ser Ser Arg Arg Gly Arg
65                  70                  75                  80

Arg Gly Gly Cys Ala Gly Gly Ala Ser Ser Pro Leu Gly Met Met Phe
                85                  90                  95

Asp Thr Leu Ala Glu Asn Met Ala Gly Val Ala Asn Leu Phe Thr Gly
            100                 105                 110

Gln Lys Thr Ile Thr Glu Ser Ser Val Glu Gly Ala Leu Asn Glu Val
        115                 120                 125

Lys Arg Ala Leu Leu Asp Ala Asp Leu Asn Leu Met Val Thr Asn Thr
    130                 135                 140

Leu Val Asp Ala Val Lys Ser Lys Ala Val Gly Met Lys Leu Val Asp
145                 150                 155                 160

Gly Val Thr Ala Lys Gln Gln Phe Val Asn Val Met Asn Asp Glu Leu
                165                 170                 175

Val Glu Ile Met Gly Ala Glu Gln Ala Pro Leu Ala Arg Arg Thr Asp
            180                 185                 190

Gly Lys Pro Thr Val Ile Leu Leu Ala Gly Leu Gln Gly Thr Gly Lys
        195                 200                 205

Thr Thr Ala Ala Ala Lys Leu Ala Lys Tyr Leu Gln Gln Glu Glu Glu
    210                 215                 220

Pro Lys Lys Val Leu Leu Val Ala Gly Asp Val Tyr Arg Pro Ala Ile
225                 230                 235                 240

Asp Gln Leu Ile Ser Leu Gly Lys Arg Ile Asp Val Glu Val Phe Ser
                245                 250                 255
```

-continued

```
Met Gly Gln Gly Val Asp Pro Val Glu Ile Thr Lys Ala Gly Leu Glu
            260                 265                 270

Arg Ala Val Glu Gly Glu Phe Asp Thr Val Ile Val Asp Thr Ala Gly
        275                 280                 285

Arg Gln Val Val Asp Asp Thr Leu Met Thr Glu Leu Lys Asp Ile Gln
    290                 295                 300

Val Ala Ser Glu Ala Asp Glu Val Leu Leu Val Val Asp Ala Met Thr
305                 310                 315                 320

Gly Gln Glu Ala Ala Thr Leu Ala Ser Val Phe Asn Glu Lys Ile Gly
                325                 330                 335

Ile Thr Gly Ala Val Leu Thr Lys Met Asp Gly Asp Thr Arg Gly Gly
            340                 345                 350

Ala Ala Leu Ser Val Gln Gly Val Ser Gln Lys Pro Ile Lys Phe Val
        355                 360                 365

Gly Ile Gly Glu Lys Met Ser Glu Glu Glu Ala Ala Lys Leu Ala Lys
    370                 375                 380

Lys Met Ile Asn Ala Glu Phe Asp Phe Asn Asp Phe Leu Lys Gln Ala
385                 390                 395                 400

Lys Met Met Lys Gly Met Gly Ser Leu Gly Gly Val Ala Asn Met Ile
                405                 410                 415

Pro Gly Met Ala Gly Lys Ile Thr Pro Gln Gln Leu Asn Gln Ala Glu
            420                 425                 430

Glu Gly Val Gln Arg Ala Glu Gly Leu Ile Lys Phe Met Thr Pro Glu
        435                 440                 445

Glu Arg Arg Thr Pro Lys Leu Leu Ile Leu Asp Pro Thr Ser Gln Ala
    450                 455                 460

Arg Cys Arg Arg Ile Ala Arg Asp Ala Gly Val Lys Leu Ser Ala Val
465                 470                 475                 480

Ser Ala Phe Leu Lys Glu Phe Gln Ala Met Gln Ser Asn Met Ser Arg
                485                 490                 495

Met Gly Lys Gln Met Ala Asp Gly Asp Pro Asn Ala Gly Pro Gly Gly
            500                 505                 510

Gln Pro Ser Pro Phe Gln Gly Leu Gly Gly Asp Thr Ala Pro Gly Ala
        515                 520                 525

Ala Pro Ser Met Asn Arg Gln Gln Arg Arg Gln Ser Lys Lys Asn Lys
    530                 535                 540

Ala Gly Arg Ser Ala Ala Pro Ser Lys Gly Phe Gly
545                 550                 555
```

<210> SEQ ID NO 86
<211> LENGTH: 28452
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 86

```
cgtctgatta aaccacgctg ggagattaga taatgaagcg tgcgcctgtt attccaaaac      60

atacgctcaa tactcaaccg gttgaagata cttcgttatc gacaccagct gccccgatgg     120

tggattcgtt aattgcgcgc gtaggagtaa tggctcgcgg taatgccatt actttgcctg     180

tatgtggtcg ggatgtgaag tttactcttg aagtgctccg gggtgatagt gttgagaaga     240

cctctcgggt atggtcaggt aatgaacgtg accaggagct gcttactgag gacgcactgg     300

atgatctcat cccttctttt ctactgactg gtcaacagac accggcgttc ggtcgaagag     360
```

```
tatctggtgt catagaaatt gccgatggga gtcgccgtcg taaagctgct gcacttaccg    420
aaagtgatta tcgtgttctg gttggcgagc tggatgatga gcagatggct gcattatcca    480
gattgggtaa cgattatcgc ccaacaagtg cttatgaacg tggtcagcgt tatgcaagcc    540
gattgcagaa tgaatttgct ggaaatattt ctgcgctggc tgatgcggaa aatatttcac    600
gtaagattat tacccgctgt atcaacaccg ccaaattgcc taaatcagtt gttgctcttt    660
tttctcaccc cggtgaacta tctgcccggt caggtgatgc acttcaaaaa gcctttacag    720
ataaagagga attacttaag cagcaggcat ctaaccttca tgagcagaaa aaagctgggg    780
tgatatttga agctgaagaa gttatcactc ttttaacttc tgtgcttaaa acgtcatctg    840
catcaagaac tagtttaagc tcacgacatc agtttgctcc tggagcgaca gtattgtata    900
agggcgataa aatggtgctt aacctggaca ggtctcgtgt tccaactgag tgtatagaga    960
aaattgaggc cattcttaag gaacttgaaa agccagcacc ctgatgcgac ctcgttttag   1020
tctacgttta tctgtcttta cttaatgtcc tttgttacag gccagaaagc ataactggcc   1080
tgaatattct ctctgggccc actgttccac ttgtatcgtc ggtctgataa tcagactggg   1140
accacggtcc cactcgtatc gtcggtctga ttattagtct gggaccacgg tcccactcgt   1200
atcgtcggtc tgattattag tctgggacca cggtcccact cgtatcgtcg gtctgataat   1260
cagactggga ccacggtccc actcgtatcg tcggtctgat tattagtctg ggaccatggt   1320
cccactcgta tcgtcggtct gattattagt ctgggaccac ggtcccactc gtatcgtcgg   1380
tctgattatt agtctggaac cacggtccca ctcgtatcgt cggtctgatt attagtctgg   1440
gaccacggtc ccactcgtat cgtcggtctg attattagtc tgggaccacg atcccactcg   1500
tgttgtcggt ctgattatcg gtctgggacc acggtcccac ttgtattgtc gatcagacta   1560
tcagcgtgag actacgattc catcaatgcc tgtcaagggc aagtattgac atgtcgtcgt   1620
aacctgtaga acggagtaac ctcggtgtgc ggttgtatgc ctgctgtgga ttgctgctgt   1680
gtcctgctta tccacaacat tttgcgcacg gttatgtgga caaaatacct ggttacccag   1740
gccgtgccgg cacgtgatcg cgcaggctca gctgcacagc agacgcaagg gacagctcag   1800
catctggaac cgccgacacc aggtgctgag gatgctgcac ctttggcaac cccaataggt   1860
gcttttgggc gtactgctgt gcctgcgcct agggacattg actggtggcg ggtcccgaag   1920
gagctgatgg gaagctacgc acaagctgaa gctggagaca gcagctccac caatgttgac   1980
ttctctgggg agcctccggc cagcagcgtg tacaacgaga gggggacgc gttagtggag   2040
caggaggtga aggcagcaac ggcgggtgtg gattttgctg gcaggaggag ggccaggggg   2100
ttgttggaca atgctgagcc tcccgatctt gataatggcc ctggagagca gccagcaggg   2160
gcaacagtga gttggagctg gaggcgattc agggataggc agggataggc agtgtagtgg   2220
ccagaactgg ctgctggaac ctggggttac tcagggtgaa cgcaggcaaa ggggtgcagg   2280
tgtattgaag ctcttaatat aagagagatg cgtcgaacat atatggtgat agtcttgagt   2340
ggtgtgttgg gtggaaggct gctgtttacg gtgcaggaag ttttcctggt acggtcgtta   2400
tgtaatgcag cagcacgtat gtaagaacca gtcgacattt aacctatgca gtagcatata   2460
gttatgtgtc aaaatcataa attggcccta tttgtggcga gcctatcttt caaatactac   2520
tgttcctcgc actgtcctct aaaatttctc caaacaacgt tgtaaaggtg ctgatgttag   2580
catatcatct ctggcataac tggatgcacc cagccggcta acagtgggaa gatgaagagg   2640
ggcttgtaca ctacactttt cttgccaaga ctgttagctt gcccaagcca gcacagcgat   2700
```

```
tttcttgcaa caaacgtgag ccttgcatct gcttttgatt gcaacggccg actggtgagt   2760
tattgtgcaa gcagtgttct gctaaactgt tcagaccagg ttcgcagctg gctaagatcg   2820
gtatctggaa agctccaacg aacaggtttt caatacgtgc tgcgtcaata tgcccttctt   2880
gttcactaca gcgacctttc caatgttgga tgtgaacaaa tgtcgaagcg cacaataacc   2940
tgaaagacat tgttgctcat tccctttct ttggtagcgt aggtttgtat atttagagtt   3000
ccagttctgt actagttgct ctgcggcaac gattgaagtg tgtaccttat actgcacgtt   3060
aaatatgata ggttcagcgc ggttctttaa atgacaaaat aaatagtatt caacaaaaaa   3120
aaatagttgt ttgacatgtc actttttctt ttacataggt agcatgtcgt caaatcgtca   3180
atgcaaacca gcttgcgact aacgtaagca gtacagggga tagtacaatg agtttttcac   3240
cagcaatttg gtccagtgtt ttcgcaccgc cgtgaagcgc attcacatta aagtagcatc   3300
gctacacctg ttctcatctt gttaggttca aattttgcaa cgtgtagcta caaagtggca   3360
acagcgcagg ctgttggtca ctcgctaagg cttgcattgg caccctcgtt gctctgtgta   3420
ggagcgtgca tttgtgctca agactgttat ttttgacttc aaaaacttta tcgatagcgc   3480
actgcctcgt ttttacaaga tagccttctg tgagcagccc tgccccatgc gcctttaggc   3540
tttctgtggc aatgtctggt tcagctggat cgggccaggc tactctcaga catgacggtg   3600
gctctgctgg cggcagtggg cctgtctcag acggtttttc accggccggc ctgaaggtaa   3660
agtagaaaga cactcataca catcttggtt cggcgttgaa agtaggtcat taacatactc   3720
tataaccaat atttgtaggt tctggtcgtg gacgacgagt taaccttgga aatccctacc   3780
aggctattct ccacagcccg aaccccttaa gctagacgaa cacagttagc ataacttcgt   3840
ataggatact ttatacgaag ttatgcggcc gcccaccatg gggggaggttt gaagtgtgcg   3900
cctgatataa tcatacacct aaaagcacca cttgctgatt gtgaagggac tatgtcgttt   3960
atgacgggac gttacgctgg ccgatggttt gaatttggac gctgtggtag aatgttatat   4020
ggacgtaaag gttggcatat tgaaaatcgt cttcacaggc aaacttctag acgtgtgacc   4080
caccggtaaa acgacaagcg tggcgcgtcg attgcgcttt gaacgtcgtt tgttggactc   4140
cagatgaacc tcaaaatcaa agcggtgatt gacgaaaatc aaatgacagc ccgcaaaatt   4200
tcatcagcct tcggatcgga ttctcagaat ctgattgtcc ctgctggcta catttatgaa   4260
atttcgtaca ttttggcaga aatgtcccaa taccatagca ctgccgcctg agctcacccg   4320
agcaatgcat actgggtacc tcgcccatct cgccctcttt ccaagcccag tgctgttgta   4380
aatagccaaa gggctcagta acaatggcca aactgacatc cgctgttcct gtgttgacag   4440
caagagatgt tgcaggtgca gtggagtttt gtgagttctg agaagctgat tgttgtttaa   4500
cttctttgaa agctttatcg aagattctgc aagcgatgaa cattgcttgt caagaccgag   4560
agctgcatgc ccacttgaca tccagctttg aacggctctt catgtttgat ttgtttctga   4620
ttgtagggac agatagactg gggtttagca gggactttgt ggaggacgat tttgcaggag   4680
tggtgaggga tgatgtgaca ctgtttatct cagcagtgca ggatcaagtg agtgcagcgt   4740
cagctgtggc agttgttggc tttcgtctca gtcagtagtt tgctgggatt gattatggag   4800
ggcacagttg caattttgag ttgcacgttg cgacaagcgt gttgacaaag cgtggtcaag   4860
ccggccagtc ttgccggtgg cgggtggctt ggtctaactt ccgctctaca gcaatcgttt   4920
tgttcatggt tacggggctg gcgtgccaga aagtcctggt cagccaccct cgcttcaaag   4980
ccgtagccca acaactttgc gaatatgttc gatttgcagg tggtgcccga taatacactg   5040
gcatgggttt gggtgagagg tacagctctg cgtgcaacag gttgcaagat gcagcgcagg   5100
```

```
tcttccctgg tcaaacgatg tatgcagagt tgagaggcac ttgagctggg tgaatggcgt   5160
gggctcgtag gtagtgtgca gggcaggaag ggcagccaat tttggagttg tggtccggtg   5220
tcgttgcttc gagccttatt aggactcttg ctcatcaaag cgttagttgt gaataagttg   5280
atctgaaagg atgttatgta cagcaagcag cagcagttaa gagtctgggg agtagctgca   5340
cagggcgagg tgtcaagatg ggaagggtcc tgcctcctta tgtgttttc cctgtagggg   5400
aggaagcctc ttatgggcaa tggttgggca tattttccag ccagcccttc tttctatagg   5460
ggccagggtg ggcccagctc gtcttggctt ccaccaccag gagagtgagg gcattgaagg   5520
gccataaata gtcctcccat ctacgtgcac cagagggtgt cgtctaggct gtgcatgcca   5580
cgaggggaag gagccaagaa tgagtgtatg ggttgttttc atgtttaggc tgggataaaa   5640
ctgttttcaa ttgcgcctgc cgggtgaaaa ccacagcagc atcagcaagc ttggagaagg   5700
ccagcccgcc cagcacaggc tcacgttccc actcaggcgg tcagtcgggc gggggtgtga   5760
gtcaggcagg cgagggtgtc tgtgcctgac atcagcacct ctgcttagcc actgcagccc   5820
ctggagcagg gtagggcgtc atttgcagca atcacctgct gcctcacacg tcgcagcttg   5880
gaatttcaac gaccatcagc gctggggttg ttgagggatc atagcagatt ttggtgcagc   5940
ctggttgtca tgctctttgt ggaatggcct ctatgttcga gcaattcgtt ggatgttgag   6000
gtgcttgggg acagagagtc gaatgatggg ccagggtcaa acatgcgagc gtttggctga   6060
gtcagcggtt tttgctggtc actttttctt ttgtttctta tttaggtttg atggatgtgt   6120
tttgtgctgc tgccctgaag ctgcagcagc gtgtctgccc tgcgctactg cgggcaccaa   6180
ggctatgtgc tggtgcactc ggctgcgctg cacctgtgca cctcgcactc cgtccagcct   6240
ccatgcagca cacgtactca cggtgtcctc ctgacctgtc gtacgctatt ccaaacttgc   6300
tcttttgctg ccgctgctct cgtacacaat tgctgttgat tatcgatatc taatcgagcg   6360
cctgctgact gaactccgca ggtttggatg aactgtatgc agagtggtct gaagtggtga   6420
gcaccaactt taggtgggtg ggctctgaag gaggaggagg gagcgggtga ttaaacaggg   6480
cctgcatgaa gaggagcagg ggctgcatgg acagcagggg gaaggtgcag aagggagggt   6540
caagcggggt tcaggtggct gtgggtttct gcacgagcag tgaaagaagc tgtatccttc   6600
cacctgcttt cactggcgaa aggttgaaaa caggatgtcg cagctggaaa gatgttgcgc   6660
tgtcaagtgc aagccatggt tgagggtatg cctgtgtgca tgtgcttctt aaagttactc   6720
ctgttctatg gttctgggtg cttgttgttt gtggtgcagg gatgcaagcg gacctgcaat   6780
gacagagatt ggagaacaac cttggggaag ggagtttgca ttgagagatc ctgcaggtga   6840
gggggcatgt aagcaatggc aggcaattca agaacgaatc attgctgcaa atgctgggat   6900
ggtatgcagc tgaggtatct attgccttgt attttgtctc gcattgcatc ggtggtgcgt   6960
tctgtggcct gaggcacagt tcttgctgtt tgataagggt tcgactgagt tgtcgtgtgt   7020
gctgtgctgc aggcaattgc gtgcactttg ttgcagaaga acaggactga gcatagcatc   7080
agcctgtggc agggttgtgg tagggctgag tggcagggtt aaaggggttg cctaccccac   7140
ccctactctc atgacaccag caacagcagc agctcatgca gtactcaaat cactgatgtc   7200
aatggtgtga cacatttggt taaggctgct ttttaaagtg ctgctttggg ggcagtgact   7260
gtgcagagct tggagcgtat ccccatgtaa tcagaaccga cgagagttcg gggcaacctt   7320
tcatcttcac attttttgtg atcagctaca gagtctgaaa tcaaatagag gctgccatct   7380
aaacgcagga gtcacaacga aggcgaaaac tccaattgct gtactcaatg cactaagtga   7440
```

-continued

```
ttgttcaatg gataaataca ctatgctcaa ttcatgccag cagagctgct ccttccagcc   7500
agctacaatg gctttttcca cgccttttga agtatgaatg ttcagcttgc tgtgcttgat   7560
gcatcaccat aaacacaatt ctacaacatt tcatgccaac aacagtacgg gctttccctg   7620
caggcagttg gtacggcata ttatggttta aacatctatc ctccagatca ccagggccag   7680
tgaggccagt ttgcatagtt aagtatgctg gctattgcag taccttatat gcaaacaagt   7740
gctcaatctg tttcatcatt gtctgtgggc aaattgcctg ccaatattct ccagttattg   7800
cctgttgttt caaatgattg aaattggaag ttgtattgct ctacattttt gacttgtgat   7860
tttttcattt gttgatatct gacaactgtg aactgcactg aacttgctgt gcttataaat   7920
gcattttttt gttttgggcc acgttgattc cttgtgatac tttcctgcta tcaaaccaaa   7980
aatatactct catgactgac gtgcaacaaa tgcatggaag ctttcaacgt tacgacagct   8040
gcttgccccc catcagctat tctacatgtg taacctacct tgcatggcca ccacaacgct   8100
actgcatgca agatctggcg caactggatg tcccaatagt agaagtatcc ggattatctc   8160
cgagagtttt acatatgtaa tcgacgccat ttctgtcatc aactataaat ccattgctcc   8220
tgcatttctg gcactgacat tctaccacaa gcaataccaa tgttggagag cgacgagagc   8280
ggcctgcccg ccatggagat cgagtgccgc atcaccggca ccctgaacgg cgtggagttc   8340
gagctggtgg gcggcggaga gggcaccccc gagcagggcc gcatgaccaa caagatgaag   8400
agcaccaaag gcgccctgac cttcagcccc tacctgctga gccacgtgat gggctacggc   8460
ttctaccact tcggcaccta ccccagcggc tacgagaacc ccttcctgca cgccatcaac   8520
aacggcggct acaccaacac ccgcatcgag aagtacgagg acggcggcgt gctgcacgtg   8580
agcttcagct accgctacga ggccggccgc gtgatcggcg acttcaaggt gatgggcacc   8640
ggcttccccg aggacagcgt gatcttcacc gacaagatca tccgcagcaa cgccaccgtg   8700
gagcacctgc accccatggg cgataacgat ctggatggca gcttcacccg caccttcagc   8760
ctgcgcgacg gcggctacta cagctccgtg gtggacagcc acatgcactt caagagcgcc   8820
atccacccca gcatcctgca gaacgggggc cccatgttcg ccttccgccg cgtggaggag   8880
gatcacagca acaccgagct gggcatcgtg gagtaccagc acgccttcaa gaccccggat   8940
gcagatgccg gtgaagaata agcagcagct tgttatgcct tccccatggg catcagcatg   9000
ctgcaagctg tctagatatc cagctttcag tggaggttga gcgagggtca gcagcggttc   9060
cctggcgatg gcggtcagct tttctggaag ccttcactag gactgcgccc agcgcatgtg   9120
acgccaatcg aacttgtgtg caaggccaaa ttttgtgacc ctgtgctgca cttcatgtat   9180
tcaagaattg agaagaaatt tcattgctgc ccttctttca ctttaatttc catccctgga   9240
tccacctccc accattgtgg ttgatgggta ggggttttgg gtaggtgcag ttcgttgtgc   9300
acgttgacat gtgtaacggt gagcaaagga attgctgggc aagtagctat tgcagcttaa   9360
gggcatggtg aaacacttgt gctgtattta cagaggaagc cagacaggta aggagtgtgt   9420
ggcagcttgg aacaggaggg ctggtcgcaa caagtatgca tatcccatga ttgttgacat   9480
aagagcagca ggtgcatatt gccagccttt gtgaaagtgg attgaaaatc aattagttgg   9540
tgtgatagct gaggctaggc actgccaacc tgcagtgaaa tgaggctcca agaccgggta   9600
ataatacagg caatcgaatc cagttgaaat tacggcgatt aaatccaagc gagcgttgta   9660
agaacatctg cacctgtctg aagtagtgag cggataatga gcattgcttg ccttctatca   9720
ctatacctga cagttacgtg tcacacactc tcaagcacaa cacacagcgg caaagttact   9780
tgctaaacct cacagtcaag ctgaaaataa aggctaaatt acgtgagacc ggcgcgccat   9840
```

```
aacttcgtat aggatacttt atacgaagtt atcaccagat ataggtgacc cgataactta   9900
attaatcttg cgaagattga attgctaata gaaggttctc atctatacat gagttaccag   9960
tgaaccccat atctgctcta taatatagtc cccgctgagg cgcagtgctg aggttccagc  10020
tcgaacgagc cagtagggct tcgactcacg gctcatttat tttagagcta ggttgacttc  10080
ccagtctcat gcaatacatg agagcaggtg ttggtcgcac gcctctctca cggtgcctct  10140
tgattttcgg ccccttgcac ccgctctcat atgacatatt cgcgctgcac ccttgctcag  10200
agcaggcgca gcatgtggag tagcgggcgc aagccgtaat gaggagtctc agctcaacat  10260
gattgaggtc agcatcactg taacaataca aatcattgtg gtgccttata tatttggtaa  10320
atgctcgctg cagtattcaa atcgaccttc actgcaagca actcgattga actacgcgcg  10380
ttattgaagg cacatacaac cgggagttca gaggagtatg cccaagaaga agcggaaagt  10440
cgggagcaat ctgttgaccg tgcatcaggt atcgagaaga actaaagagc gttcaaacgc  10500
atcaatattt tgctaaagag ctttacatct ttttggggct attttctggc tactcggtag  10560
tgacttgacc actttcttcc caagtggggg caagccgata agccgctgtg accgttgatt  10620
tttttataaa agacgtagac atgttcaatc agccacaatt gatatgcttg aatacagaac  10680
ctgcccgcat tgcctgttga cgcaacatct ggtgagctgc ggttgctatc ctcccaatat  10740
aacctgaagt catgcatata ttcgcactaa tctacatccc atgttgtgtt gagctattcg  10800
gtattgatgc cagctcagtg aactaattat caaatgtata tcggtgctgc cagaatcgat  10860
ccatgtatca atgccacaag taactggaga tacatttgct acatgtagat gaggtgcgca  10920
agaacctgat ggacatgttt agggaccgcc aagccttcag cgagcataca tggaagatgc  10980
tgctgagcgt gtgcagatct tgggcagcat ggtgtaagct gaacaaccgc aagtggttcc  11040
cagcagaacc cgaaggtatg cctgggtaac tgtcaaaatc atgtatattc ccgcaatgca  11100
agtggttcat tgttgtgctt tacgttaaag acgtgtcagc tgcaggagaa ttattttgag  11160
gatgattgtc cgttgttggc gatgtcttgc attgtgaagt atgttttgaa gtcatacagg  11220
aagtgtgaaa tcccaaagca gctggctgcc gctgcatgcg accagtcatt cacctgcatt  11280
gtgtgtgctg tagatgtgag ggactatctg ctgtacctgc aagcaagggg actggcagtg  11340
aagaccattc agcagcatct gggacagctg aacatgctgc ataggaggtc tggactgcct  11400
aggccaagcg atagcaatgc agtgtctctg gtgatgcgcc gcattagaaa ggagaacgtg  11460
gatgctgggg agagggcaaa acaagcactg gcatttgagc gcaccgactt tgaccaagtg  11520
aggtgggctt cgcaactgct gcctgaactt cctgttcctg tgcatgtaca tgagagtcgg  11580
ttggaacagg ctcatactgc gcctgattga taggctgtcc cacattgttt tatttgctgt  11640
atcgatgtat tcattttgca ttgggtcctt tctgctcatg aagcaccaag aaggctggct  11700
gtcaatggca tgccagctca tgccatctgg atgacattat gcaagaccag tgttgactcg  11760
aacatgaatc ttactggaaa ctttaatgaa tgctttcgag ctttttgtgc aggtctctga  11820
tggagaactc agaccgctgc caagacatcc gcaatctggc atttctgggg atcgcctaca  11880
acacactgct gaggattgcc gagatcgcac gcattagggt gaaggacatt agccgcacag  11940
atggagggag gatgctgatc catatcggga ggacaaagac cctggtgagc acagctggag  12000
tggagaaagc actgtctctg ggagtgacca aggtaagctt accatgtgtt tatatgaagc  12060
tgatatttgg aagaaaggag gaagcaacga caacaagggc ggtgcacaat ctattgccgc  12120
ttttgaatct tgcccgcaaa ggcagtcgat gattgctcac tgtatcaggt tgatttagtt  12180
```

gatgaggtgt agctggggaa gctccaatcc ccagtccaga tagccttggt tatgaattgc 12240
ataatgtagg caccacttgc actggtccta aaccccagtt cattcctgtc cttctcgtgc 12300
attttgtcaa atgaacatgc aaccgagtgt gttttcctac tcgacatgtg tgcgattgcc 12360
cacgtgtgct gcagctggtg gaacggtgga ttagcgtgtc tggagtggca gatgacccca 12420
acaactacct gttttgccgc gtgcgcaaga atggagttgc tgcacctagc gcaaccagtc 12480
aactgtctac aagggcactg gaggggatct ttgaggcaac acatcgcctg atctacgggg 12540
caaaggatga ttctgggcag aggtatctgg cctggtctgg acattctgca agggttggag 12600
cagcaaggga catggcaaga gctggagtga gcattcccga gatcatgtga gaggccccag 12660
caaaaacaac agcactagct gttgctgctc agtttgtgct cgtgatgttt gaaaggaatg 12720
gacaaggttc atccatgatg ttcattatct gggctggtct tgtacatggg gttattctat 12780
actaaacagg agcgatacaa ataacaaaca atcaatgtct atatacacat atacttggct 12840
aaatttttct cccggcctta catacataac aaaggctaaa ctaattgacc caaaataatt 12900
gtatgaataa tcaaattgat gcatacaaat aatcctaaaa atgaaaaaaa tttcattgaa 12960
ataagtatag aaataacaaa tgtttgaccc acagccctca ctctccaacc caatcctgcc 13020
tctcacaaga cttgccatgt accaacttac aatgacagcg agctacaaca agttccatca 13080
aggtgtgggt tgctattagt tggtggaacg tttgtacatt tcacagttgg acatgcactt 13140
gcgaaaaagg cgttggcttc agtgaggcag tgcttgctcg tatcccctcc aagcatgcct 13200
tgtgcaccca ttttgcaacg caggcaagct ggagggtgga caaacgtgaa catcgtgatg 13260
aactacatcc gcaacctgga cagcgagact ggagcaatgg tgagactgct ggaggatggg 13320
gattaatcag gatgttttga gcggttgtag gttctgtagt tgtatggtag gttgcatgga 13380
ggaaataggc caacaacaat tccaaatcaa aggagattgt agcgttgctc ttggtccccc 13440
tgaaaatttt tgttgttatg tgtctataaa tctagttctg caccttgcaa actgtgggat 13500
gccctgtcca gagcagaagg taatcccaaa acagtcgaga aagtctcgtt gggtggttgt 13560
gtaaagtaca aatgtatgtt ttccaccttg tctttgtatt gtgcacgagc tacagcattg 13620
gtggaagggc ttatagctgc tgggtcatca tgctgtcctg ttcttgatgg tttaggtgtc 13680
atccctttca ctgactcagc gaaatcggat gcgtaccatt catgaacggt gttgcacttg 13740
ctgtttgtga aaggtactgc atgtgcattg tacaatagac tactataatg tctcatgcac 13800
gtggtcaatg atgtagattt ctggaatatg catcgtgtaa ttgattcgat gaacccctcg 13860
tttggaactc tatttgaaaa gcaatcgagt gtcattatcc ataatggatg atgatcatga 13920
gcattgcaaa tagcaccatt agaacaaact gaatattgta caccttgacc tggatatgca 13980
tccgtccttc atcccacttt attaaggcag gttataattg gcaaggagtc ggcagaatag 14040
tcgtttggtt ataccccagt tttagtgggg cctttggcag ctatattatg gtcgcgactg 14100
taaccgggtc cgtttaaagt tcgattacat ctcagaaata taattgggct gcatgttaga 14160
aacttttcgc cgggtataac cggggtataa tcggcatact gcccaatgac ggccagccgc 14220
tggtcagtga ccgtcaaacg gtcggacggt ctgcatcgca tgtgcgctga catgtcaagt 14280
gcatgcttct cttacattca ggcaaaagac tacaagtcat tgaagaattg tcaactcagt 14340
aagctgacaa ttacgttcat gaaggtcagt cgtatgaaac tcgtatttct ccctaagtcg 14400
ttactatgga aagtacatcg tgccacgtca tcgtcatcgt ggcaatgaca gatgatggat 14460
agggtggggt tggcattaat tgctatcatt ttctttgcag aaaacaaata cctggcacat 14520
aatttgttga taatcatatg tatgtatgtc cacatgtcaa cgttatatgt ataaaaatca 14580
agacttgttt gcttaactct aaatttaatg taagaatttc ggtaataatc tgatctacat 14640
tatcacttgt gattaatgtt gaaatttgtt atccttaatt atcgtgcttg gcacaacttt 14700
cagattttgt ctgctgtcac attcatgcag tttcatttgc agtaaattct caatcattta 14760
tgtagttgat aagaatattt gatctgcttt tcattaagca aattttgtta gctttctccc 14820
cttgattgtt cattcaatga gattacattg aatgatgtct acacatataa taagaacgca 14880
tgtctacaca aatctaaaaa tcagctgcac gctcccaatt actatcgcac actctgacac 14940
cagaccgtgc tgtgacaata taagctgcac tgacaaattt ggaaaacaca agattcagaa 15000
gaaaacaaat actggaaccc ctcacacacc acctttctac agcacaaaca cgaagcagta 15060
gccaaggtaa gaaaatccga tcaaaataca ttaaatcatg tctaatatac agcataagta 15120
tagctaatga aatcgttggt cgggccttaa taacacacag tctaccaaca cctagttggt 15180
aaataccgtt gctgatattg ctctgtacca gtaaaagagg gctgcgatga gcgtttttag 15240
tgcacttctt caacacggaa tatttttcac aaattggtat gagaaccaat tttgcaaaat 15300
gttcgccctg taaagtatcg ctctgggacg atcagcttga cgtaattgta ggcgaaaagg 15360
gcgttcaaag tgcagcttta tgtatgaacg tcataaaata taaagcatag cacaatcact 15420
gatagaaaat atttgtgcgc attaaaactc tcacttctgt tgcggataca acgacggaaa 15480
tgagaagctt gtgtaagaag caattcaagt tttcattttg tcatctaagg tgtgatcctc 15540
cgatattcat taccgaatgc tgatctgagt tggaaagatg gcaatattta gctgtgcaca 15600
ctttgacctc caggccttgg cgggaattta gtattctagc tttcctattg gaacgatagg 15660
ccagccaagt ctccagcttg tatacgctac accagcagac atgctctcaa tttagctgac 15720
agtgtcttca tatttgtatt atctgttgtg tctatgccga agaagaagcg caaggtgggc 15780
gactacaagg acgacgacga caagctggag ccaggtatgc ataacctttc aatagatgct 15840
gccgcgcctt gggttcgctg cctgtgtcct gaagtacttt tcaccaggtc tacatgcatg 15900
cagcaactaa tcgttagttg ttcctttgta aacagcgttt tctgtcttta ccatgattca 15960
ggcgagaagc cgtacaagtg tccagagtgc ggcaagagct tcagccagtc aggagcactg 16020
acccgccacc agagaacaca tacacgcgac aagaagtaca gcatcggcct ggacatcggc 16080
accaactctg ttggttgggc ggtgatcacc gacgagtaca aggtgccgag gtatgttatc 16140
tttgattgca ctacttgcag tcctggtggg cactattgtt gtgcataggc gctcttttgc 16200
attcatgtat tgaatgtaga gaagttgtac actcctccta ggagactagc tgatggagtc 16260
ctgtattaaa tttgttcaca tcatatgcct tacagcatga tccattagaa gtaactaaat 16320
ttctaagcac ccagtctgag aaaccagatc gatggcaagt tgctcttggc ttgctgtgct 16380
tgcagcaaga agttcaaggt gctgggcaac accgaccgcc acagcatcaa gaagaacctg 16440
atcggcgcgc tgctgttcga ttctggcgag acagcagagg cgacacgcct gaagagaaca 16500
gcacgcagac gctacacacg ccgcaagaac cgcatctgct acctccagga gatcttcagc 16560
aacgagatgg cgaaggtgga cgacagcttc ttccacaggc tggaggagtc gttcctggtg 16620
gaggaggaca agaagcacga gcgccacccg gtaagtcgcg tgccaagcac tagtttacca 16680
tcccacaaat gacaggtctg ggtgggacat ctgcacctga aaatggctta cgacagctgc 16740
ttctcaattc gagtgtgcat attgcaagca ttagattttt tcctgcagat cttcggcaac 16800
atcgtggatg aggtggcgta ccacgagaag tacccgacca tctaccacct gcgcaagaag 16860
ctggtggaca gcaccgacaa ggcggacctg agactgatct acctggcact ggcgcacatg 16920

-continued atcaagttcc gcggccactt cctgatcgag ggtgagtgtg gaatgcatca cagtggaaac 16980
tgctttgtag tacaatttgt ttgtgaagtt tgtgtctaga tgtccatttg atctgtggaa 17040
tgaatgtgct agctctcatg cacagcagta tttggaatgc tgaattacag tgtttccttt 17100
gttggtgtca ggcgatctga acccggacaa cagcgacgtg gacaagctgt tcatccagct 17160
ggtgcagacc tacaaccagc tgttcgagga gaacccgatc aacgcaagcg gcgtggacgc 17220
aaaggtgtct tgatgtaaag tcgaacattg catttgaacg aaggagctcc cttgttggct 17280
aagcatgggt attgactcta ccccagcagg gaatcatctt gctgcaacag ctcacgtcgt 17340
atttgtatgt ggtgcaggcg attctgagcg caaggctgag caagagccgc agactggaga 17400
acctgatcgc gcaactgcca ggcgagaaga agaacggcct gttcggcaac ctgatcgcgc 17460
tgtcactggg cctgacgccg aacttcaaga gcaacttcga cctggcggag gacgcgaagc 17520
tgcaactgag caaggtgaac gtccccctcg gccctgtgct ggtgtgcctg ctgtccaatg 17580
gcacgtttgt gcttcacaat tctacaggtt gatgcaatgt aggttggttg tgctgatgcc 17640
agagatgcac tcaaccaaca ccgtgttgct ttgttggttc ccaaccagcc tgcaatgcaa 17700
cctgtgaatc gtgcaccata cgatctgcat gcaggacacc tacgacgacg acctggacaa 17760
cctgctggcg caaatcggcg accagtacgc agacctgttc ctggcagcga agaacctgag 17820
cgacgcgatt ctgctgagcg acattctgta agtctcagag cacatcacct gcatcacaca 17880
ggatttcttt tgtcagcata tcctgccttt tcgggtcatg tttggatgcc gtgcggctgt 17940
gtgccactgg tccaggcgta ctgggctttc tgacaagctg gatgttatgc ttatattgca 18000
ggcgcgtgaa caccgagatc accaaggtga gccgcacact tgctattgct cgctttcaca 18060
aaatacccgt cgtgaaaacg tcatgtgaag gttgctatca tcgggtcaga gagtatatta 18120
catcatgaac aggctgcaag ggtttgattc ctgcaggcac cactgagcgc gagcatgatc 18180
aagcggtacg acgagcacca ccaggacctg acactgctga aggcactggt gaggcagcag 18240
cttccggaga aatacaagga gatcttcttc gaccagagca agaacggcta cgcgggctac 18300
atcgatggcg gtgcatctca agaggagttc tacaaattca tcaaggtatg tttggcacac 18360
cattgacaga aggggcatgt cttgcccagt gtgcactgct gtcaggtcga tgagagaagt 18420
ggcaatgaaa aattttggtt tgacaacaaa tatgaggggg tactcgggac tgattggcaa 18480
tgcgttagaa actccgtaag atcaaatttc tgaagtggta gcagtggaag ttcctagctg 18540
agggtgtcac tcactcttat ttctgcagcc gatcctggag aagatggacg gcaccgagga 18600
gctgctggtg aagctgaacc gcgaggatct gctgcgcaag cagcgcacat tcgacaatgg 18660
cagcatcccg caccagatcc atctgggtga gctgcacgcg attctgagaa ggcaggagga 18720
cttctacccg ttcctgaagg acaaccgcga gaagatcgag aagatcctgg tacgtggccc 18780
gggttcacct gttgcgtgca tgttgacttc aggacaaagt tagcattatt acacagcggc 18840
agcacagtga gggtcatcat gtggctggct ttccaattgc tccgagggaa taatcggttg 18900
aatgtgtgtt tctcttgcca gtgtgtcctt ggaggtgcgt gcgtgcttcg caaaaaagga 18960
gtacccaata acccttgaaa caaccagttt tgggctgcaa caacacaaga ccgcggttta 19020
ctgcctgact atgcagacgt tccgcatccc gtactacgtc ggtccactgg cacgcggcaa 19080
cagcagattt gcgtggatga cccgcaagag cgaggagaca atcaccccgt ggaacttcga 19140
ggaggtggtg gataagggtg cgtggccagt accagctgca ccccacaggc ggttgttttg 19200
acatttaaac cgctttcagg aagcgtttgt acactcatgc gcttcatggt ctaccagcag 19260
gaggtctgga acacattcag atctaacatg aaatcaagct tgcatttcaa aagcggggca 19320
tccaagtgca gcggggatga actgctgtct catttctatg caggcgcgtc tgcacagagc 19380
ttcatcgagc gcatgaccaa cttcgacaag aacctgccga acgagaaggt gctgccgaag 19440
catagcctgc tgtacgagta tttcaccgtg tacaacgagc tgaccaaggt gaagtacgtg 19500
accgagggca tgcgcaagcc ggcatttctg agcggtgagc aaaagaaggt gggtggtgca 19560
caatgttgat gcagatttga cgctgtatca ctgctgtctc gctgtacagc atctgataca 19620
ctgctgttcc cgctccccgc aggccatcgt ggacctgctg ttcaagacca accgcaaggt 19680
gaccgtgaag cagctgaagg aggactactt caagaagatc gagtgcttcg acagcgtgga 19740
gatcagcggc gtggaggatc gctttaacgc gagtctgggc acctaccacg acctgctgaa 19800
gatcatcaag gacaaggact tcctggacaa cgaggaggtg attgtgggtg gagtgcaccg 19860
cgaatgaatg gggcactgca gcacaatgga gcacacatcc aatccgcaat gagctctcct 19920
gagacttttt ttggctcctg aagcaaacca gacaatgtgc gcctatttca cggacctggc 19980
gcatggaagt agtctggcaa ctatggctgg agcacaacaa tttctggtta ttttgattgg 20040
aatgattggg ggaaaaaaca atgtgttgcc cgcagcacag gccctggtgc agttgagtta 20100
gctgtagcag tagcagaagg catgtcatcg aaaaagtacc gaattgtgcc atcatcccca 20160
ccctgctgca gaacgaggac atcctggagg acatcgtgct gaccctgacc ctgttcgagg 20220
atcgcgagat gatcgaggag cgcctgaaga catacgcgca cctgtgagtg gttgccctgg 20280
acactggaga tttcttgcat gttgggtgtg gctgattgtg cctgcatcac tggatgattg 20340
tggcacattt tcggtttaat attcagggta ctgctgcaaa cgagcttggt tcaactgacg 20400
tacctgaacc agtcgttttg ctgcttgcag gttcgacgac aaggtaagct gtgacaggac 20460
aagctggcag attcttcact tgcacctgtc cagctgaatc tacaaccatg ggtgaaggat 20520
gctgccgttg ctggcagcca cacctgtttg aaactaaaat gggagcaacc tgtgcagcaa 20580
ggtcctacga tatcatacct gcttcttcaa ccatctgatg cccctttatca acaagcgcac 20640
cctgcaggaa ttacccttgc accaaaacct gggcacgttg cctgccgctt gccagaacta 20700
gctgtctgtg ccactcccaa catgtgccta gcatctgtga tatctgctac aggtgatgaa 20760
gcagctgaag cgccgccgct atacaggttg gggtagactg agccgcaagc tgatcaacgg 20820
catccgcgac aagcagagcg gcaagacaat cctggacttc ctgaagagcg acggcttcgc 20880
aaaccgcaac ttcatgcagc tgatccacga cgacaggtga gccaggggag gtgcattcct 20940
agcctgtgct tgcttgtgtg gaccctattt gggaggagga agattgacct ggtatgaaat 21000
gtgaggctag acaacacatg cgactatttc tctccagcag cactggcagg acgatgggac 21060
tgcatgtgag ggcatgtctt gacatgaaat gtcttgccac cagtttgatg tgttgacatc 21120
gaacatcagc ccccctccc cagctattat ctagttctgg tcctatcaga ccatgcgcaa 21180
tctgctggcg gtctcatctt taaaagcatt cttgtcatca ggctgtgcag tggagccagc 21240
aataaaacca acctattgtt ttgcagcctg accttcaagg aggacatcca gaaggcgcag 21300
gtgtctggtc agggcgatag ccttcacgag cacatcgcga acctggcagg ctcaccagcg 21360
atcaagaagg gcatcctgca gaccgtgaag gtggtggatg agctggtgaa ggtgatgggc 21420
cgccacaaac cggagaacat cgtgatcgag atggcgcgcg agaaccagac aacccaaaag 21480
ggccagaaga acagccgcga gcggtacgca gaactctggc gtagccacgc aaatcatgtt 21540
tgcagatgaa agttttgtca tatgcgcaag accagggacc ttctatgtat caaaaggctt 21600
aacagtgtgt tgttggttat gttgtgcagc atgaagcgca tcgaagaggg catcaaggag 21660

-continued

```
ctgggtgagt catgtggaaa ggtatcatac attagatggt gttcccctgt tgtacaagat  21720
ctggcagcat ttggatgctg ccattggaga tttcatgaga tattcagtta aactaaaagc  21780
gtgagttttc gcagcagagg atagagccaa actcacaaat cattttggct tggtgcaggc  21840
agccagatcc tgaaggagca tccagtggag aacacccagc tgcagaacga gaagctgtac  21900
ctgtactacc tgcagaacgg ccgcgacatg tacgtggatc aggagctgga catcaaccgc  21960
ctgagcgact acgacgtgga ccacattgtg ccgcagtcgt tcctgaagga cgacagcatc  22020
gacaacaagg tgctgacccg cagcgacaag aatcgcggca agagcgacaa cgtgccgtct  22080
gaagaggtga ggcatcgcac aggatataca gtgggttcca tgagtgctgt tgtgttgtgc  22140
attgcttcga cccgctttcc aacctgtgcg tggtgtatgg gtttgcacca tggcgtgcac  22200
gggcacaggc atgtcatgct gcaagcaaca gggccgccaa gcttccttca cctgctcggt  22260
gatctttgtc ccttcctcca ccctcccttt ttccccgccc caggtggtga agaagatgaa  22320
gaactactgg cgccagctgc tgaacgcgaa gctgatcaca cagcgcaagt tcgacaacct  22380
gaccaaggca gagaggggtg gcctgtctga gctggataag gcgggcttca tcaagcgcca  22440
gctggtggag acacgccaga tcacaaagca cgtggcgcag atcctggaca gccgcatgaa  22500
caccaagtac gacgagaacg acaagctgat ccgcgaggtg tgacccgggt gtattagaga  22560
gatgcgcaac gcgtgctggt tgttgttgcc gttgcaccta gggagtaggt cgaatgccgc  22620
gttggtgccc gctggggtgg ctgtatcatg ctggatgggg ttgcaatcag acccgggtaa  22680
gaatgaagtg tggagctcac tgttccgtcg agcgcttcag cctgcttgat ggtgatgccg  22740
gtttggcgca ggtgaaggtg atcaccctga agagcaagct gtgagtggcg tgctgcacaa  22800
ttgtttgtca agtgcacttg ttcttgatac aaagttgggc tcgccattga tagcaagaaa  22860
aagaacttgc cacctggata gctgcgtctg gaacatgttg catggaggga attttatggt  22920
gacacccatg gtgacactct tcatggaacc tgctggccac ctgctggtat gcctcttgag  22980
gctggatgat caacaaatga tgtgccgcag tctacagtca atttcagttc acccagtagc  23040
tgtttttcat tcgtgctgca gggtgagcga cttccgcaag gacttccagt tctacaaggc  23100
aagtgccttc tagggttcag atctaagcca gagcagtgaa caactggtgc tattatatcg  23160
tacatatggt gctaattcgc ctgcttgcag ctcagcaggc accattggtg cacaggaaaa  23220
tcggcgcatg atccaagtgc agctgcgcct cgcagcttgt acccctgctg agttttcttt  23280
cggctgttgc ccatgcaggt gcgcgagatc aacaactacc accacgcgca cgacgcctac  23340
ctgaatgcag tggttggcac cgcgctgatc aagaagtacc cgaagctgga gagcgagttc  23400
gtgtacggcg actacaaggt gtacgacgtg cgcaagatga tcgcgaagag cgaggtgagc  23460
actcacaggc agttctgtta ccaacatctg cgattttctt gggcagagag tgtatcttag  23520
acctcattca cctcagattc ctgagcgagc tgcaatgccc gttgtcagcc tgtgcaatga  23580
aggaaaaacc tgtcgtaatg cttgcagcag gagatcggca aggcaaccgc gaagtatttc  23640
ttctactcga acatcatgaa cttcttcaag accgagatca ccctggcgaa cggcgagatt  23700
gtgagtgtca cagtagtgtg catcttcgtt tgatccagtt tgatccacgt gcagctgccc  23760
atcaagtcca ggttgtggac cttcatcttt ggactggcag tgtatgaaaa gtccactggg  23820
aacctgctct ttttcatacc gcatcatgca tatcgtgtcc catcgtgcgt acttcatgag  23880
ttgtccctat ttttattact gtcgtcatca cttccaacgt ccacagagcc aacacgactt  23940
gtgctgaata aaggaatgaa atcgcctatt taatataaac tggtattgtg ggacaaagtc  24000
caattcgcaa gtctgatgcg cacctgtgca gaggaagagg ccgctgatcg agaccaacgg  24060
```

```
cgagacaggc gagatcgtgt gggataaggg ccgcgacttt gcgacagtgc gcaaggttct  24120
gagcatgcca caggtgaaca tcgtgaagaa gaccgaggtg cagaccggcg gcttcagcaa  24180
agagagcatc ctgccaaagc gcaacagcga caagctgatc gcgcgcaaga aggactggga  24240
cccgaagaag tatggcggct tcgacagccc aaccgtggca tatagcgtgc tggtggtggc  24300
gaaggtggag aagggcaaga gcaagaagct gaagagcgtg aaggagctgc tgggtgagcg  24360
gccagcacat gcacctaggt tgcctatcac atggcaccaa attgcatagc catttcaggg  24420
tgattcactt cccggtaaca ggcattgtct ggcagcctca tcgtatgcat gaatggagat  24480
gggtcaattc aagcttgcat ttcaaaagca gggcatccaa gtgcagctgg gatcaactgc  24540
tgtctcattt ctatgcaggc atcaccatca tggagaggag cagcttcgag aagaacccca  24600
tcgacttcct ggaggcgaag ggctacaagg aggtgaagaa ggacctgatc atcaagctgc  24660
cgaagtacag cctgttcgag ctggagaatg gccgcaagcg catgctggca tctgcaggtg  24720
ggtggtgcac aatgttgatg atagtgccct gatgtagtgc gcagatttga cgctgtatca  24780
ctgctgtctc gctgtacagc atctgataca ctgctgttcc cgctccccgc aggtgagctg  24840
caaaagggca acgagctggc actgccgagc aagtacgtga acttcctgta cctggcgagc  24900
cactacgaga agctgaaggg ctcaccggag gacaacgagc agaagcagct gttcgtggag  24960
cagcacaagc actacctgga cgagatcatc gagcagatca gcgagttcag caagcgcgtg  25020
atcctggcag acgcgaacct ggataaggta ggaattttcc cctccctgca ggtggccagg  25080
gaaatgaacc ggtcaccatg taccgggtag cacgggtgga cacacggcag tggccaggga  25140
atcgtactgc tgagggtccc cctgcatgca gactgtgggg gttccctcag gctccgtctt  25200
tgttgcacat gcaatggttt gatcggtctc agttggcatc tctattgaaa ctgctatatt  25260
cctatgccag tgacgcagag gtgaggatgg ttgacaaggt tttgacgtag tgggtgttga  25320
gggtgctgtg caggtgctga gcgcgtacaa caagcaccgc gacaagccaa tccgcgagca  25380
agcagagaac atcatccacc tgttcacgct gaccaacctg ggcgcaccag cagcgttcaa  25440
atatttcgac accaccatcg accgcaagcg gtacacaagc accaaggtac tacctgcctg  25500
cccaaatgct gttgggcttt gcagcacaaa ggaaaattct ccagccaggg tttttcctgc  25560
tgcaacactg ttgtatgatc gctcacaata agggggaaat aggtttccaa gtcatggttg  25620
tgacagtgga aaccaagtct tttttgcctc caccaagttt ttgtcctcaa atttaattca  25680
atggtggttt gtaggaggtg ctggacgcga ccctgatcca tcagagcatc acaggtacag  25740
tgcagcagca caatccctcg tcaagcttac ttgtgttgca ttgccaaatt gcccaatttc  25800
ctatgaagtt tgctgtacat ttgatcatgc gctaaattgc ttttacgttc tatcgctttg  25860
tatgcatgca ggcctgtacg agacccgcat cgacctgtct caactgggtg gcgactgagg  25920
tgcgaatagt gcttcagtaa aaaagtagca acttggtgca atatcgtcag ggtcgtgtgg  25980
tctgctcgcc agcaagtttt ttggcacagg agagcgcttt ttccgagtac cgccaaagtt  26040
caagcatgtg ctgtgattcg ctgttgcctc ttatgataat tgctcaaagt ttccaagcat  26100
tctatgtcca ccctgcacca ctaagttgta tggtgcttat tctgcagggg atgattcatg  26160
gtgcctaaaa attttgtgct gctgtcgcgt ctgttttctg tcgcagttta gtgaatgtaa  26220
ctccaaatac caaacttttc atcacaatca tattgatgcc tttgtaagtg aattacagcg  26280
tttttgcca taaaaagaag taccgtgaca ttggggtcgt cataacaaga agctttatga  26340
acaagcagct tgatctacga gacttataca taaatggttt cgggtaactc ctaatacggg  26400
```

gctacgttag ttcagcagct gagaacgacc acgaacggga agaattccag ccatgttgaa 26460
gaggtgcagc tatcaaggtg aggtctttac tggtgtctgt tattgctgta acatcatttc 26520
gctgttgcac aatttaaaca tttgtaattt actgttgtta ttgcagtggc cacttgtagc 26580
agtggcagcg aggcactgac acttctacgt gaacgcaacg aggacggatc ctccgaccag 26640
ttcgacctcg tactgtcaga tgtttacatg ccgggtatgt cgtattcctt tgtaaacttt 26700
acaatatgcg tctagtttga cgcgtacact ttgtacactt tgcaaaaacg caccctgcga 26760
ggtctgccat ttggtcacta caacttggcc accttggttg caagtttgca agttcgctct 26820
acgtcaacgc tgcaaaatga accaattgtt ttgcactgac cctgccaacc ttcatttgtg 26880
gctgcagaca tggacggttt caagctgctt gaacacatcg gtctagagtt ggagcttccc 26940
gttatcagta agttgatcga gccgagtcca gagcgaagcc tgcttctata ctattagcag 27000
ctgtcttttg atatttgaca gcttgacttg atatggtcac agagcatact tgcaaccagg 27060
ttacctgttg aactagcaac tgtgcccaag catctcttca agcacctccg tcagtccata 27120
gggtactgtt gatttgtact ctgcaatact gcactgtaat gcgctgtgaa tcactgccct 27180
tcacctctag atggtgcttc cctggagccc tcccccacct ccgcctcaag cccctcacat 27240
gcctctcccc cccctgcagt gatgtcatcc aacggggaca cgaatgtcgt gctgcggggg 27300
gtcacccacg gggctgtgga ctttctgatc aagcccgttc gaattgagga gctgcggaac 27360
gtgtggcagc acgtggtgcg tcgtcgttcc atggcgctgg ccaggacgcc agacgagggg 27420
ggacactcgg acgaggactc tcaggtgccc ttggcagctt ctgggcggct tgctgtgtcg 27480
gatgccactt ggactgggga tgcacgaggg gtggggggac aatgggagat gggccatagt 27540
aggccagagt tgatggcagt ggtggtgggg gggagtaggc gggagagaag cagccatcct 27600
ggtgttggtt ttgatgattg agtgcatggg gatgatgcac aggtgagctg actggatgcc 27660
ttgtcttgct gtgctgcgct gcagcggcac agtgtgaaac gcaaggagtc ggagcagagc 27720
ccgctgcagc tcagcacaga gcagggcggg aacaagaagc caagagtggt gtggtcggtg 27780
gagatgcacc aacaggtgtg cttgcgggcg ggtgtatacg ggggaggggg gccagctgct 27840
ggctgacctg gcgtgcgcgg tgcattgcac ttggcgatga ggggcgtgct tcagtatgta 27900
gctgggacgc aattggttgt gctgtgtgac cagtgcacaa aatacatccc tgaattccag 27960
tgggttgaac agagttgtcc tggaggtggg aagcaaacgc gcacgtggta gaggggagca 28020
gggtgcagaa cagccgcagc aggggtgttg cgcagtgtgc aggtatcctg cctccatgcc 28080
ccgggccatg ggcatactac gctggtaccg tcaggatggg cgttgagcct ggcttggggg 28140
gcagggggcg agcgaatgcg gaatgggagc ggcaggtgct gggagggtgg ctgactggct 28200
tgcaggagcg caagtcctgt cgggggcgtc gtcctgttcc ctcctgcccg cttcacccac 28260
gttcactctc atgcctccac actcctgctg ctgacacacc tgtcgccacc tccgctgcag 28320
tttgtgaacg cggtcaactc cctgggcatt gacaaggcgg tgcccaagcg gattctggac 28380
ctgatgaacg tggaggggct gacgcgcgag aacgtggcca gccatctgca ggtgcctgcc 28440
atgacccgcg at 28452

<210> SEQ ID NO 87
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 87
aggctactct cagacatgac ggtggctctg 30

<210> SEQ ID NO 88
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 88
gccacaaatg aaggttggca gggtcagtgc 30

<210> SEQ ID NO 89
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 89
acaccacctt aaggcacatg agg 23

<210> SEQ ID NO 90
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 90
ggcgtgggac atggtgcgca agg 23

<210> SEQ ID NO 91
<211> LENGTH: 55
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 91
tgaagcaccc cccggcctct ccccccgcag ggccgcccct cccgcctcgt cgtgc 55

<210> SEQ ID NO 92
<211> LENGTH: 56
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 92
cgcaacgctc tccctcccca ccccccagcc tcacatccgc ctcaagcagc gccctg 56

<210> SEQ ID NO 93
<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 93
caagctatgc gaggaaggga gggtc 25

<210> SEQ ID NO 94
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 94
ctgccgcaag tgagtgtgct gtc 23

<210> SEQ ID NO 95
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 95
caccagatat aggtgacccg ataac 25

<210> SEQ ID NO 96
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 96
aaaactccac tgcacctgca acat 24

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 97
tgcggtgaag cttggagctg 20

<210> SEQ ID NO 98
<211> LENGTH: 59
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 98
ttgccgtcga cgagacttcg gggcgcgcat ttatcgactc tcttgaagat acaccggtt 59

<210> SEQ ID NO 99
<211> LENGTH: 65
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 99

```
tccaattgta gatatcatat tgtttccgga cctaccttac gcactgagtg ctgccagatg     60

ttctt                                                                 65


<210> SEQ ID NO 100
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100

gaggtgggtg gtagtgcttc gcgaggtg                                        28


<210> SEQ ID NO 101
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101

atcacagctc acagggcaga cactgcgtc                                       29


<210> SEQ ID NO 102
<211> LENGTH: 7
<212> TYPE: PRT
<213> ORGANISM: Unknown
<220> FEATURE:
<223> OTHER INFORMATION: Description of Unknown: 'SHAQKYF' class family
      protein sequence

<400> SEQUENCE: 102

Ser His Ala Gln Lys Tyr Phe
1               5


<210> SEQ ID NO 103
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103

gggacatggt gcgcaaggac ggg                                             23


<210> SEQ ID NO 104
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104

tgcggtgaag cttggagctg tgg                                             23


<210> SEQ ID NO 105
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 105

```
acaccacctt aaggcacatg agg                                              23
```